(12) United States Patent
Cook et al.

(10) Patent No.: US 8,835,424 B2
(45) Date of Patent: Sep. 16, 2014

(54) SELECTIVE AGENTS FOR PAIN SUPPRESSION

(75) Inventors: James Cook, Whitefish Bay, WI (US); Shengming Huang, Milpitas, CA (US); Rahul Edwankar, Milwaukee, WI (US); Ojas A. Namjoshi, Milwaukee, WI (US); Zhi-Jian Wang, Milwaukee, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 197 days.

(21) Appl. No.: 12/779,449

(22) Filed: May 13, 2010

(65) Prior Publication Data

US 2010/0317619 A1    Dec. 16, 2010

Related U.S. Application Data

(60) Continuation-in-part of application No. 12/684,845, filed on Jan. 8, 2010, which is a continuation of application No. 11/929,860, filed on Oct. 30, 2007, now abandoned, which is a division of application No. 11/458,855, filed on Jul. 20, 2006, now abandoned, which is a continuation of application No. 10/402,538, filed on Mar. 28, 2003, now Pat. No. 7,119,196.

(60) Provisional application No. 60/368,408, filed on Mar. 28, 2002, provisional application No. 61/177,818, filed on May 13, 2009.

(51) Int. Cl.
*A61K 31/5517* (2006.01)
*C07D 487/02* (2006.01)

(52) U.S. Cl.
USPC ........... 514/220; 540/561; 540/562; 540/563; 540/564; 540/566

(58) Field of Classification Search
USPC ........... 514/220; 540/561, 562, 563, 564, 566
See application file for complete search history.

(56) References Cited

FOREIGN PATENT DOCUMENTS

WO    2006061428 A2    6/2006

OTHER PUBLICATIONS

UWE Rudolph et al., Benzodiazepine Actions Mediated by Specific Aminobutyric Acid Receptor Subtypes, Nature Oct. 1999, vol. 401, pp. 796-800, Macmillan Magazines Ltd.

Karin Low et al., Molecular and Neuronal Substrate for the Selective Attenuation of Anxiety, Science Oct. 2000, vol. 290, pp. 131-134, www.sciencemag.org.
R.M. McKernan et al., Sedative but not Anxiolytic Properties of Benzodiazepines are Mediated by the GABA Receptor, Subtype, Nature Neuroscience, Jun. 2000, vol. 3, No. 6, Nature America Inc., pp. 587-592, http://neurosci.nature.com.
F. Crestani et al., Trace Fear Conditioning Involves Hippocampal GABA Receptors, Institute of Pharmacology, Jun. 2002, vol. 99, No. 13, pp. 8980-8985, www.pnas.org.
Mark S. Chambers et al., Identification of a Novel, Selective GABA a5 Receptor Inverse Agonist Which Enhances Cognition, J. Med. Chem 2003, 46, pp. 2227-2240.
Ulrike B. Zeilhofer, Julia Knabl et al., Reversal of Pathological Pain Through Specific Spinal GABA Receptor Subtypes, Nature vol. 451/17, Jan. 2008, Nature Publishing Group, pp. 330-335.
Julia Knabl et al., Genuine Antihyperalgesia by Sysemic Diazepam Revealed by Experiments in GABA Receptor Point-Mutated Mice, Pain 141, 2009, Int'l Assoc for the Study of Pain, Elsevier B.V., pp. 233-238.
Vesa K. Kontinen et al., Effect of Midazolam in the Spinal Nerve Ligation Model of Neuropathic Pain in Rats, Pain 85, 2009, Int'l Assoc for the Study of Pain, Elsevier B.V., pp. 425-431.
Adam P. Tucker et al., Intrathecal Midazolam II: Combination with Intrathecal Fentanyl for Labor Pain, Anesth Analg International Anesthesia Research Society 2004, pp. 1521-1527.
Heike A. Wieland et al., A Single Histidine in GABA Receptors is Essential for Benzodiazepine Agonist Binding, The Journal of Biological Chemistry, vol. 267, No. 3, Jan. 1992, pp. 1426-1429.
E.A. Barnard et al., International Union of Pharmacology. XV. Subtypes of y-Aminobutyric Acid Receptors: Classification on the Basis of Subunit Structure and Receptor Function, Pharmacological Reviews, vol. 50, No. 2, 1998, pp. 291-313.
P. Scott-Stevens et al., Rodent Pharmacokinetics and Receptor Occupancy of the GABAa Receptor Subtype Selective Benzodiazepine Site Ligand L-838417; Biopharmaceutics & Drug Disposition, 26: 2005, pp. 13-20, www.interscience.wiley.com.
Felix M. Rivas et al., Antiseizure Activity of Novel y-Aminobutyric Acid (A) Receptor Subtype-Selective Benzodiazepine Analogues in Mice and Rat Models, J. Med. Chem, American Chemical Society, Mar. 2009, 52, pp. 1795-1798.
E.A. Barnard, The Molecular Architecture of GABA Receptors, Pharmacology of GBA and Glyci, 2001, vol. 150, pp. 77-99.

*Primary Examiner* — Brenda Coleman
(74) *Attorney, Agent, or Firm* — Boyle Fredrickson, S.C.

(57)    ABSTRACT

In preferred embodiments, the present invention provides methods of treatment and pharmaceutical compositions for the suppression, alleviation and prevention of the often chronic, severe and debilitating pain that can accompany inflammatory diseases and neuropathic insults, pain that is often unresponsive to conventional analgesic treatment. The preferred embodiments of the present invention further relate to methods of treatment and pharmaceutical compositions using benzodiazepine derivatives that provide suppression, alleviation and prevention of neuropathic pain, migraine-related pain and inflammatory pain with reduced sedative and ataxic side effects.

11 Claims, 40 Drawing Sheets

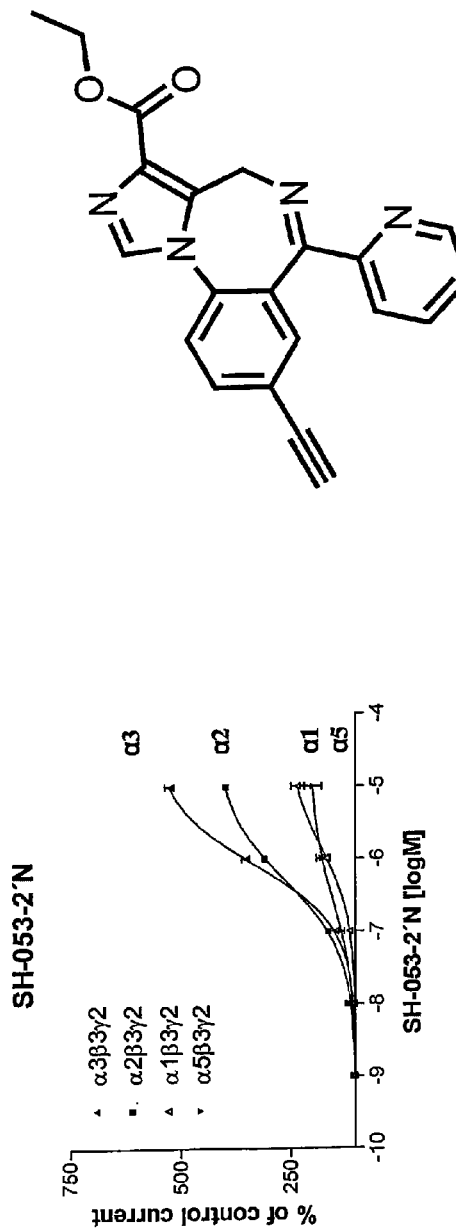

JY-XHE-053
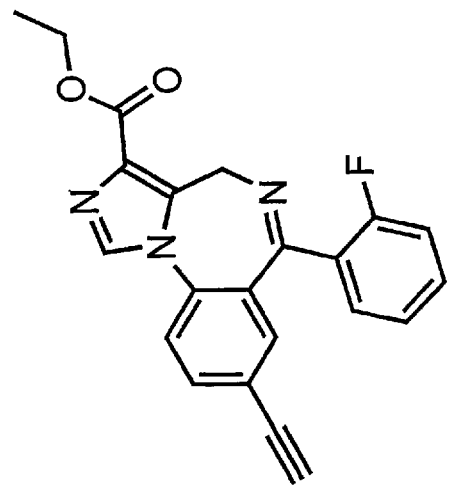
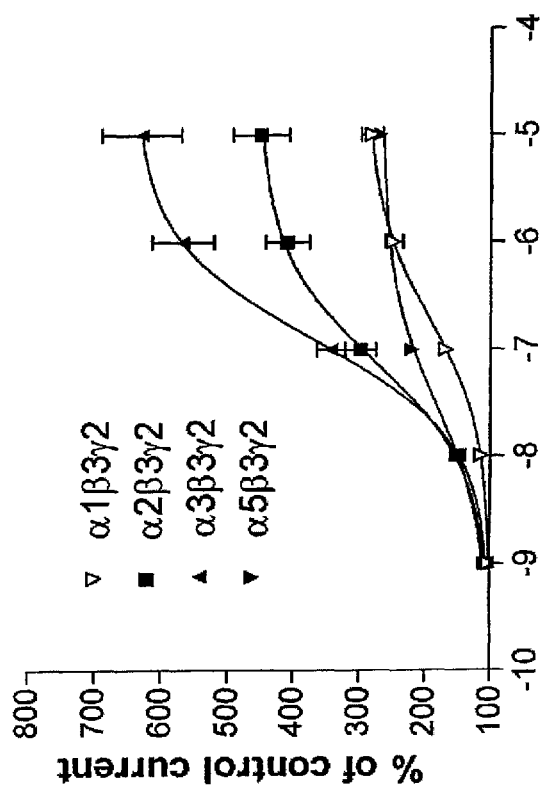
Fig. 6
Binding affinity at α$_x$β3γ2 GABAA/BzR Receptor Subtypes (Values are reported in nM):
| Compound | α1 | α2 | α3 | α4 | α5 | α6 |
|---|---|---|---|---|---|---|
| JY-XHE-053 | 21.99 | 12.34 | 34.9 | ND | 0.671 | ND |

SH-053-2'F-S-CH3
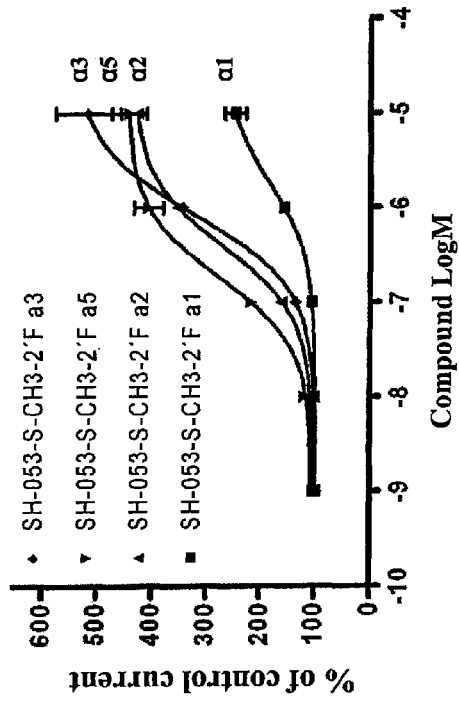
*SH-053-2'F-S-CH3*
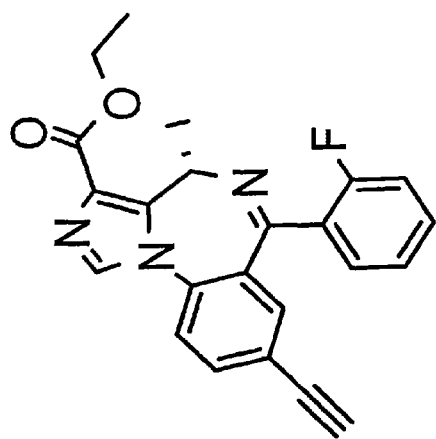
Binding affinity at α$_x$β3γ2 GABAA/BzR Receptor Subtypes (Values are reported in nM):
| Compound | α1 | α2 | α3 | α4 | α5 | α6 |
|---|---|---|---|---|---|---|
| SH-053-2'F-S-CH3 | 350 | 141 | 1237 | >5000 | 16 | 5000 |
| SH-053-2'F-S-CH3 | 468.2 | 33.27 | 291.5 | >5000 | 19.2 | >5000 |
Fig. 12

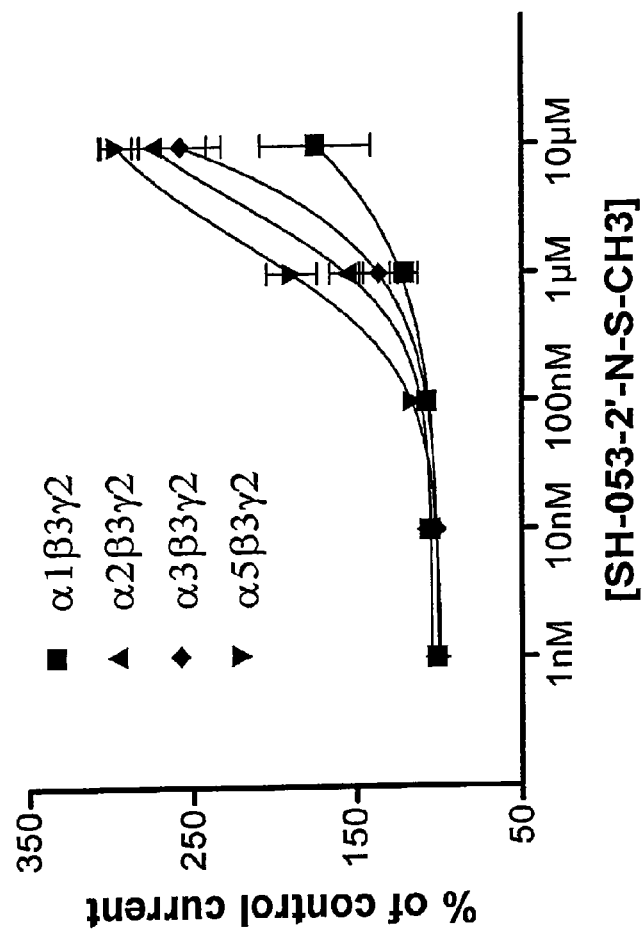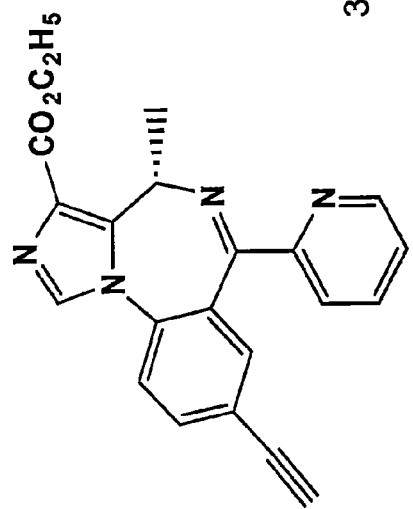
FIG. 14

PS-1-37

Binding affinity at αxβ3γ2 GABAA/BzR Receptor Subtypes (Values are reported in nM):

| Compound | α1 | α2 | α3 | α4 | α5 | α6 |
|---|---|---|---|---|---|---|
| PS-1-37 | 193 | 35 | 435 | ND | 22 | 5000 |

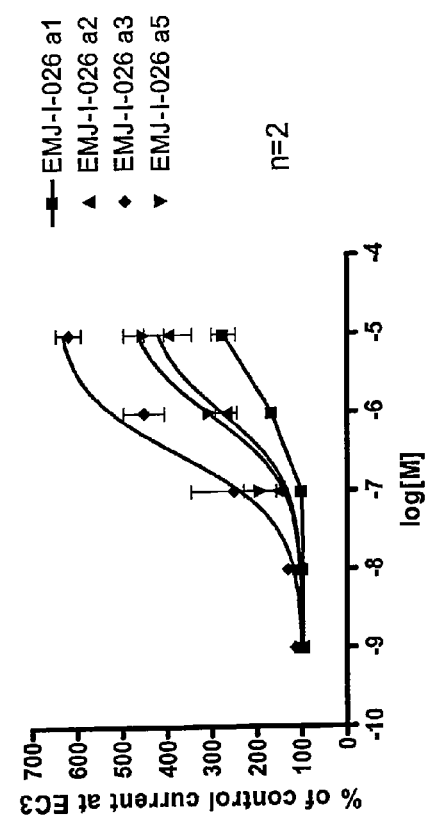
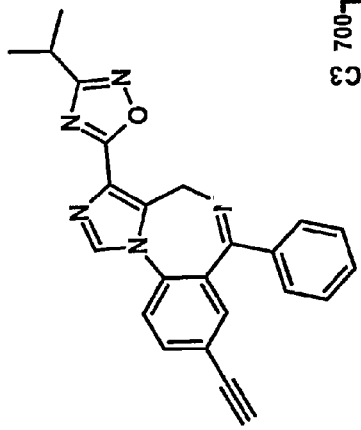
FIG. 16

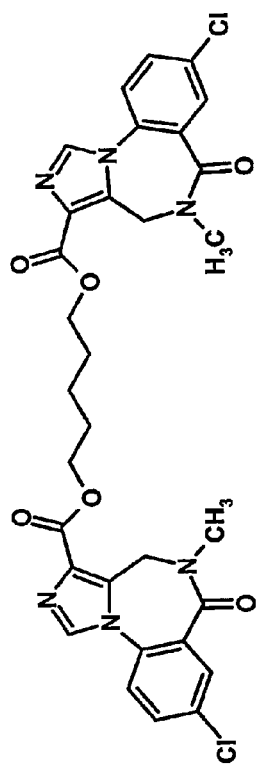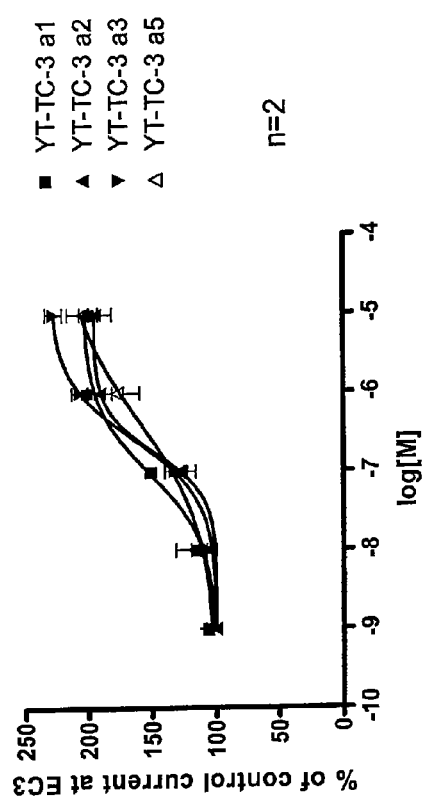
Fig. 19

YT-II-794
| $\alpha_1$ | $\alpha_2$ | $\alpha_3$ | $\alpha_4$ | $\alpha_5$ | $\alpha_6$ |
|---|---|---|---|---|---|
| 4536 | 126.2 | 4981 | ND | 932.8 | ND |
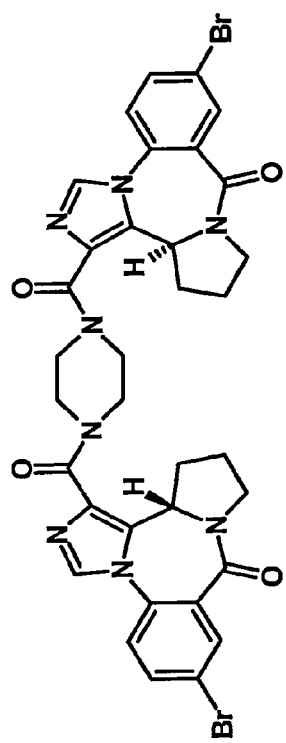
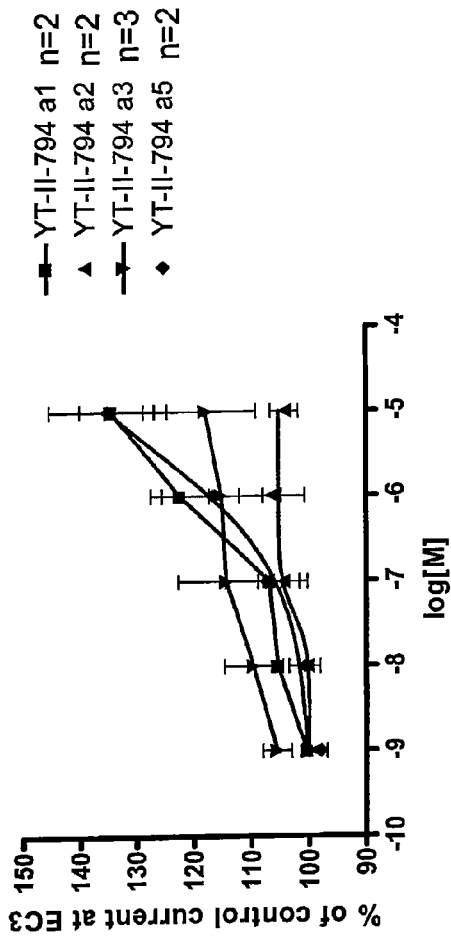
FIG. 20

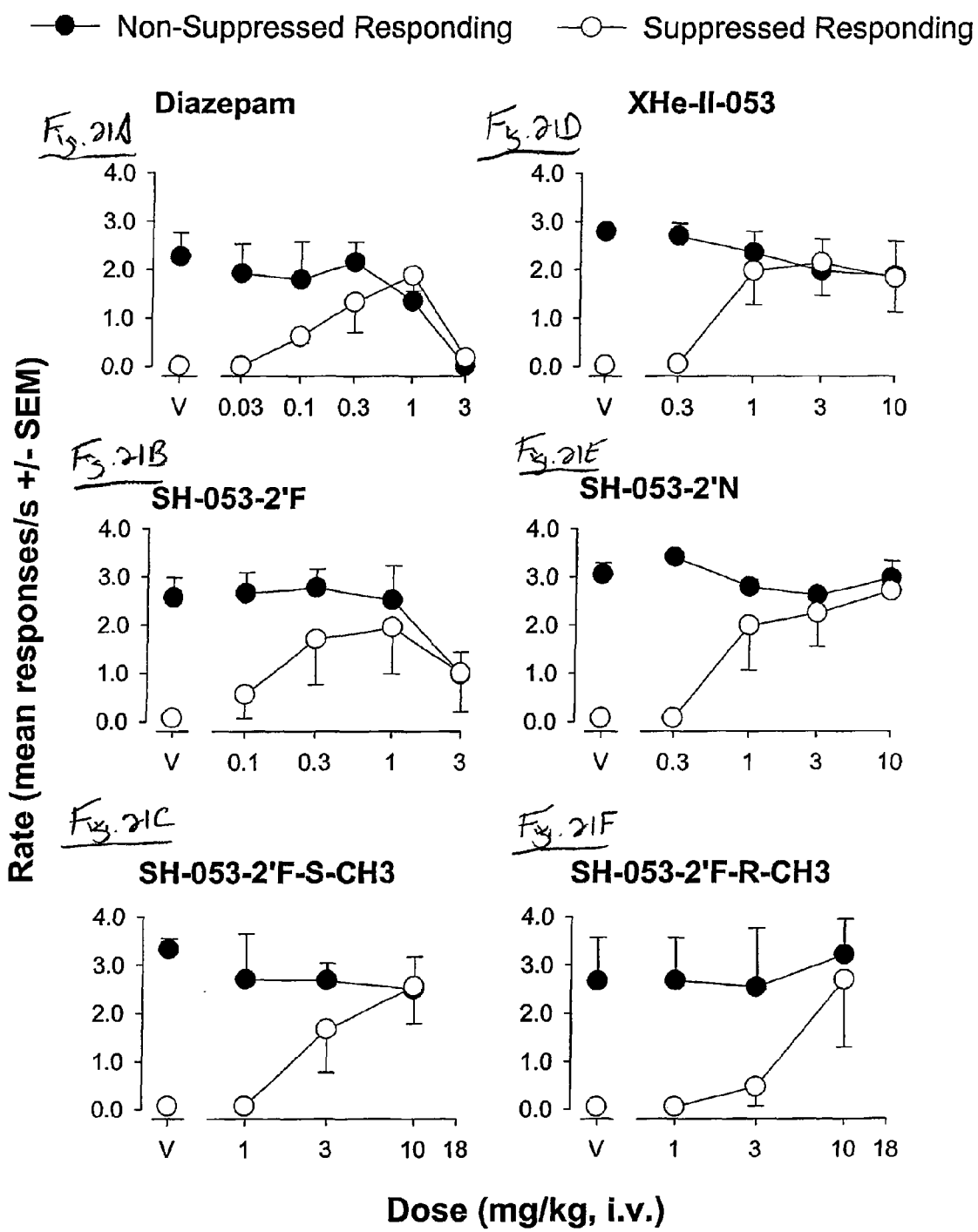

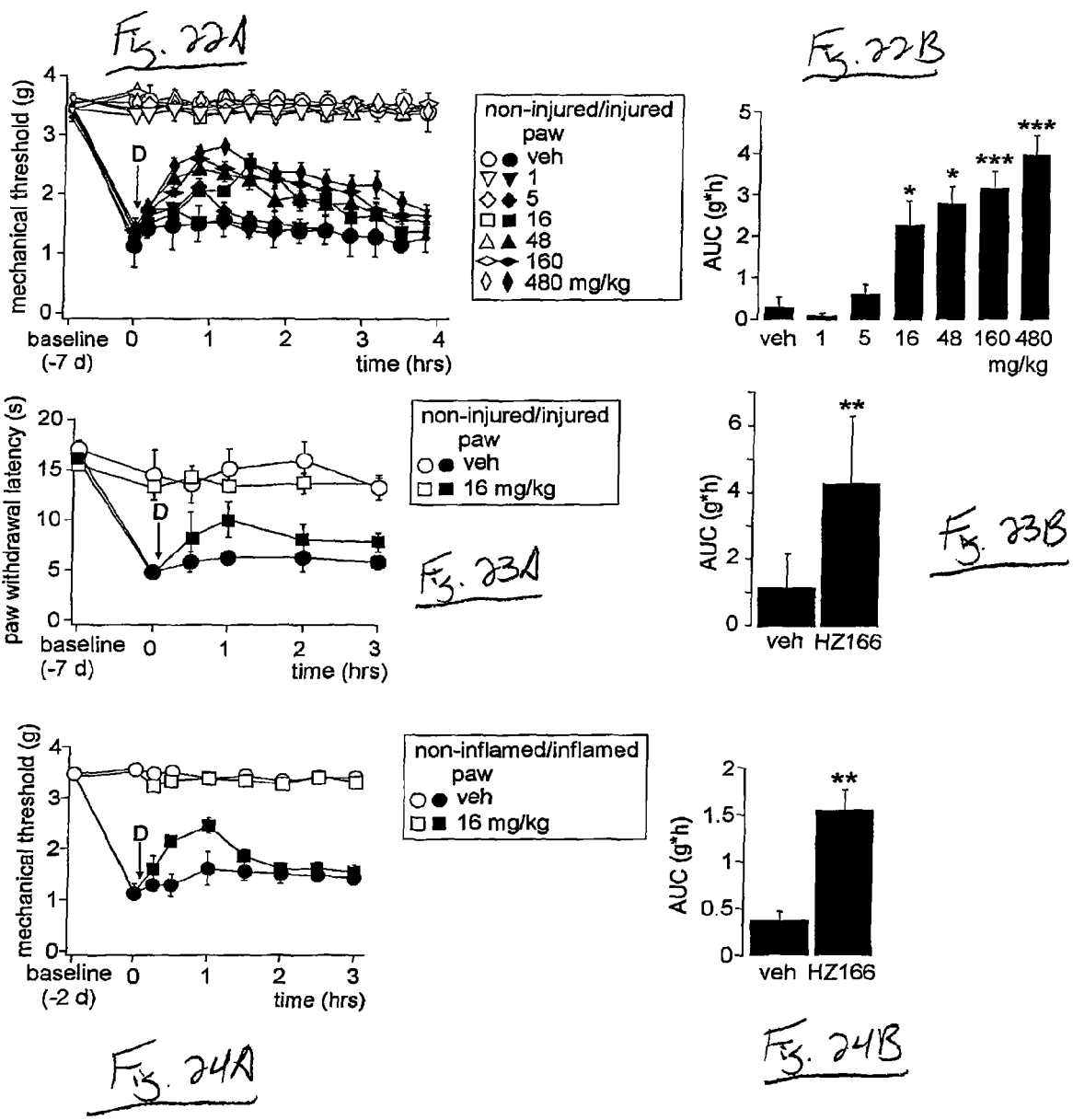

FIG. 27B
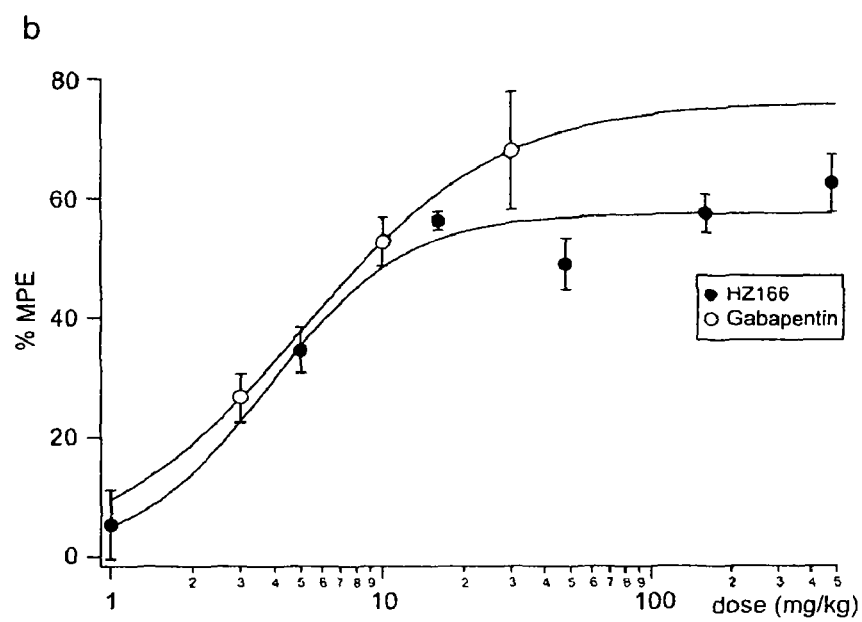
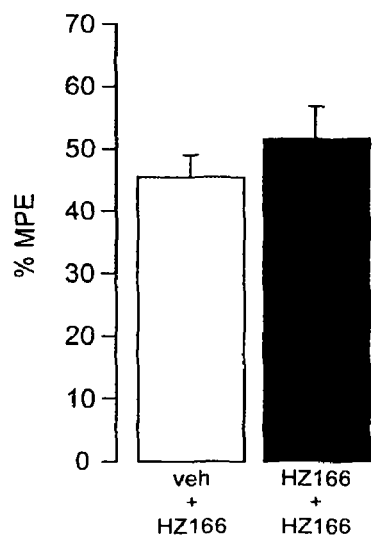
FIG. 27D

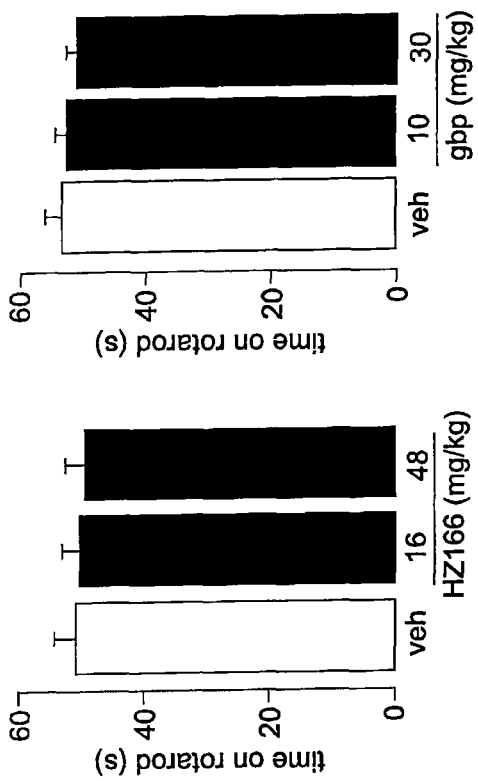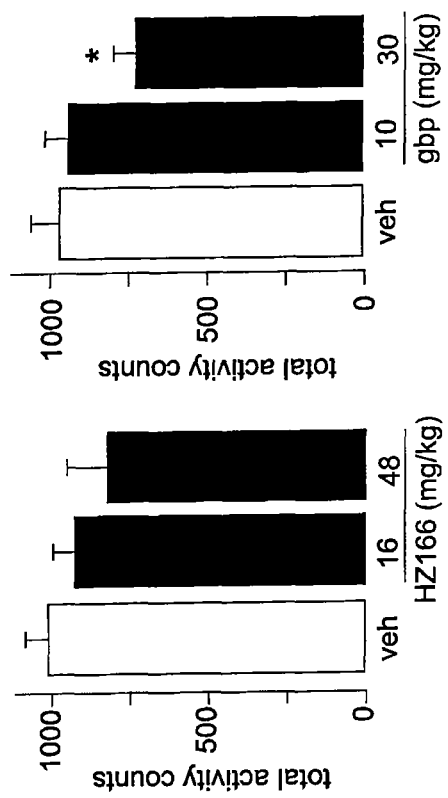
Fig. 28
Fig. 29
Fig. 30
Fig. 31

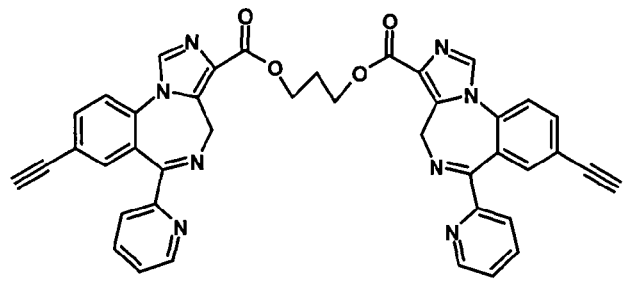
SR-II-57
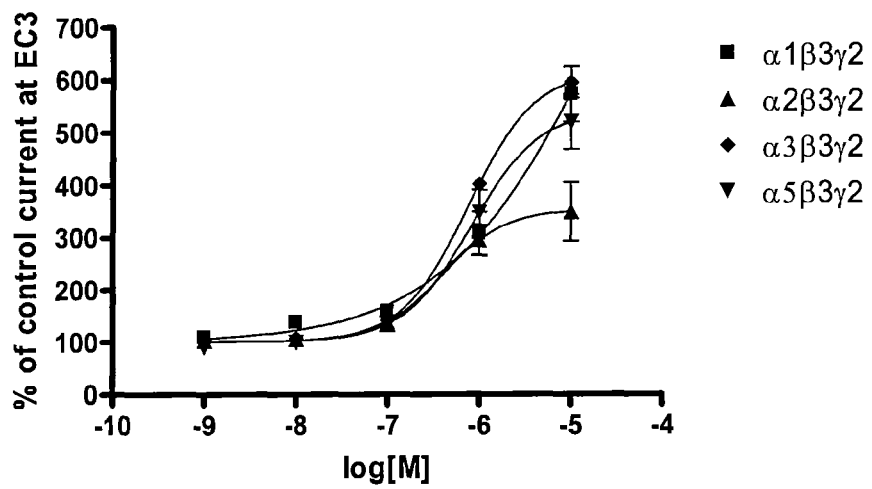
FIG. 34
|  |  | α1β3γ2 | α2β3γ2 | α3β3γ2 | α5β3γ2 |
|---|---|---|---|---|---|
| SR-II-57 | EC$_{50}$ | >17μM | 390nM | >754nM | 816nM |
|  | 95%CI |  |  |  | (418-1592) |
|  | Nh |  |  |  | 1.2 |
|  | 1nM | 10nM | 100nM | 1μM | 10μM |
|---|---|---|---|---|---|
| α1 |  | 137±2 | 159±3 | 307±41 | 572±52 |
| α2 |  |  | 137±8 | 295±30 | 349±56 |
| α3 |  |  | 141±1 | 402±1 | 594±30 |
| α5 |  |  | 135±14 | 347±44 | 520±52 |
| c | Structure | a1 | a2 | a3 | a4 | a5 | Amt(mgs) |
|---|---|---|---|---|---|---|---|
| SR-II-57 | 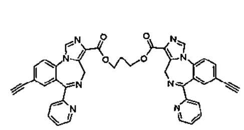 | 169.2 | 480.8 | 667.1 | ND | 729.5 | 20 |

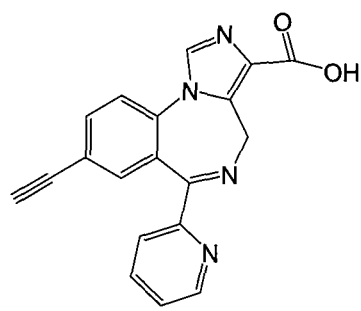
SR-II-54
FIG. 35
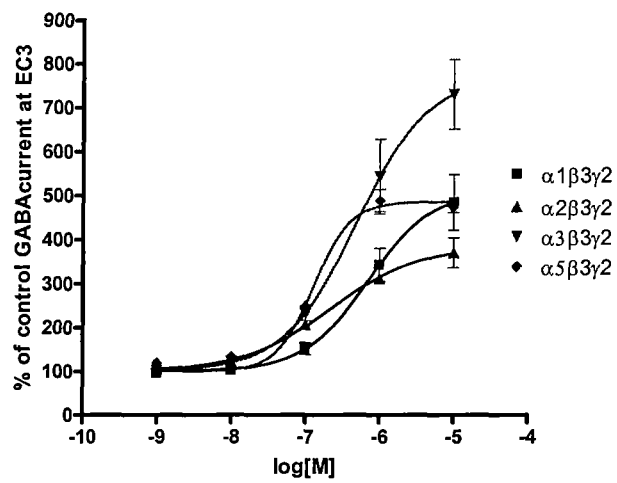
|  |  | α1β3γ2 | α2β3γ2 | α3β3γ2 | α5β3γ2 |
|---|---|---|---|---|---|
| SR-II-54 | EC$_{50}$ | 0.69μM | 0.22μM | 0.48μM | 0.13μM |
|  | 95%CI | (0.26-1.8) | (0.09-0.53) | (0.17-1.38) | (0.08-0.21) |
|  | Nh | 1.01 | 0.74 | 0.89 | 1.76 |
|  | 1nM | 10nM | 100nM | 1μM | 10μM |
|---|---|---|---|---|---|
| α1 |  | 103±2 | 139±2 | 297±50 | 492±37 |
| α2 | 105±4 | 121±3 | 206±4 | 311±6 | 370±34 |
| α3 | 102±2 | 123±5 | 231±15 | 543±85 | 731±80 |
| α5 | 118±5 | 133±3 | 248±7 | 489±25 | 473±12 |
| Compound | Structure | a1 | a2 | a3 | a4 | a5 | Amt(mgs) |
|---|---|---|---|---|---|---|---|
| SR-II-54 | 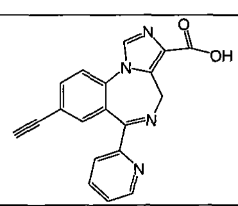 | 174.1 | 363.2 | 946.4 | ND | 966.6 | 20 |

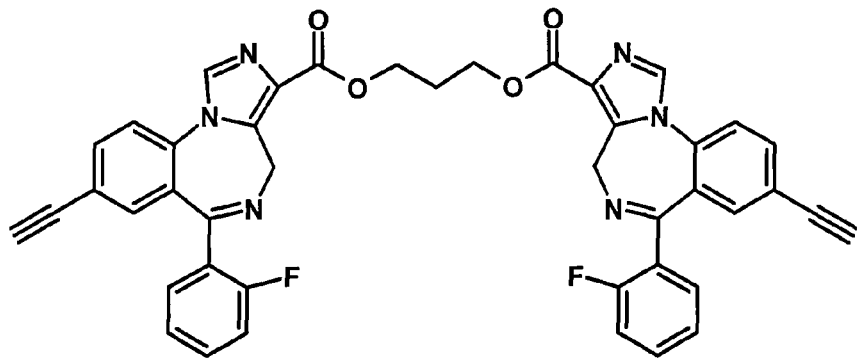
YT-III-271
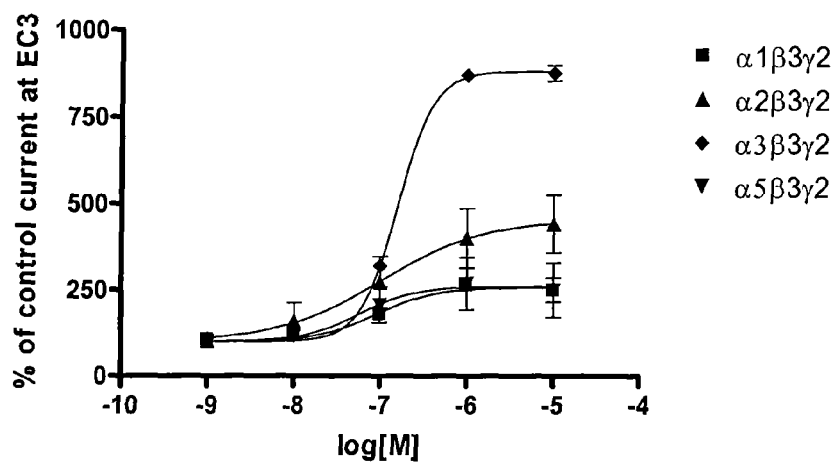
FIG. 36
N=2 for each receptor type
|  |  | α1β3γ2 | α2β3γ2 | α3β3γ2 | α5β3γ2 |
|---|---|---|---|---|---|
| YT-III-271 | EC$_{50}$ | 91nM | 103nM | 157nM | 58nM |
|  | 95%CI | (29-283) | (8-1416) | (112-218) | (4-854) |
|  | Nh | 1.27 | 0.74 | 2.1 | 1.36 |
|  | 10nM | 100nM | 1μM | 10μM |
|---|---|---|---|---|
| α1 | ns | 180±4 | 263±5 | 251±35 |
| α2 | ns | 272±75 | 401±86 | 442±84 |
| α3 | 133±1 | 321±3 | 870±15 | 877±22 |
| α5 | ns | 207±52 | 269±76 | 250±79 |
Binding affinity at αxβ3γ2 GABA$_A$/BzR subtypes (Values are reported in nM).
| Compound | α1 | α2 | α3 | α4 | α5 | α6 |
|---|---|---|---|---|---|---|
| YT-III-271 | 32.54 | 1.26 | 2.35 | ND | 103 | ND |

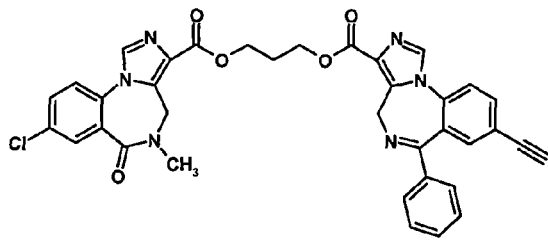
| MW | 659.09 |
|---|---|
| Log P | 4.09 |
| CLog P | 3.57 |
FIG. 37
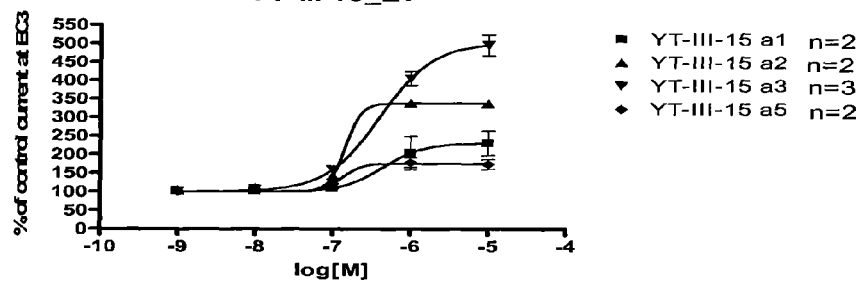
YT-III-15_ZV
|  | YT-III-15 a1 | YT-III-15 a2 | YT-III-15 a3 | YT-III-15 a5 |
|---|---|---|---|---|
| BOTTOM | 100.0 | 100.0 | 100.0 | 100.0 |
| TOP | 231.5 | 338.5 | 502.7 | 176.4 |
| LOGEC50 | -6.353 | -6.842 | -6.396 | -6.881 |
| HILLSLOPE | 1.662 | 4.163 | 1.254 | 3.377 |
| EC50 | 4.438e-007 | 1.437e-007 | 4.013e-007 | 1.315e-007 |
|  |  | α1β3γ2 | α2β3γ2 | α3β3γ2 | α5β3γ2 |
|---|---|---|---|---|---|
| YT-III-15 | EC50 | 444nM | 144 nM | 401nM | 132nM |
|  | 95%CI | 86-2290 |  | 280-576 |  |
|  | Nh | 1.1 |  | 0.2 |  |
|  | 10nM | 100nM | 1μM | 10μM |
|---|---|---|---|---|
| α1 | ns | 110±2 | 205±44 | 231±33 |
| α2 | ns | 143±1 | 339±6 | 338±6 |
| α3 | ns | 159±8 | 406±19 | 496±28 |
| α5 | ns | 122±13 | 179±13 | 174±13 |
Binding affinity at αxβ3γ2 GABA$_A$/BzR subtypes (Values are reported in nM).
| Compound | $α_1$ | $α_2$ | $α_3$ | $α_4$ | $α_5$ | $α_6$ |
|---|---|---|---|---|---|---|
| YT-III-15 | 73.19 | 90.45 | 141.4 | ND | 114 | ND |

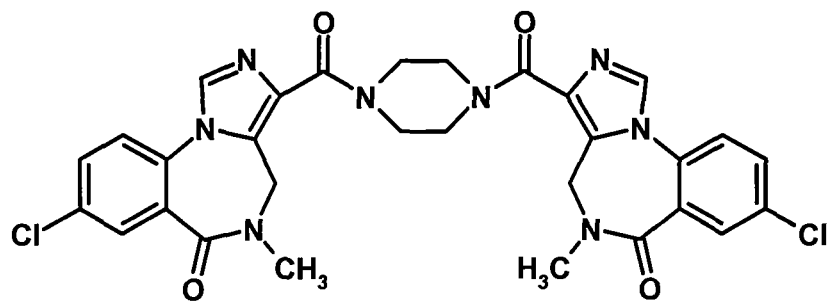
YT-TC-4
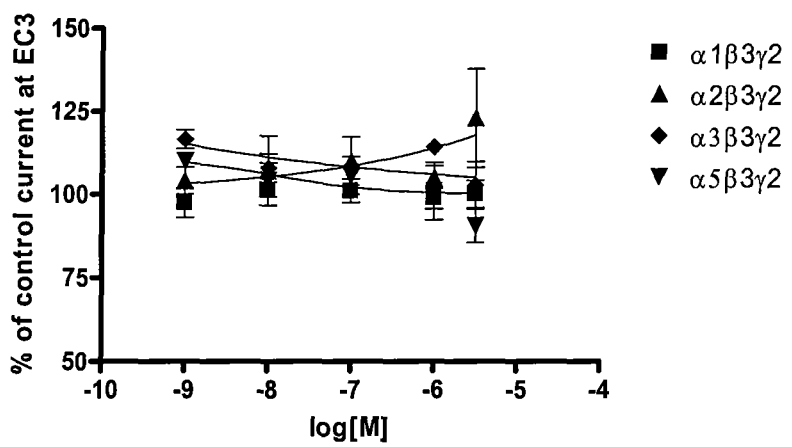
N=2 for each receptor type
FIG. 38
Binding affinity at $\alpha x\beta 3\gamma 2$ GABA$_A$/BzR subtypes (Values are reported in nM).
| Comp | α1 | α2 | α3 | α4 | α5 | α6 |
|---|---|---|---|---|---|---|
| YT-TC-4 | 6291 | 3315 | 352.2 | ND | 2881 | ND |

N=2 for each receptor type

|  |  | α1β3γ2 | α2β3γ2 | α3β3γ2 | α5β3γ2 |
|---|---|---|---|---|---|
| YT-III-38 | EC₅₀ 95%CI | >15μM | >15μM | >754nM | >1mM |
|  | Nh |  |  |  |  |

|  | 10nM | 100nM | 1μM | 10μM |
|---|---|---|---|---|
| α1 | ns | ns | 181±11 | 502±45 |
| α2 | 109±4 | 139±8 | 252±18 | 525±65 |
| α3 | 139±11 | 201±29 | 509±60 | 753±36 |
| α5 | 120±4 | 151±7 | 282±5 | 660±9 |

Binding affinity at αxβ3γ2 GABA$_A$/BzR subtypes (Values are reported in nM).

| Compound | α1 | α2 | α3 | α4 | α5 | α6 |
|---|---|---|---|---|---|---|
| YT-III-38 | 1461 | 18.21 | 14.63 | ND | 3999 | ND |

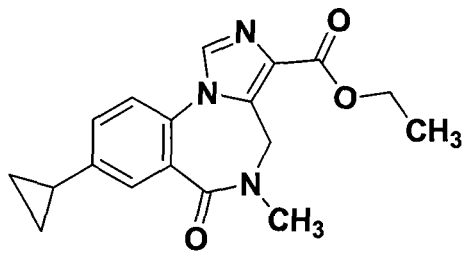
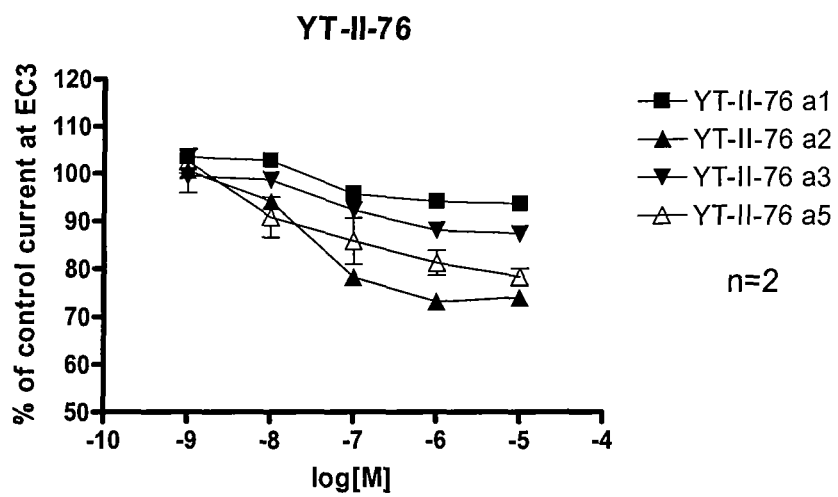
FIG. 40
|   | 10nM | 100nM | 1μM | 10μM |
|---|---|---|---|---|
| α1 | ns | 96±1 | 94±1 | 94±1 |
| α2 | ns | 78±1 | 73±1 | 74±1 |
| α3 | ns | 92±1 | 88±1 | 87±2 |
| α5 | 91±4 | 86±5 | 81±3 | 78±2 |
Binding affinity at $\alpha x\beta 3\gamma 2$ $GABA_A$/BzR subtypes (Values are reported in nM).
| Compound | α1 | α2 | α3 | α4 | α5 | α6 |
|---|---|---|---|---|---|---|
| YT-II-76 | 95.34 | 2.797 | 0.056 | ND | 0.04 | ND |

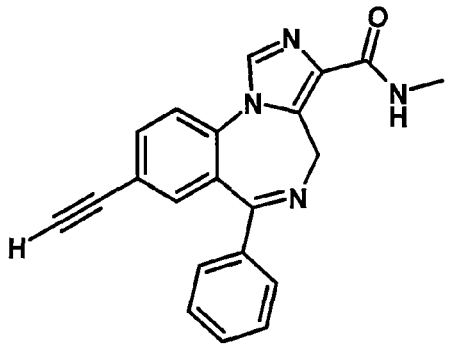
YT-III-31
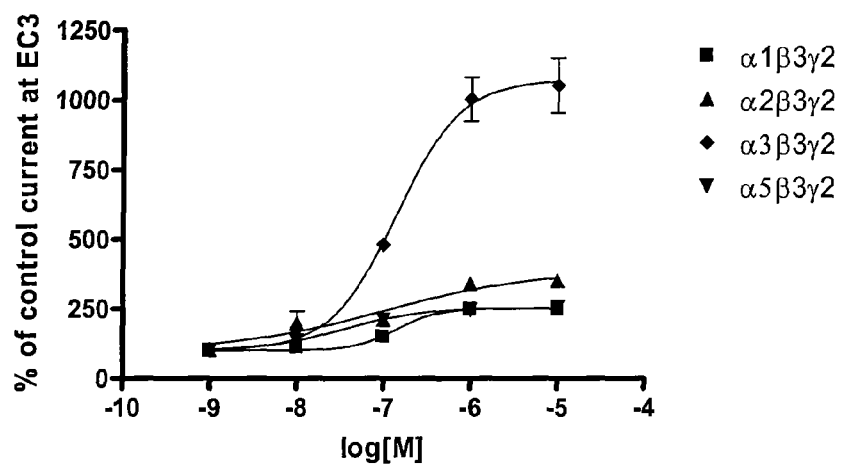
FIG. 41
N=2 for each receptor type
|  |  | α1β3γ2 | α2β3γ2 | α3β3γ2 | α5β3γ2 |
|---|---|---|---|---|---|
| YT-III-31 | EC$_{50}$ | 142nM | 103nM | 140nM | 36nM |
|  | 95%CI | (46-438) | (5-1980) | (80-244) | (26-50) |
|  | Nh | 1.85 | 0.51 | 1.17 | 0.97 |
|  | 10nM | 100nM | 1μM | 10μM |
|---|---|---|---|---|
| α1 | 112±2 | 151±4 | 249±1 | 248±24 |
| α2 | 200±41 | 211±23 | 339±4 | 351±20 |
| α3 | 176±2 | 481±22 | 1003±79 | 1052±98 |
| α5 | 132±4 | 211±3 | 246±1 | 254±10 |
Binding affinity at αxβ3γ2 GABA$_A$/BzR subtypes (Values are reported in nM).
| Compound | α1 | α2 | α3 | α4 | α5 | α6 |
|---|---|---|---|---|---|---|
| YT-III-31 | 36.39 | 67.85 | 129.7 | ND | 7.59 | ND |

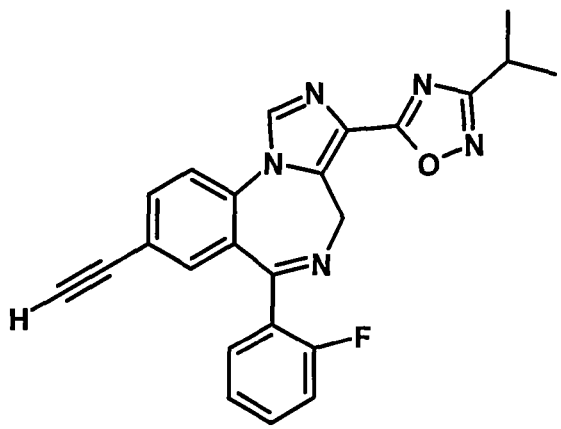
YT-III-42
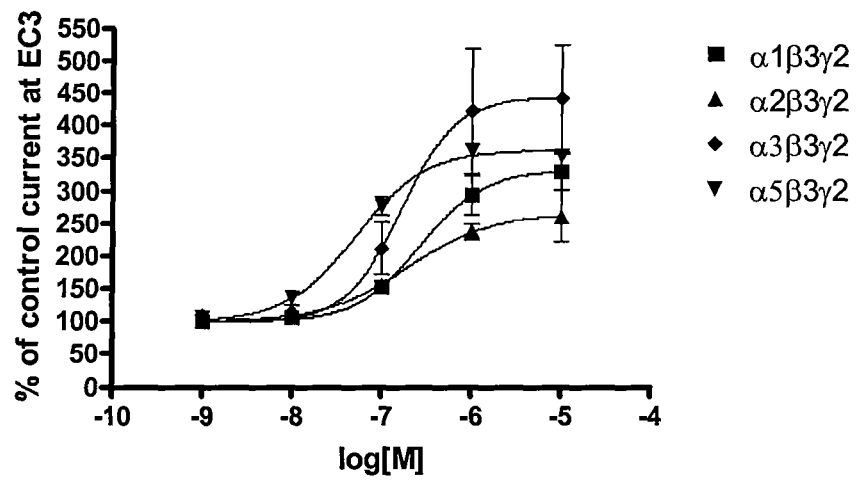
FIG. 42
N=2 for each receptor type
|  |  | α1β3γ2 | α2β3γ2 | α3β3γ2 | α5β3γ2 |
|---|---|---|---|---|---|
| YT-III-42 | EC$_{50}$ | 271nM | 198nM | 165nM | 51nM |
|  | 95%CI | 120-613 | 50-778 | 26-1034 | 37-70 |
|  | Nh | 1,22 | 0,92 | 1,42 | 1,12 |
|  | 10nM | 100nM | 1μM | 10μM |
|---|---|---|---|---|
| α1 | ns | 152±7 | 294±32 | 330±27 |
| α2 | 112±1 | 156±2 | 237±13 | 261±40 |
| α3 | ns | 212±40 | 422±99 | 441±82 |
| α5 | 138±5 | 276±14 | 363±5 | 354±8 |

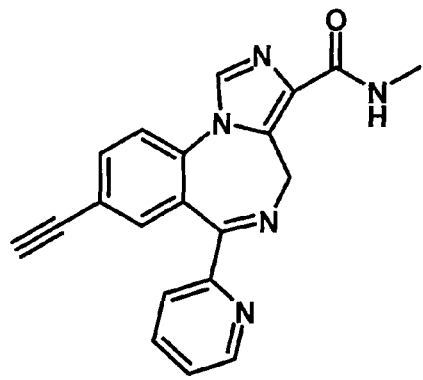
FIG. 43
HJ-I-40
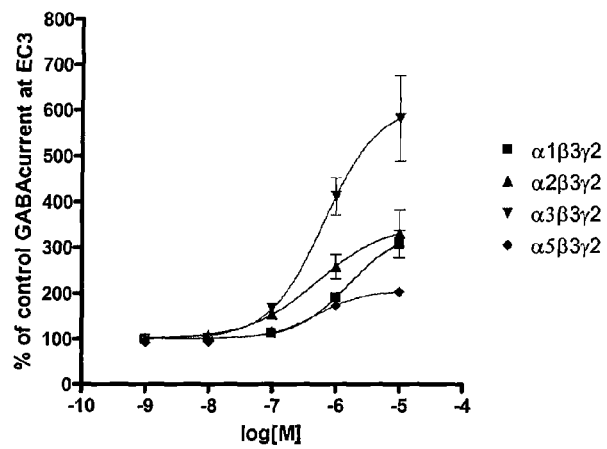
| | | α1β3γ2 | α2β3γ2 | α3β3γ2 | α5β3γ2 |
|---|---|---|---|---|---|
| HJ-I-040 | EC$_{50}$ | 1.6μM | 0.5μM | 0.6μM | 0.5μM |
| | 95%CI | (0.4-6.4) | (0.09-2.8) | (0.24-1.8) | (0.26-0.98) |
| | Nh | 1.1 | 0.81 | 1.0 | 1.2 |
| | 1nM | 10nM | 100nM | 1μM | 10μM |
|---|---|---|---|---|---|
| α1 | | 102±6 | 112±1 | 191±5 | 308±30 |
| α2 | | 108±1 | 154±10 | 259±26 | 331±50 |
| α3 | | 101±0 | 168±9 | 412±40 | 582±93 |
| α5 | | 94.2±3 | 115±5 | 173±9 | 203±7 |
| Compound | Structure | a1 | a2 | a3 | a4 | a5 | Amt(mgs) |
|---|---|---|---|---|---|---|---|
| HJ-I-040 | 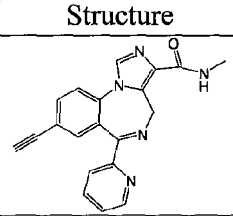 | 1070 | 869.4 | 1123.6 | ND | 1065 | 20 |

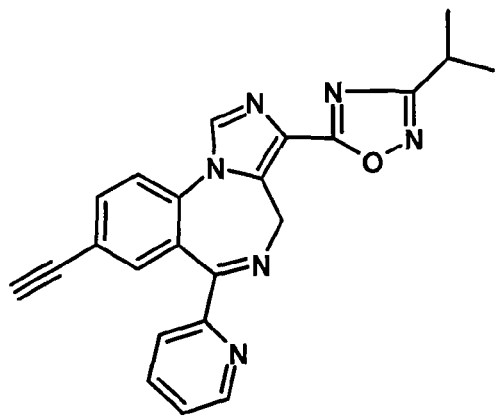
FIG. 44
ZJW-II-40
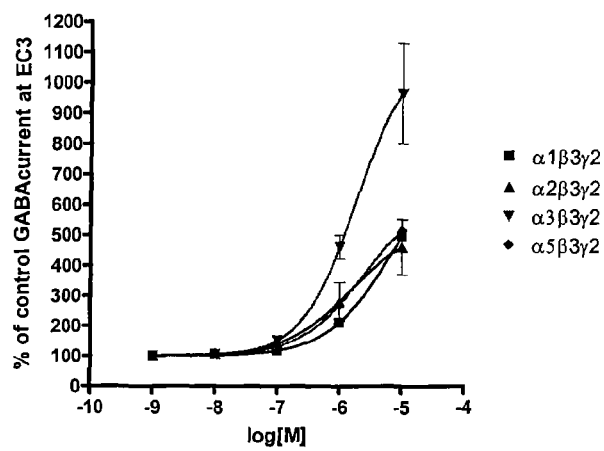
| | | α1β3γ2 | α2β3γ2 | α3β3γ2 | α5β3γ2 |
|---|---|---|---|---|---|
| ZJW-II-40 | EC$_{50}$ | 6.8μM | 1.5μM | 1.7μM | 2.4μM |
| | 95%CI | (1-45) | (0.05-46) | (0.38-8.2) | (1.2-4.7) |
| | Nh | 0.86 | 0.84 | 1.03 | 0.88 |
| | 1nM | 10nM | 100nM | 1μM | 10μM |
|---|---|---|---|---|---|
| α1 | | 104±1 | 117±1 | 209±3 | 495±14 |
| α2 | | 107±3 | 140±14 | 280±65 | 460±91 |
| α3 | | 106±2 | 150±2 | 460±39 | 964±164 |
| α5 | | 106±1 | 130±1 | 270±7 | 514±15 |
| Compound | Structure | a1 | a2 | a3 | a4 | a5 | Amt(mgs) |
|---|---|---|---|---|---|---|---|
| ZJW-II-040 | 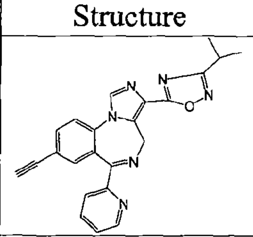 | 4753 | 25.54 | 31.43 | ND | 275.4 | 20 |

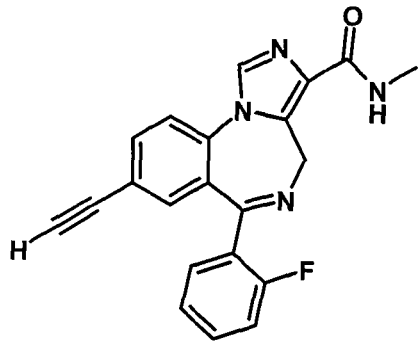
| α1 | α2 | α3 | α4 | α5 | α6 |
|---|---|---|---|---|---|
| 22.16 | 44.06 | 38.48 | ND | 12.15 | ND |
FIG. 45
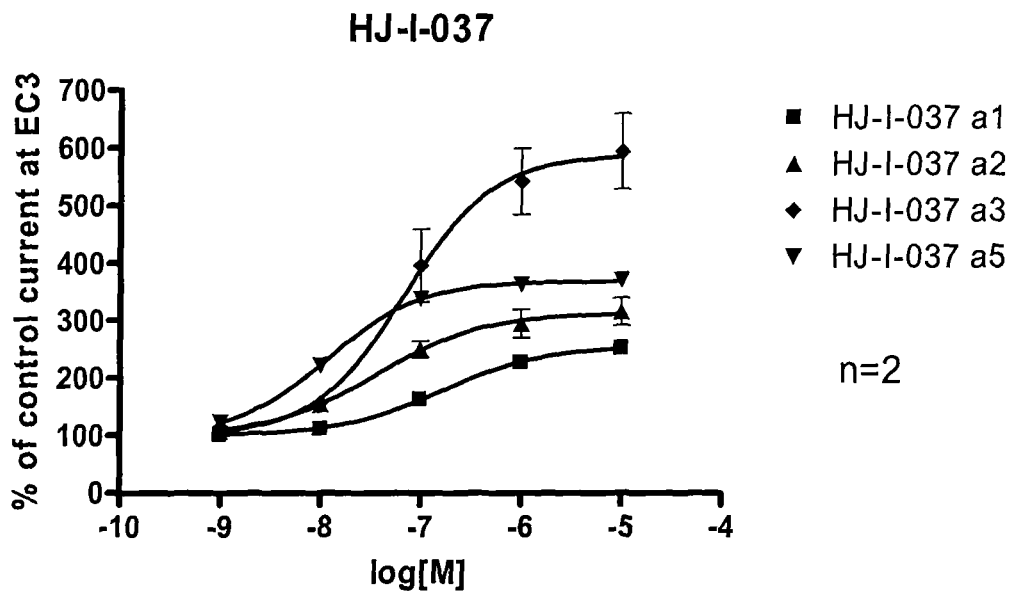

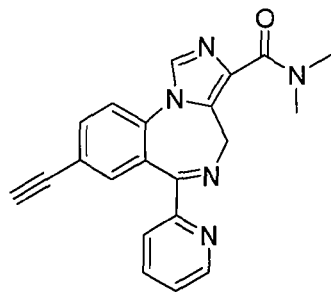
ZJW-II-061  FIG. 46
| α1 | α2 | α3 | α4 | α5 | α6 |
|---|---|---|---|---|---|
| 2116 | 402.3 | 382.7 | ND | 1153 | ND |
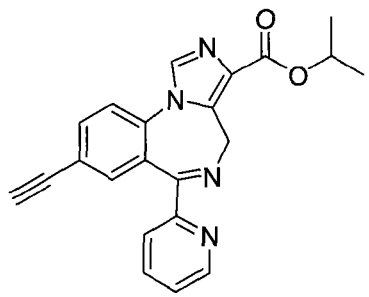
ZJW-II-063  FIG. 47
| α1 | α2 | α3 | α4 | α5 | α6 |
|---|---|---|---|---|---|
| 2036 | 1303 | 1371 | ND | 1030 | ND |
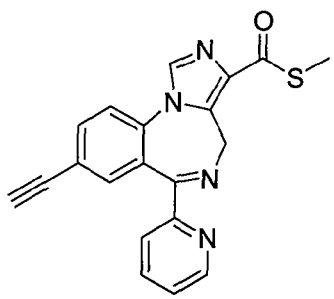
ZJW-II-065  FIG. 48
| α1 | α2 | α3 | α4 | α5 | α6 |
|---|---|---|---|---|---|
| 1144 | 961.2 | 640.9 | ND | 1403 | ND |

FIG. 49

Diazepam

Binding Affinity at αxβ3γ2 (nM)
| α1 | α2 | α3 | α4 | α5 | α6 |
|---|---|---|---|---|---|
| 14 | 7.8 | 13.9 | ND | 13.4 | ND |

Oocyte Efficacy (Emax values)
| α1 | α2 | α3 | α5 |
|---|---|---|---|
| 255±17 | 413±14 | 551±7 | 194±4 |

JY-Xhe-053

Binding Affinity at αxβ3γ2 (nM)
| α1 | α2 | α3 | α4 | α5 | α6 |
|---|---|---|---|---|---|
| 22 | 12.3 | 34.9 | ND | 0.7 | >1000 |

Oocyte Efficacy (Emax values)
| α1 | α2 | α3 | α5 |
|---|---|---|---|
| 290±1 | 447±9 | 668±3 | 266±12 |

Xhe-II-053

Binding Affinity at αxβ3γ2 (nM)
| α1 | α2 | α3 | α4 | α5 | α6 |
|---|---|---|---|---|---|
| 247 | 40 | 90 | >1000 | 13 | >1000 |

Oocyte Efficacy (Emax values)
| α1 | α2 | α3 | α5 |
|---|---|---|---|
| 253±4 | 393±9 | 629±5 | 226±5 |

HZ-166

Binding Affinity at αxβ3γ2 (nM)
| α1 | α2 | α3 | α4 | α5 | α6 |
|---|---|---|---|---|---|
| 118 | 148 | 365 | >5000 | 77 | >500 |

SH-053-2'F-S-CH3

Binding Affinity at αxβ3γ2 (nM)
| α1 | α2 | α3 | α4 | α5 | α6 |
|---|---|---|---|---|---|
| 468.2 | 33.3 | 291.5 | ND | 19.2 | >5000 |

Oocyte Efficacy (Emax values)
| α1 | α2 | α3 | α5 |
|---|---|---|---|
| 2944±11 | 458±14 | 534±24 | 446±12 |

SH-053-2'F-R-CH3

Binding Affinity at αxβ3γ2 (nM)
| α1 | α2 | α3 | α4 | α5 | α6 |
|---|---|---|---|---|---|
| 759.1 | 948.2 | 768.8 | ND | 95.2 | ND |

Oocyte Efficacy (Emax values)
| α1 | α2 | α3 | α5 |
|---|---|---|---|
| 262±20 | 321±44 | 352±36 | 589±20 |

SELECTIVE AGENTS FOR PAIN SUPPRESSION

CROSS-REFERENCE TO RELATED APPLICATIONS

This application claims priority from U.S. Provisional Patent Application Ser. No. 61/177,818, filed on May 13, 2009, in addition to being a continuation-in-part of U.S. Non-Provisional patent application Ser. No. 12/684,845, filed on Jan. 8, 2010, which is a continuation of U.S. Non-Provisional patent application Ser. No. 11/929,860, filed on Oct. 30, 2007 now abandoned, which is a divisional of U.S. Non-Provisional patent application Ser. No. 11/458,855, filed on Jul. 20, 2006 now abandoned, which is a continuation of U.S. Non-Provisional patent application Ser. No. 10/402,538, filed on Mar. 28, 2003, now U.S. Pat. No. 7,119,196, which claims priority from U.S. Provisional Patent Application Ser. No. 60/368,408, filed Mar. 28, 2002, the entirety of which are each expressly incorporated by reference herein.

STATEMENT REGARDING FEDERALLY SPONSORED RESEARCH OR DEVELOPMENT

This invention was made with United States government support under NIMH grant number MH46851. The United States government has certain rights to this invention.

BACKGROUND OF THE INVENTION

In certain aspects, the present invention relates to compositions including a class of benzodiazepine derivatives that are subunit-selective $GABA_A$ receptor agonists. Such compositions are useful for the treatment of neuropathic pain, migraine related pain and inflammatory pain, with reduced sedative, hypnotic, and ataxic side effects. In other aspects, the present invention relates to methods of treatment or prevention of neuropathic pain, migraine related pain and inflammatory pain, using such benzodiazepine derivatives that are subunit-selective $GABA_A$ receptor agonists.

Inflammatory diseases and neuropathic insults are frequently accompanied by severe and debilitating pain, which can become chronic and often unresponsive to conventional analgesic treatment. Pain usually results from activation of nociceptive afferents (pain receptors) by actually or potentially tissue-damaging stimuli. Pain may also arise by activity generated within the nervous system without adequate stimulation of its peripheral sensory endings. For this type of pain, the International Association for the Study of Pain introduced the term neuropathic pain, defined as "pains resulting from disease or damage of the peripheral or central nervous systems, and from dysfunction of the nervous system."

Neuropathic pain encompasses a range of painful conditions of diverse origins including diabetic neuropathy, post-herpetic neuralgia, nerve injuries after surgery, pain following paraplegia, hypersensitivity to non-painful stimuli (allodynia), e.g. after surgery or during migraine attacks, spontaneous pain, hyperalgesia, diffuse muscle tenderness of myofacial syndromes, sensory abnormalities of the gastrointestinal tract, e.g. in irritable bowel disease, or chest pain and a large proportion of back pain. Cancer pain and AIDS-associated pain also qualify as neuropathic pain. The most commonly prescribed drugs for the treatment of pain include tricyclic antidepressants, anti-epileptic drugs, opioid analgesics and, in case of local pain, cream and patches delivering analgesics. These analgesics are of limited use in the treatment of neuropathic pain. Currently prescribed drugs for neuropathic pain are not effective for all patients, have various side effects and frequently provide only modest pain relief. Accordingly, there is a significant unmet medical need for drugs to specifically treat neuropathic pain.

Inflammatory pain is triggered by nerve endings that become irritated when surrounded by inflamed tissue. Inflammatory pain is most commonly associated with conditions such as trauma, osteoarthritis, rheumatoid arthritis, post surgery recovery and some forms of cancer pain. The most significant innovation in the treatment of inflammatory pain over the last years has been the introduction of selective cyclooxygenase inhibitors (COX-2 inhibitors). However, the efficacy of current COX-2 inhibitors is less substantial than first suggested, and the side effect profile causes concern. The treatment of inflammatory pain requires new therapeutic means with an improved side effect profile.

Migraine-associated pain attacks affect about 10 to 20% of the middle European population. Pain attacks are believed to originate from the sensitization of meningeal nociceptors by neuropeptides and/or their excitation by dilated meningeal blood vessels. At present migraine pain is usually treated with cyclooxygenase inhibitors and 5-hydroxytryptamine (serotonin) agonists (so called triptans). Pain relief is often unsatisfactory and treatment with both groups of agents bares significant gastrointestinal and cardiovascular risks.

Gamma-aminobutyric acid (GABA) is the major inhibitory neurotransmitter in the central nervous system. GABA receptors are heteromeric, and are divided into three main classes: (1) $GABA_A$ receptors, which are members of the ligand-gated ion channel superfamily; (2) $GABA_B$ receptors, which may be members of the G-protein linked receptor superfamily; and (3) $GABA_C$ receptors, also members of the ligand-gated ion channel superfamily, but their distribution is confined to the retina. Benzodiazepine receptor ligands do not bind to $GABA_B$ and $GABA_C$ receptors. Since the first cDNAs encoding individual $GABA_A$ receptor subunits were cloned the number of known members of the mammalian family has grown to 21 including $\alpha$, $\beta$, and $\gamma$ subunits ($6\alpha$, $4\beta$, $4\gamma$, $1\delta$, $1\epsilon$, $1\pi$, $1\theta$, and $3\rho$).

A characteristic property of $GABA_A$ receptors is the presence of a number of modulatory sites, one of which is the benzodiazepine (BZ) site. The benzodiazepine binding site is the most explored of the $GABA_A$ receptor modulatory sites, and is the site through which benzodiazepine-based anxiolytic drugs exert their effect. Before the cloning of the $GABA_A$ receptor gene family, the benzodiazepine binding site was historically subdivided into two subtypes, BENZODIAZEPINE1 and BENZODIAZEPINE2, on the basis of radioligand binding studies on synaptosomal rat membranes. The BENZODIAZEPINE1 subtype has been shown to be pharmacologically equivalent to a $GABA_A$ receptor comprising the $\alpha 1$ subunit in combination with a $\beta$ subunit and $\gamma 2$. It has been indicated that an $\alpha$ subunit, a $\beta$ subunit and a $\gamma$ subunit constitute the minimum requirement for forming a functional $GABA_A$ receptor.

Receptor subtype assemblies for BZ-sensitive $GABA_A$ receptors include amongst others the subunit combinations $\alpha 1\beta 2\gamma 2$, $\alpha 2\beta 2,3\gamma 2$, $\alpha 3\beta 2,3\gamma 2$, $\alpha 2\beta g3$, and $\alpha 5\beta 3\gamma 2,3$. Subtype assemblies containing an $\alpha 1$ subunit ($\alpha 1\beta 2\gamma 2$) are present in most areas of the brain and are thought to account for 40-50% of $GABA_A$ receptors in the rat. Subtype assemblies containing $\alpha 2$ and $\alpha 3$ subunits respectively are thought to account for about 25% and 17% $GABA_A$ receptors in the rat. Subtype assemblies containing an $\alpha 5$ subunit ($\alpha 5\beta 3\gamma 2$) are expressed predominately in the hippocampus and cortex and are thought to represent about 4% of $GABA_A$ receptors in the rat. Two other major populations are the $\alpha 2\beta 2/3\gamma 2$ and $\alpha 3\beta 2/3\gamma 2/3$ subtypes. Together these constitute approximately a further 35% of the total $GABA_A$ receptor population. Pharmacologically this combination appears to be equivalent to the BENZODIAZEPINE2 subtype as defined previously by radioligand binding, although the BENZODIAZEPINE2 subtype may also include certain α5-containing subtype assemblies.

The present pharmacology of agonists acting at the BZ site of $GABA_A$ receptors suggests that al containing receptors mediate sedation, anticonvulsant activity and anterograde amnesia, while α2 and/or α3 $GABA_A$ receptors mediate anxiolytic activity. The α5 containing $GABA_A$ receptors are involved in memory functions (U. Rudolph et al., Nature 1999, 401, 796; K. Löw et al., Science 2000, 290, 131; McKernan Nature Neurosci. 2000, 3, 587; F. Crestani et al., Proc. Nat. Acad. Sci. USA 2002, 99, 8980; M.S. Chambers et al., J. Med. Chem. 2003, 46, 2227).

The demonstration of the pharmacology of $GABA_A$ receptor subtypes has been achieved in vitro by studying ligand induced currents in oocytes that express mRNA for specific $GABA_A$ receptor subunits, or in vivo, by studying mice in which either the α1, α2, α3 or a 5 $GABA_A$ receptor is rendered diazepam-insensitive by a histidine to arginine point mutation, respectively α1(H101R), α2(H101R), α3(H126R), or α5(H105R). In the point-mutated mice the benzodiazepine pharmacology related to the respective receptor is absent as compared to wild type mice. In the following, the point mutated mouse mutants are referred to as $GABA_A$ receptor mutant mice, receptor mutant mice or mutant mice.

It is believed that agents acting selectively as benzodiazepine agonists at $GABA_A/α2$, $GABA_A/α3$, and/or $GABA_A/α5$ receptors, possess desirable properties. Compounds which are modulators of the benzodiazepine binding site of the $GABA_A$ receptor by acting as benzodiazepine agonists are referred to hereinafter as "$GABA_A$ receptor agonists." The $GABA_A/α1$-selective (α1β2γ2) agonists alpidem and zolpidem are clinically prescribed as hypnotic agents, suggesting that at least some of the sedation associated with known anxiolytic drugs which act at the BENZODIAZEPINE1 binding site is mediated through $GABA_A$ receptors containing the α1 subunit.

There have been suggestions that some compounds that are selectively $GABA_A/α2$ and/or $GABA_A/α3$ receptor agonists rather than $GABA_A/α1$ receptor agonists may be effective in the treatment of pain with a reduced propensity to cause sedation. An indication of this can be found in PCT published application WO2006061428, published Jun. 16, 2006, which discloses the use of are $GABA_A/α2$, or $GABA_A/α3$ receptor agonists including 1,2,4-triazolo[4,3-b]pyridazines, e.g. L-838,417, TPA 023 or CL-218,872, 1H-pyrido[3,4-b]indole derivatives, e.g. SL 651498, and pyrazolo[1,5-a]pyrimidines, e.g. ocinaplon, for the prevention and treatment of neuropathic, inflammatory and migraine associated pain. However, no disclosure was made of benzodiazepine derivatives that might be useful for the suppression, alleviation or prevention of neuropathic pain, migraine related pain and inflammatory pain.

SUMMARY OF THE INVENTION

In preferred embodiments, the present invention provides methods of treatment and pharmaceutical compositions for the suppression, alleviation and prevention of the often chronic, severe and debilitating pain that can accompany inflammatory diseases and neuropathic insults, pain that is often unresponsive to conventional analgesic treatment. The preferred embodiments of the present invention further relate to methods of treatment and pharmaceutical compositions using benzodiazepine derivatives that provide suppression, alleviation and prevention of neuropathic pain, migraine-related pain and inflammatory pain with reduced sedative and ataxic side effects.

In certain aspects, the present invention provides methods for the treatment and prevention of neuropathic pain, inflammatory pain and migraine-associated pain comprising administering to a patient in need of such treatment a $GABA_A$ receptor agonist, such as an agonist or partial agonist acting at the BZ site of the α2 $GABA_A$ receptors and/or α3 $GABA_A$ receptors, for the preparation of a medicament for the prevention and treatment of neuropathic and inflammatory pain, and to a method of prevention and treatment of neuropathic and inflammatory pain using a $GABA_A$ receptor agonist.

In particular, the invention relates to such a use, wherein the $GABA_A$ receptor agonist is an agonist or partial agonist of the α2 $GABA_A$ receptors and/or of the α3 $GABA_A$ receptors and preferably has less binding affinity to α1 or less efficacy of receptor activation at al compared to α2 or α3 $GABA_A$ receptors, and further mayor may not have binding affinity to α5 or efficacy of receptor activation at α5 $GABA_A$ receptors. The $GABA_A$ receptor agonist may also act at the GABA binding site and on modulatory sites other than the benzodiazepine binding site of $GABA_A$ receptors. Preferred are $GABA_A$ receptor agonists having anxiolytic efficacy of the classical non-selective benzodiazepines, but which are not sedating, amnesic or ataxic, and preferably displaying less other side effects than classical non-selective benzodiazepines.

Diminished pain control by glycinergic and γ-aminobutyric acid (GABA)-ergic neurons in the spinal cord is a major contributing factor to chronic pain of inflammatory and neuropathic origin (Zeilhofer, 2008). Restoring synaptic inhibition should therefore be a rational strategy for the treatment of such conditions. Previous work from several groups has shown that local spinal (intrathecal) or systemic application of BDZ-site agonists alleviates inflammatory or neuropathic pain in animals (Kontinen and Dickenson, 2000; Knabl et al., 2008; Knabl et al., 2009), and labor pain in human patients (Tucker et al., 2004). However, the wide-spread expression of $GABA_A$ receptors throughout the CNS and various central side effects including sedation, memory impairment, and addiction strictly limit or even preclude the use of classical BDZs in chronic pain patients.

Advances in our understanding of the molecular diversity of $GABA_A$ receptors have raised hopes that a separation of desired and undesired actions of classical BDZs could become possible through the development of subtype-selective or partial BDZ-site agonists. BDZ-sensitive $GABA_A$ receptors contain at least one of the following α subunits α1, α2, α3 or α5, together with a β subunit and a γ2 subunit in a 2:2:1 stoichiometry (Wieland et al., 1992; Barnard et al., 1998; Barnard, 2001). Work in $GABA_A$ receptor point-mutated mice, in which the different subtypes of α subunits have been rendered diazepam-insensitive, has shown that the sedative action of BDZs is mediated by $GABA_A$ receptors containing an α1 subunit (α1-$GABA_A$ receptor) (Rudolph et al., 1999), whereas α2-$GABA_A$ receptors were found to be responsible for the anxiolytic properties of classical BDZs (Low et al., 2000). Using these $GABA_A$ receptor point-mutated mice, we could recently demonstrate that α2- or α3-$GABA_A$ receptors are largely responsible for the spinal anti-hyperalgesic actions of classical BDZs, while α1-$GABA_A$ receptors do not contribute (Knabl et al., 2008). Conversely, pronounced analgesia against formalin induced pain has also been observed after systemic treatment with diazepam in α1-$GABA_A$ receptor point-mutated mice, which are protected from the sedative effects of diazepam. These results suggest that al sparing (non-sedative) BDZ-site agonists should exert a genuine analgesic effect after systemic treatment (Knabl et al., 2009).

In rats, we have previously tested such a non-sedative BDZ-site ligand, L-838,417, which has been developed in the quest for non-sedative anxiolytics (McKernan et al., 2000).

L-838,417 showed good antihyperalgesic activity in a rat neuropathic pain model without losing efficacy after repeated treatment (Knabl et al., 2008). However, this compound possesses poor pharmacokinetics in mice with very low bioavailability and very short half-life (Scott-Stevens et al., 2005). Recently, a class of novel 8-substituted triazolo- and imidazobenzodiazepines has been synthesized with the aim to develop novel anticonvulsant BDZ-site ligands with a better side effect profile (Rivas et al., 2009). One of these compounds (HZ166, ligand 2 in Rivas et al., 2009) is a non-sedative partial BDZ-site agonist with preferential activity at α2- and α3-$GABA_A$ receptors. It exhibits good anticonvulsive activity at non-sedative doses with minimal toxicity and suitable pharmacokinetics in mice and rats after intraperitoneal (i.p.) application. Here, we have evaluated potential antihyperalgesic effects of HZ166 in mouse models of neuropathic and inflammatory pain, and compared these effects with those of gabapentin, a drug frequently used in neuropathic pain patients.

More particularly, the invention relates to methods of treatment and pharmaceutical compositions for administration to a patient for the treatment and prevention of neuropathic pain, inflammatory pain and migraine-associated pain an effective amount, where the composition is a compound of the formula

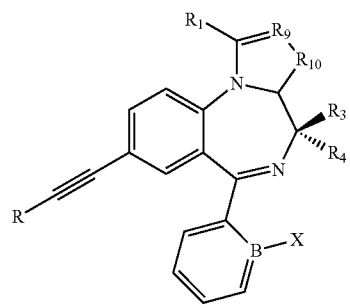

or a salt thereof, where R is H or $Si(CH_3)_3$,
$R_1$ is —H, —$CH_3$ or =O, $R_3$ and $R_4$ are both H, or $R_3$ is H and $R_4$ is S—$CH_3$, or $R_3$ is R—$CH_3$ and $R_4$ is H,
$R_9$ is N, or

$R_{10}$ is N, C—$CO_2CH_2CH_3$, C—$CO_2CH_2CF_3$, C—$CO_2C(CH_3)_3$, C—$CO_2CH(CH_3)_2$, C—$CO_2CH_2CH(CH_3)_2$, C—$CON(CH_3)_2$, C—$CONHCH_3$, C—$COSCH_3$, C—$R_{15}$, C—$R_{16}$, or

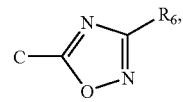

$R_6$ is $CH(CH_3)_2$, $CH_2CH_3$, or $CH_3$, and B is C or N, and X is absent, H, F, Cl, or Br, and when $R_{10}$ is C—$R_{15}$, $R_{15}$ is

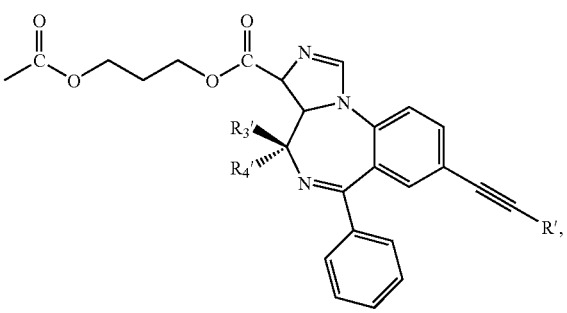

$R_1$ is H, R' is H or $Si(CH_3)_3$, $R'_3$ and $R'_4$ are both H, or $R'_3$ is H and $R'_4$ is S—$CH_3$, or $R'_3$ is R—$CH_3$ and $R'_4$ is H, and when $R_{10}$ is C—$R_{15}$, $R_{15}$ is $R_{16}$ is

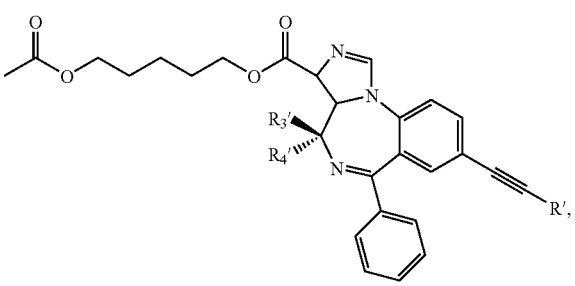

$R_1$ is H, R' is H or $Si(CH_3)_3$, $R'_3$ and $R'_4$ are both H, or $R'_3$ is H and $R'_4$ is S—$CH_3$, or $R'_3$ is R—$CH_3$ and $R'_4$ is H.

In preferred embodiments, preferred compounds for the practice of the present invention include

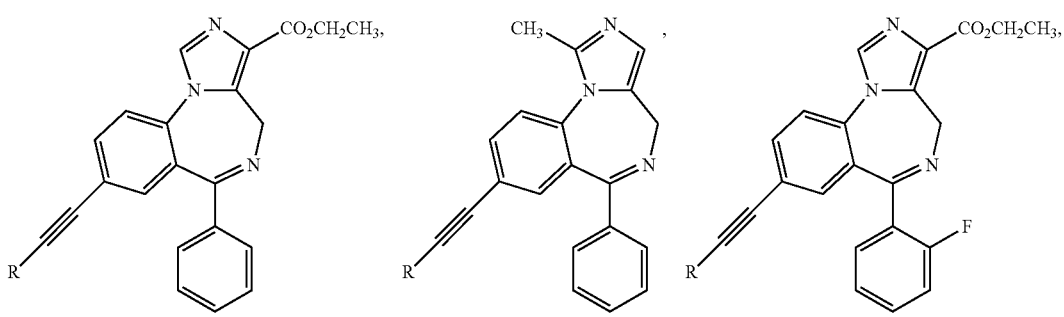

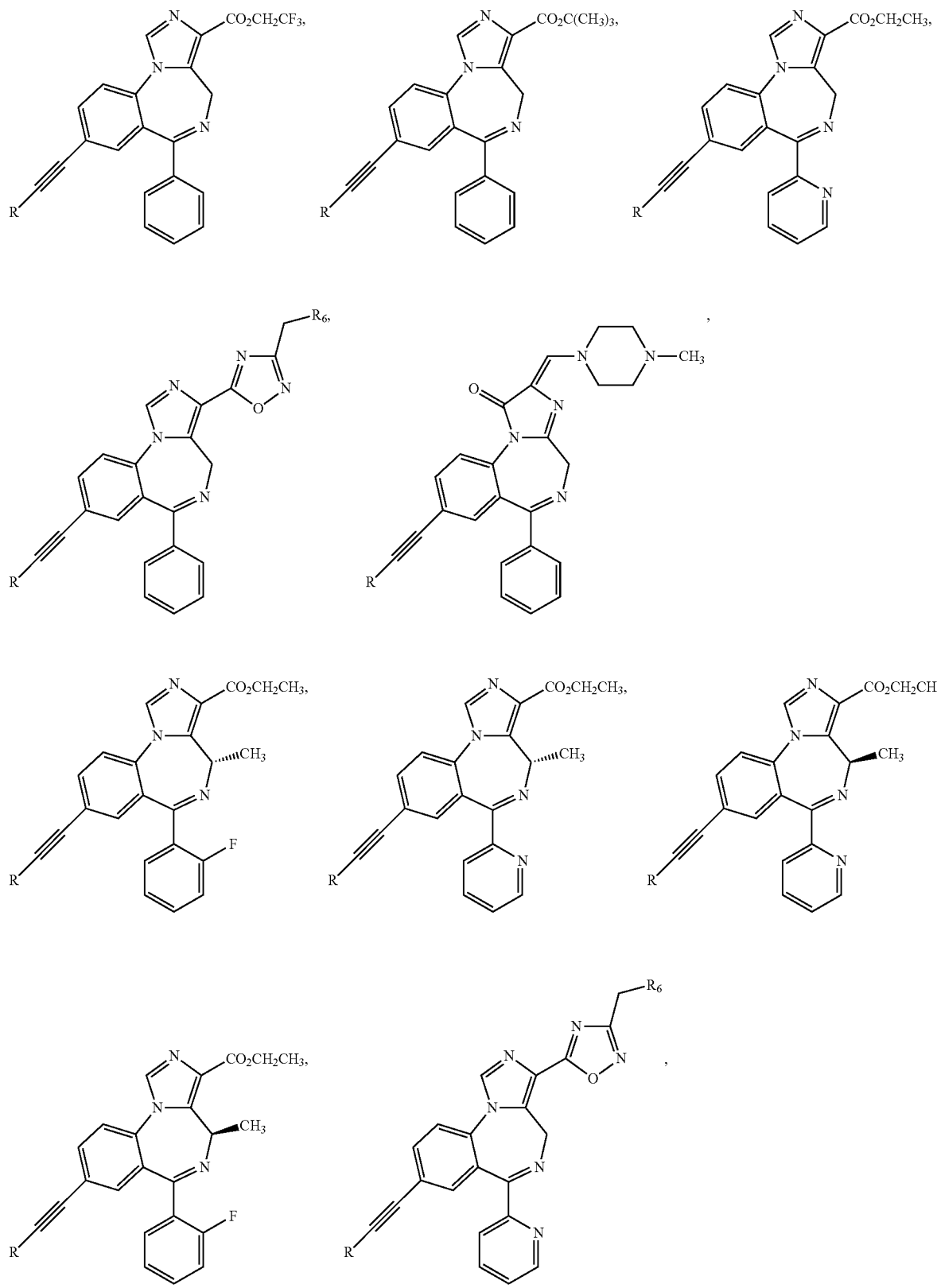

-continued

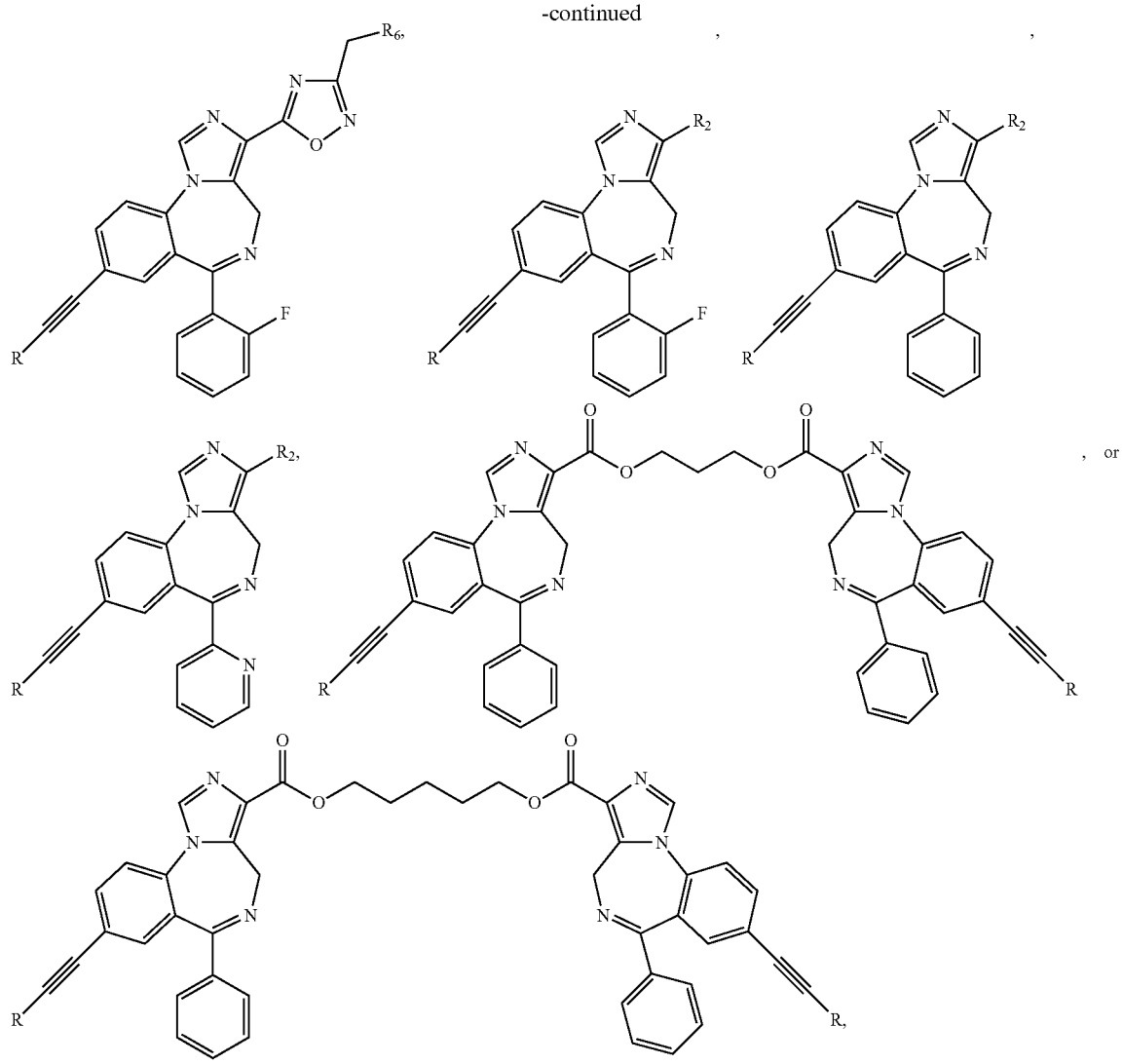

and salts thereof, where R is H or Si(CH$_3$)$_3$, where R$_6$ is CH(CH$_3$)$_2$, CH$_2$CH$_3$, or CH$_3$ and R$_2$ is CO$_2$CH(CH$_3$)$_2$, CO$_2$CH$_2$CH(CH$_3$)$_2$, CON(CH$_3$)$_2$, CONHCH$_3$, or COSCH$_3$.

Particularly preferred compounds are characterized in Table 1, below.

TABLE 1

| Compound | R | R$_1$ | R$_3$ | R$_4$ | R$_9$ | R$_{10}$ | B | X |
|---|---|---|---|---|---|---|---|---|
| XHE-II-053 | H | —H | H | H | N | C—CO$_2$CH$_2$CH$_3$ | C | H |
| XHE-II-048 | Si(CH$_3$)$_3$ | —H | H | H | N | C—CO$_2$CH$_2$CH$_3$ | C | H |
| XLI-270 | H | —CH$_3$ | H | H | N | N | C | H |
| Xli-JY-DMH | H | —CH$_3$ | H | H | N | N | C | Cl |
| JY-XHE-053 | H | —H | H | H | N | C—CO$_2$CH$_2$CH$_3$ | C | F |
| JY-038 | Si(CH$_3$)$_3$ | —H | H | H | N | C—CO$_2$CH$_2$CH$_3$ | C | F |
| dm-II-20 | H | —H | H | H | N | C—CO$_2$CH$_2$CF$_3$ | C | H |
| XLI-225 | H | —H | H | H | N | C—CO$_2$C(CH$_3$)$_3$ | C | H |
| HZ-166 | H | —H | H | H | N | C—CO$_2$CH$_2$CH$_3$ | N | — |
| PS—I-26 | H | —H | H | H | N | 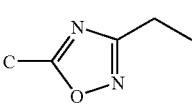 | C | H |

TABLE 1-continued

| Compound | R | $R_1$ | $R_3$ | $R_4$ | $R_9$ | $R_{10}$ | B | X |
|---|---|---|---|---|---|---|---|---|
| PS—I-37 | H | =O | H | H | 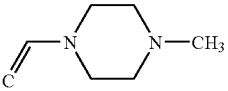 | | N | C | H |
| PS—I-36 | Si(CH$_3$)$_3$ | =O | H | H | 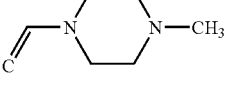 | | N | C | H |
| DMH-D-053 | H | —H | H | H | N | C—$R_{15}$ | C | H |
| dm-III-97 | H | —H | H | H | N | C—$R_{16}$ | C | H |
| SH-053-2'F—S—CH3 | H | —H | H | S—CH$_3$ | N | C—CO$_2$CH$_2$CH$_3$ | C | F |
| SH—I-055 | Si(CH$_3$)$_3$ | —H | H | S—CH$_3$ | N | C—CO$_2$CH$_2$CH$_3$ | C | F |
| SH-053-2'N—S—CH3 | H | —H | H | S—CH$_3$ | N | C—CO$_2$CH$_2$CH$_3$ | N | — |
| SH-053-2'N—R—CH3 | H | —H | R—CH$_3$ | H | N | C—CO$_2$CH$_2$CH$_3$ | N | — |
| SH—I-061 | H | —H | H | S—CH$_3$ | N | C—CO$_2$CH$_2$CH$_3$ | N | — |
| SH-053-2'F—R—CH3 | H | —H | R—CH3 | H | N | C—CO$_2$CH$_2$CH$_3$ | C | F |
| SH—I-060 | Si(CH$_3$)$_3$ | —H | R—CH$_3$ | H | N | C—CO$_2$CH$_2$CH$_3$ | C | F |

In preferred embodiments, because we have found analgesic effects of the subtype-selective benzodiazepine-site ligand JY-XHE-053 in the chronic constriction injury model of neuropathic pain, a preferred compound for the practice of the present invention is JY-XHE-053:

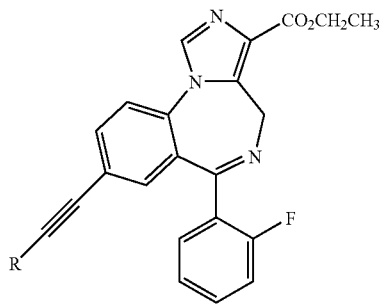

where R is H or Si(CH$_3$)$_3$.

In other preferred embodiments, because we have found analgesic effects of the subtype-selective benzodiazepine-site ligand Hz 166 in the chronic constriction injury model of neuropathic pain, a preferred compound for the practice of the present invention is Hz 166:

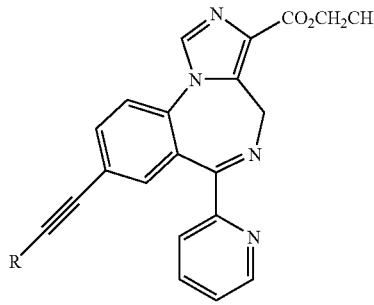

where R is H or Si(CH$_3$)$_3$.

In further preferred embodiments, because we have found analgesic effects of the subtype-selective benzodiazepine-site ligand Xli-JY-DMH in the chronic constriction injury model of neuropathic pain, a preferred compound for the practice of the present invention is Xli-JY-DMH:

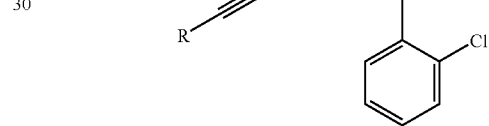

where R is H or Si(CH$_3$)$_3$.

In yet other preferred embodiments, because we have found analgesic effects of the subtype-selective benzodiazepine-site ligand XHE-II-053 in the chronic constriction injury model of neuropathic pain, a preferred compound for the practice of the present invention is XHE-II-053:

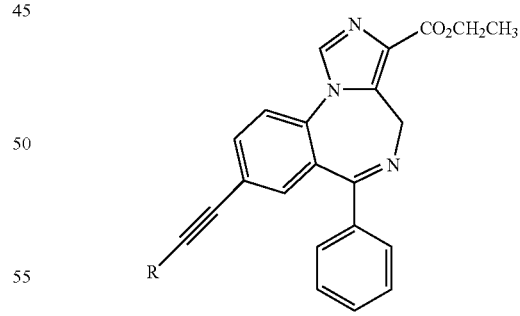

where R is H or Si(CH$_3$)$_3$.

In other aspects, the present invention provides methods for the treatment and prevention of neuropathic pain, inflammatory pain and migraine-associated pain comprising administering to a patient in need of such treatment an effective amount of a compound selected from the group consisting of compounds according to Formulas A, B, C, D, I, III, or IV or a salt thereof,

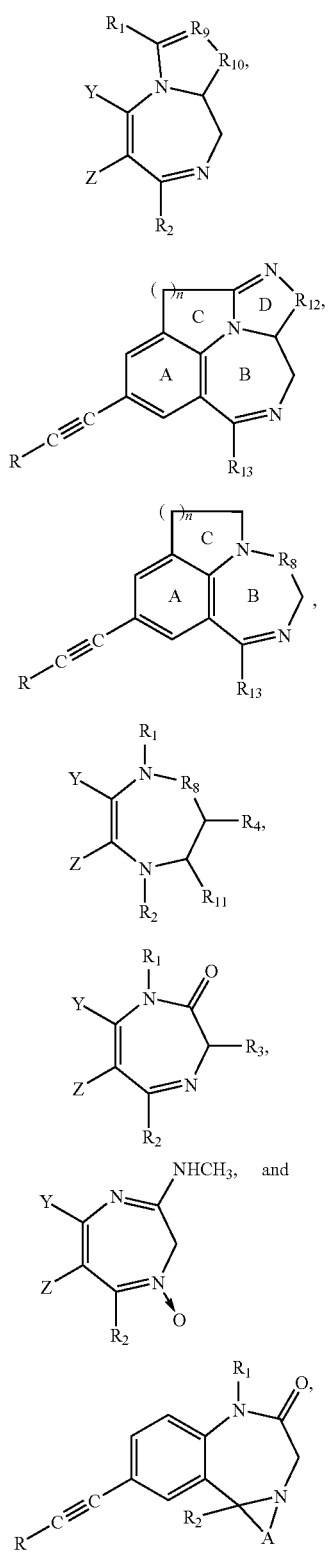
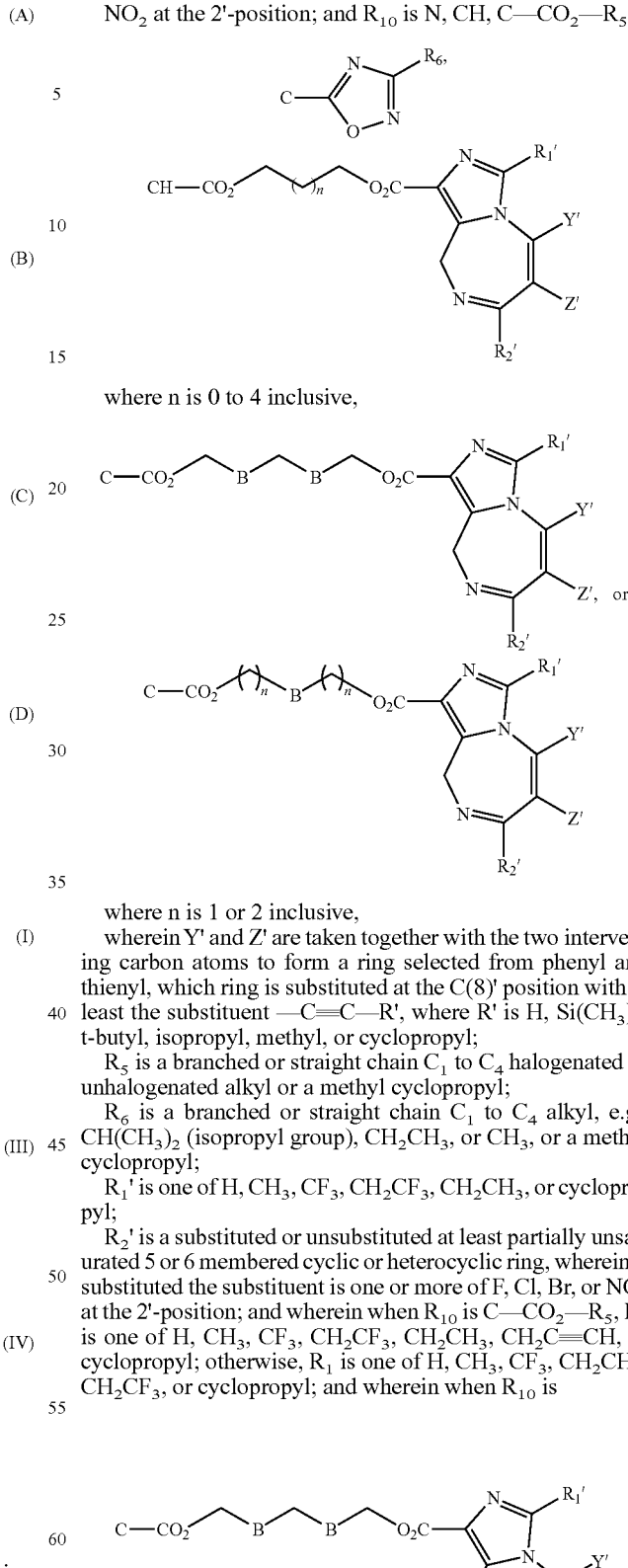

wherein Y and Z are taken together with the two intervening carbon atoms to form a ring selected from phenyl and thienyl, which ring is substituted at the C(8) position with at least the substituent —C≡C—R, where R is H, Si(CH$_3$)$_3$, t-butyl, isopropyl, methyl, or cyclopropyl;

R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position; and R$_{10}$ is N, CH, C—CO$_2$—R$_5$, where n is 0 to 4 inclusive, where n is 1 or 2 inclusive, wherein Y' and Z' are taken together with the two intervening carbon atoms to form a ring selected from phenyl and thienyl, which ring is substituted at the C(8)' position with at least the substituent —C≡C—R', where R' is H, Si(CH$_3$)$_3$, t-butyl, isopropyl, methyl, or cyclopropyl;

R$_5$ is a branched or straight chain C$_1$ to C$_4$ halogenated or unhalogenated alkyl or a methyl cyclopropyl;

R$_6$ is a branched or straight chain C$_1$ to C$_4$ alkyl, e.g., CH(CH$_3$)$_2$ (isopropyl group), CH$_2$CH$_3$, or CH$_3$, or a methyl cyclopropyl;

R$_1$' is one of H, CH$_3$, CF$_3$, CH$_2$CF$_3$, CH$_2$CH$_3$, or cyclopropyl;

R$_2$' is a substituted or unsubstituted at least partially unsaturated 5 or 6 membered cyclic or heterocyclic ring, wherein if substituted the substituent is one or more of F, Cl, Br, or NO$_2$ at the 2'-position; and wherein when R$_{10}$ is C—CO$_2$—R$_5$, R$_1$ is one of H, CH$_3$, CF$_3$, CH$_2$CF$_3$, CH$_2$CH$_3$, CH$_2$C≡CH, or cyclopropyl; otherwise, R$_1$ is one of H, CH$_3$, CF$_3$, CH$_2$CH$_3$, CH$_2$CF$_3$, or cyclopropyl; and wherein when R$_{10}$ is B is O or NH and wherein —BCH$_2$B— is optionally replaced with —N(R$_7$)—N(R$_7$)—, where R$_7$ is one of H, CH$_3$, alkyl, or cycloalkyl; and when R$_{10}$ is

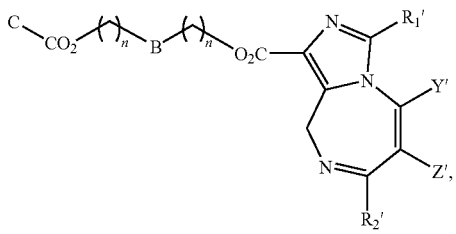

B is O or NH or —N(R$_7$)—N(R$_7$)—, where R$_7$ is one of H, CH$_3$, alkyl, or cycloalkyl; and R$_9$ is N or

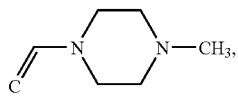

wherein when R$_9$ is

R$_1$ is =O and R$_{10}$ is N; R$_3$ is one of —H, —OH, —OCON(CH$_3$)$_2$, —COOH, —COOCH$_3$, —COOC$_2$H$_5$,

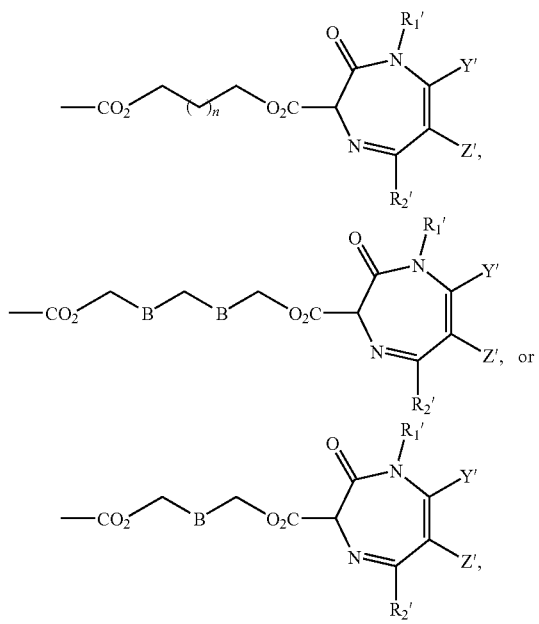

wherein if R$_3$ is

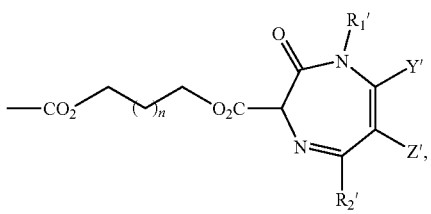

n is 0 to 4; Y' and Z' are taken together with the two intervening carbon atoms to form a ring selected from phenyl and thienyl, which ring is substituted at the C(7)' position with at least the substituent —C≡C—R', where R' is H, Si(CH$_3$)$_3$, t-butyl, isopropyl, methyl, or cyclopropyl;

R$_1$ and R$_1$' are independently one of H, CH$_3$, CF$_3$, CH$_2$CF$_3$, CH$_2$CH$_3$, or cyclopropyl;

R$_2$ and R$_2$' are independently a substituted or unsubstituted at least partially unsaturated 5 or 6 membered cyclic or heterocyclic ring, wherein if substituted the substituent is at least one of F, Cl, Br, or NO$_2$ at the 2'-position, or wherein if R$_3$ is

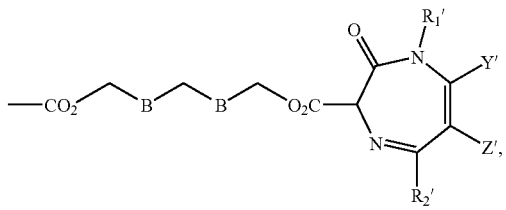

Y' and Z' are taken together with the two intervening carbon atoms to form a ring selected from phenyl and thienyl, which ring is substituted at the C(7)' position with at least the substituent —C≡C—R', where R' is H, Si(CH$_3$)$_3$, t-butyl, isopropyl, methyl, or cyclopropyl; R$_1$ and R$_1$' are independently one of H, CH$_3$, CF$_3$, CH$_2$CH$_3$, CH$_2$CF$_3$ or cyclopropyl; R$_2$ and R$_2$' are independently a substituted or unsubstituted at least partially unsaturated 5 or 6 membered cyclic or heterocyclic ring, wherein if substituted the substituent is at least one of F, Cl, Br, or NO$_2$ at the 2'-position; B is O or NH and wherein —BCH$_2$B— is optionally replaced with —N(R$_7$)—N(R$_7$)—, where R$_7$ is one of H, branched or straight chain C$_1$ to C$_4$ alkyl, cyclopropyl or methyl cyclopropyl, wherein if R$_3$ is

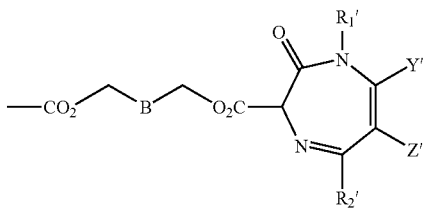

Y' and Z' are taken together with the two intervening carbon atoms to form a ring selected from phenyl and thienyl, which ring is substituted at the C(7)' position with at least the substituent —C≡C—R', where R' is H, Si(CH$_3$)$_3$, t-butyl, isopropyl, methyl, or cyclopropyl;

R$_1$ and R$_1$' are independently one of H, CH$_3$, CF$_3$, CH$_2$CH$_3$, CH$_2$CF$_3$ or cyclopropyl; R$_2$ and R$_2$' are independently a substituted or unsubstituted at least partially unsaturated 5 or 6 membered cyclic or heterocyclic ring, wherein if substituted the substituent is one or more of F, Cl, Br, or NO$_2$ at the 2'-position;

B is O, NH, or —N(R$_7$)—N(R$_7$)—, where R$_7$ is one of H, branched or straight chain C$_1$ to C$_4$ alkyl, cyclopropyl or methyl cyclopropyl, wherein R$_2$ is not phenyl when R$_3$ is H, R$_1$ is H or CH$_3$ and Y and Z taken together form a phenyl ring; wherein R$_8$ is C=O, C=S, or C—NHCH$_3$;

R$_{11}$ is O or N and R$_4$ is H, O or C, wherein when R$_{11}$ is O, R$_4$ is H, and R$_8$ is C=O;

when R$_{11}$ is N, R$_4$ is C and R$_{11}$ and R$_4$ are taken together with an intervening nitrogen atom to form a pyrazole ring;

when R$_{11}$ is N, R$_4$ is O and R$_{11}$ and R$_4$ are taken together with an intervening carbon atom to form an oxazole ring; or when R$_{11}$ is N, R$_4$ is C and R$_{11}$ and R$_4$ are taken together with two intervening carbon atoms to form a pyridine ring;

and $R_{12}$ is N or CH, $R_{13}$ is phenyl, 2-thienyl, 3-thienyl, 2-pyridyl, or 2-pyridyl N—O, and if the compound is according to Formula B or C, n is an integer from 1 to 2 inclusive and ring C is saturated or unsaturated.

The compounds described herein have been synthesized based on a modified version of the computer modeling disclosed in Cook, et al *J. Med. Chem.*, 1996, 39, 1928-1934. These compounds obtained by modifying elements, described herein, of the known benzodiazepine agents, have increased binding selectivity for the $GABA_A/\alpha 2$, $GABA_A/\alpha 3$, and/or $GABA_A/\alpha 5$ receptors described above, and/or altered efficacy at one or more $GABA_A$ receptors described above, and/or altered selectivity at one or more ion channels. Further details of the synthesis of these compounds are found in U.S. Pat. No. 7,119,196, and published patent application WO 2003/082832, WO 2006/004945, and US 2006/0003995, all of which are incorporated by reference herein in their entirety.

Suitable compounds for the practice of embodiments of the present invention have binding selectivity for the $GABA_A/\alpha 2$, $GABA_A/\alpha 3$ receptors over $GABA_A/\alpha 1$ receptors. In another aspect, suitable compounds for the practice of embodiments of the present invention have higher physiological efficacy at $GABA_A/\alpha 2$, $GABA_A/\alpha 3$ receptors than at $GABA_A/\alpha 1$ receptors.

Suitable compounds for the practice of embodiments of the present invention include compounds of formula I, or a salt or prodrug thereof,

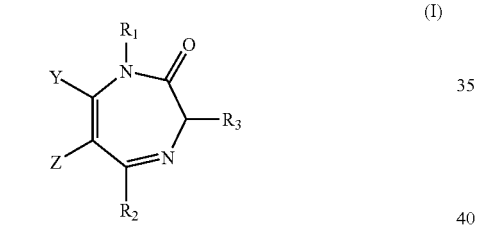

(I)

wherein Y and Z are taken together with the two intervening carbon atoms to form a ring selected from phenyl and thienyl, which ring is substituted at the C(7) position with at least the substituent —C≡C—R, where R is H, Si(CH$_3$)$_3$, t-butyl, isopropyl, methyl, or cyclopropyl; $R_1$ is one of H, CH$_3$, C$_2$H$_4$N(C$_2$H$_5$)$_2$, CH$_2$CF$_3$, CH$_2$C≡CH, or an alkyl cyclopropyl; $R_2$ is a substituted or unsubstituted at least partially unsaturated 5 or 6 membered cyclic or heteorcyclic ring, wherein if substituted the substituent is one or more of F, Cl, Br, or NO$_2$ at the 2'-position; and $R_3$ is one of H, OH, OCON(CH$_3$)$_2$, COOCH$_3$, or COOC$_2$H$_5$. Preferred compounds according to formula I include:

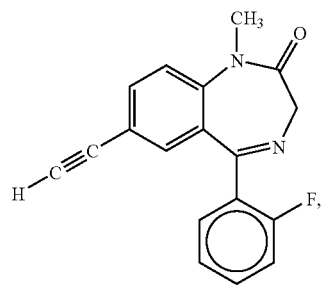

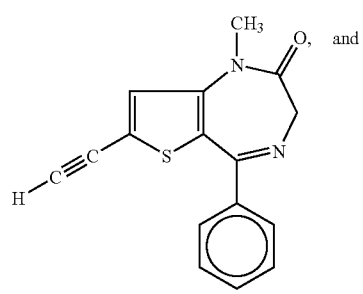

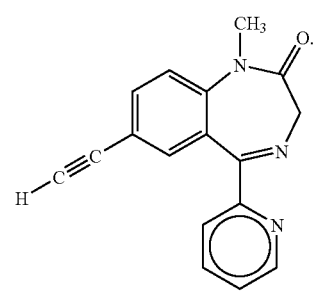

Suitable compounds for the practice of embodiments of the present invention include compounds of formula II, or a salt or prodrug thereof,

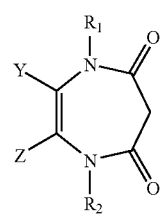

(II)

wherein Y and Z are taken together with the two intervening carbon atoms to form a ring selected from phenyl and thienyl, which ring is substituted at the C(7) position with at least the substituent —C≡C—R, where R is H, Si(CH$_3$)$_3$, t-butyl, isopropyl, methyl, or cyclopropyl; $R_1$ is one of H, CH$_3$, C$_2$H$_4$N(C$_2$H$_5$)$_2$, CH$_2$CF$_3$, CH$_2$C≡CH, or an alkyl cyclopropyl; and $R_2$ is a substituted or unsubstituted at least partially unsaturated 5 or 6 membered cyclic or heterocyclic ring, wherein if substituted the substituent is one or more of F, Cl, Br, or NO$_2$ at the 2'-position. Preferred compounds according to formula II include:

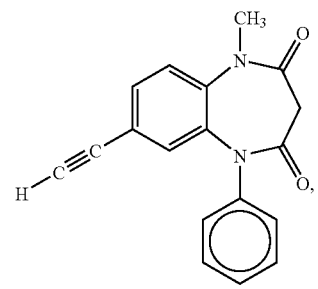

-continued

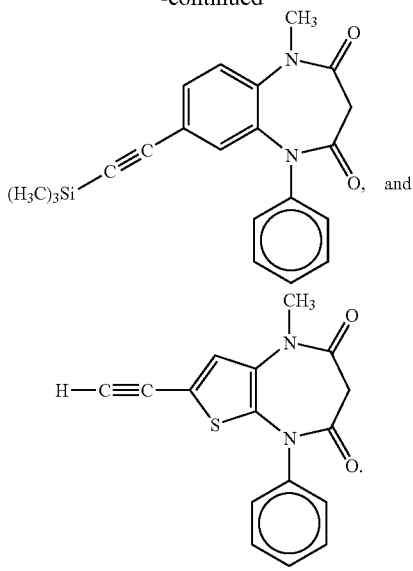

, and

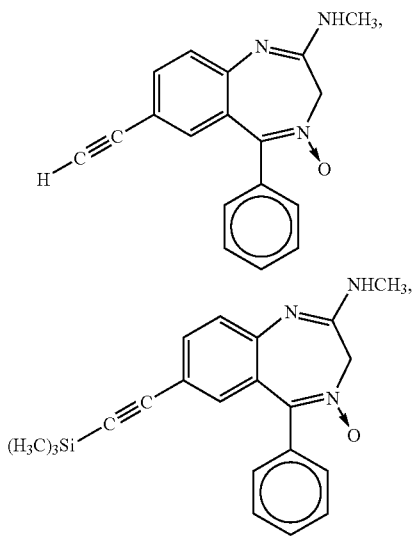

.

Suitable compounds for the practice of embodiments of the present invention include compounds of formula III, or a salt or prodrug thereof,

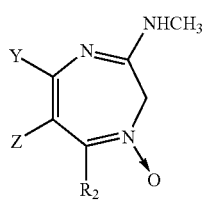

(III)

wherein Y and Z are taken together with the two intervening carbon atoms to form a ring selected from phenyl and thienyl, which ring is substituted at the C(7) position with at least the substituent —C≡C—R, where R is H, Si(CH$_3$)$_3$, t-butyl, isopropyl, methyl, or cyclopropyl; and R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position. Preferred compounds according to the formula III include:

-continued

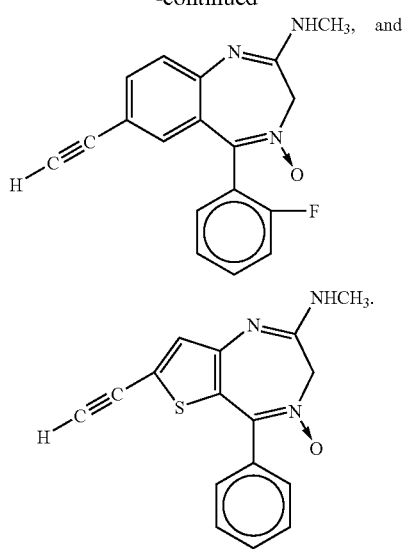

Suitable compounds for the practice of embodiments of the present invention include compounds of formula IV, or a salt or prodrug thereof,

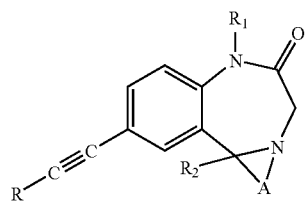

(IV)

wherein R is H, Si(CH$_3$)$_3$, t-butyl, isopropyl, methyl, or cyclopropyl; R$_1$ is one of H, CH$_3$, C$_2$H$_4$N(C$_2$H$_5$)$_2$, CH$_2$CF$_3$, CH$_2$C≡CH, or an alkyl cyclopropyl; R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position; and A is an ethoxide or a propoxide. Preferred compounds according to the formula IV include:

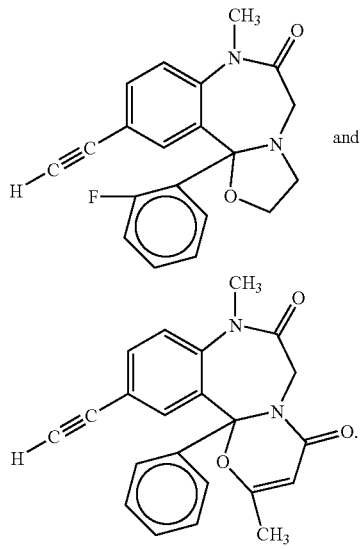

Suitable compounds for the practice of embodiments of the present invention include compounds of formula V, or a salt or prodrug thereof,

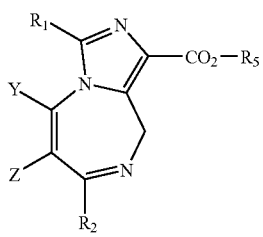

wherein Y and Z are taken together with the two intervening carbon atoms to form a ring selected from phenyl and thienyl, which ring is substituted at the C(8) position with at least the substituent —C≡C—R, where R is H, Si$(CH_3)_3$, t-butyl, isopropyl, methyl, or cyclopropyl; $R_1$ is one of H, $CH_3$, $CF_3$, $CH_2CH_3$, $CH_2CF_3$, $CH_2C\equiv CH$, an alkyl, or cyclopropyl; $R_2$ is a substituted or unsubstituted at least partially unsaturated 5 or 6 membered cyclic or heterocyclic ring, wherein if substituted the substituent is one or more of F, Cl, Br, or $NO_2$ at the 2'-position; and $R_5$ is a branched or straight chain $C_1$ to $C_4$ halogenated or unhalogenated alkyl or a methyl cyclopropyl. Preferred compounds according to formula V include:

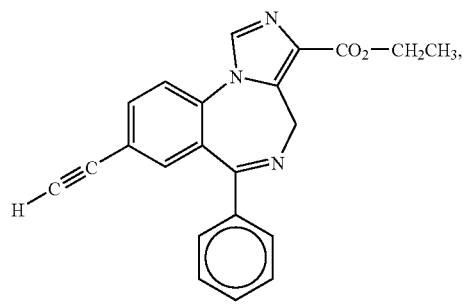

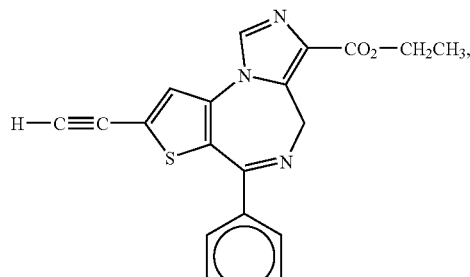

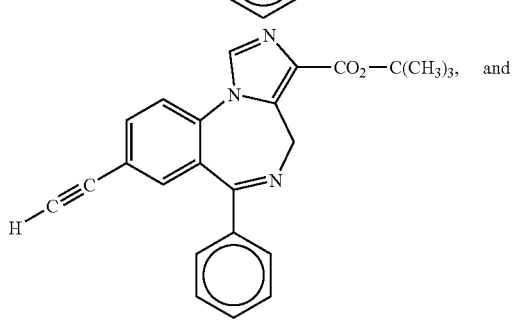

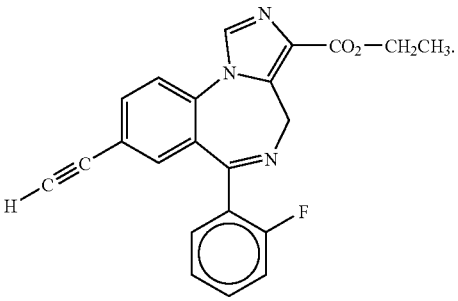

Suitable compounds for the practice of embodiments of the present invention include compounds of formula VI, or a salt or prodrug thereof,

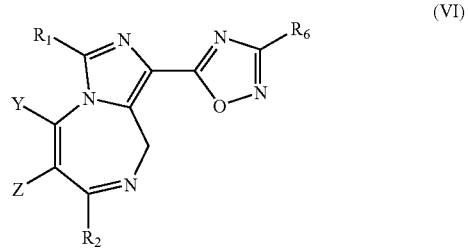

wherein Y and Z are taken together with the two intervening carbon atoms to form a ring selected from phenyl and thienyl, which ring is substituted at the C(8) position with at least the substituent —C≡C—R, where R is H, Si$(CH_3)_3$, t-butyl, isopropyl, methyl, or cyclopropyl; $R_1$ is one of H, $CH_3$, $CF_3$, $CH_2CH_3$, $CH_2CF_3$, or cyclopropyl;

$R_2$ is a substituted or unsubstituted at least partially unsaturated 5 or 6 membered cyclic or heterocyclic ring, wherein if substituted the substituent is one or more of F, Cl, Br, or $NO_2$ at the 2'-position; and $R_6$ is a branched or straight chain $C_1$ to $C_4$ alkyl, e.g., $CH(CH_3)_2$ (isopropyl group), $CH_2CH_3$, or $CH_3$, or a methyl cyclopropyl.

Preferred compounds according to formula VI include:

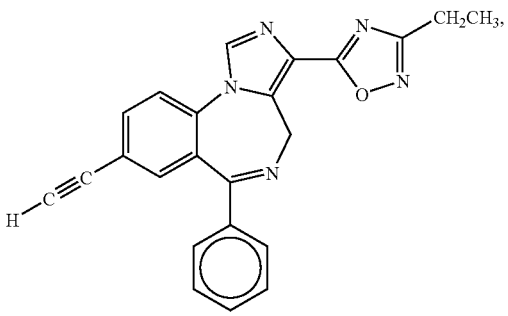

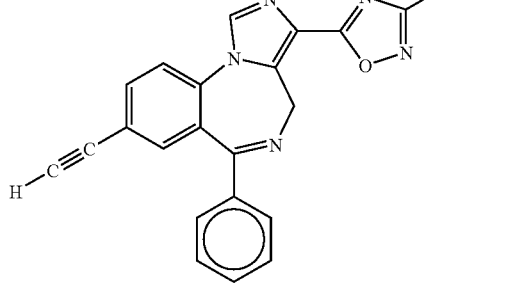

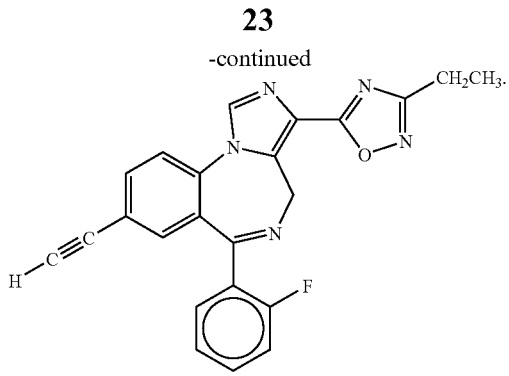

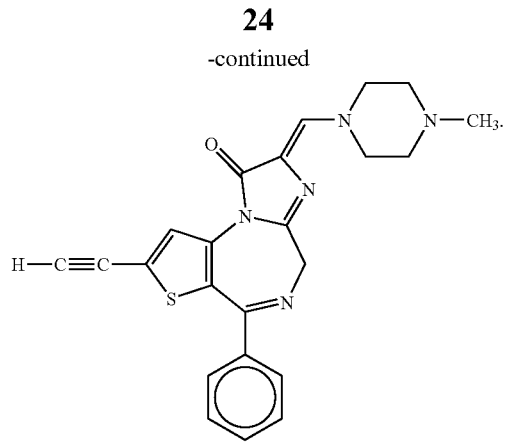

Suitable compounds for the practice of embodiments of the present invention include compounds of formula VII, or a salt or prodrug thereof,

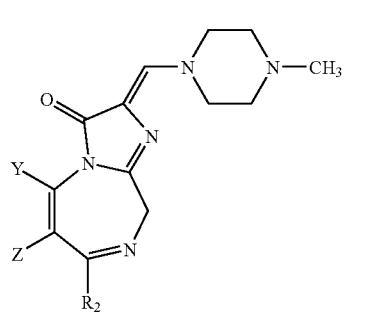

(VII)

Suitable compounds for the practice of embodiments of the present invention include compounds of formula VIII, or a salt or prodrug thereof,

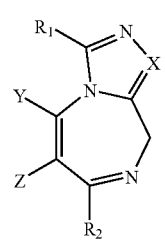

(VIII)

wherein Y and Z are taken together with the two intervening carbon atoms to form a ring selected from phenyl and thienyl, which ring is substituted at the C(8) position with at least the substituent —C≡C—R, where R is H, Si(CH$_3$)$_3$, t-butyl, isopropyl, methyl, or cyclopropyl; and R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position. Preferred compounds according to formula VII include:

wherein Y and Z are taken together with the two intervening carbon atoms to form a ring selected from phenyl and thienyl, which ring is substituted at the C(8) position with at least the substituent —C≡C—R, where X is N or CH, where R is H, Si(CH$_3$)$_3$, t-butyl, isopropyl, methyl, or cyclopropyl; R$_1$ is H, CH$_3$, CF$_3$, CH$_2$CH$_3$, CH$_2$CF$_3$, or cyclopropyl; R$_2$ is a substituted or unsubstituted at least partially unsaturated 5 or 6 membered cyclic or heterocyclic ring, wherein if substituted the substituent is one or more of F, Cl, Br, or NO$_2$ at the 2'-position. Preferred compounds according to formula VIII include:

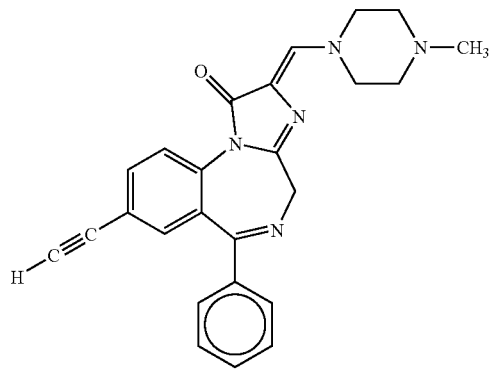

and

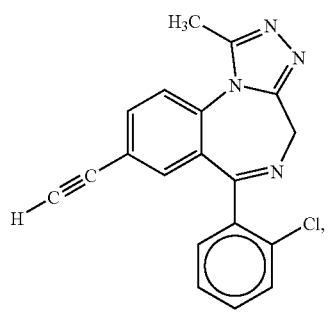

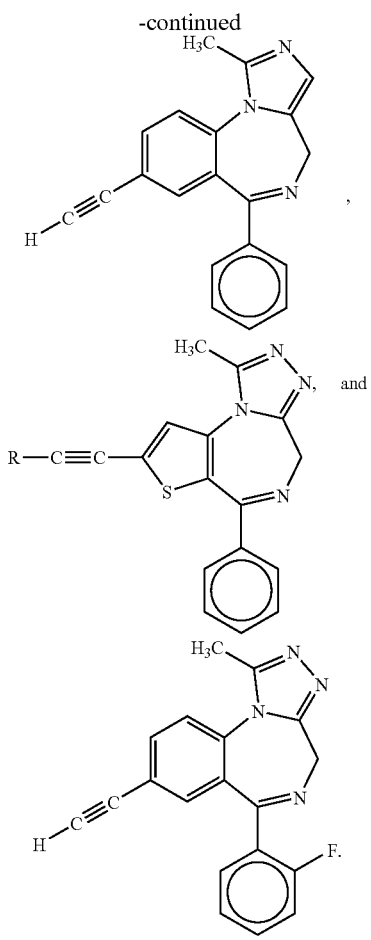

Suitable compounds for the practice of embodiments of the present invention include compounds of formula IX, or a salt or prodrug thereof,

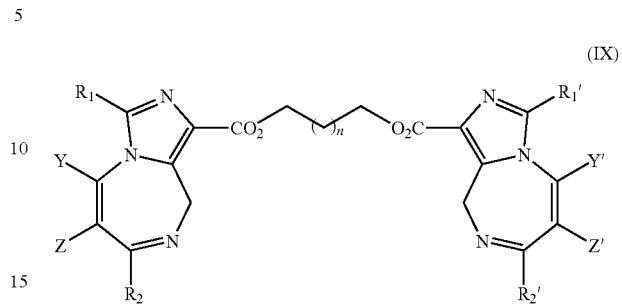

wherein n is 0 to 4; Y and Z are taken together with the two intervening carbon atoms to form a ring selected from phenyl and thienyl, which ring is substituted at the C(8) position with at least the substituent —C≡C—R, where R is H, Si(CH$_3$)$_3$, t-butyl, isopropyl, methyl, or cyclopropyl; Y' and Z' are taken together with the two intervening carbon atoms to form a ring selected from phenyl and thienyl, which ring is substituted at the C(8)' position with at least the substituent —C≡C—R', where R' is H, Si(CH$_3$)$_3$, t-butyl, isopropyl, methyl, or cyclopropyl; R$_1$ and R$_1$' are independently one of H, CH$_3$, CF$_3$, CH$_2$CF$_3$, CH$_2$CH$_3$, or cyclopropyl; and R$_2$ and R$_2$' are independently a substituted or unsubstituted at least partially unsaturated 5 or 6 membered cyclic or heterocyclic ring, wherein if substituted the substituent is one or more of F, Cl, Br, or NO$_2$ at the 2'-position. Preferred compounds according to formula IX include:

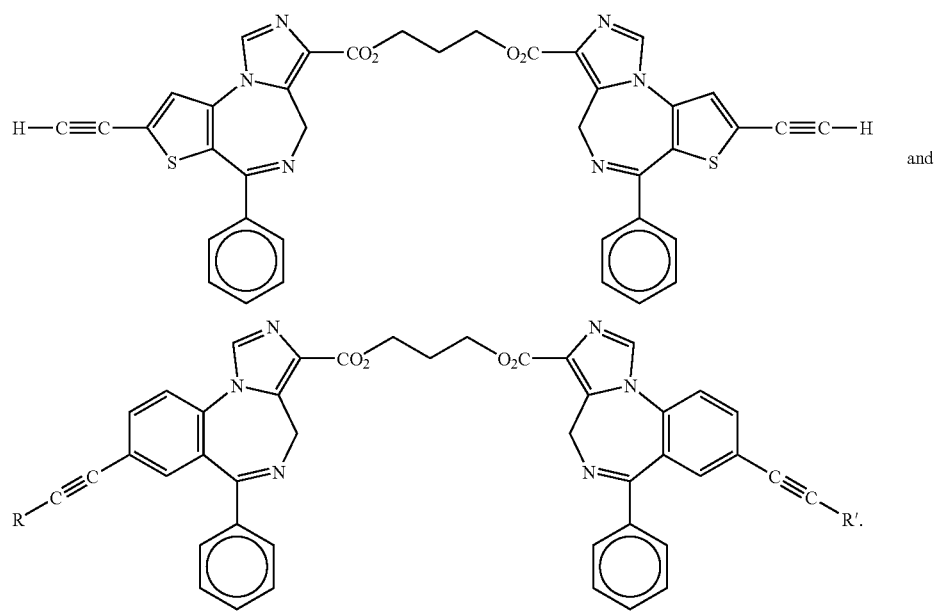

R is H or Si(CH$_3$)$_3$
R' is H or Si(CH$_3$)$_3$

Suitable compounds for the practice of embodiments of the present invention include compounds of formula X, or a salt or prodrug thereof,

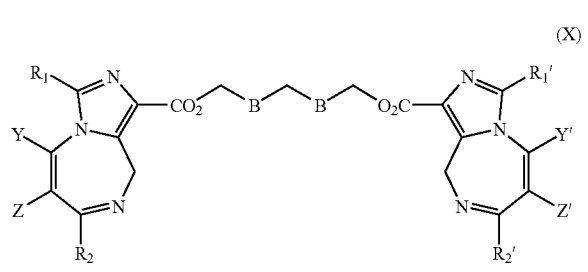

(X)

wherein Y and Z are taken together with the two intervening carbon atoms to form a ring selected from phenyl and thienyl, which ring is substituted at the C(8) position with at least the substituent —C≡C—R, where R is H, Si (CH$_3$)$_3$, t-butyl, isopropyl, methyl, or cyclopropyl; Y' and Z' are taken together with the two intervening carbon atoms to form a ring selected from phenyl and thienyl, which ring is substituted at the C(8)' position with at least the substituent —C≡C—R' where R' is H, Si(CH$_3$)$_3$, t-butyl, isopropyl, methyl, or cyclopropyl; R$_1$ and R$_1$' are independently one of H, CH$_3$, CF$_3$, CH$_2$CH$_3$, CH$_2$CF$_3$, or cyclopropyl; R$_2$ and R$_2$' are independently a substituted or unsubstituted at least partially unsaturated 5 or 6 membered cyclic or heterocyclic ring, wherein if substituted the substituent is one or more of F, Cl, Br, or NO$_2$ at the 2'-position; and B is O or NH and wherein —BCH$_2$B— is optionally replaced with —N(R$_7$)—N(R$_7$)—, where R$_7$ is one of H, CH$_3$, alkyl, or cycloalkyl. Preferred compounds according to formula X include:

Suitable compounds for the practice of embodiments of the present invention also include compounds of formula XI, or a salt or prodrug thereof,

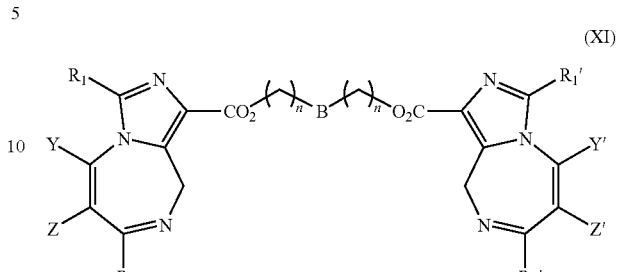

(XI)

wherein n is 1 or 2; wherein Y and Z are taken together with the two intervening carbon atoms to form a ring selected from phenyl and thienyl, which ring is substituted at the C(8) position with at least the substituent —C≡C—R, where R is H, Si (CH$_3$)$_3$, t-butyl, isopropyl, methyl, or cyclopropyl; Y' and Z' are taken together with the two intervening carbon atoms to form a ring selected from phenyl and thienyl, which ring is substituted at the C(8)' position with at least the substituent —C≡C—R', where R' is H, Si(CH$_3$)$_3$, t-butyl, isopropyl, methyl, or cyclopropyl; R$_1$ and R$_1$' are independently one of H, CH$_3$, CF$_3$, CH$_2$CH$_3$, CH$_2$CF$_3$, or cyclopropyl; R$_2$ and R$_2$' are independently a substituted or unsubstituted at least partially unsaturated 5 or 6 membered cyclic or heterocyclic ring, wherein if substituted the substituent is one or more of F, Cl, Br, or NO$_2$ at the 2'-position; and B is O, NH, or —N(R$_7$)—N(R$_7$)—, where R$_7$ is one of H, CH$_3$, alkyl, or cycloalkyl. Preferred compounds according to formula XI include:

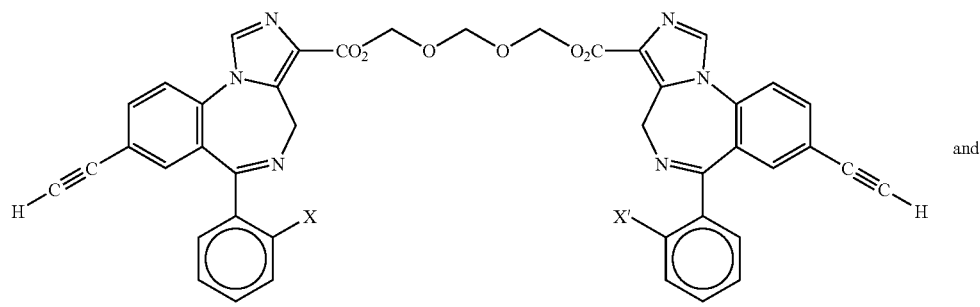

X and X' are each independently H or F and

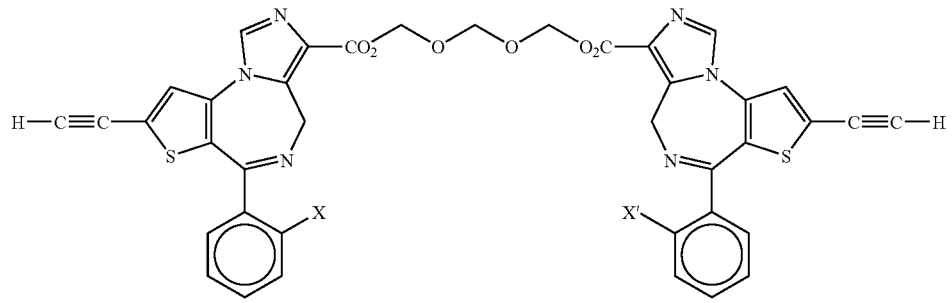

X and X' are each independently H or F

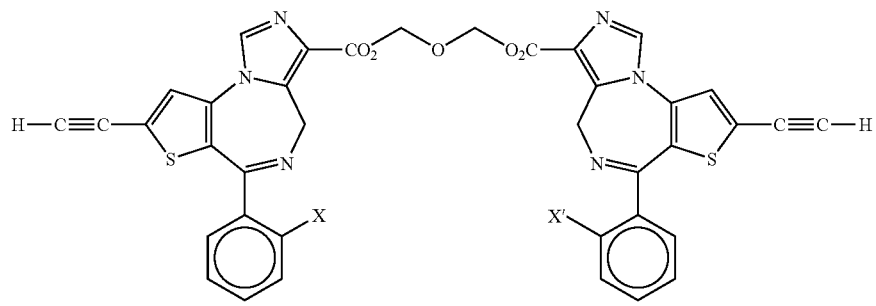

X and X' are each independently H or F

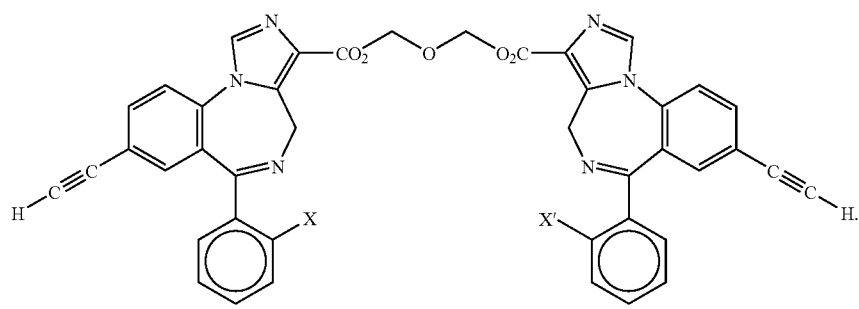

X and X' are each independently H or F

Suitable compounds for the practice of embodiments of the present invention include compounds of formula XII, or a salt or prodrug thereof,

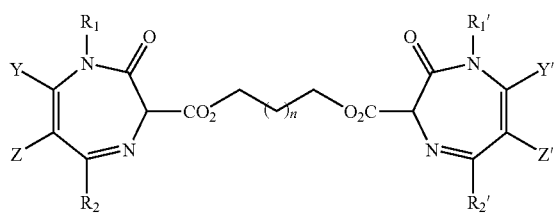

(XII)

wherein n is 0 to 4; Y and Z are taken together with the two intervening carbon atoms to form a ring selected from phenyl and thienyl, which ring is substituted at the C(7) position with at least the substituent —C≡C—R, where R is H, $Si(CH_3)_3$, t-butyl, isopropyl, methyl, or cyclopropyl; Y' and Z' are taken together with the two intervening carbon atoms to form a ring selected from phenyl and thienyl, which ring is substituted at the C(7)' position with at least the substituent —C≡C—R', where R' is H, $Si(CH_3)_3$, t-butyl, isopropyl, methyl, or cyclopropyl; $R_1$ and $R_1'$ are independently one of H, $CH_3$, $CF_3$, $CH_2CF_3$, $CH_2CH_3$, or cyclopropyl; and $R_2$ and $R_2'$ are independently a substituted or unsubstituted at least partially unsaturated 5 or 6 membered cyclic or heterocyclic ring, wherein if substituted the substituent is one or more of F, Cl, Br, or $NO_2$ at the 2'-position. Preferred compounds according to formula XII include:

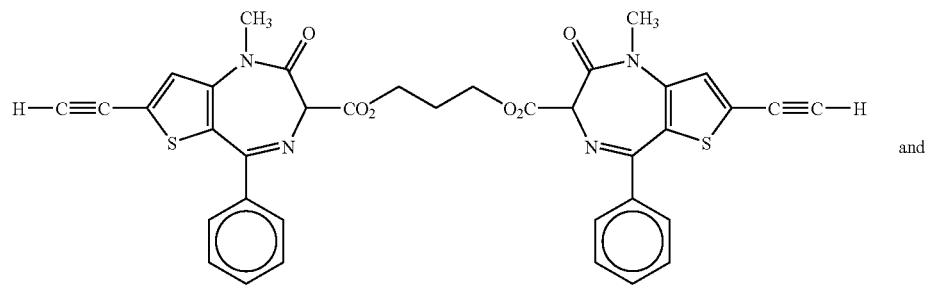

and

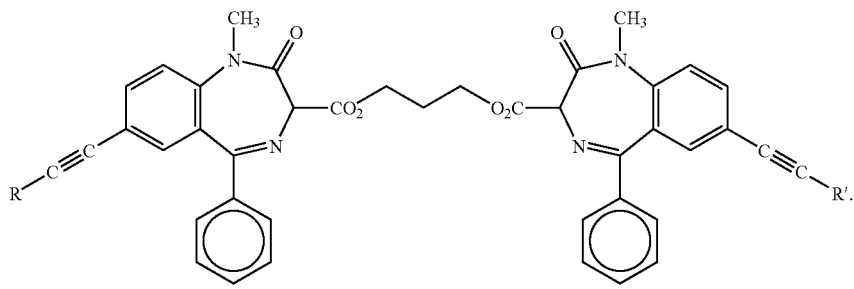

R is H or Si(CH₃)₃
R' is H or Si(CH₃)₃

Suitable compounds for the practice of embodiments of the present invention include compounds of the formula XIII, or a salt or prodrug thereof,

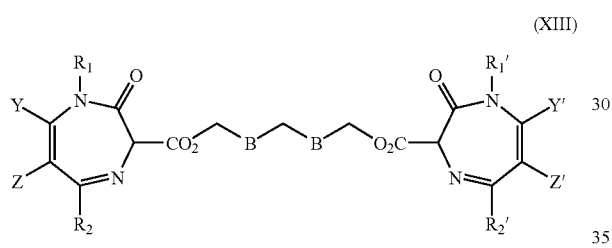

(XIII)

wherein Y and Z are taken together with the two intervening carbon atoms to form a ring selected from phenyl and thienyl, which ring is substituted at the C(7) position with at least the substituent —C≡C—R, where R is H, Si(CH₃)₃, t-butyl, isopropyl, methyl, or cyclopropyl; Y' and Z' are taken together with the two intervening carbon atoms to form a ring selected from phenyl and thienyl, which ring is substituted at the C(7)' position with at least the substituent —C≡C—R', where R' is H, Si(CH₃)₃, t-butyl, isopropyl, methyl, or cyclopropyl; $R_1$ and $R_1'$ are independently one of H, $CH_3$, $CF_3$, $CH_2CH_3$, $CH_2CF_3$, or cyclopropyl; $R_2$ and $R_2'$ are independently a substituted or unsubstituted at least partially unsaturated 5 or 6 membered cyclic or heterocyclic ring, wherein if substituted the substituent is one or more of F, Cl, Br, or $NO_2$ at the 2'-position; and B is O or NH and wherein —BCH₂B— is optionally replaced with —N(R₇)—N(R₇)—, where R₇ is one of H, CH₃, alkyl, or cycloalkyl. Preferred compounds according to formula XIII include:

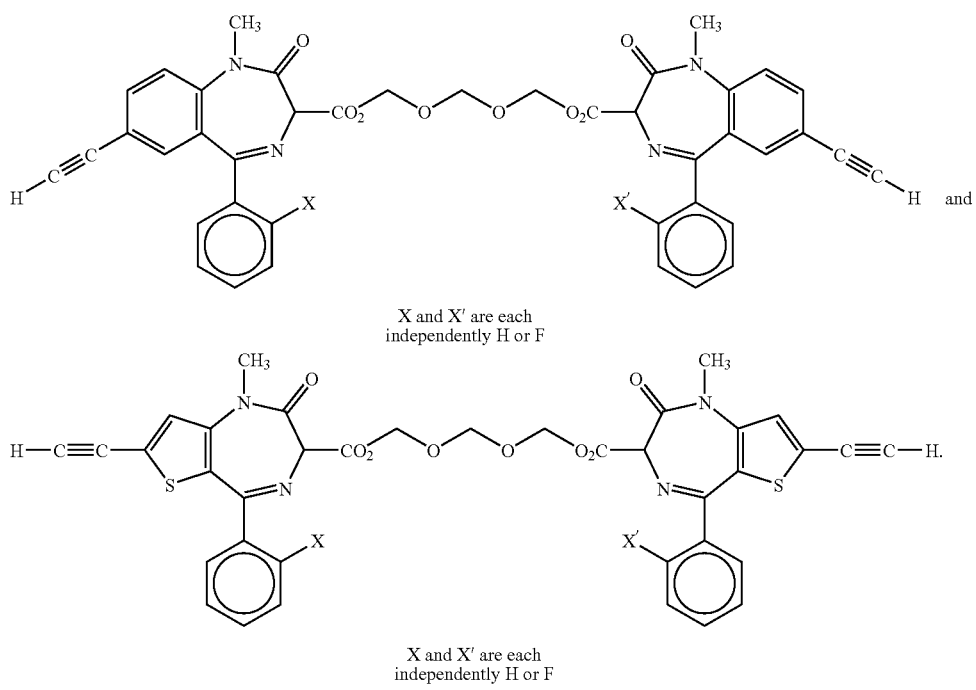

X and X' are each independently H or F

X and X' are each independently H or F

Yet other suitable compounds for the practice of embodiments of the present invention include compounds of the formula XIV, or a salt or prodrug thereof,

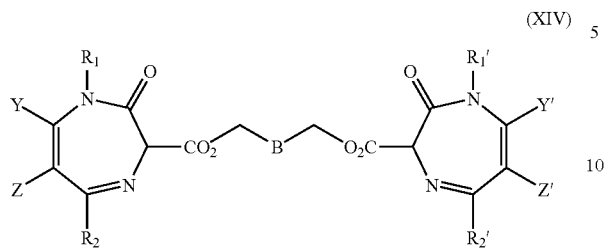
(XIV)

wherein Y and Z are taken together with the two intervening carbon atoms to form a ring selected from phenyl and thienyl, which ring is substituted at the C(7) position with at least the substituent —C≡C—R, where R is H, Si(CH$_3$)$_3$, t-butyl, isopropyl, methyl, or cyclopropyl; Y' and Z' are taken together with the two intervening carbon atoms to form a ring selected from phenyl and thienyl, which ring is substituted at the C(7)' position with at least the substituent —C≡C—R', where R' is H, Si(CH$_3$)$_3$, t-butyl, isopropyl, methyl, or cyclopropyl; R$_1$ and R$_1$' are independently one of H, CH$_3$, CF$_3$, CH$_2$CH$_3$, CH$_2$CF$_3$, or cyclopropyl; R$_2$ and R$_2$' are independently a substituted or unsubstituted at least partially unsaturated 5 or 6 membered cyclic or heterocyclic ring, wherein if substituted the substituent is one or more of F, Cl, Br, or NO$_2$ at the 2'-position; and B is O, NH, or —N(R$_7$)—N(R$_7$)—, where R$_7$ is one of H, CH$_3$, alkyl, or cycloalkyl. Preferred compounds according to formula XIV include:

Yet other suitable compounds for the practice of embodiments of the present invention include compounds of the formula XV, or a salt or prodrug thereof,

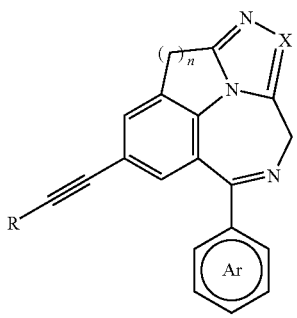

where n is 1-2 inclusive, R is H, Si(CH$_3$)$_3$, t-butyl, or cyclopropyl, Ar is phenyl, 2'-fluorophenyl, 2-thienyl, 3-thienyl, 2-pyridyl, 2-pyridyl N—O, and X is N or CH.

Yet other suitable compounds for the practice of embodiments of the present invention include compounds of the formula XVI, or a salt or prodrug thereof,

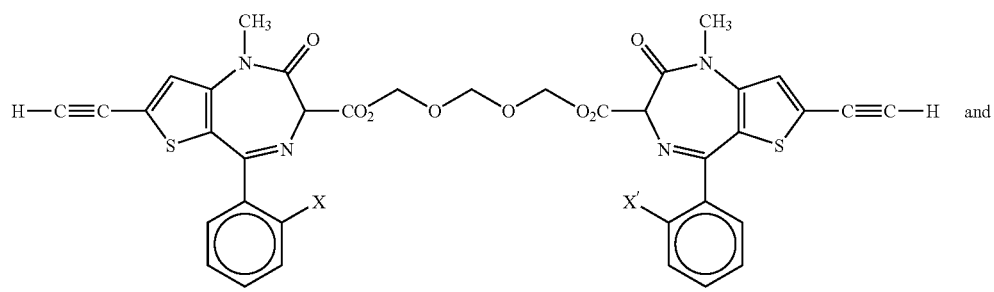

and

X and X' are each independently H or F

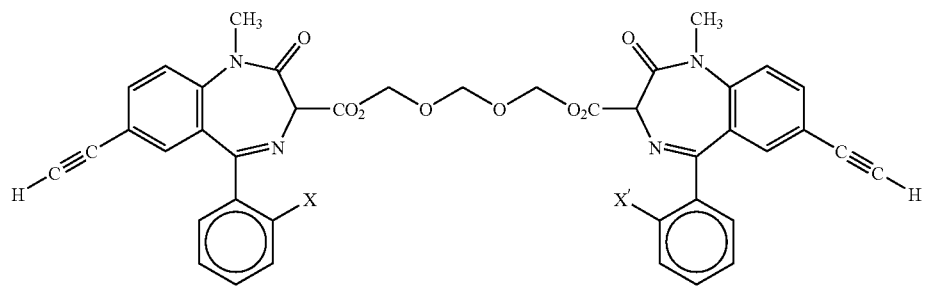

X and X' are each independently H or F

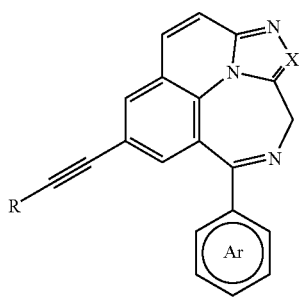

where R is H, Si(CH$_3$)$_3$, t-butyl, or cyclopropyl, Ar is phenyl, 2'-fluorophenyl, 2-thienyl, 3-thienyl, 2-pyridyl, 2-pyridyl N—O, and X is N or CH.

Further suitable compounds for the practice of embodiments of the present invention include compounds of the formula XVII, or a salt or prodrug thereof,

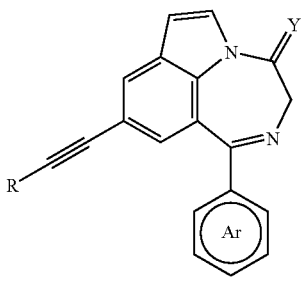

where R is H, Si(CH$_3$)$_3$, t-butyl, or cyclopropyl, Ar is phenyl, 2'-fluorophenyl, 2-thienyl, 3-thienyl, 2-pyridyl, 2-pyridyl N—O, and Y is O, S or NHCH$_3$.

Further suitable compounds for the practice of embodiments of the present invention include compounds of the formula XVIII, or a salt or prodrug thereof,

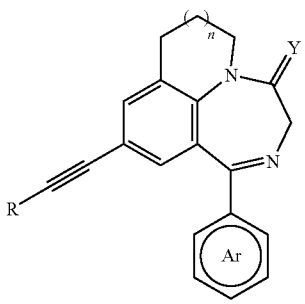

where n is 1-2 inclusive, R is H, Si(CH$_3$)$_3$, t-butyl, or cyclopropyl, Ar is phenyl, 2'-fluorophenyl, 2-thienyl, 3-thienyl, 2-pyridyl, 2-pyridyl N—O, and Y is O, S or NHCH$_3$.

Other suitable compounds for the practice of embodiments of the present invention include compounds of the formula XIX, or a salt or prodrug thereof, where R is H, Si(CH$_3$)$_3$, t-butyl, or cyclopropyl, Ar is phenyl, 2'-fluorophenyl, 2-thienyl, 3-thienyl, 2-pyridyl, 2-pyridyl N—O, and Y is O, S or NHCH$_3$.

Other suitable compounds for the practice of embodiments of the present invention include compounds of the formula XX, or a salt or prodrug thereof, where R is H, Si(CH$_3$)$_3$, t-butyl, or cyclopropyl, Ar is phenyl, 2'-fluorophenyl, 2-thienyl, 3-thienyl, 2-pyridyl, 2-pyridyl N—O, and Y is O, S or NHCH$_3$.

Further suitable compounds for the practice of embodiments of the present invention include compounds of the formula XXI, or a salt or prodrug thereof, where R is H, Si(CH$_3$)$_3$, t-butyl, or cyclopropyl, Ar is phenyl, 2'-fluorophenyl, 2-thienyl, 3-thienyl, 2-pyridyl, 2-pyridyl N—O, and Y is O, S or NHCH$_3$.

Compounds (XV) to (XXI) above can also have R as CF$_3$, CCl$_3$, or CBr$_3$.

A still further aspect of the present invention provides compositions comprising compounds of the above kind in a pharmaceutically acceptable carrier. Such pharmaceutically acceptable carriers are well known in the art.

In the above embodiments by "alkyl" we mean a straight or branched halogenated or unhalogenated alkyl group having 1-6 carbon atoms. By "cycloalkyl" we mean one containing 3-7 carbon atoms. Also, in the above embodiments by "cyclic" we prefer a phenyl group and by "heterocyclic" we prefer a 2-pyridine or a 2- or 3-thiophene.

The compounds of the present invention are $GABA_A$ receptor ligands which exhibit anxiolytic activity due to increased agonist efficacy at the $GABA_A/\alpha2$ and $GABA_A/\alpha3$ receptors, and optionally the $GABA_A/\alpha5$ receptors. The compounds in accordance with this invention may possess at least 2-fold, suitably at least 5-fold, and advantageously at least a 10-fold, selective efficacy for the $GABA_A/\alpha2$, $GABA_A/\alpha3$, and/or $GABA_A/\alpha5$ receptors relative to the $GABA_A/\alpha1$ receptors. However, compounds which are not selective in terms of their agonist efficacy for the $GABA_A/\alpha2$, $GABA_A/\alpha3$, and/or $GABA_A/\alpha5$ receptors are also encompassed within the scope of the present invention. Such compounds will desirably exhibit functional selectivity by demonstrating anxiolytic activity with decreased sedative-hypnotic/muscle relaxant/ataxic activity due to decreased efficacy at $GABA_A/\alpha1$ receptors.

For use in medicine, the salts of the compounds of formulas (I)-(XXI) will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts.

The present invention includes within its scope prodrugs of the compounds of formulas (I)-(XXI) above. In general, such prodrugs will be functional derivatives of the compounds of formulas (I)-(XXI) which are readily convertible in vivo into the required compound of formulas (I)-(XXI). Conventional procedures for the selection and preparation of suitable prodrug derivatives are described, for example, in *Design of Prodrugs*, ed. H. Bundgaard, Elsevier, 1985.

Where the compounds according to the invention have at least one asymmetric center, they may accordingly exist as enantiomers. Where the compounds according the invention possess two or more asymmetric centers, they may additionally exist as diastereoisomers. It is to be understood that all such isomers and mixtures thereof in any proportion are encompassed within the scope of the present invention. The examples of the use of stereroisomeric compounds in the practice of the present invention disclosed herein are illustrative examples, and are not limiting.

Practice of the embodiments of the invention also involves pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds of the present invention may be incorporated into transdermal patches designed to deliver the appropriate amount of the drug in a continuous fashion. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid performulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage from affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium caboxymethylcellulose, methylcellulose, polyvinylpyrrolidone or gelatin.

Suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day, or on a continuous basis via, for example, the use of a transdermal patch.

BRIEF DESCRIPTION OF THE DRAWINGS

FIG. 7 is a graph of dose-response curves of the patch clamp current (expressed as percent of the control current) produced by various concentrations of HZ-166 (SH-053'2'N) when applied to $Xenopus$ oocytes expressing $\alpha1\beta3\gamma2$ (●), $\alpha2\beta3\gamma2$ (■), $\alpha3\beta3\gamma2$ (▲) or $\alpha5\beta3\gamma2$ (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 8 is a graph of dose-response curves of the patch clamp current (expressed as percent of the control current) produced by various concentrations of JY-XHE-053 when applied to $Xenopus$ oocytes expressing $\alpha1\beta3\gamma2$ (●), $\alpha2\beta3\gamma2$ (■), $\alpha3\beta3\gamma2$ (▲) or $\alpha5\beta3\gamma2$ (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 12 is a graph of dose-response curves of the patch clamp current (expressed as percent of the control current) produced by various concentrations of SH-053-2'F—S—CH3 when applied to $Xenopus$ oocytes expressing recombinant $GABA_A/\alpha_1$ receptors, $GABA_A/\alpha_2$ receptors, $GABA_A/\alpha_3$ receptors or $GABA_A/\alpha_5$ receptors.

FIG. 14 is a graph of dose-response curves of the patch clamp current (expressed as percent of the control current) produced by various concentrations of SH-053-2'N—S—CH3 when applied to $Xenopus$ oocytes expressing recombinant $GABA_A/\alpha_1$ receptors, $GABA_A/\alpha_2$ receptors, $GABA_A/\alpha_3$ receptors or $GABA_A/\alpha_5$ receptors.

FIG. 18 is a graph of dose-response curves of the patch clamp current (expressed as percent of the control current) produced by various concentrations of EMJ-I-026 when applied to $Xenopus$ oocytes expressing $\alpha1\beta3\gamma2$ (□), $\alpha2\beta3\gamma2$ (■), $\alpha3\beta3\gamma2$ (▲) or $\alpha5\beta3\gamma2$ (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 19 is a graph of dose-response curves of the patch clamp current (expressed as percent of the control current) produced by various concentrations of YT-TC-3 when applied to $Xenopus$ oocytes expressing $\alpha1\beta3\gamma2$ (□), $\alpha2\beta3\gamma2$ (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

FIG. 20 is a graph of dose-response curves of the patch clamp current (expressed as percent of the control current) produced by various concentrations of YT-II-794 when applied to *Xenopus* oocytes expressing α1β3γ2 (□), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

FIGS. 21A-21F are graphs of the results for rates of non-suppressed and suppressed responses at various dosage concentrations of diazepam, XHE-II-053, JY-XHE-053, Hz-166, SH-053-2'F—S—CH3 and SH-053-2'F—R—CH3.

FIGS. 22A and 22B are graphs of the antihyperalgesic effects of HZ166 where neuropathic pain is assessed in the CCI model illustrating the mechanical sensitization and where PWTs (g, mean±SEM) in response to mechanical stimulation with dynamic von Frey filaments were measured before CCI surgery (baseline), on day 7 after surgery before drug administration and for 4 hours after drug injection. Left: time course. HZ166 (1 [▼, ∇], 5 [♦,], 16 [■, □], 48 [▲, Δ], 160 [,], 480 [,] mg/kg body weight) or vehicle (●, ○) were injected i.p. Filled symbols, ipsilateral paw; open symbols, contralateral paw. n=6 mice per group. Right: statistical analysis. AUC (g*h, mean±SEM). ANOVA followed by Scheffe's post hoc test, F (6, 35)=17.14; P<0.001*, P<0.05; , P<0.01; *, P<0.001.

FIGS. 23A and 23B are graphs of the antihyperalgesic effects of HZ166 where neuropathic pain is assessed in the CCI model illustrating the thermal hyperalgesia, and where PWLs (s, mean±SEM) in response to a defined radiant heat stimulus. Left: time course. On day 7 after CCI surgery, HZ166 (▼, ∇, 16 mg/kg body weight) or vehicle (●, ○) were injected i.p. and PWTs were monitored for 3 hours after injection. n=6 mice per group. Right: statistical analysis. AUC (g*h, mean±SEM). **, P<0.01 (unpaired t-test).

FIGS. 24A and 24B are graphs of the antihyperalgesic effects of HZ166 where neuropathic pain is assessed in the inflammatory hyperalgesia induced by subcutaneous zymosan A injection into the plantar side of the left hindpaw, and where left: mechanical PWTs (g, mean±SEM) in response to stimulation with dynamic von Frey filaments were monitored before and 2 days after injection of zymosan A. On day 2, HZ166 (▼, ∇, 16 mg/kg body weight) or vehicle (●, ○) were injected i.p. and PWTs were monitored for 3 hours after HZ166 injection. n=6 mice per group. Right: statistical analysis. AUC (g*h, mean±SEM). **, P<0.01 (unpaired t-test).

FIG. 27B is a graph of the percent maximum possible effect of HZ166 and gabapentin on mechanical sensitization after chronic constriction injury.

FIG. 27D is a graph of the percentage maximum possible effect of HZ166 (acute treatment: vehicle+HZ166, chronic treatment: HZ166+HZ166) on mechanical sensitization after C (ipsilateral paw values after drug injection are compared with pre-surgery values). n=6 mice per group.

FIG. 28 is a graph of the effects of HZ166 on motor coordination and locomotor activity of the total time spent on rotarod (mean±SEM) measured 60 min after the injection of HZ166 (16 and 48 mg/kg body weight, i.p.) or vehicle. n=10 mice per group.

FIG. 29 is a graph of the effects of gabapentin on motor coordination and locomotor activity of the total time spent on rotarod (mean±SEM) measured 60 min after the injection of gabapentin (10 and 30 mg/kg body weight, i.p.) or vehicle.

FIG. 30 is a graph of the effects of HZ166 on motor coordination and locomotor activity of the total activity counts (mean±SEM) in the open field test measured for 60 min starting 60 min after the injection of HZ166 (16 and 48 mg/kg body weight, i.p.) or vehicle. n=10 mice per group.

FIG. 31 is a graph of the effects of gabapentin on motor coordination and locomotor activity of the total activity counts (mean±SEM) in the open field test measured for 60 min starting 60 min after the injection gabapentin (10 and 30 mg/kg body weight, i.p.), or vehicle. ANOVA followed by Scheffe's post hoc test, F (2, 27)=4.79; *, P<0.05, significantly different from vehicle-treated controls.

FIG. 34 is a graph of dose-response curves of the patch clamp current (expressed as percent of the control current) produced by various concentrations of SR-II-57 when applied to *Xenopus* oocytes expressing α1β3γ2 (■), α2β3γ2 (■), α3β3γ2 (▲) or α5β3γ2 (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 35 is a graph of dose-response curves of the patch clamp current (expressed as percent of the control current) produced by various concentrations of SR-II-54 when applied to *Xenopus* oocytes expressing α1β3γ2 (■), α2β3γ2 (■), α3β3γ2 (▲) or α5β3γ2 (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 36 is a graph of dose-response curves of the patch clamp current (expressed as percent of the control current) produced by various concentrations of YT-III-271 when applied to *Xenopus* oocytes expressing α1β3γ2 (□), α2β3γ2 (■), α3β3γ2 (▲) or α5β3γ2 (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 37 is a graph of dose-response curves of the patch clamp current (expressed as percent of the control current) produced by various concentrations of YT-III-15 when applied to *Xenopus* oocytes expressing α1β3γ2 (■), α2β3γ2 (■), α3β3γ2 (▲) or α5β3γ2 (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 38 is a graph of dose-response curves of the patch clamp current (expressed as percent of the control current) produced by various concentrations of YT-TC-4 when applied to *Xenopus* oocytes expressing α1β3γ2 (■), α2β3γ2 (■), α3β3γ2 (▲) or α5β3γ2 (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 40 is a graph of dose-response curves of the patch clamp current (expressed as percent of the control current) produced by various concentrations of YT-II-76 when applied to *Xenopus* oocytes expressing α1β3γ2 (■), α2β3γ2 (■), α3β3γ2 (▲) or α5β3γ2 (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 41 is a graph of dose-response curves of the patch clamp current (expressed as percent of the control current) produced by various concentrations of YT-III-31 when applied to *Xenopus* oocytes expressing α1β3γ2 (■), α2β3γ2 (■), α3β3γ2 (▲) or α5β3γ2 (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 42 is a graph of dose-response curves of the patch clamp current (expressed as percent of the control current) produced by various concentrations of YT-III-42 when applied to *Xenopus* oocytes expressing α1β3γ2 (■), α2β3γ2 (■), α3β3γ2 (▲) or α5β3γ2 (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 43 is a graph of dose-response curves of the patch clamp current (expressed as percent of the control current) produced by various concentrations of HJ-I-40 when applied to *Xenopus* oocytes expressing α1β3γ2 (■), α2β3γ2 (■), α3β3γ2 (▲) or α5β3γ2 (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 44 is a graph of dose-response curves of the patch clamp current (expressed as percent of the control current) produced by various concentrations of ZJW-II-40 when applied to *Xenopus* oocytes expressing α1β3γ2 (■), α2β3γ2 (■), α3β3γ2 (▲) or α5β3γ2 (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 45 is a graph of dose-response curves of the patch clamp current (expressed as percent of the control current) produced by various concentrations of HJ-I-037 when applied to *Xenopus* oocytes expressing α1β3γ2 (■), α2β3γ2 (■), α3β3γ2 (▲) or α5β3γ2 (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 46 is a representation of the binding affinity of ZJW-II-061.

FIG. 47 is a representation of the binding affinity of ZJW-II-063.

FIG. 48 is a representation of the binding affinity of ZJW-II-065.

FIG. 49 is an illustration of both the binding affinities and oocyte efficacies of JY-XHE-053, XHE-II-053, HZ-166, SH-053-2'F—S—CH3 and SH-053-2'F—R—CH3, and the binding affinity of diazepam.

DETAILED DESCRIPTION OF THE INVENTION

Figure 1:
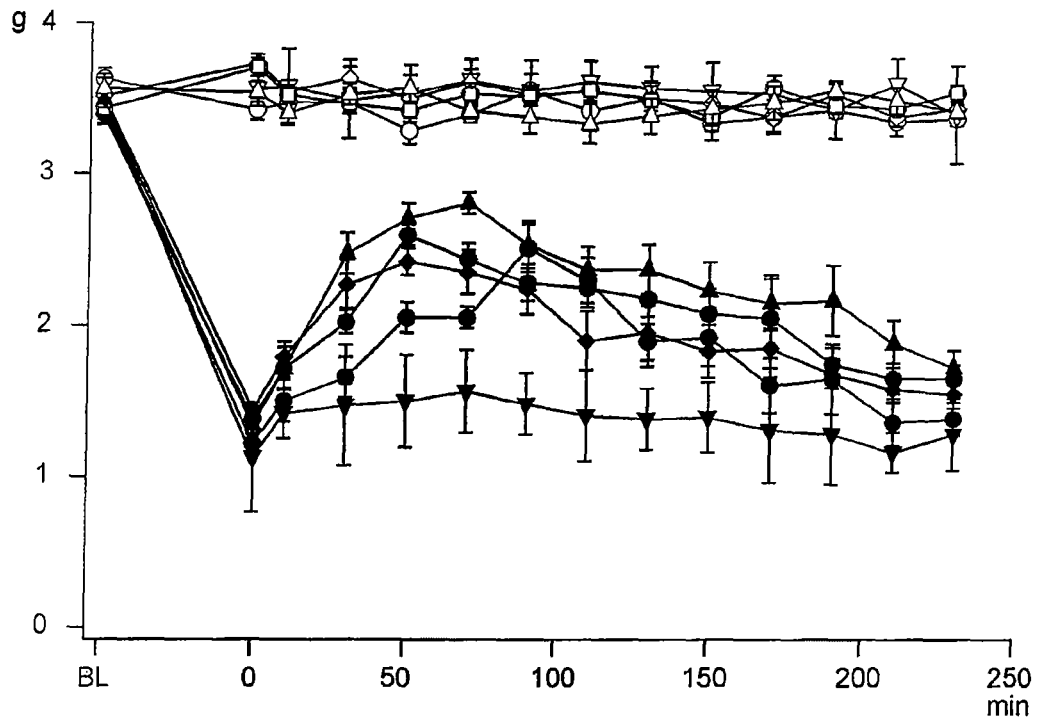
FIG. 1 is a graph of the antinociceptive effect of systemic HZ-166 in the chronic constriction injury (CCI) model. Paw withdrawal thresholds (g, mean±SEM) in response to mechanical stimulation are monitored before (BL) and 7 days after nerve ligation. On day 7, HZ166 (16 [●], 48 [◆], 160 [■], 480 [▲] mg/kg body weight) or vehicle (▼) are injected intraperitoneally and paw withdrawal thresholds are monitored for 230 minutes after HZ-166 injection. Filled symbols, ipsilateral paw; open symbols, contralateral paw.

In the present invention ligands of $GABA_A$ receptor subtypes are shown to modulate and/or regulate neuropathic and inflammatory pain and mediate pain suppression. Compounds which are ligands of the $GABA_A$ receptors acting as agonists or partial agonists are referred to hereinafter as "$GABA_A$ receptor agonists" or "$GABA_A$ receptor partial agonists" or "agonists" or "partial agonists". In particular these are compounds which are ligands of the benzodiazepine (BZ) binding site of the $GABA_A$ receptors, and hence acting as BZ site agonists or partial agonists. Such ligands also include compounds acting at the GABA site or at modulatory sites other than the benzodiazepine site of $GABA_A$ receptors.

The novel pain-suppressing agents act preferably by selectively or preferentially activating as agonists or partial agonists the $GABA_A/\alpha_2$ receptors and/or $GABA_A/\alpha_3$ receptors as compared to the $GABA_A/\alpha_1$ receptors. A selective or preferential therapeutic agent has less binding affinity to the $GABA_A/\alpha_1$ receptors compared to the $GABA_A/\alpha_2$ or $GABA_A/\alpha_3$ receptors. Alternatively, the agent binds to $GABA_A/\alpha_1$, $GABA_A/\alpha_2$ and $GABA_A/\alpha_3$ receptors with a comparable affinity but exerts preferential efficacy of receptor activation at $GABA_A/\alpha_2$ and $GABA_A/\alpha_3$ receptors compared to the $GABA_A/\alpha_1$ receptors. A selective agent of the present invention can also have a greater or lesser ability to bind or to activate $GABA_A/\alpha_5$ receptors relative to $GABA_A/\alpha_2$ and $GABA_A/\alpha_3$ receptors. The pain-modulating agent acts at the benzodiazepine site of the respective $GABA_A$ receptors but is not restricted to this drug binding domain in its receptor interactions.

Pain suppression is evaluated in the mouse formalin test, which is a model of chemically induced tonic pain and in the model of sciatic nerve ligation, which is considered to be prototypic for neuropathic pain. When the BZ ligand diazepam is administered, the level of pain response is strongly reduced. This effect of diazepam is attenuated in mice in which the $GABA_A/\alpha_2$ and $GABA_A/\alpha_3$ receptor has been rendered diazepam insensitive by a point mutation ($\alpha_2$ H102R, $\alpha_3$ H126R). These results suggest that $GABA_A/\alpha_2$ and $GABA_A/\alpha_3$ receptors are mediators of pain suppression, but some contribution to pain suppression $GABA_A/\alpha_5$ and receptors is not excluded. One aspect of the invention relates to a method of treatment or prevention of neuropathic and inflammatory pain comprising administering a subunit selective $GABA_A$ receptor agonist as defined hereinbefore in a quantity effective against neuropathic, migraine associated and inflammatory pain to a mammal in need thereof, for example to a human requiring such treatment.

The treatment may be for prophylactic or therapeutic purposes. For the administration, the subunit selective $GABA_A$ receptor agonist is preferably in the form of a pharmaceutical preparation comprising the subunit selective $GABA_A$ receptor agonist in chemically pure form and optionally a pharmaceutically acceptable carrier and optionally adjuvants. The subunit selective $GABA_A$ receptor agonist is used in an amount effective against neuropathic and inflammatory pain. The dosage of the active ingredient depends upon the species, its age, weight, and individual condition, the individual pharmacokinetic data, the mode of administration, and whether the administration is for prophylactic or therapeutic purposes. In the case of an individual having a body weight of about 70 kg the daily dose administered is from approximately 1 mg to approximately 500 mg, preferably from approximately 1 mg to approximately 100 mg, of a subunit selective $GABA_A$ receptor agonist.

Pharmaceutical compositions for enteral administration, such as nasal, buccal, rectal or, especially, oral administration, and for parenteral administration, such as intravenous, intramuscular, subcutaneous, peridural, epidural or intrathecal administration, are especially preferred. The pharmaceutical compositions comprise from approximately 1% to approximately 95% active ingredient, preferably from approximately 20% to approximately 90% active ingredient.

For parenteral administration including intracoronary, intracerebrovascular, or peripheral vascular injection/infusion preference is given to the use of solutions of the subunit selective $GABA_A$ receptor agonist, and also suspensions or dispersions, especially isotonic aqueous solutions, dispersions or suspensions which, for example, can be made up shortly before use. The pharmaceutical compositions may be sterilized and/or may comprise excipients, for example preservatives, stabilizers, wetting agents and/or emulsifiers, solubilizers, viscosity-increasing agents, salts for regulating osmotic pressure and/or buffers and are prepared in a manner known per se, for example by means of conventional dissolving and lyophilizing processes.

For oral pharmaceutical preparations suitable carriers are especially fillers, such as sugars, for example lactose, saccharose, mannitol or sorbitol, cellulose preparations and/or calcium phosphates, and also binders, such as starches, cellulose derivatives and/or polyvinylpyrrolidone, and/or, if desired, disintegrators, flow conditioners and lubricants, for example stearic acid or salts thereof and/or polyethylene glycol. Tablet cores can be provided with suitable, optionally enteric, coatings. Dyes or pigments may be added to the tablets or tablet coatings, for example for identification purposes or to indicate different doses of active ingredient. Pharmaceutical compositions for oral administration also include hard capsules consisting of gelatin, and also soft, sealed capsules consisting of gelatin and a plasticizer, such as glycerol or sorbitol. The capsules may contain the active ingredient in the form of granules, or dissolved or suspended in suitable liquid excipients, such as in oils.

Transdermal application is also considered, for example using a transdermal patch, which allows administration over an extended period of time, e.g. from one to twenty days.

Another aspect of the invention relates to the use of a $GABA_A$ receptor agonist in the method of treatment or prevention of neuropathic and inflammatory pain and in the manufacture of medicaments for treating neuropathic and inflammatory pain. Such medicaments are manufactured by methods known in the art, especially conventional mixing, coating, granulating, dissolving or lyophilizing. A subunit selective $GABA_A$ receptor agonist can be administered alone or in combination with one or more other therapeutic agents, possible combination therapy taking the form of fixed combinations of a subunit selective $GABA_A$ receptor agonist and one or more other therapeutic agents known in the treatment of neuropathic and inflammatory pain, the administration being staggered or given independently of one another, or being in the form of a fixed combination.

Possible combination partners considered are non-steroid anti-inflammatory agents, opioid analgesics, anticonvulsants (e.g. carbamazepine), anti-depressants (e.g. amitriptyline), blockers of voltage gated calcium channels, in particular N-type channels, and blockers of voltage gated sodium channels, in particular Nav 1.3, 1.8, 1.9, such as ligands of the alpha2delta subunit of voltage gated $Ca^{2+}$ channels, e.g. gabapentin and pregabaline.

The following examples serve to illustrate the invention without limiting the invention in its scope.

EXPERIMENTAL METHODS

The methods and models for the study the alleviation and prevention of neuropathic pain, migraine-related pain and inflammatory pain are known in the art. See, Knabl, J., Witschi, R., Hösl, K., Reinold, H., Zeilhofer, U., B., Ahmadi, S., Brockhaus, J., Sergejeva, M., Hess, A., Brune, K., Fritschy, J.-M. Rudolph, U., Mohler, H., & Hanns Ulrich Zeilhofer, H.

U., Reversal of pathological pain through specific spinal GABA$_A$ receptor subtypes, Nature, doi:10.1038/nature06493 in press, 2008, and WO 2006/061428.

A genetic approach in combination with behavioral tests and electrophysiological experiments is used to identify the GABA$_A$ receptor isoforms involved in the control of nociception. Behavioral and electrophysiological experiments are performed in wild type (wt) mice and in genetically engineered mice, which carry a point mutation in benzodiazepine-sensitive GABA receptor subunits ($\alpha$1, $\alpha$2, $\alpha$3, or $\alpha$5) that render the corresponding receptors insensitive to diazepam. Wild-type mice and GABA$_A$ receptor mutant mice ($\alpha$1 (H101R), $\alpha$2(H101R), $\alpha$3(H126R) and $\alpha$5(H105R)) 10-12 are maintained on a 129X1/SvJ background. Behavioral experiments are performed on adult mice and Wistar rats. Conversely, in vitro assays, either competitive binding to recombinant GABA$_A$ receptors of known subunit composition or modulation of the GABA elicited currents through GABA$_A$ receptors of known subunit composition inserted into cell membranes, serve to provide an indication of in vivo action of a test compound in behavioral studies.

Electrophysiology of Spinal Cord Slices. 250 μm thick transverse slices of the lumbar spinal cord are prepared from 14-21 day old mice. GABAergic membrane currents are recorded from superficial dorsal horn neurons (laminae I and II) as described previously. Alternatively, dissociated dorsal root ganglion cells (DRGs) are plated on poly-(L-lysine)-coated cover slips (for details see Zeilhofer, H. U., Kress, M. & Swandulla, D. Fractional Ca$^{2+}$ currents through capsaicin- and proton-activated ion channels in rat dorsal root ganglion neurons. J. Physiol. (Lond.) 503, 67-78 (1997)). GABA-induced currents are recorded from capsaicin sensitive DRG neurons 3-30 h after plating. Whole-cell patch-clamp recordings are performed from neurons identified under visual control using the infrared gradient contrast technique coupled to a video microscopy system. In both preparations, GABA (1 mM) is applied to the some of the recorded neuron via a glass pipette by short (10 ms) electronically controlled puffer applications at a frequency of 0.07 Hz. Slices are continuously superfused with external solution, which contains 125 mM NaCl, 26 mM NaHCO$_3$, 1.25 mM NaH$_2$PO$_4$, 2.5 mM KCl, 2 mM CaCl$_2$, 1 mM MgCl$_2$, 10 mM glucose (pH 7.30, 315 mosmol/l) and is bubbled with 95% O$_2$, 5% CO$_2$. Patch pipettes (4-5 M Ohm are filled with internal solution containing 130 mM K-gluconate, 20 mM KCl, 2 mM MgCl$_2$, 0.05 mM EGTA, 3 mM Na-ATP, 0.1 mM Na-GTP, and 10 mM Na-HEPES (pH 7.30). 5 mM QX-314 are added to the internal solution to block voltage-activated sodium currents. The test compounds are applied by bath perfusion at a rate of 1-2 ml/min. Recordings are made in the presence of the GABA$_B$ receptor antagonist CGP-55,845 (200 mM).

Chemically induced pain is assessed in the formalin test: The T22 formalin test (Hunskaar S, Fasmer OB, Hole K (1985) Formalin test in mice, a useful technique for evaluating mild analgesics. J Neurosci Methods 14:69-76) involves injection of 0.5% formalin into the mouse hind paw. This elicits a distinct bi-phasic behavioral profile in response to the formalin injection characterized by licking of the affected paw, and the number of licks is measured as a proxy for perceived pain. The first (acute) phase is thought to correspond to the direct stimulation of peripheral fibers while the second (inflammatory) phase is caused by the release of inflammatory mediators from the damaged tissue and nerve endings. Thus, this model is ideally suited for efficacy of an investigational AED against the acute and chronic hyper-responsive neuronal discharges following activation of peripheral nerve fibers.

The results of the formalin test are given both as raw data ("Response") and in an aggregate, analyzed form ("Analysis"). In the Response section, each Trial involves sixteen animals, eight controls given an i.p. injection of vehicle and eight given the compound at a specified dose. Thus, for multiple doses of the compound, there will also be multiple control groups. The data recorded for each animal is the amount of time(s) spent licking the affected hind paw in a two minute period. These two minute periods occur at five minute intervals and continue for 45 minutes. Plotting the time spent licking versus time reveals the characteristic biphasic response. From this plot, we can then determine the area under the curve (AUC) for each animal during both the acute and inflammatory stages. The AUC for each phase is shown in the analysis section of the data sheet for both control and drug-treated animals The AUC for each drug-treated animal is compared to the average result from the control group, yielding an average percent of control (reported with the SEM and p value). Significant reductions in this number indicate a reduction in licking and, presumably, a reduction of perceived pain.

Inflammatory pain is assessed in the zymosan A model. See Hargreaves, K., Dubner, R., Brown, F., Flores, C. & Joris, J. A new and sensitive method for measuring thermal nociception in cutaneous hyperalgesia. Pain 32, 77-88 (1988). Inflammatory pain is induced by subcutaneous injection of zymosan A (0.06 mg in mice; 1 mg in rats) into one hindpaw. In mice, 0.06 mg of zymosan A suspended in 20 ml of 0.9% NaCl is injected subcutaneously into the plantar side of the left hind-paw. The model is also used in rats, but 1 mg of zymosan A is used. Heat hyperalgesia is assessed 24 h and 6 h after induction of inflammation in mice and rats, respectively.

Neuropathic pain. The pro- or antinociceptive effects of the compounds of the present invention are analyzed in two manners. First, using the T23 Partial Ligation of the Sciatic Nerve model (Z. Seltzer, R. Dubner and Y. Shir, A novel behavioural model of neuropathic pain disorders produced in rats by partial sciatic nerve injury. Pain 43 (1990), pp. 205-218), animals will be anesthetized with sodium pentobarbital and the depth of anesthesia monitored by their response to a tail pinch and observation of the depth of respiration. Sterile technique will be used throughout the surgery. The upper thigh will be shaved and wiped off with ethanol and betadine. A small incision will then be made in the skin. The underlying muscle of the upper thigh will be separated and the sciatic nerve exposed. The nerve is separated from the surrounding connective tissue and slightly elevated by a pair of fine, curved forceps. Approximately ⅓ to ½ of the nerve is tied off by passing a needle (7.0) and nylon suture through the nerve. The muscle and skin incision are closed off separately with 5.0 suture and the animals kept warm until they have recovered from the anesthesia. This procedure is routinely done on the right side (ipsilateral) while a sham surgery is performed on the left hind leg (contralateral). The latter involves a similar procedure with the exception that the sciatic nerve on this side is only exposed. The rats will be closely monitored daily for the development of infection or untoward effects of the surgery in which case the animals will be immediately euthanized After an appropriate time for recovery (7 days) the animals will be tested for the development of mechanical allodynia (abnormal response to a non-noxious stimulus). The animals are each put in a bottomless plexiglass box placed on a wire mesh (¼") platform. After 30-60 minutes in which to acclimate, a baseline mechanical sensitivity is determined. This procedure is done by applying a series of calibrated Von Frey fibres perpendicularly to the plantar surface of each hind paw and holding it there for about 6 secs with enough force to slightly bend the fibre. After a positive response (withdrawal of the foot) is noted a weaker fibre is applied. This is repeated until a 50% threshold for withdrawal can be determined The allodynic threshold is then redetermined after intraperitoneal administration of an investigational AED. Testing will be conducted at the time-to-peak effect of the AED as determined in the acute seizure model.

In addition, the pro- or antinociceptive effects of the compounds of the present invention are analyzed in the chronic constriction injury (CCI) model. The $GABA_A$ receptor subunit selective test compounds of the present invention are analysed in the CCI model in 7-8-week-old C57BL/6 mice. See Bennett, G. J. & Xie, Y. K. A peripheral mononeuropathy in rat that produces disorders of pain sensation like those seen in man. Pain 33, 87-107 (1988). Seven to eight week old mice are anesthetized with isofluran. Unilateral constriction injury of the left sciatic nerve just proximal to the trifurcation is performed with three loose ligatures. In sham-operated animals the sciatic nerve is exposed and the connective tissue is freed, but no ligatures are applied. In these sham-operated animals only a minor and transient hyperalgesia has been shown to occur. Heat hyperalgesia, cold allodynia and mechanical sensitization are assessed 7-9 days after surgery. Mechanical sensitivity is assessed with electronic von Frey filaments (IITC).

Heat hyperalgesia is assessed by measuring paw withdrawal latencies on exposure to a defined radiant heat stimulus are measured with a commercially available apparatus (Plantar Test; Ugo Basile). Four or five measurements are taken in each animal for every time point. Measurements of paw withdrawal latencies of the inflamed or injured paw and of the contralateral paw are made alternately.

Cold allodynia is measured as the time spent lifting, shaking or licking the paw (seconds per minute) for 5 min after the application of a drop of acetone onto the affected paw. Triple measurements of paw withdrawal thresholds (g) are made for each time point and animal.

Locomotor activity. Locomotor activity is tested with a commercially available microprocessor-controlled activity cage (Actiframe; Gerb Elektronik). Mice are placed in the apparatus 15 min before testing. Motor activity is measured 10-40 min and 40-80 min after intrathecal and oral drug application, respectively.

Motor impairment. A possible impairment of motor function is assessed with the rotarod test. See Bonetti, E. P. et al. Ro 15-4513: partial inverse agonism at the BZR and interaction with ethanol. Pharmacol. Biochem. Behav. 31, 733-749 (1988). Rats are trained on day zero and the maximum speed tolerated for at least 2 min is determined for each rat. On the following day, rotarod performance is determined again 30 min after treatment with test compound or vehicle (administered orally).

Drugs. For intraperitoneal injection HZ-166, JY-XHE-053 or XHE-II-053 are suspended in 5% methylcellulose, 95% water, sonicated for 10 min and administered intraperitoneally in a total volume of 10 µl/g body weight. Benzodiazepine and thiodiazepine derivatives suitable for use in the methods of the present invention are synthesized and characterized in detail below.

Competitive Binding Assays Competitive binding assays were performed in a total volume of 0.5 mL at 4° C. for 1 hour using [$^3$H]flunitrazepam as the radiolabel. For these binding assays, 20-50 mg of membrane protein harvested with hypotonic buffer (50 mM Tris-acetate pH 7.4 at 4 degree) was incubated with the radiolabel as previously described (Choudhary, M. S., Craigo. S., Roth, B. L., Identification of receptor domains that modify ligand binding to 5-hydroxy-tryptamine-2 and 5-hydroxytryptamine-1c serotonin receptors, Mol Pharmacol. 1992 October; 42(4):627-33). Nonspecific binding was defined as radioactivity bound in the presence of 100 µM diazepam and represented less than 20% of total binding. Membranes were harvested with a Brandel cell harvester followed by three ice-cold washes onto polyethyleneimine-pretreated (0.3%) Whatman GF/C filters. Filters were dried overnight and then soaked in Ecoscint, a liquid scintillation cocktail (National Diagnostics; Atlanta, Ga.). Bound radioactivity was quantified by liquid scintillation counting. Membrane protein concentrations were determined using an assay kit from Bio-Rad (Hercules, Calif.) with bovine serum albumin as the standard.

Cloning of $GABA_A$ receptor subunits. Cloning of $GABA_A$ receptor subunits α1, β3 and γ2 into pCDM8 expression vectors (Invitrogen, CA) has been described elsewhere. See Li, X.; et al., Synthesis, in vitro affinity, and efficacy of a bis 8-ethynyl-4H-imidazo[1,5a]-[1,4]benzodiazepine analogue, the first bivalent alpha5 subtype selective BzR/$GABA_A$ antagonist. J Med. Chem. 2003, 46, (26), 5567-70; El Hadri, A.; et al., N-Substituted 4-amino-3,3-dipropyl-2(3H)-furanones: new positive allosteric modulators of the $GABA_A$ receptor sharing electrophysiological properties with the anticonvulsant loreclezole. J Med. Chem. 2002, 45, (13), 2824-31. $GABA_A$ receptor subunit α4 was cloned in an analogous way. cDNAs for subunits α2, α3 and α5 were gifts from P. Malherbe and were subcloned into a pCI-vector. cDNA for subunit α6 was a gift from P. Seeburg and was subcloned into the vector pGEM-3Z (Promega). After linearizing the cDNA vectors with appropriate restriction endonucleases, capped transcripts were produced using the mMessage mMachine T7 transcription kit (Ambion, TX). The capped transcripts were polyadenylated using yeast poly(A) polymerase (USB, OH) and were diluted and stored in diethylpyrocarbonate-treated water at −70° C.

In Vitro Expression of $GABA_A$ Receptor Subunits The methods used for isolating, culturing, injecting and defolliculating of the oocytes were identical with those described by E. Sigel. See Fuchs, K.; et al., Endogenous [3H]flunitrazepam binding in human embryonic kidney cell line 293. European journal of pharmacology 1995, 289, (1), 87-95; Sigel, E.;& Baur, R., Allosteric modulation by benzodiazepine receptor ligands of the $GABA_A$ receptor channel expressed in Xenopus oocytes. J. Neurosci. 1988, 8, (1), 289-95; Sigel, E.; & Minier, F., The Xenopus oocyte: System for the study of functional expression and modulation of proteins. Molecular Nutrition & Food Research 2005, 49, (3), 228-234. Mature female Xenopus laevis (Nasco, WI) were anaesthetized in a bath of ice-cold 0.17% Tricain (Ethyl-m-aminobenzoate, Sigma, MO) before decapitation and removal of the frog ovary. Stage 5 to 6 oocytes with the follicle cell layer around them were singled out of the ovary using a platinum wire loop. Oocytes were stored and incubated at 18° C. in modified Barths medium (MB, containing 88 mM NaCl, 10 mM HEPES-NaOH (pH 7.4), 2.4 mM $NaHCO_3$, 1 mM KCl, 0.82 mM $MgSO_4$, 0.41 mM $CaCl_2$, 0.34 mM $Ca(NO_3)_2$) that was supplemented with 100 Units/mL penicillin and 100 µg/mL streptomycin. Oocytes with follicle cell layers still around them were injected with 50 mL of an aqueous solution of the cRNA. This solution contained the transcripts for the different alpha subunits and the beta 3 subunit at a concentration of 0.0065 ng/nL as well as the transcript for the gamma 2 subunit at 0.032 ng/nL. After injection of the cRNA, oocytes were incubated for at least 36 h before the enveloping follicle cell layers were removed. To this end, oocytes were incubated for 20 minutes at 37° C. in MB that contained 1 mg/mL collagenase type IA and 0.1 mg/mL trypsin inhibitor I-S (both Sigma). This was followed by osmotic shrinkage of the oocytes in doubly concentrated MB medium supplied with 4 mM Na-EGTA. Finally, the oocytes were transferred to a culture dish containing MB and were gently pushed away from the follicle cell layer that stuck to the surface of the dish. After removal of the follicle cell layer, oocytes were allowed to recover for at least 4 h before being used in electrophysiological experiments.

Voltage Clamp Recordings From *Xenopus* Oocytes. For electrophysiological recordings, oocytes were placed on a nylon-grid in a bath of *Xenopus* Ringer solution (XR, containing 90 mM NaCl, 5 mM HEPES-NaOH (pH 7.4), 1 mM $MgCl_2$, 1 mM KCl and 1 mM $CaCl_2$). The oocytes were constantly washed by a flow of 6 mL/min XR that could be switched to XR containing GABA and/or drugs. Drugs were diluted into XR from DMSO-solutions resulting in a final concentration of 0.1% DMSO perfusing the oocytes. Drugs were preapplied for 30 seconds before the addition of GABA, which was coapplied with the drugs until a peak response was observed. Between two applications, oocytes were washed in XR for up to 15 minutes to ensure full recovery from desensitization. For current measurements the oocytes were impaled with two microelectrodes (2-3 mΩ) that were filled with 2 mM KCl. All recordings were performed at rt at a holding potential of −60 mV using a Warner OC-725C two-electrode voltage clamp (Warner Instruments, Hamden, Conn.). Data were digitized, recorded and measured using a Digidata 1322A data acquisition system (Axon Instruments, Union City, Calif.). Results of concentration response experiments were fitted using GraphPad Prism 3.00 (GraphPad Software, San Diego, Calif.). The equation used for fitting concentration response curves was Y=Bottom+(Top−Bottom)/(1+10^((Log EC50−X)*HillSlope)); X represents the logarithm of concentration, Y represents the response; Y starts at Bottom and goes to Top with a sigmoid shape. This is identical to the "four parameter logistic equation."

Results of Studies in Pain Models

Formalin test: The antinociceptive effects of HZ-166, JY-XHE-053 and XHE-II-053 were tested in the T22 formalin test described above with results shown below in Table 2.

Neuropathic pain: For the T23 sciatic ligation tests done using the shown in Table 1, the results indicated that ADDs 351015-6 were significantly protective against neuropathic pain caused by sciatic ligation. The effects from ADD 351017 were considered insignificant.

Figure 2:
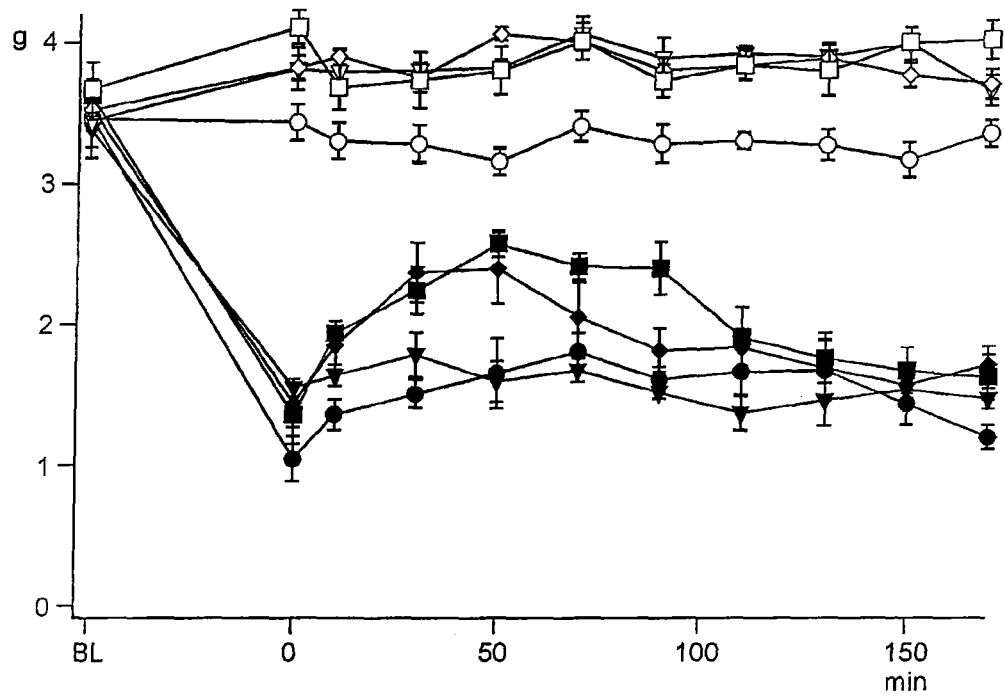
FIG. 2 is a graph of the antinociceptive effect of systemic JY-XHE-053 in the chronic constriction injury (CCI) model. Paw withdrawal thresholds (g, mean±SEM) in response to mechanical stimulation are monitored before and 7 days after nerve ligation. On day 7, JY-XHE-053 (8 [●], 30 [◆], 100 [■] mg/kg body weight) or vehicle (▼) are injected intraperitoneally and paw withdrawal thresholds are monitored for 170 minutes after JY-XHE-053 injection. Filled symbols, ipsilateral paw; open symbols, contralateral paw.
Figure 3:
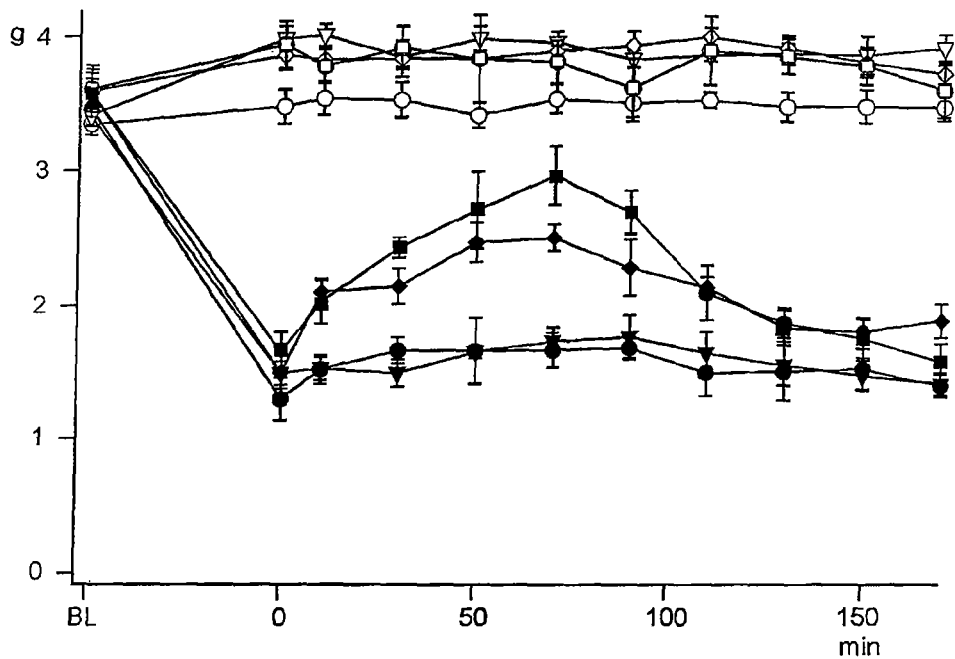
FIG. 3 is a graph of the antinociceptive effect of systemic XHE-II-053 in the chronic constriction injury (CCI) model. Paw withdrawal thresholds (g, mean±SEM) in response to a mechanical stimulation are monitored before and 7 days after nerve ligation. On day 7, XHE-II-053 (1[●], 10[♦], 30[■] mg/kg body weight) or vehicle (▼) are injected intraperitoneally and paw withdrawal thresholds are monitored for 170 minutes after XHE-II-053 injection. Filled symbols, ipsilateral paw; open symbols, contralateral paw.

The potential analgesic effects of HZ-166, JY-XHE-053 or XHE-II-053 were also tested in the chronic constriction injury (CCI) model of neuropathic pain as described above. Mechanical sensitivity (withdrawal threshold upon mechanical stimulation of the hindpaws of the operated (neuropathic) or non-operated (non-operated) side were tested with von Frey filaments. HZ-166 elicited significant analgesia at doses of 48 mg/kg, 160 mg/kg and 480 mg/kg injected intraperitoneally (i.p.) (FIG. 1). JY-XHE-053 exerted significant analgesic effect at doses of 8 mg/kg and 30 mg/kg (i.p.) (FIG. 2). Similarly, XHE-II-053 was significantly analgesic at 10 mg/kg (i.p.) (FIG. 3). These results indicate that all three subtype-selective benzodiazepine-site ligands exert significant analgesic effects against neuropathic pain.

Figure 4:
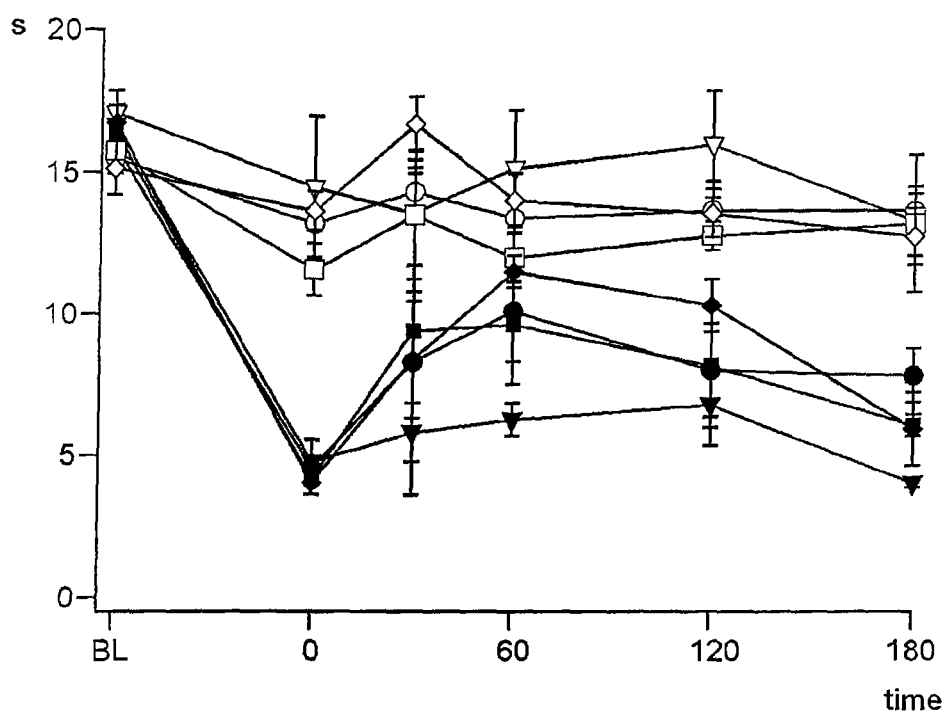
FIG. 4 is a graph of the effects of systemic HZ-166, JY-XHE-053 and XHE-II-053 against thermal hyperalgesia in the chronic constriction injury (CCI) model. (A) Paw withdrawal latencies (s, mean±SEM) in response to a defined radiant heat stimulus are monitored before and 7 days after nerve ligation. On day 7, HZ-166 (●, 16 mg/kg body weight), JY-XHE-053 (■, 30 mg/kg body weight) XHE-II-053 (♦, 10 mg/kg body weight) or vehicle (▼) are injected intraperitoneally and paw withdrawal thresholds are monitored for 3 hours after injection. Filled symbols, ipsilateral paw; open symbols, contralateral paw.

Further, the effects of systemic HZ-166, JY-XHE-053 and XHE-II-053 against thermal hyperalgesia in the chronic constriction injury (CCI) model are shown in FIG. 4. (A) Paw withdrawal latencies (s, mean±SEM) in response to a defined radiant heat stimulus are monitored before and 7 days after nerve ligation. On day 7, HZ-166 (●, 16 mg/kg body weight), JY-XHE-053 (■, 30 mg/kg body weight) XHE-II-053 (♦, 10 mg/kg body weight) or vehicle (▼) are injected intraperitoneally and paw withdrawal thresholds are monitored for 3 hours after injection. Filled symbols, ipsilateral paw; open symbols, contralateral paw.

Spinal cord $GABA_A$ receptors: Whole-cell patch-clamp electrophysiology recordings are performed in spinal cord slices of $GABA_A$ receptor mutant mice and of corresponding wt mice. Membrane currents activated by exogenous GABA are recorded from neurons located in the superficial dorsal horn to assess their sensitivity to diazepam. GABA-induced membrane currents are evoked by external application of GABA (3 mM) to neurons located in the superficial layers (lamina I and II) of the spinal cord dorsal horn. In wild-type

TABLE 2

| ADD | | | 351015 (HZ-166) | 351016 (JY-XHE-053) | 351017 (XLI-JY-DMH) |
|---|---|---|---|---|---|
| T22 Formalin Pain (mouse, i.p.) | Acute | Dose (mg/kg) | 16 | 10 | 1 |
| | | Change (% of Control) ± SEM | 66.8 ± 6.79 | 98.41 ± 12.8 | 87.6 ± 12.15 |
| | | p value | <0.05 | >0.05 | >0.05 |
| T22 Formalin Pain (mouse, i.p.) | Inflammatory | Dose(mg/kg) | 16 | 10 | 1 |
| | | Change (% of Control) ± SEM | 63 ± 20.59 | 84.58 ± 10.18 | 111.9 ± 17.58 |
| | | p value | >0.05 | >0.05 | >0.05 |
| T23 Sciatic Ligation | | Dose (mg/kg) | 35.5 | 18 | 1 |
| | | TPE (hr) | 2 | 2 | 2 |
| | | Change (% of Control) ± SEM | 210 ± 42 | 132 ± 7 | 136 ± 18 |
| | | Significance | yes | yes | no |

Based on the results for the formalin tests, ADD 351015 showed significant protection at the acute phase of chemically induced pain. ADDs 351016 and 351017 would be considered insignificant (p>0.05). Further, in the inflammatory pain model, each of ADDs 351015-351017 would be considered insignificant (p>0.05).

mice, diazepam (1 μM) potentiates GABA induces currents by 150.1±7.54% (mean±SEM, n=11). This potentiation is nearly identical in $α_1$ mutant mice (165±22.3%), but is almost abolished in $α_2$ and $α_3$ mutant mice (106.9±3.6% and 102.5±6.6%) and reduced in $α_5$ mutant mice (126±13.0%). Thus, $GABA_A/α_2$, $GABA_A/α_3$, $GABA_A/α_5$, receptor subtypes are preponderant mediators of benzodiazepine action in the superficial dorsal horn. A contribution of $GABA_A/\alpha_2$, $GABA_A/\alpha_3$, $GABA_A/\alpha_5$ receptors located in other areas of the CNS to the antinociceptive effect of diazepam is not excluded.

In a separate study, the antihypealgesic effects of HZ-166 were evaluated in comparison with, gabapentin, a drug widely used in the clinical management of neuropathic pain.

Drugs: HZ166 was synthesized as described previously (Cook et al., 2006). Flumazenil was purchased from Tocris Bioscience. For i.p. injection HZ166, flumazenil and gabapentin (Neurontin®) were suspended in 0.5% methyl cellulose and 0.9% NaCl and applied in a total volume of 10 ml/kg body weight.

In vivo studies: Behavioral experiments were performed in 7-12 weeks old male mice kept at a 12/12 h light/dark cycle with free access to food and water. Permission for the animal experiments has been obtained from the Veterinaramt des Kantons Zürich (ref no. 121/2006 and 135/2009). All efforts were made to minimize animal suffering. In all behavioral tests, the observer was blinded to the drug treatment.

Pain studies—Neuropathic pain: HZ166 and gabapentin were analyzed in the chronic constriction injury (CCI) model. Unilateral constriction injury of the left sciatic nerve just proximal to the trifurcation was performed as described previously (Bennett and Xie, 1988). Anesthesia was induced and maintained by 2% isoflurane, combined with oxygen (30%). The sciatic nerve was exposed at the mid-thigh level proximal to the sciatic trifurcation by blunt dissection through the biceps femoris muscle. 5±7 mm of nerve were freed of adhering tissue and three chromic gut ligatures (4/0) (Ethicon) were loosely put around the nerve with about 1 mm spacing. The ligatures were tied until they elicited a brief twitch in the hindlimb. The surgical wound was closed in layers. Heat hyperalgesia and mechanical sensitization were assessed 7-16 days after surgery.

Pain Studies—Inflammatory pain: Inflammatory pain was studied in the zymosan A model (Meller and Gebhart, 1997). 0.06 mg zymosan A (Sigma Chemicals) suspended in 20 µl 0.9% NaCl was injected subcutaneously into the plantar side of the left hindpaw. Mechanical sensitization was assessed 48 hours after induction of inflammation.

Pain Studies—Heat hyperalgesia: Paw withdrawal latencies upon exposure to a defined radiant heat stimulus were measured using a commercially available apparatus (Plantar Test, Ugo Basile, Comerio, Italy). 4-5 measurements were taken in each animal for every time point and averaged. Measurements of paw withdrawal latencies of the inflamed or injured paw and of the contralateral paw were made alternately.

Pain Studies—Mechanical sensitization: Mechanical sensitivity was assessed with dynamic von Frey filaments (IITC, Woodland Hills, Calif.). 4-5 measurements were made for each time point and animal and averaged. Measurements of paw withdrawal thresholds of the injured paw and of the contralateral paw were made alternately.

Tolerance development: Possible development of tolerance against the antihyperalgesic effect of HZ166 was investigated in the CCI model. Starting from day 7 after CCI surgery, HZ166 at the dose of 16 mg/kg or vehicle were administered intraperitoneally once daily for 9 consecutive days. On day 10, each group (vehicle and HZ166) was subdivided in 2 subgroups: one received vehicle and the other HZ166 at the dose of 16 mg/kg. After the last injection, mechanical sensitivity was assessed for 3 hours.

Motor impairment: A possible impairment of motor function was analyzed in the rotarod test. Mice were trained on the rotarod (diameter 3 cm, 2 rpm) for 2 days. Animals capable of remaining on the rotarod in the absence of treatment for at least 2 min were selected for drug testing. On the test day, the latency to fall off the rod was recorded before and 60 minutes after treatment with vehicle, HZ166 or gabapentin.

Locomotor activity: Spontaneous locomotor activity was tested using a commercially available microprocessor equipped activity cage (actiframe, Gerb Elektronik). Mice were placed in the activity cage 15 min before testing. Locomotor activity was measured for 1 h after intraperitoneal administration of vehicle, gabapentin or HZ166 during the early light phase of the day-night cycle.

Statistical Analysis: For all different doses and vehicle, baseline paw withdrawal thresholds/latencies on day 7 after nerve ligation or on day 2 after zymosan A injection were subtracted from all later withdrawal thresholds and the area under the curve (AUC) was calculated. Drug effects were expressed as percent maximum possible effect (MPE) calculated from comparisons of paw withdrawal latencies or thresholds obtained prior to surgery or inflammation and before and after drug treatment. $ED_{50}$ values were calculated by fitting the experimental data to Hill's equation with a Hill coefficient of $H_n=1$. Unless otherwise indicated, statistical comparisons were made with one-way analysis of variance (ANOVA) followed by Scheffe's post hoc test. P values<0.05 were considered significant.

Results

Antihyperalgesic Effects of HZ166 in Neuropathic Mice:

Antihyperalgesic actions of HZ166 were evaluated in mice, which had undergone chronic constriction injury (CCI) surgery of the left sciatic nerve. Following surgery, operated mice developed progressive behavioral signs of mechanical sensitization (quantified as a decrease in the paw withdrawal threshold [PWT] in response to stimulation with von Frey filaments) and of thermal hyperalgesia (quantified as a decrease in the paw withdrawal latency [PWL] in response to a radiant heat stimulus). Mechanical PWTs and thermal PWLs decreased from 3.45±0.04 g and 16.28±1.23s pre-surgery to 1.43±0.02 g and 4.67±0.53 s, respectively (mean±sem, n=6).

On day 7 after surgery, when sensitization of the ipsilateral paw had reached a plateau, HZ166 was administered i.p. and mechanical sensitivities of the ipsi- and contralateral paws were assessed for 3 hours at 30 min intervals (FIGS. 22A-22B). To quantify the analgesic effects of HZ166, the area under the curve (AUC) was calculated for each mouse. HZ166 significantly increased ipsilateral PWTs in a dose-dependent manner with a maximum effect about 1 h after injection and an ED50 of 3.83±0.94 mg/kg. Statistically significant antihyperalgesic effects were obtained for doses≥16 mg/kg. Saturation of the antihyperalgesic effect was reached at doses≥160 mg/kg. PWTs of the contralateral paw were not affected (compare FIGS. 22A-22B).

The effect of systemic HZ166 against heat hyperalgesia was assessed in the plantar test (FIGS. 23A-23B). Here, we tested a dose of 16 mg/kg, which was the lowest effective dose against mechanical hyperalgesia. HZ166 was administered 7 days after surgery, when the PWL of the CCI-lesioned ipsilateral paw (ipsi) was stable and significantly lower (presurgery) than that of the contralateral, non-lesioned paw. HZ166 significantly increased PWLs with a peak effect at 1 hr after the administration. The AUC calculated for the injured paw (4.33±1.95 s*h; n=6) was significantly different from the vehicle (1.18±0.89 s*h; n=6; P<0.01, unpaired t-test).

Antihyperalgesic effects of HZ166 in the zymosan A model of inflammatory pain: Zymosan A injected subcutaneously into the plantar side of the left hindpaw at a dose of 0.06 mg in 20 μl induced a local inflammatory reaction accompanied by swelling of the paw and thermal and mechanical sensitization. 48 hours after injection of zymosan A, HZ166 (16 mg/kg) or vehicle were given i.p. and mechanical PWTs were assessed for 3 hours (FIGS. 24A-24B). The AUC determined in HZ166 treated mice 1.55±0.21 g*h; n=6 mice) was significantly different from that of vehicle treated mice (0.38±0.08 g*h; n=6; P<0.01, unpaired t-test).

Figures 25A, 25B:
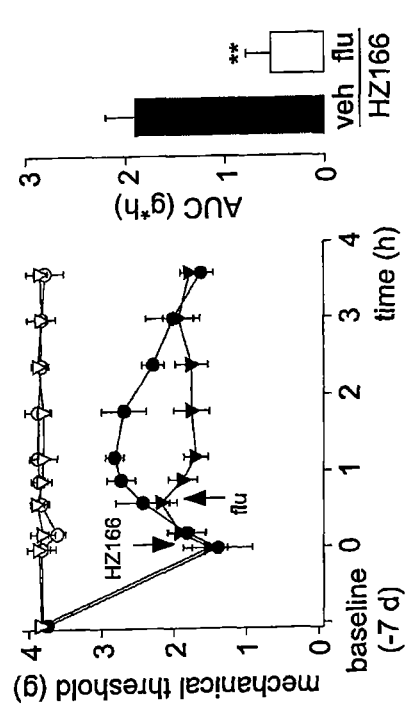
FIGS. 25A and 25B are graphs illustrating the reversal of HZ166-induced antihyperalgesia by the BDZ-site antagonist flumazenil, where left: PWTs (g, mean±SEM) in response to von Frey filament stimulation were monitored before and 7 days after nerve ligation. On day 7, HZ166 (16 mg/kg body weight) was injected i.p. 45 min later flumazenil (∇, Δ10 mg/kg body weight) or vehicle (●, ○) were injected i.p. PWTs were monitored for 3 hours after injection. n=6 mice per group. Right: statistical analysis. AUC (g*h, mean±SEM) was calculated for the time interval between administration of flumazenil or vehicle (45 min) and the end of the experiment (4 hours). **, P<0.01 (unpaired t-test).
Figure 26A:
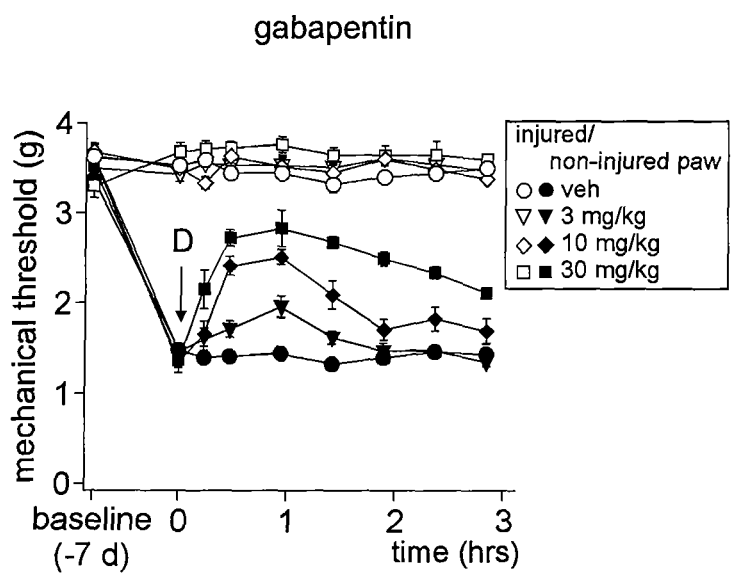
FIGS. 26A and 26B are graphs of the effect of gabapentin on mechanical sensitization after chronic constriction injury where PWTs (g, mean±SEM) in response to von Frey filament stimulation were monitored before and 7 days after CCI surgery. On day 7, gabapentin and HZ166 (3 [▼, ∇], 10 [♦, ◊] or 30 [■, □] mg/kg body weight) or vehicle (●, ○) were injected i.p. and PWTs were monitored for 3 hours after gabapentin injection. n=6 mice per group.
Figure 26B:
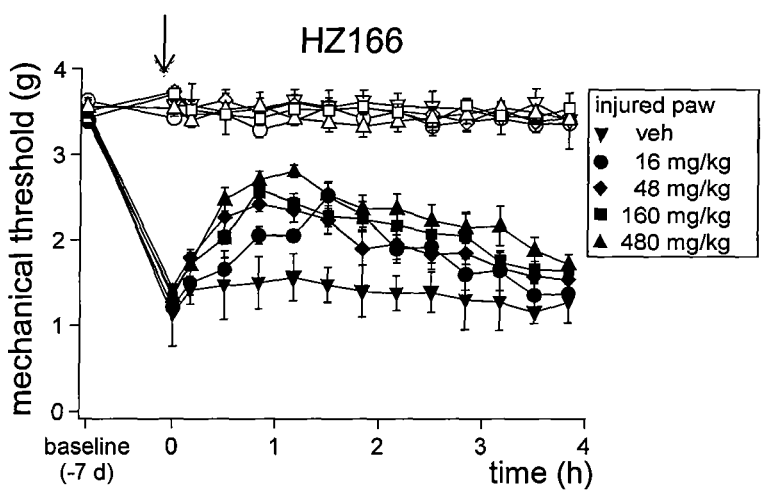
Figure 27A:
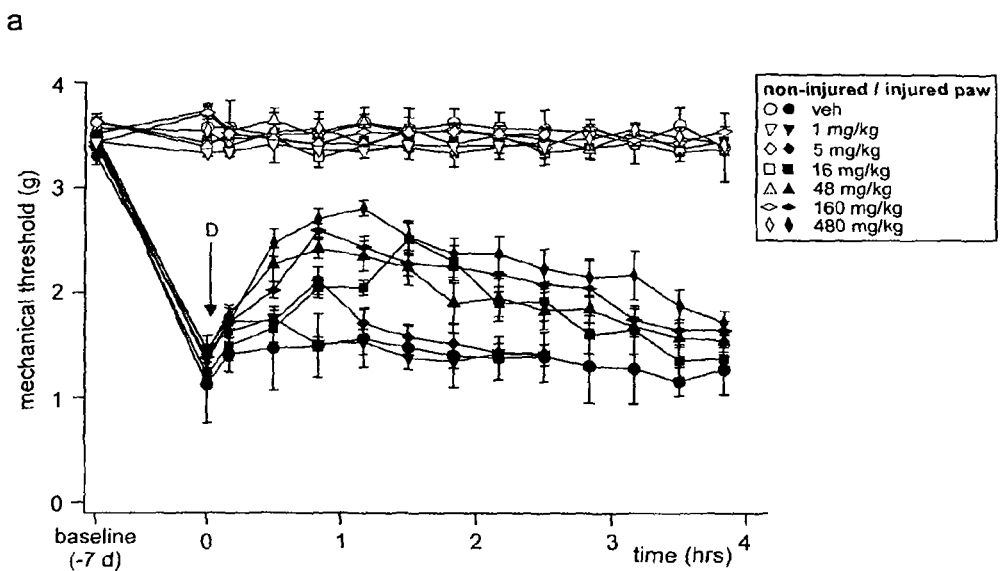
FIG. 27A is a graph of the effect of HZ166 on mechanical sensitization after chronic constriction injury (CCI). Paw withdrawal thresholds (g, mean±SEM) in response to mechanical stimulation are monitored before and 7 days after CCI. On day 7, HZ166 (1[▼], 5[♦], 16[■], 48[▲], 160[۱], 480[ﻝ] mg/kg body weight) or vehicle (●) are injected intraperitoneally and paw withdrawal thresholds are monitored for 4 hours after HZ166 injection. Filled symbols, ipsilateral paw; open symbols, contralateral paw. n=6 mice per group
Figure 27C:
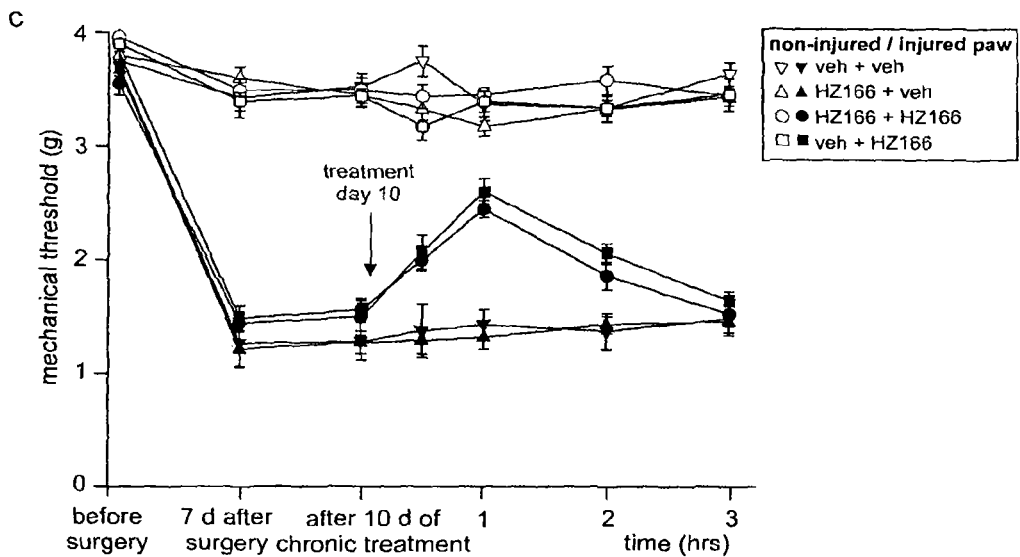
FIG. 27C is a graph of the effect of HZ166 on mechanical sensitization in CCI model after chronic treatment. Paw withdrawal thresholds (g, mean±SEM) in response to mechanical stimulation are monitored before surgery, 7 days after surgery and 10 days after chronic treatment. On day 10 after chronic treatment, HZ166 (16 mg/kg body weight) or vehicle are injected intraperitoneally in 4 different subgroups (chronic vehicle+vehicle [▼], chronic vehicle+HZ166 [■], chronic HZ166+HZ166 [●], chronic HZ166+vehicle [▲]) and paw withdrawal thresholds are monitored for 3 hours after drug injection. Filled symbols, ipsilateral paw; open symbols, contralateral paw. n=6 mice per subgroup.

Involvement of the BDZ-binding site: To verify that the antihyperalgesic effects of HZ166 came from its interaction with the BDZ-site of GABA$_A$ receptors, we tested the effect of flumazenil, a competitive BDZsite antagonist (FIGS. 25A-2B). Flumazenil (10 mg/kg, i.p.) almost completely reversed the antihyperalgesic effect of HZ166 (16 mg/kg). The AUC calculated in flumazenil treated mice (0.54±0.25 g*h; n=6) was significantly different from that of vehicle treated mice (1.90±0.29 g*h; n=6; P<0.01, unpaired t-test).

Comparison of the antihyperalgesic effects of HZ166 and gabapentin: We next compared the antihyperalgesic efficacy of HZ166 in the CCI model with that of gabapentin, a drug routinely used in the clinical treatment of neuropathic pain (FIGS. 26A-26B, 27A-27D).

Gabapentin was injected i.p. in mice at doses of 3, 10 and 30 mg/kg. Its effects on mechanical PWTs were measured for 3 hours after injection. Both HZ166 and gabapentin caused a dose-dependent reversal of mechanical hypersensitivity. Both compounds exhibited similar antihyperalgesic potencies, but the maximum antihyperalgesic effect (efficacy), which was reached in the case of gabapentin only with sedative doses (compare next paragraph), was higher for gabapentin. The percentage maximum possible effect of HZ166 and gabapentin on mechanical sensitization after CCI (ipsilateral paw values after drug injection are compared with pre-surgery values) are displayed in FIG. 27B. (n=6 mice per group). Sedative effects of gabapentin were observed at 30 mg/kg, whereas HZ166 did not impair spontaneous locomotor activity at doses≤48 mg/kg.

HZ-166 has been shown to exert antihyperanalgesic activity (FIG. 28A-28C) in a mouse model of neuropathic pain comparable to that of sub sedative doses of gabapentin, a drug frequently used in neuropathic pain patients. It was not sedating and did not develop tolerance. This is the same α2/α3 BzR agonist that was anticonvulsant (Rivas, Stables, Cook et al., *J. Med. Chem.*, 2009), but did not develop tolerance (Cook, Stables, Enthalpy Inc), because it was nearly silent at α1 and α5 receptors. It is the lack of efficacy at α1 and α5 receptors that is responsible for the lack of tolerance. The sole metabolite (HZ-166 acid) of HZ-166 was also an anticonvulsant (even orally) in rats (Stables, Cook et al.), and it has recently been shown that HZ-166 had a good Cyp profile. In addition, this ligand has been shown (Rowlett, Cook et al.) to be an anxiolytic in rhesus monkeys (conflict paradigm) with no sign of sedation even up to 10 mg/kg.

Effect of HZ166 on Mechanical Sensitization after Chronic Constriction Injury (CCI).

Paw withdrawal thresholds (g, mean±SEM) in response to mechanical stimulation are monitored before and 7 days after CCI. On day 7, HZ166 (1[▼], 5[♦], 16[■], 48[▲], 160[⊡], 480[⋈] mg/kg body weight) or vehicle (●) are injected intraperitoneally and paw withdrawal thresholds are monitored for 4 hours after HZ166 injection. Filled symbols, ipsilateral paw; open symbols, contralateral paw. n=6 mice per group Effect of HZ166 on Mechanical Sensitization in CCI Model after Chronic Treatment Paw withdrawal thresholds (g, mean±SEM) in response to mechanical stimulation are monitored before surgery, 7 days after surgery and 10 days after chronic treatment. On day 10 after chronic treatment, HZ166 (16 mg/kg body weight) or vehicle are injected intraperitoneally in 4 different subgroups (chronic vehicle+vehicle [▼], chronic vehicle+HZ166 [■], chronic HZ166+HZ166 [●], chronic HZ166+vehicle [▲]) and paw withdrawal thresholds are monitored for 3 hours after drug injection. Filled symbols, ipsilateral paw; open symbols, contralateral paw. n=6 mice per subgroup.

Percentage maximum possible effect of HZ166 (acute treatment: veh+HZ166, chronic treatment: HZ166+HZ166) on mechanical sensitization after C (ipsilateral paw values after drug injection are compared with pre-surgery values). n=6 mice per group.

Motor coordination and locomotor activity: We used the rotarod test to assess possible drug-induced changes in motor performance (FIGS. 28 and 29). Neither HZ166 (16 and 48 mg/kg) nor gabapentin (10 and 30 mg/kg) interfered with rotarod performance. The propensity of HZ166 and gabapentin to cause sedation was evaluated using a commercially available microprocessor equipped activity cage (actiframe, Gerb Elektronik) (FIGS. 30 and 31). At doses with a maximum analgesic effect (16 and 48 mg/kg), HZ166 did not significantly impair spontaneous motor activity, whereas a significant reduction in locomotor activity was found for gabapentin at doses≥30 mg/kg.

Figures 32, 33:
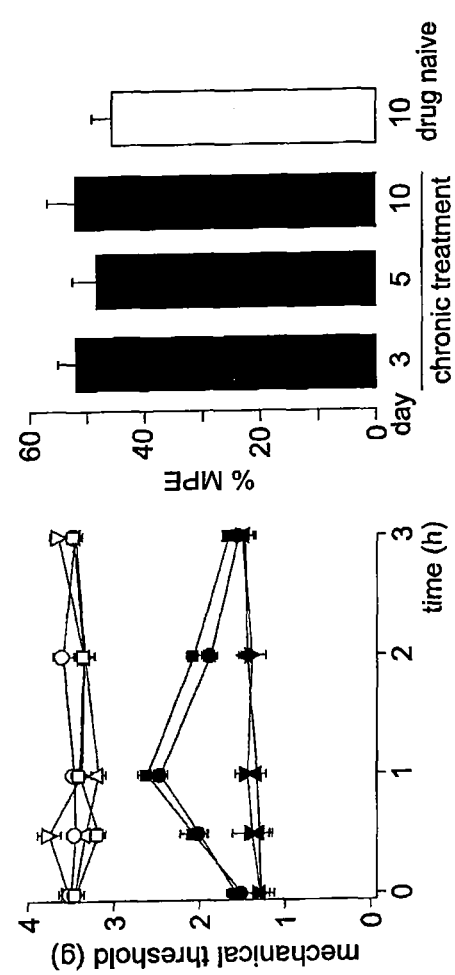
FIG. 32 is a graph of the lack of tolerance development where PWTs (g, mean±SEM) in response to von Frey filament stimulation were assessed in mice 17 days after CCI surgery. Mice had undergone 10 days of chronic i.p. treatment with either HZ166 (16 mg/kg body weight) or vehicle and were treated acutely on day 17 with either HZ166 (16 mg/kg body weight) or vehicle. 4 groups of mice were analyzed (chronic vehicle/acute vehicle [▼, ∇], chronic vehicle/acute HZ166 [■, □], chronic HZ166/acute HZ166 [●, ○], chronic HZ166/acute vehicle [▲, Δ]). PWTs were monitored for 3 hours after drug injection. Filled symbols, ipsilateral paw; open symbols, contralateral paw. n=6 mice per group.
FIG. 33 is a graph of the lack of tolerance development where the percent maximum possible effect (MPE) of HZ166 after 3, 5 and 10 days of chronic treatment with HZ166 (black bars) and in mice chronically treated with vehicle for 10 days (white bar). n=6 mice per group. ANOVA followed by Scheffe's post hoc test, F (3, 20)=1.50.

Tolerance development: Long-term administration of BDZs is often associated with a progressive loss of activity (tolerance development). Here, we investigated the liability of HZ166 to tolerance development (FIGS. 32 and 33). Mice were chronically treated with HZ166 at a dose of 16 mg/kg once daily or with vehicle for 9 days starting from day 7 after CCI surgery. After 10 days of chronic drug or vehicle treatment, mechanical sensitivity was measured in both groups after administration of HZ166 to compare its analgesic activity in drug-naïve mice and in mice chronically exposed to HZ166. HZ166 exerted virtually the same analgesic activity in both groups. Measurements of mechanical sensitivity were also performed at day 3 and 5 during chronic treatment to monitor the antihyperalgesic activity of HZ166 over time. At neither one of these time points any signs of reduced antihyperalgesic activity were found.

Our previous studies in GABA$_A$ receptor point-mutated mice have shown that spinal α2- and/or α3-GABA$_A$ receptors mediate most of the anti-hyperalgesic activity observed with spinally administered diazepam, while sedative α1-GABA$_A$ receptors do not contribute. After systemic treatment with diazepam, a strong antihyperalgesic action was retained in α1-GABA$_A$ receptor point-mutated mice suggesting that non-sedative (α1 sparing) BDZ site agonists should exert pronounced antihyperalgesic effects (Knabl et al., 2009). Such pharmacological data have hitherto largely been missing in mice, which precluded a comparison of genetic and pharmacological data within the same species. To address this issue, we have now used HZ166a novel non-sedative BDZ-site partial agonist with preferential activity at α2- and α3-GABA$_A$ receptors and suitable pharmacokinetic properties in mice (Rivas et al., 2009). These experiments demonstrated that HZ166 possesses significant dose-dependent activity against thermal and mechanical hyperalgesia in models of inflammatory and neuropathic pain in the absence of sedation or motor impairment. Reversal by flumazenil, a competitive BDZ-site antagonist, indicates that these effects were specifically mediated by GABA$_A$ receptors. These data are in line with previous results obtained in rats by our group with L-838,417 (Knabl et al., 2008) or by others with NS11394 (Munro et al., 2008), which is another subtypeselective BDZ-site ligand (Mirza et al., 2008). Together, they indicate that profound antihyperalgesia can be obtained in different rodent species with non-sedative BDZ-site ligands in various pain models.

Similar to what we and other have seen with intrathecal injections of diazepam in mice (Knabl et al., 2009) or with systemic administration of subtype-selective agents in rats (Knabl et al., 2008; Munro et al., 2008), HZ166 did not change responses of noninflamed or uninjured paws confirming that a facilitation of GABA$_A$ receptor-mediated inhibition at the spinal cord level produces anti-hyperalgesia rather than general analgesia.

In order to compare the antihyperalgesic efficacy of HZ166 to that of drugs already established in the treatment of neuropathic pain, we compared the effects of HZ166 with those of gabapentin, an anticonvulsant drug which is widely used in the treatment of different forms of neuropathic pain. Its clinical effectiveness has been described in a variety of pain syndromes, including painful diabetic neuropathy, postherpetic neuralgia and phantom limb pain (Jensen et al., 2009). Gabapentin is generally well tolerated but sedation and dizziness are reported adverse effects. Here, we found that at non-sedative doses, the antihyperalgesic activities of gabapentin and HZ166 were similar. Nevertheless, the maximum possible antihyperalgesic effect of gabapentin was higher, but only at doses, which significantly reduced locomotor activity in the open field test and which were thus considered to be sedative.

Apart from sedation, major side effects of classical BDZs as well as of most centrally acting analgesics include tolerance development and addiction. We have previously reported that repeated administration of L-838,417 (once per day for nine days) did not diminish its analgesic effect, while complete tolerance developed during the same time period against morphine-induced analgesia (Knabl et al., 2008). Here, we found again no loss of antihyperalgesic activity of HZ166 during a 9-day treatment period in neuropathic mice. Although the lack of tolerance development likely results from reduced activity at α1-GABA$_A$ receptors (Mirza and Nielsen, 2006), pharmacokinetic properties (time of exposure of the receptors to the drug) and a generally lower intrinsic activity (as compared to diazepam) may also contribute (Licata and Rowlett, 2008).

We did not test for potential addictive properties of HZ166, but available pharmacological evidence again suggests that α1 sparing agonists should be devoid of addictive properties (Ator et al., 2010). A critical role of α1 GABA$_A$ receptors in reinforcing properties of BDZs has also been demonstrated in a recent neurobiological study (Tan et al., 2010), which used mice carrying point-mutated (diazepam-nsensitive) GABA$_A$ receptor subunits. This study analyzed drug-induced increases in dopamine release in the ventral tegmental area, which constitute the basis of the re-enforcing properties of many addictive drugs. Their findings provide direct evidence that diazepam and most likely other BDZs cause addiction through an α1-GABA$_A$ receptor-induced disinhibition of dopaminergic neurons in the ventral tegmental area.

In summary, our findings suggest that future subtype-selective (α1 sparing) BDZs may constitute a novel approach to the treatment of chronic pain. Drug companies have already tried to identify and develop α1 sparing compounds for about 10 years in the sake for novel non-sedative anxiolytics (Atack, 2005). This strategy has yielded only rather limited success so far, partly because most known subtype-selective BDZ-site agonists differ primarily in their intrinsic activity at GABA$_A$ receptor subtypes while traditional drug screening relied on differences in affinity. The recent advent of novel technologies in electrophysiology which allow high through-put screening of agents acting on ion channels (Dunlop et al., 2008) should significantly facilitate the identification of such compounds.

Synthesis of GABA$_A$ Receptor Subunit Selective Benzodiazepine Derivatives.

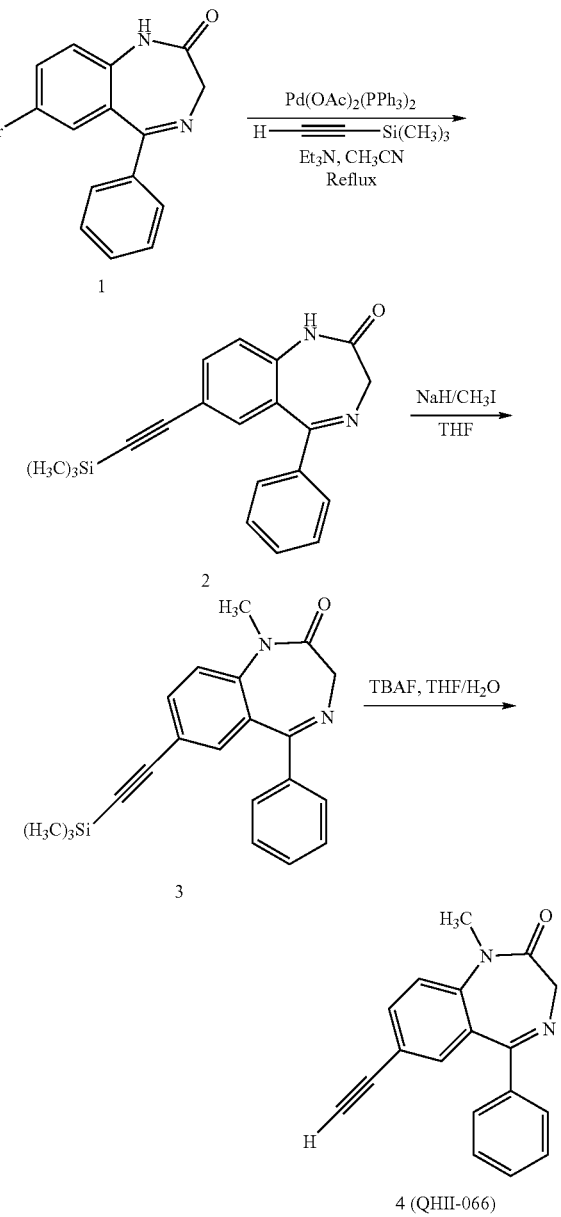

The bromide 1 available was reacted with trimethylsilyacetylene in the presence of a palladium catalyst to provide trimethylsilyl analog 2. This product was methylated with methyl iodide/sodium hydride to give the N-methyl benzodiazepine 3. This was subjected to fluoride-mediated desilation to furnish 4 (QHII-066).

Procedure for QHII-066

7-Trimethylsilylacetyleno-5-phenyl-1,3-dihydrobenzo[e]-1,4-diazepin-2-one 2. A mixture of 1 (1 g, 3.17 mmole) in triethyl amine (30 mL) and CH$_3$CN (20 mL) with trimethylsilylacetylene (622.7 mg, 6.34 mmole) and bis(tri-phenylphosphine)-palladium (II) acetate (118 mg, 0.16 mmol) was heated to reflux under nitrogen. After 12 hours, the reaction mixture was cooled to room temperature and filtered. The filtrate was concentrated in vacuum and the residue was treated with a saturated aqueous solution of NaHCO$_3$ (30 mL), and extracted with CH$_2$Cl$_2$ (3×50 mL). The organic layers were combined and washed with brine and dried (Na$_2$SO$_4$). After removal of solvent under reduced pressure, the residue was purified via flash chromatography (silica gel, EtOAc/hexanes: 1/1) to furnish 3 as a yellow powder (791 mg, 75%): mp: 190-191.5° C.; IR (KBr) 3011, 2281, 1686, 1610, 1486, 1325, 1249, 839, 700 cm$^{-1}$; 1H NMR (CDCl$_3$) δ 0.21 (s, 9H), 4.31 (s, 2H), 7.09 (d, 1H, J=8.25 Hz), 7.21-7.61 (br, 7H), 10.17 (s,1H); MS (CI) m/e (relative intensity) 333 (M$^+$+1, 100). This material was used in the next step.

1-Methyl-7-trimethylsilylacetyleno-5-phenyl-1,3-dihydrobenzo[e]-1,4-diazepin-2-one 3. A mixture of 2 (485 mg, 1.46 mmol) was dissolved in dry THF (20 mL) at 0° C. and NaH (60% in mineral oil, 70 mg, 1.75 mmol) was added to the solution in one portion. The slurry was then stirred for 20 min at 0° C. and CH$_3$I (311 mg, 2.19 mmol) was added to the mixture and it was warmed up to room temperature. After the mixture stirred for 3 hours at room temperature, the THF was then removed under reduced pressure. The residue was purified by flash chromatography [hexanes/EtOAc (1:4)] to provide the title compound 3 (303 mg, 60%) as a white solid: mp: 177-178° C.; IR (KBr) 2954, 2147, 1687, 1612, 1491, 1382, 1115, 1075, 839, 700 cm$^{-1}$; 1HNMR (CDCl$_3$) δ (ppm), 3.18 (s, 3H), 3.54 (d, 1H, J=10.8 Hz), 4.60 (d, 1H. J=10.8 Hz), 7.05 (s, 1H), 7.07 (d, 1H, J=8.58 Hz), 7.20-7.27 (m, 3H), 7.37-7.42 (m, 3H); MS (EI) m/e 346 (M$^+$, 90), 318 (100), 303(19), 165(22), 151(20). Anal. Calcd. for C$_{21}$H$_{22}$N$_2$OSi: C, 72.79; H, 6.40; N, 8.08. Found: C, 72.50; H, 6.68; N, 8.04.

1-Methyl-7-acetyleno-5-phenyl-1,3-dihydro-benzo[e]-1,4-diazepin-2-one 4 (QHII-066). A solution of 3 (100 mg), in THF (30 mL) was treated with tetrabutylammonium fluoride (1 M in THF). The mixture was stirred for 20 minutes at room temperature before water (30 mL) was added. The mixture was then extracted with EtOAc (3×30 mL). The combined organic extracts were washed with brine and dried (Na$_2$SO$_4$). The solvent was removed under vacuum and the residue which resulted was passed through a wash column (silica gel, EtOAc/hexanes: 4/1) to give 4 (QHII-066) as light yellow crystals (71 mg, 90%): mp: 163-165° C.; IR (KBr) 2965, 1680, 1605, 1387, 1121, 833, 747 cm$^{-1}$; 1HNMR (CDCl$_3$) δ (ppm) 3.38 (s, 3H), 3.75 (d, 1H, J=10.8 Hz), 4.80 (d, 1H, J=10.9 Hz), 5.28 (s, 1H), 7.29 (d, 1H, J=8.5 Hz), 7.35-7.45 (m, 4H), 7.55-7.59 (m, 2H), 7.62 (dd, 1H, J=8.5 Hz, 2.0 Hz); MS (D) m/e (relative intensity) 274 (M$^+$, 100), 259 (12), 246 (100), 189 (12). 122(19), 105 (42). Anal. Calcd. for C$_{18}$H$_{14}$N$_2$O.2/3H$_2$O, Calculated: C, 75.51; H, 4.89; N, 9.78. Found: C, 75.59; H, 5.17; N, 9.62.

Scheme 2 (XHeII-053)

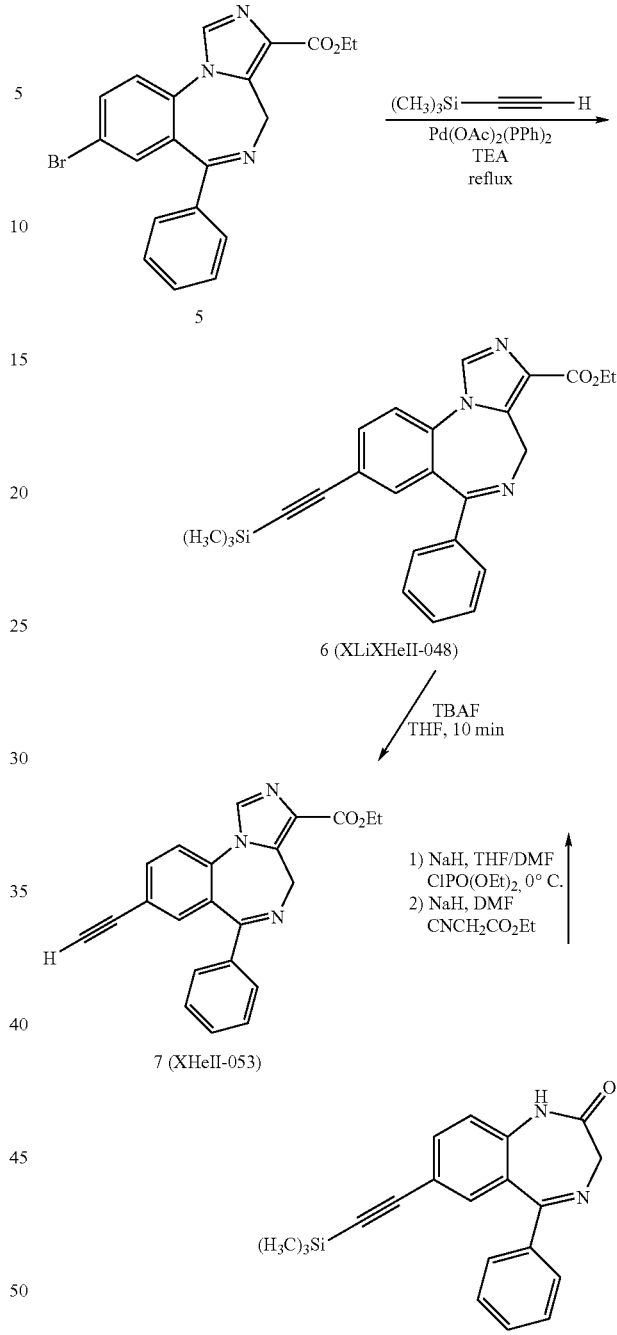

The bromide 1 was reacted with diethylphosphorochloridate in the presence of sodium hydride, followed by addition of ethyl isocyanoacetate to provide the ester 5. This was converted to the trimethylsilylacetyleno compound 6 (XLiX-HeII-048) under standard conditions (Pd-mediated, Heck-type coupling).[8] Treatment of 6 with fluoride gave the title compound 7 (XHeII-053).

Procedure for XHe-II-053

Ethyl 8-bromo-6-phenyl-4H-benzo[f]imidazo[1,5-a][1,4]diazepine-3-carboxylate 5. This benzodiazepine 5 was obtained in 45% yield from 1 analogous to the literature procedure as a white solid. 2: mp: 174-175° C.; IR (KBr) 2978, 1712, 1609, 1491 cm$^{-1}$; $^1$H NMR (CDCl$_3$) δ 1.44 (t, 3H, J=7.1 Hz), 4.09 (d, 1H, J=12.1 Hz), 4.38-4.49 (m, 2H), 6.08 (d, 1H, J=12.3 Hz), 7.40-7.53 (m, 6H), 7.60 (d, 1H, J=2.2 Hz), 7.82 (dd, 1H, J=8.6 Hz and 2.2 Hz), 7.95 (s, 1H); MS (EI) m/e (relative intensity) 411 (34), 410 (M+, 8), 409 (34), 365 (61), 363 (61), 337 (100), 335 (100), 285 (21), 232, (17). Anal. Calcd. for $C_{20}H_{16}BrN_3O_2$: C, 58.55; H, 3.93; N, 10.24. Found: C, 58.30, H, 3.91; N, 9.90.

Ethyl 8-trimethylsilylacetylenyl-6-phenyl-4H-benzo[f]imidazo[1,5-a][1,4]diazepine-3-carboxylate 6 (XLiXHeII-048). A mixture of bromide 5 (0.3 g, 0.73 mmol), trimethylsilylacetylene (0.143 g, 1.46 mmol) and bis(triphenylphosphine)-palladium-(II) acetate (55 mg, 0.073 mmol) in a mixed solvent system of toluene (20 mL) and anhydrous TEA (50 mL) was heated to reflux under argon. After stirring for 12 hours at reflux, the mixture was cooled to room temperature and the precipitate which formed was removed by filtration. The filtrate was concentrated under reduced pressure and the residue was treated with a saturated aqueous solution of $NaHCO_3$ (20 mL), and extracted with $CHCl_3$ (3×25 mL). The combined extracts were washed with brine and dried ($Na_2SO_4$). After removal of solvent under reduced pressure, the residue was purified by flash chromatography (silica gel, EtOAc) to afford 6 (XLiXHeII-048) as a white solid (0.29 g, 93%). This benzodiazepine can also be obtained from 2 in 45% yield by following the same procedure 6 (XLiXHeII-048): mp: 170-172° C.; IR (KBr) 2958, 2152, 1718 cm$^{-1}$; $^1$H NMR (CDCl$_3$) δ 0.23 (s, 9H), 1.42 (t, 3H, J=7.2 Hz), 4.04 (d, 1H, J=12.6 Hz), 4.41 (m, 2H, J=7.2 Hz), 6.23 (d, 1H, J=12.6 Hz), 7.35-7.55 (m, 7H), 7.73 (dd, 1H, J=8.3 Hz, J=1.9 Hz), 7.93 (s, 1H); MS (EI) m/e (relative intensity) 427 (M+, 76), 412 (5), 381 (55), 353 (100) 303 (10), 287 (7). Anal. Calcd. for $C_{25}H_{25}N_3O_2Si.1/3$ EtOAc: C, 69.22; H, 6.01; N, 9.20. Found: C, 68.87; H, 5.81; N, 9.37.

Ethyl 8-acetylenyl-6-phenyl-4H-benzo[f]imidazo[1,5-a][1,4]diazepine-3-carboxylate 7 (XHeII-053). A solution of 6 (XLiXHeII-048) (0.17 g, 0.41 mmol), in THF (15 mL) was treated with $Bu_4NF.H_2O$ (0.16 g, 0.62 mmol). The mixture which resulted was allowed to stir for 30 min at room temperature after which the mixture was added to $H_2O$ (10 mL) and extracted with EtOAc (3×25 mL). The combined organic extracts were washed with brine (25 mL) and dried ($Na_2SO_4$). After removal of solvent under reduced pressure, the residue was purified by a wash column (silica gel, EtOAc) to furnish 7 (XHeII-053) (0.12 g, 85%) as a white solid: mp 237-239° C.; IR (KBr) 3159, 3107, 2092, 1721, 1606 cm$^{-1}$; $^1$H NMR (CDCl$_3$) δ 1.44 (t, 3H, J=7.1 Hz), 3.20 (s, 1H), 4.13 (d, 1H, J=10.22 Hz), 4.41-4.48 (m, 2H), 6.11 (d, 1H, J=12 Hz), 7.42-7.63 (m, 7H), 7.81 (dd, 1H, J=8.3 Hz and 1.8 Hz), 8.03 (s, 1H); MS (D) m/e (relative intensity) 355 (M+, 83), 309 (70), 281 (100), 253 (12), 231 (18), 178 (20). Anal. Calcd. for $C_{22}H_{17}N_3O_2.3/4H_2O$: C, 71.63; H, 5.05; N, 11.39. Found: C, 71.27; H, 4.71; N, 11.03. The bromide 1, available from reference 1, was stirred with the di-4-morpholino-phosphinic chloride, followed by addition of acetylhydrazide to furnish triazolo-benzodiazepine 8. This material 8 was subjected to a Heck-type coupling reaction (TMS-C≡CH, Pd-mediated)$^{4,7,8}$ to furnish ligand 9. This analog was converted into 10 (XLi270) on stirring with fluoride anion as shown in Scheme 3.

Procedure for XLi 270:

8-Bromo-1-methyl-6-phenyl-4H-s-triazolo[4,3-a][1,4]benzodiazepine 8. A solution of 1 (1 g, 3.07 mmol of 7-bromo-5-phenyl-1,4-benzodiazepine-2-one) in dry THF (20 mL) was cooled in an ice-water bath and a 60% dispersion of sodium hydride (152.2 mg) was added in one portion. After 20 minutes, di-4-morpholinylphosphinic chloride$^3$ (943.9 mg, 4.76 mmol) was added at 0° C. and this was stirred for 30 minutes and allowed to warm to room temperature. The mixture was stirred for 1.5 hours. To this mixture was then added a solution of acetylhydrazide (521.9 mg, 7.14 mmol) in dry butanol (5 mL) and stirring was continued at room temperature for 10 min. The solvents were evaporated and the residue was dissolved in butanol (10 mL) and heated to reflux for 5 hours. Butanol was removed under reduced pressure and the residue was partitioned between $CH_2Cl_2$ (50 mL) and water (50 mL). The water layer was extracted by $CH_2Cl_2$ (3×30 mL). The combined organic layer was washed by brine (30 mL). The organic layer was dried ($Na_2SO_4$) and the solvent was removed under vacuum. The residue was purified by flash chromatography (silica gel) to provide pure 8 [539.5 mg (40% yield)] as a white solid: mp 268.5-270° C.; IR (KBr) 2358, 1607, 1538, 1484, 1311, 1000, 801, 697 cm$^{-1}$; $^1$H NMR (CDCl$_3$) δ 2.82 (s, 3H), 4.11 (d,1H, J=12.8 Hz), 5.49 (d,1H, J=12.8 Hz), 7.21-7.68(m, 7H), 7.75 (dd, 1H, J=0.58 Hz, J=1.5 Hz); MS (EI) m/e (relative intensity) 354 (34), (M+, 16), 352 (34), 325(33), 323 (34), 273 (63), 245 (31), 232 (19), 204 (100), 183(23), 177 (36), 151 (24). Anal. Calcd. for $C_{17}H_{13}BrN_4$: C, 57.81; H, 3.71; N, 15.86. Found C, 57.57; H, 3.64: N, 15.70.

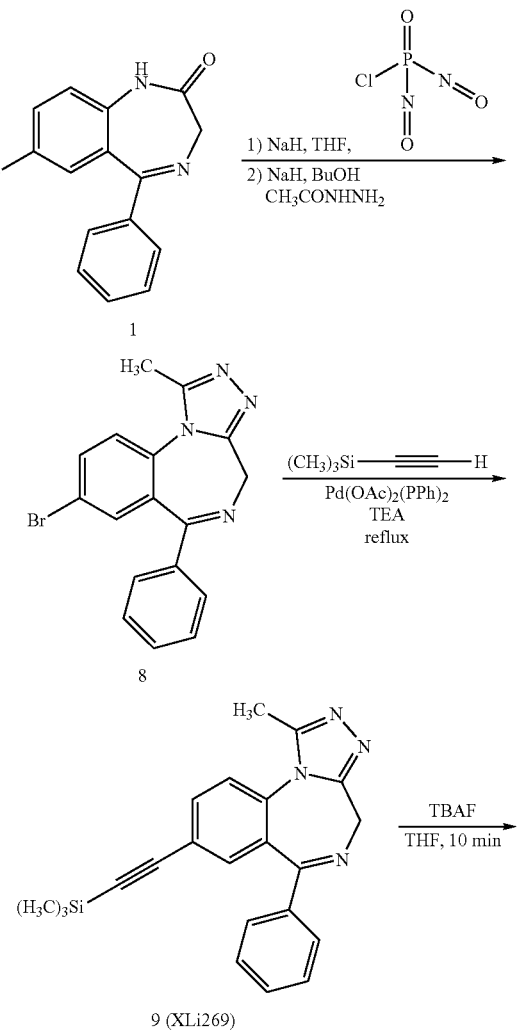

-continued

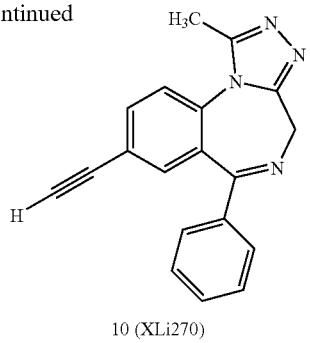

10 (XLi270)

8-Trimethylsilylacetylenyl-1-methyl-6-phenyl-4H-s-triazolo[4,3-a][1,4]-benzodiazepine 9. (XLi269). A mixture of 8 (8-bromo-1-methyl-6-phenyl-4-H-s-triazolo-[4,3-a][1,4] benzodiazepine, 300 mg, 0.85 mmol), trimethylsilylacetylene (208.5 mg, 2.12 mmol) and bis(triphenylphosphine)-palladium (II) acetate in a mixed solvent system of $EtN_3$ (5 mL) and $CH_3CN$ (8 mL) was heated to reflux under nitrogen. After stirring for 6 hours at reflux. The mixture was cooled to room temperature. The mixture was concentrated under reduced pressure and $H_2O$ (30 mL) was added. The mixture was extracted with $CH_2Cl_2$ (3×50 mL). The combined extracts were washed with brine and dried ($Na_2SO_4$). After removal of solvent under reduced pressure, the residue was purified by flash chromatography (silica gel, EtOH/EtOAc) to afford benzodiazepine 9 (185 mg, 60% yield) as a white solid: mp 229-233° C.; IR (KBr) 2957, 2156, 1609, 1537, 1491, 1424, 1315, 1249, 881, 844, 750 cm$^{-1}$; $^1$H NMR (CDCl$_3$) δ 0.23 (s, 9H), 2.68 (s, 3H), 4.11 (d, 1H, J=12.5 Hz), 5.49 (d, 1H, J=13.0 Hz), 7.21-7.68(m, 7H), 7.75(dd, 1H, J=8.5 Hz, J=1.5 Hz); MS (EI) m/e (relative intensity) 370 (M$^+$, 80), 355 (44), 341 (60), 286 (34), 177 (51), 163 (52) 143 (100), 129 (19), 115 (28). Anal. Calcd. for $C_{22}H_{22}N_4Si$: C, 71.31; H, 5.98; N, 15.12. Found: C, 70.90; H, 5.93; N, 15.08.

8-Acetylenyl-1-methyl-6-phenyl-4H-s-triazolo[4,3-a][1,4]benzodiazepine 10 (XLi-270). A solution of 9 [trimethylsilylacetylenyl-1-methyl-6-phenyl-4H-s-triazolo-[4,3-a]-[1,4]-benzodiazepine (106.4 mg, 0.288 mmol)] in dry THF (20 mL) was treated with Bu$_4$NF (1.0 M in THF, 112.8 mg, 0.431 mmol). The mixture which resulted was allowed to stir for 5 min at room temperature after which the mixture was added to $H_2O$ (10 mL) and extracted with $CH_2Cl_2$ (3×25 mL). The combined organic extracts were washed with brine (25 mL) and dried ($Na_2SO_4$). After removal of solvent under reduced pressure, the residue was crystallized from EtOAc to provide benzodiazepine 10 (XLi270) (66.8 mg, 80% yield) as a white solid: mp>250° C. (dec); IR (KBr) 3198, 2158, 1609, 1538, 1491, 1425, 1317, 1002, 838, 748, 695 cm$^{-1}$; $^1$H NMR (CDCl$_3$) δ 2.78 (s, 3H), 3.15 (s, 1H), 4.11 (d, 2H, J=12.8 Hz), 5.91 (d, 1H, J=12.8 Hz), 7.35-7.85 (m, 8H); MS (EI) (relative intensity) 298 (M$^+$, 100), 269 (78), 230 (48), 228 (65), 201 (20), 127 (65), 115 (42), 101 (54). Anal. Calcd. for $C_{19}H_{14}N_4$·1/2 $CH_3OH$: C, 74.50; H, 5.13; N, 17.82. Found: C, 74.33; H, 4.83; N, 17.77.

Scheme 4

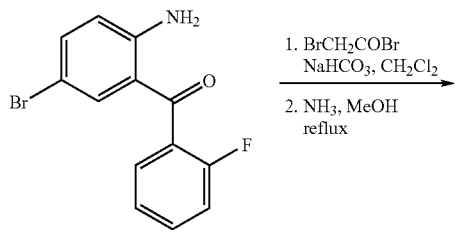

11

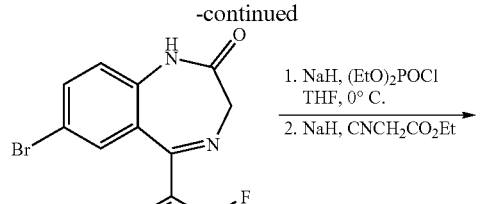

12
(this material was available from reference one)

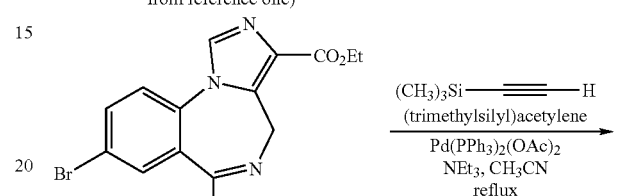

13 (JYI-032)

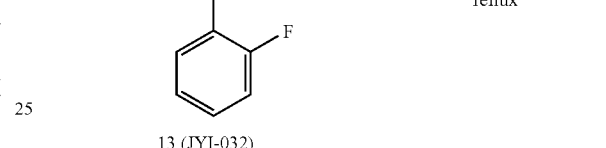

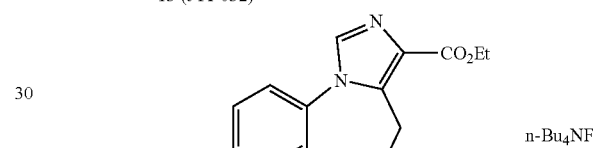

14 (JYI-038)

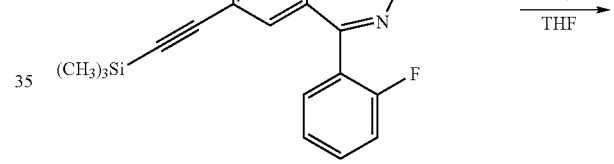

15 (JY-XHE-053

The 7-bromo-2'-fluorobenzodiazepine 12 was reacted with sodium hydride and diethylphosphorochloridate and this was followed by addition of ethyl isocyanoacetate to provide benzimidazo intermediate 13 (JYI-032), as illustrated in Scheme 4. This material was heated with trimethysilylacetylene in a Heck-type coupling reaction to provide the trimethylsilyl analog 14 (JYI-038). The silyl group was removed from 14 on treatment with fluoride anion to furnish 15, a 2'-fluoro analog of XHeII-053, in excellent yield.

Procedure:

Ethyl 8-bromo-6-(2'-fluorophenyl)-4H-benzo[f]imidazo[1,5-a][1,4]diazepine-3-carboxylate 13 (JYI-032). A solution of 12 (7.0 g, 21.0 mmol) in THF (50 mL) was cooled in ice-water, and sodium hydride (1.0 g, 25.2 mmol) was added in one portion. After 30 min, diethyl phosphorochloridate (5.62 g, 31.5 mmol) was added dropwise, and the solution which resulted was stirred continuously for 30 min with cooling from an ice bath. A solution of ethyl isocyanoacetate (4.22 g, 25.2 mmol) and sodium hydride (1.17 g, 29.4 mmol) in THF (10 mL), which had stirred for 30 min with ice-bath cooling, was added slowly via a cannula. After stirring for another 30 min with cooling, the reaction mixture was allowed to stir at room temperature overnight. The mixture was then added to $H_2O$ (10 mL) and extracted with EtOAc (3×50 mL). The combined organic extracts were washed with brine (2×50 mL) and dried ($Na_2SO_4$). The solvent was evaporated under reduced pressure and the residue was purified by flash chromatography (silica gel, hexanes/EtOAc: 2/1) to afford 13 (JYI-032, 5.2 g, 58%) as a white solid: mp 200-201.5° C.; IR (KBr) 2977, 1718, 1610, 1491, 1450 cm$^{-1}$; $^1$H NMR (DMSO-$d_6$) δ 1.30 (t, 3 H, J=4.2 Hz), 4.28 (bs, 1 H), 4.30 (q, 2 H, J=4.2 Hz), 5.75 (bs, 1 H), 7.20 (t, 1 H, J=5.6 Hz), 7.30 (t, 1 H, J=4.5 Hz), 7.40 (s, 1 H), 7.54 (m, 2 H), 7.85 (d, 1 H, J=5.2 Hz), 7.96 (dd, 1 H, J=5.2 Hz and 1.3 Hz), 8.44 (s, 1 H); MS (EI) m/e (relative intensity) 428 (7), 381 (58), 355 (100), 303 (37), 274 (36), 247 (35), 234 (52), 154 (71), 127 (62). Anal Calcd. for $C_{20}H_{15}N_3O_2FBr$: C, 56.09; H, 3.53; N, 9.81. Found: C, 56.02; H, 3.51; N, 9.58.

Ethyl 8-trimethylsilylacetylenyl-6-(2'-fluorophenyl)-4H-benzo[f]-imidazo[1,5-a][1,4]diazepine-3-carboxylate 14 (JYI-038). A mixture of bromide 13 (JYI-032, 1.40 g, 3.3 mmol), trimethylsilylacetylene (0.65 g, 6.6 mmol) and bis(triphenylphosphine)-palladium (II) acetate (0.25 g, 0.33 mmol) in a mixed solvent system of $CH_3CN$ (80 mL) and anhydrous triethylamine (50 mL) was heated to reflux under argon. After stirring for 2 h at reflux, the mixture was cooled to room temperature and the precipitate which formed was removed by filtration. The filtrate was concentrated under reduced pressure and the residue was treated with a saturated aqueous solution of $NaHCO_3$ (40 mL), and extracted with $CHCl_3$ (3×50 mL). The combined organic extracts were washed with brine (2×20 mL) and dried ($Na_2SO_4$). After removal of solvent under reduced pressure, the residue was purified by flash chromatography (silica gel, hexanes/EtOAc: 3/1) to afford 14 (JYI-038, 1.2 g, 82%) as a white solid: mp 196-197.5° C.; IR (KBr) 2959, 2157, 1709, 1613, 1494, 1451, 1252 cm$^{-1}$; $^1$H NMR (DMSO-$d_6$) δ 0.20 (s, 9 H), 1.32 (t, 3 H, J=7.1 Hz), 4.18 (bs, 1 H), 4.32 (q, 2 H, J=7.1 Hz), 5.78 (bs, 1 H), 7.25 (t, 1 H, J=11.5 Hz), 7.30-7.35 (m, 4 H), 7.81 (d, 1 H, J=6.6 Hz), 7.93 (d, 1 H, J=8.4 Hz), 8.49 (s, 1 H); MS (EI) m/e (relative intensity) 445 (37), 399 (51), 371 (100), 235 (71), 192 (66), 178 (75). Anal. Calcd. for $C_{25}H_{24}N_3O_2FSi$: C, 67.39; H, 5.42; N, 9.43. Found: C, 66.98; H, 5.46; N, 9.19.

8-Acetyleno-6-(2'-fluorophenyl)-4H-benzo[f]imidazo[1,5-a][1,4]diazepine-3-carboxylate 15 (JY-XHE-053). A solution of 14 (JYI-038, 80 mg, 0.18 mmol) in THF (5 mL) was treated with $Bu_4NF$ (0.5 mL, 1.0M solution in THF). The mixture which resulted was allowed to stir for 5 min at room temperature after which the mixture was added to $H_2O$ (5 mL) and extracted with EtOAc (3×10 mL). The combined organic extracts were washed with brine (2×10 mL) and dried ($Na_2SO_4$). The solvent was removed under reduced pressure and the residue was purified by flash chromatography (silica gel, EtOAc) to afford 15 (JY-XHE-053, 67 mg, 80%) as a white solid: mp 223.5-224.5° C.; IR (KBr) 3288, 2979, 1712, 1621, 1491, 1255, 1190 cm$^{-1}$; $^1$H NMR (DMSO-$d_6$) δ 1.34 (t, 3 H, J=7.1 Hz), 4.27 (bs, 1 H), 4.36 (q, 2 H, J=7.1 Hz), 4.47 (s, 1 H), 5.80 (bs, 1 H), 7.22 (t, 1 H, J=8.4 Hz), 7.30-7.60 (m, 4 H), 7.85 (d, 1 H, J=8.4 Hz), 7.92 (d, 1 H, J=8.4 Hz), 8.83 (s, 1 H); MS (EI) m/e (relative intensity) 373 (28), 327 (47), 299 (100), 249(22), 178 (50). Anal. Calcd. for $C_{22}H_{16}N_3O_2F\cdot\frac{1}{2}H_2O$: C, 69.10; H, 4.48; N, 10.99. Found: C, 69.19; H, 4.39; N, 10.68.

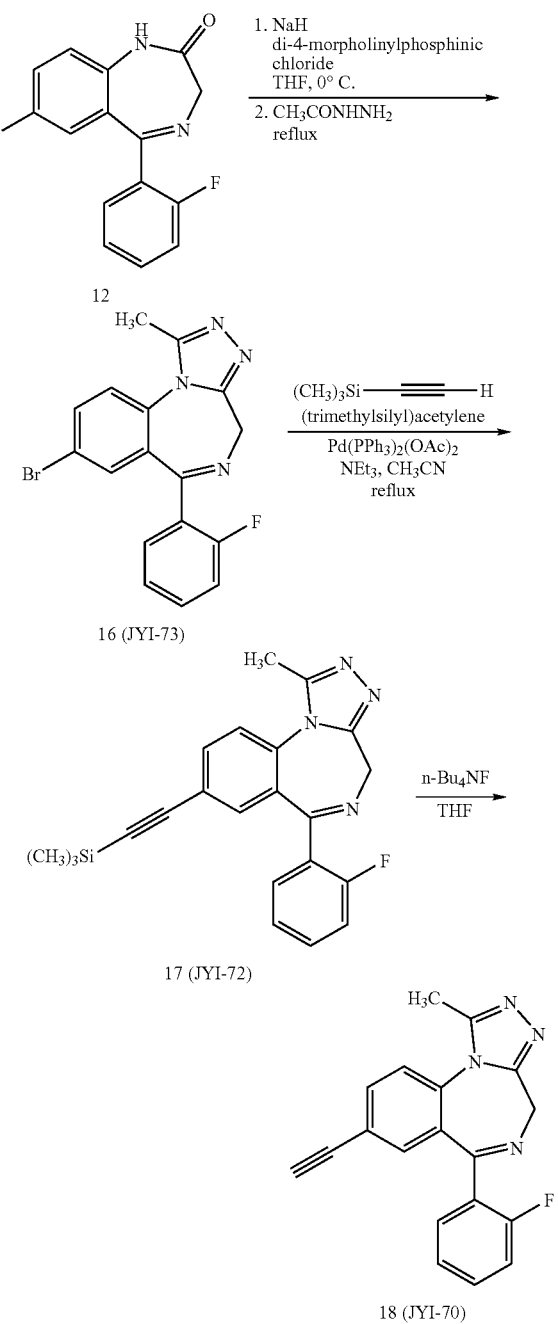

The 7-bromo-2'-fluorobenzodiazepine 12 was stirred with sodium hydride and di-4-morpholinylphosphinic chloride, followed by addition of acetic hydrazide, according to the published procedure[3] to provide triazolobenzodiazepine 16 (JYI-73), as illustrated in Scheme 5. This compound 16 underwent the palladium-mediated Heck-type coupling reaction with trimethylsilylacetylene to furnish the 8-trimethylsilyl substituted analog 17 (JYI-72). Removal of the silyl group from 17 furnished the 8-acetyleno triazolobenzodiazepine 18 (JYI-70).

Procedure:

8-Bromo-1-methyl-6-(2'-fluorophenyl)-4H-s-triazolo[4,3-a][1,4]benzodiazepine 16 (JYI-73). A solution of 12 (JYI-032, 7.0 g, 21.0 mmol) in THF (50 mL) was cooled in ice-water, and sodium hydride (0.72 g, 18 mmol) was added in one portion. After 1 hour, di-4-morpholinylphosphinic chloride (4.84 g, 22.5 mmol) was added, and the solution which resulted was stirred continuously for 2 hours at room temperature. To this mixture was then added a solution of acetic hydrazide (2.47 g, 30 mmol) in n-BuOH (20 mL) and stirring was continued at room temperature for 15 min. The solvents were evaporated and the residue was dissolved in n-BuOH (25 mL) and heated to reflux for 2 hours. n-Butanol was evaporated and the residue was partitioned between $CH_2Cl_2$ and brine. The $CH_2Cl_2$ layer was dried and removed under reduced pressure after which the residue was purified by flash chromatography (silica gel, EtOAc) to afford 16 (JYI-73, 2.2 g, 40%) as a white solid: mp 213-214° C.; IR (KBr) 1610, 1484, 1426, 1314 cm$^{-1}$; $^1$H NMR (DMSO-d$_6$) δ 2.56 (s, 3 H), 4.28 (d, 1 H, J=12.9 Hz), 5.26 (d, 1 H, J=12.9 Hz), 7.24 (t, 1 H, J=8.3 Hz), 7.29 (t, 1 H, J=7.2 Hz), 7.35 (s, 1 H), 7.43-7.60 (m, 2 H), 7.83 (d, 1 H, J=8.7 Hz), 7.98 (dd, 1 H, J=8.7 Hz and 2.3 Hz); MS (EI) m/e (relative intensity) 371 (5), 341 (34), 222 (100), 195 (19), 181 (28), 111 (72). Anal. Calcd. for $C_{17}H_{12}N_4FBr$: C, 55.01; H, 3.26; N, 15.09. Found: C, 54.76; H, 3.29; N, 14.74.

8-Trimethylsilylacetylenyl-1-methyl-6-(2'-fluorophenyl)-4H-s-triazolo[4,3-a][1,4]-benzodiazepine 17 (JYI-72). A mixture of bromide 16 (JYI-73, 1.40 g, 3.8 mmol), trimethylsilylacetylene (0.65 g, 6.6 mmol) and bis(triphenylphosphine)palladium (II) acetate (0.25 g, 0.33 mmol) in a mixed solvent system of $CH_3CN$ (80 mL) and anhydrous triethylamine (50 mL) was heated to reflux under argon. After stirring for 2 hours at reflux, the mixture was cooled to room temperature and the precipitate which formed was removed by filtration. The filtrate was concentrated under reduced pressure and the residue was treated with a saturated aqueous solution of $NaHCO_3$ (40 mL), and extracted with $CHCl_3$ (3×50 mL). The combined organic extracts were washed with brine (2×10 mL) and dried ($Na_2SO_4$). After removal of solvent under reduced pressure, the residue was purified by flash chromatography (silica gel, EtOAc) to afford 17 (JYI-72, 1.15 g, 77%) as a gray solid: mp 218-219° C.; IR (KBr) 2958, 2157, 1612, 1537, 1493, 1452, 1317, 1249 cm$^{-1}$; $^1$H NMR (DMSO-d$_6$) δ 0.21 (s, 9 H), 2.56 (s, 3 H), 4.23 (s, 1 H, J=12.9 Hz), 7.26 (t, 1 H, J=8.4 Hz), 7.29-7.83 (m, 6 H); MS (EI) m/e (relative intensity) 388 (65), 373 (14), 359 (77), 304 (44), 152 (100). Anal. Calcd. for $C_{22}H_{21}N_4SiF.0.7H_2O$: C, 65.87; H, 5.62; N, 13.94. Found: C, 65.88; H, 5.34; N, 13.94.

8-Acetyleno-1-methyl-6-(2'-fluorophenyl)-4H-s-triazolo[4,3-a][1,4]benzodiazepine 18 (JYI-70). A solution of 17 (JYI-72, 2.0 g, 5 mmol) in THF (20 mL) was treated with $Bu_4NF$ (4 mL, 1.0M solution in THF). The mixture which resulted was allowed to stir for 5 min at room temperature after which the mixture was added to $H_2O$ (20 mL) and extracted with $CH_2Cl_2$ (3×50 mL). The combined organic extracts were washed with brine (2×15 mL) and dried ($Na_2SO_4$). After removal of solvent under reduced pressure, the residue was purified by flash chromatography (silica gel, EtOAc/MeOH: 100/1) to afford 18 (JYI-70, 1.1 g, 70%) as a pale yellow solid: mp>250° C. (dec); IR (KBr) 3205, 1612, 1493, 1426, 1317 cm$^{-1}$; $^1$H NMR (DMSO-d$_6$) δ 2.54 (s, 3 H), 4.22 (d, 1 H, J=12.9 Hz), 4.39 (s, 1 H), 5.26 (d, 1 H, J=12.9 Hz), 7.22 (t, 1 H, J=8.3 Hz), 7.32-7.55 (m, 4 H), 7.97 (m, 2 H); MS (EI) m/e (relative intensity) 316 (72), 287 (100), 246 (69), 153 (16), 127 (62). Anal. Calcd. for $C_{19}H_{13}N_4F.0.6 CH_3OH$: C, 70.16; H, 4.37; N, 16.55. Found: C, 69.98; H, 4.31; N, 16.70.

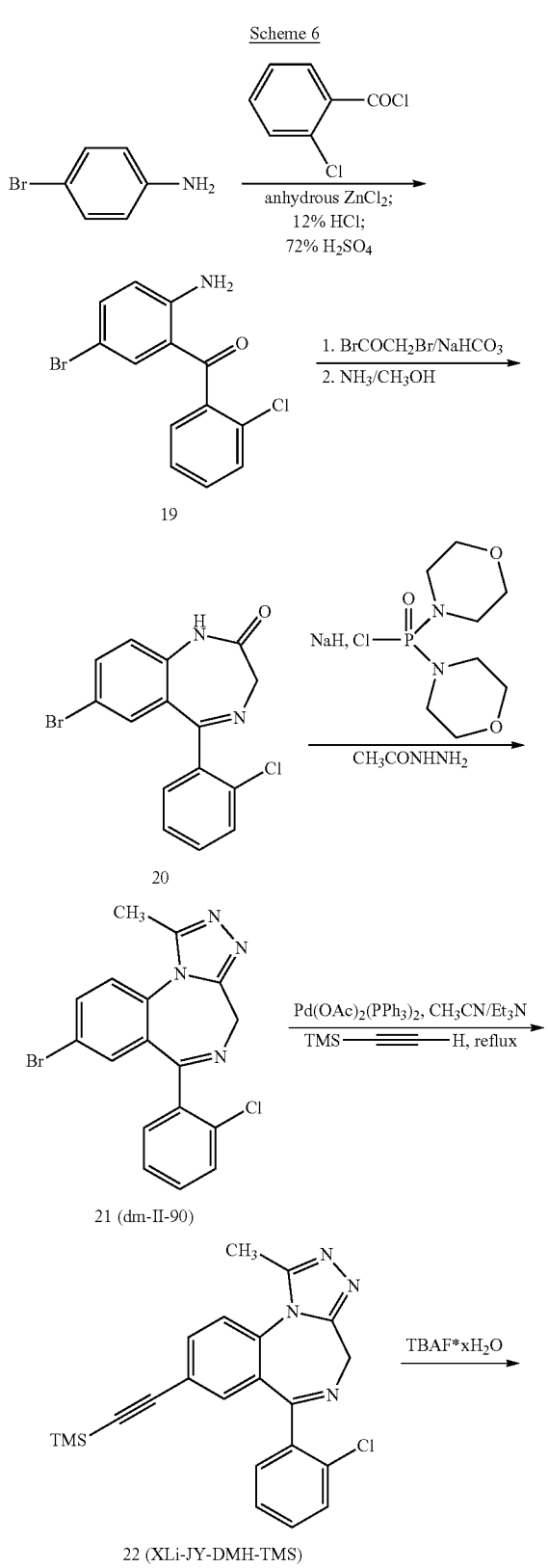

Scheme 6

-continued

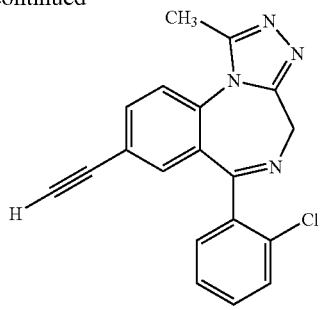

23 (XLi-JY-DMH)

2-Amino-5-bromo-2'-chlorobenzophenone 19 was obtained from simple starting materials, 4-bromoaniline and 2-chlorobenzoyl chloride, according to the improved conditions in the literature. The benzodiazepine 20, available from reference 1, was stirred with sodium hydride and di-4-morpholinophosphinic chloride, followed by addition of acetylhydrazide to furnish triazolobenzodiazepine 21 (dm-II-90). The ligand 22 (XLi-JY-DMH-TMS) was obtained by a Heck coupling reaction of 21 (dm-II-90) with trimethylsilylacetylene. This compound was converted into acetylene 23 (XLi-JY-DMH) on stirring with fluoride anion as shown in Scheme 6.

2-Amino-5-bromo-2'-chlorobenzophenone 19. 2-Chlorobenzoyl chloride (177 mL, 1.4 mol) was cooled in a 2-L flask equipped with a condenser and a thermometer to 0° C. with an ice-water bath and 4-bromoaniline (100 g, 0.58 mol) was added to the cooled solution. The mixture was heated to 120° C. and kept at this temperature for 1 h until analysis by TLC indicated 4-bromoaniline had been consumed (EtOAc: hexane, 1:4). The solution was heated to 160° C. and anhydrous $ZnCl_2$ (95 g, 0.70 mol, flamed dried) was added in one portion. The temperature was increased to 195° C. and stirring was maintained at this temperature for 3 hr until no more bubbles were evolved. The mixture was cooled to 120° C. and aq HCl (12%, 350 mL) was added dropwise slowly. The mixture was kept at reflux for 20 min, after which the aq layer was poured off. This procedure with aq HCl was repeated 4 times. Water (350 mL) was then added, and the mixture held at reflux for 20 min and then the water was poured off. This was repeated several times until the solid was not a block any more. Then $H_2SO_4$ (72%, 700 mL) was added to the residue and the mixture was heated to reflux for about 1 hr until the reaction mixture became a homogeneous dark colored solution. The hot acidic solution was poured into a mixture of ice and water with stirring. The precipitate which resulted was filtered and washed with a large amount of cold water until the pH value of the solid was about 6. The solid was then suspended in ice water and aq NaOH (40%, 290 mL) was added carefully. The mixture which resulted was stirred for 2 hrs. The solid was filtered and washed with ice water. The suspension of the solid in ice water was adjusted carefully to approximately pH=3 with aq $H_2SO_4$ (40%) dropwise. The solid which remained was filtered and washed with water to neutrality. The yellow solid 19 (66.1 g, 37.0%) was dried and used directly in the next step without further purification. $^1$H NMR (300 MHz, $CDCl_3$) δ 6.49 (s, br, 2H), 6.65 (d, 1H, J=8.82 Hz), 7.26-7.8 (m, 6H).

8-Bromo-5-(2'-chlorophenyl)-1-methyl-4H-s-triazolo[4,3-a]-1,4-benzodiazepine 21 (dm-II-90). A solution of benzodiazepine 20 (20 g, 57 mmol, available from reference 1) in dry THF (250 mL) was cooled to −5° C. and a 60% dispersion of sodium hydride (3.66 g, 92 mmol) was added in one portion. The mixture was allowed to warm to rt with stirring and the stirring was continued at rt until no more bubbles were evolved. The suspension was cooled to −5° C. after which di-4-morpholinylphosphinic chloride (21.8 g, 86 mmol) was added and this mixture was stirred for 30 min and allowed to warm to rt. The mixture was stirred for an additional 1.5 hr. To the mixture was then added a solution of acetylhydrazide (9.42 g, 114 mmol) in butanol (60 mL) and stirring was continued at rt for 10 min. The solvent was removed under reduced pressure and the residue was taken up in butanol (100 mL) and held at reflux for 2 hr. Butanol was removed under reduced pressure and the residue was partitioned between $CH_2Cl_2$ (200 mL) and $H_2O$ (100 mL). The aq layer was extracted 4 times and the organic layers combined. The organic layer was washed with brine and dried ($Na_2SO_4$). After the solvent was removed under reduced pressure, the residue was crystallized from EtOAc-$Et_2O$ to provide the pure triazolobenzodiazepine 21 (dm-II-90, 14 g, 63.2%) as a yellow solid: mp 265-267° C. [lit 274-275° C.]$^{(10)}$; IR (KBr) 3120 (br.), 1686, 1479, 1386, 1014, 827, 747 cm$^{-1}$; $^1$H NMR (300 MHz, $CDCl_3$) δ 2.42 (s, 1H), 4.18 (d, 1H, J=12.9 Hz), 5.56 (d, 1H, J=12.9 Hz), 7.36 (m, 3H), 7.43 (m, 2H), 7.61 (m, 1H), 7.80 (dd, 1H, J=2.1 Hz, 8.7 Hz); MS (EI) m/e (rel intensity) 386 (M$^+$, 45), 357 (100); Anal. Calcd. For $C_{17}H_{12}N_4BrCl.0.5H_2O$: C, 51.65; H, 3.32; N, 14.18. Found C, 51.95; H, 2.97; N, 13.91.

8-Trimethylsilylacetylenyl-5-(2'-chlorophenyl)-1-methyl-4H-s-triazolo-[4,3-a]-1,4-benzodiazepine 22 (XLi-JY-DMH-TMS). A mixture of 21 (7.75 g, 20 mmol), acetonitrile (600 mL), triethylamine (500 mL) and bis(triphenylphosphine)-palladium (II) acetate (1.2 g, 1.6 mmol) was degassed. Tri-methylsilylacetylene (5.65 mL, 40 mmol) was then added and the solution was degassed again. The solution was then heated to reflux for 4 hr until analysis by TLC indicated the starting material had disappeared. The mixture was cooled to rt and concentrated under reduced pressure. The residue was partitioned between $H_2O$ (50 mL) and EtOAc (2×200 mL). The combined organic layer was washed with brine and dried ($Na_2SO_4$). The residue was purified by flash chromatography on silica gel ($CHCl_3$) to furnish the trimethylsilyl analogue 22 (XLi-JY-DMH-TMS, 3 g, 37.0%) as white solid: mp 265-267° C.; IR (KBr) 2930, 1618, 1554, 1497, 1429, 1316, 885, 847 cm$^{-1}$; $^1$H NMR (300 MHz, $CDCl_3$) δ 0.24 (s, 9H), 2.65 (s, 3H), 4.15 (d, 1H, J=12.9 Hz), 5.52 (d, 1H, J=12.9 Hz), 7.35-7.45 (m, 5H), 7.61 (m, 1H), 7.72 (dd, 1H, J=1.8 Hz, 8.4 Hz); MS (EI) m/e (rel intensity) 404 (M$^+$, 90), 375 (100); Anal. Calcd. For $C_{22}H_{21}N_4SiCl$: C, 65.33; H, 5.24; N, 13.86. Found: C, 64.99; H, 4.98; N, 13.79.

8-Acetyleno-5-(2'-chlorophenyl)-1-methyl-4H-s-triazolo-[4,3-a]-1,4-benzodiazepine 23 (XLi-JY-DMH). A solution of benzodiazepine 22 (1.25 g, 31 mmol) in THF (250 mL) was cooled to −30° C. and treated with $Bu_4NF.xH_2O$ (0.97 g, 37 mmol). After the mixture was stirred for 5 min, analysis by TLC (silica gel; EtOAc:EtOH 4:1) indicated starting material had disappeared. Water (70 mL) was then added and the mixture was allowed to warm to rt. The mixture was then extracted with EtOAc (2×200 mL). The organic layer was washed with brine and dried ($Na_2SO_4$). After removal of the solvent under reduced pressure, the residue was washed successively with ethyl ether, ethyl acetate and chloroform. After drying, the title compound 23 (XLi-JY-DMH) was obtained (1.0 g, 97.3%) as a white solid: mp>250° C. (dec); IR (KBr) 3185, 1623, 1543, 1497, 1429, 756 cm$^{-1}$; $^1$H NMR (300 MHz, $CDCl_3$) δ 2.65 (s, 3H), 3.17 (s, 1H), 4.18 (d, 1H, J=12.9 Hz), 5.54 (d, 1H, 12.9 Hz), 7.34 (m, 2H), 7.41-7.45 (m, 3H), 7.6 (m, 1H), 7.75 (dd, 1H, J=1.8 Hz, 8.4 Hz); MS (EI) m/e (rel intensity) 332 (M$^+$, 78) 303 (100).

Scheme 7

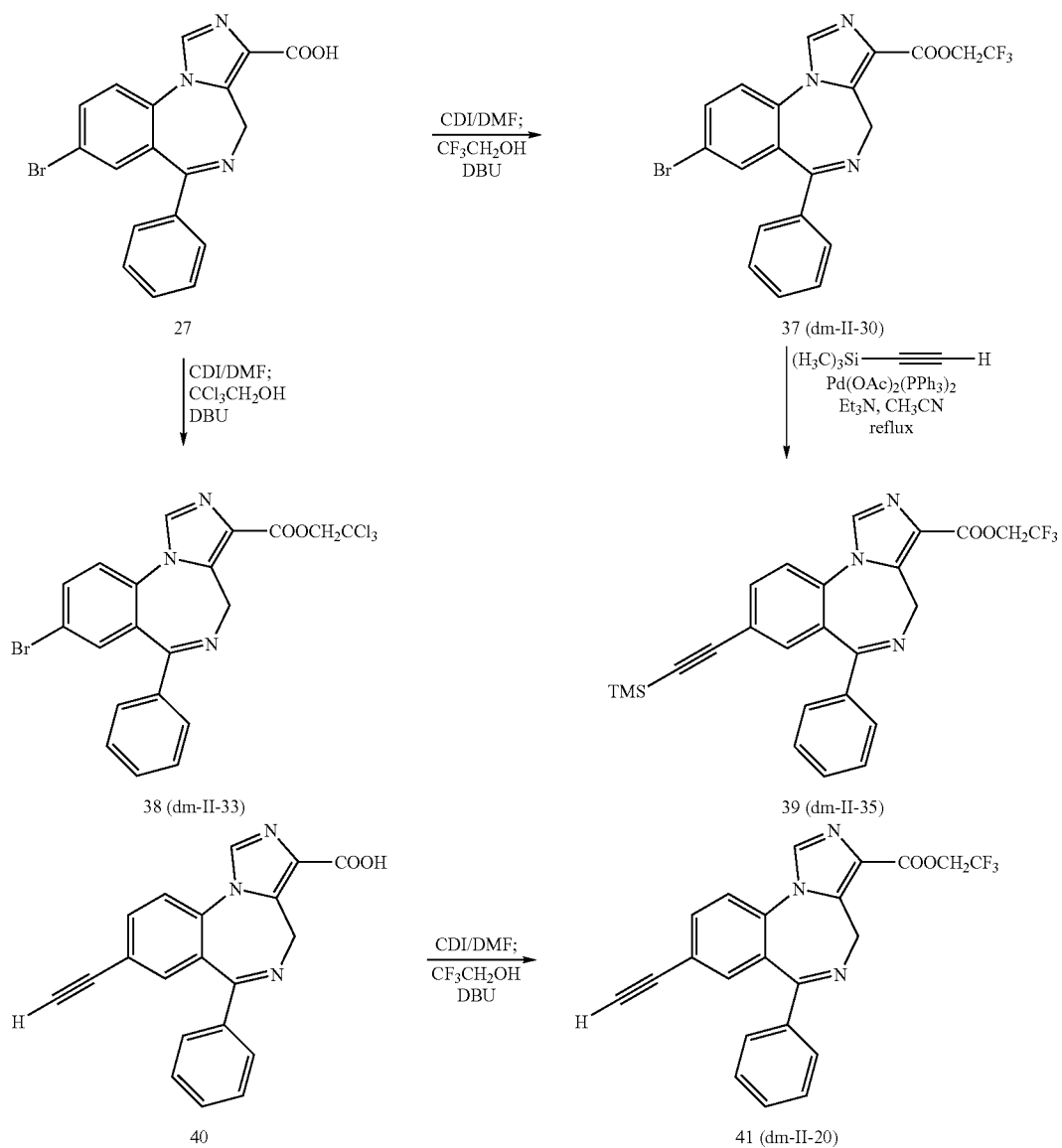

Esters 37 (dm-II-30), 38 (dm-II-33) and 41 (dm-II-20) were prepared according to the general procedure described from the starting acids and different alcohols, respectively. The bromide 37 was converted into the trimethlyacetylenyl compound 39 (dm-II-35) under standard conditions (Pd-mediated, Heck-type coupling) (Scheme 7).

General Procedure for Preparing the Esters. The acid was dissolved in DMF (10 mL/mmol S.M.) and CDI (1.2 eq) was added. The reaction mixture was stirred at room temperature for 3 h followed by addition of the alcohol (10 eq) and DBU (1 eq). The stirring was maintained until the disappearance of all the starting material as determined by TLC (EtOAc:EtOH 4:1). The reaction mixture was then quenched by adding water. The solid which precipitated was filtered and washed with ethyl ether. It was purified by flash chromatography (EtOAc) on silica gel or neutral aluminum oxide for ester 38.

Trifluoroethyl 8-bromo-6-phenyl-4H-benzo[f]imidazo[1, 5-a][1,4]diazepine-3-carboxylate 37 (dm-II-30). A white solid (69.1%) from acid 27 and 2,2,2-trifluoroethanol: mp 202-204° C.; IR (KBr) 3114, 1711, 1608, 1495, 1368, 1288, 1158 cm$^{-1}$; $^1$H NMR (300 MHz, CDCl$_3$) δ 4.10 (d, 1H, J=12.6 Hz), 4.68 (m, 1H), 4.85 (m, 1H), 6.02 (d, 1H, J=12.6 Hz), 7.41-7.54 (m, 6H), 7.62 (d, 1H, J=2.1 Hz), 7.83 (dd, 1H, J=2.1 Hz, 8.4 Hz), 7.97 (s, 1H); MS (EI) m/e (rel intensity) 463 (M$^+$, 14), 465 (14).

Trichloroethyl 8-bromo-6-phenyl-4H-benzo[f]imidazo[1, 5-a][1,4]diazepine-3-carboxylate 38 (dm-II-33). A white solid (90.9%) from acid 27 and 2,2,2-trichloroethanol: mp 113-116° C.; IR (KBr) 3434, 1728, 1610, 1493, 1270, 1146, 1128 cm$^{-1}$; $^1$H NMR (300 MHz, CDCl$_3$) δ 4.11 (d, 1H, J=12.6 Hz), 4.91 (d, 1H, J=12.0 Hz), 5.19 (d, 1H, J=12.0 Hz), 6.12 (d, 1H, J=12.6 Hz), 7.41-7.54 (m, 6H), 7.61 (d, 1H, J=2.1 Hz), 7.83 (dd, 1H, J=2.1 Hz, 8.4 Hz); MS (EI) m/e (rel intensity) 511 (M$^+$, 45).

Trifluoroethyl 8-trimethylsilylacetylenyl-6-phenyl-4H-benzo[f]imidazo[1,5-a][1,4]diazepine-3-carboxylate 39 (dm-II-35). A white solid (49.8%): mp 107-110° C.; IR (KBr) 2961, 1734, 1611, 1560, 1497, 1251, 1159, 1120, 846 cm$^{-1}$; $^1$H NMR (300 MHz, CDCl$_3$) δ 0.25 (s, 9H), 4.08 (d, 1H, J=12.3 Hz), 4.69 (m, 1H), 4.84 (m, 1H), 5.98 (d, 1H, J=12.3

Hz), 7.39-7.57 (m, 7H), 7.76 (dd, 1H, J=1.8 Hz, 8.4 Hz); MS (EI) m/e (rel intensity) 481 (M+, 100).

Trifluoroethyl 8-acetylenyl-6-phenyl-4H-benzo[f]imidazo[1,5-a][1,4]diaze-pine-3-carboxylate 41 (dm-II-20). A white solid (36.9%) from acid 40 and 2,2,2-trifluoroethanol: mp 188-190° C.; IR (KBr) 3443, 3277, 1710, 1600, 1492, 1366, 1280, 1156 cm$^{-1}$; $^1$H NMR (500 MHz, CDCl$_3$) δ 3.18 (s, 1H), 4.08 (d, 1H, J=12.5 Hz), 4.67 (m, 1H), 4.82 (m, 1H), 5.98 (d, 1H, J=12.5 Hz), 7.37-7.40 (m, 2H), 7.44-7.51 (m, 3H), 7.56-7.59 (m, 2H), 7.78 (dd, 1H, J=1.5 Hz, 8.5 Hz); MS (EI) m/e (rel intensity) 409 (M+, 28). Anal. Calcd. For C$_{22}$H$_{14}$N$_3$O$_2$F$_3$.0.25H$_2$O: C, 63.82; H, 3.72; N, 10.16. Found: C, 63.89; H, 3.37; N, 9.94.

Scheme 8:

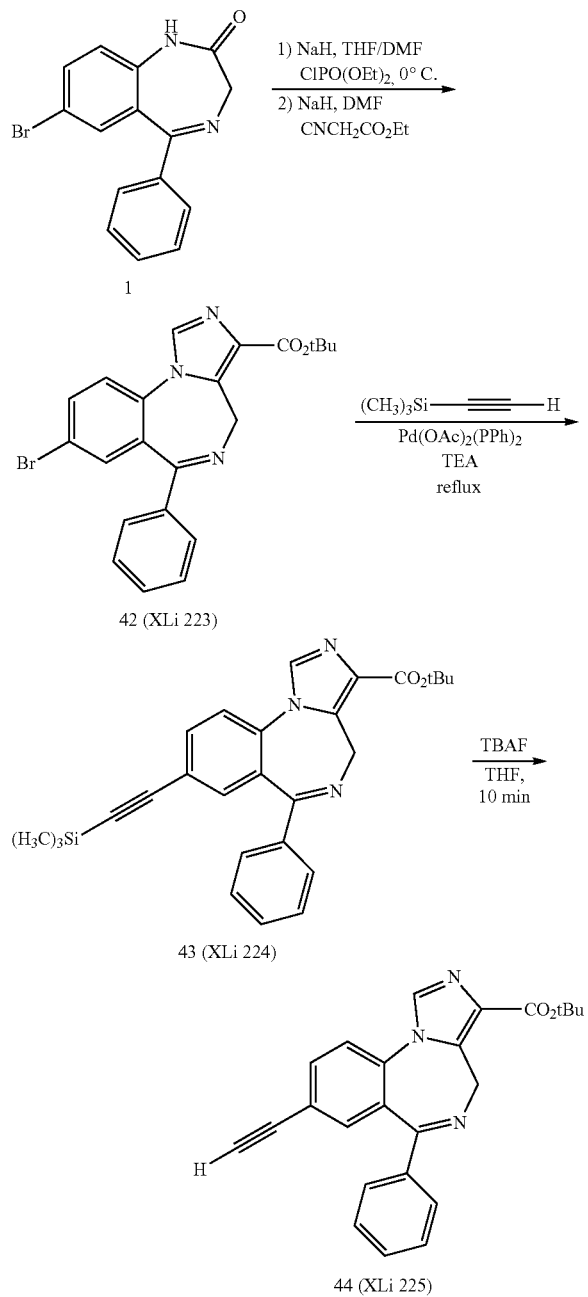

The bromide 1 was reacted with diethylphosphorochloridate in the presence of sodium hydride, followed by addition of t-butyl isocyanoacetate to provide the ester 42. This was converted into the trimethylsilylacetyleno compound 43 under standard conditions (Pd-mediated, Heck-type coupling). Treatment of 43 with fluoride gave the title compound 44.

Procedure for XL1225:

t-Butyl 8-bromo-6-phenyl-4H-benzo[f]imidazo[1,5-a][1,4]diazepine-3-carboxylate 42. This benzodiazepine 42 was obtained in 40% yield from 1 analogous to the literature procedure as a white solid. 42 (XLi223): mp: 222°-223° C.; IR (KBr) 2975, 2358, 1717, 1608, 1557, 1277, 1073, 908, 696, 652 cm$^{-1}$; $^1$H NMR (CDCl$_3$) δ 1.60 (s, 9H), 4.03 (d, 1H, J=12.5 Hz), 6.08 (d, 1H, J=12.4 Hz), 7.35-7.52 (m, 7H), 7.58 (d, 1H, J=2.2 Hz), 7.80 (dd, 1H, J=2.22 Hz and 8.55 Hz), 7.93 (s, 1H);

t-Butyl-8-trimethylsilylacetylenyl-6-phenyl-4H-benzo[f]imidazo[1,5-a][1,4]-diazepine-3-carboxylate 43 (XLi 224). A mixture of bromide 42 (1 g, 2.28 mmol, trimethylsilylacetylene (559 mg, 5.69 mmol) and bis(triphenylphosphine)-palladium-(II) acetate (55 mg, 0.073 mmol) in a mixed solvent system of CH$_3$CN (15 mL) and anhydrous TEA (25 mL) was heated to reflux under argon. After stirring for 6 hours at reflux, the mixture was cooled to room temperature and the precipitate which formed was removed by filtration. The filtrate was concentrated under reduced pressure and the residue was treated with a saturated aqueous solution of NaHCO$_3$ (20 mL), and extracted with CHCl$_3$ (3×25 mL). The combined extracts were washed with brine and dried (Na$_2$SO$_4$). After removal of solvent under reduced pressure, the residue was purified by flash chromatography (silica gel, EtOAc) to afford 43 (XLi224) as a white solid (710 mg, 68.9%). mp: 234°-236° C.; IR (KBr) 2973, 2357, 2154, 1719, 1611, 1493, 1366, 1250, 1152, 1075, 946, 880 cm$^{-1}$; $^1$H NMR (CDCl$_3$) δ 0.23 (s, 9H), 1.64 (s, 9H), 4.05 (d, 1H, J=12.7 Hz), 6.06 (d, 1H, J=12.4), 7.37-7.53 (m, 7H), 7.73 (dd, 1H, J=1.95 and 8.25 Hz), 7.92 (s, 1H); MS (EI) m/e (relative intensity) 427 (M+, 76), 412 (5), 381 (55), 353 (100) 303 (10), 287 (7).

t-Butyl 8-acetylenyl-6-phenyl-4H-benzo[f]imidazo[1,5-a][1,4]diazepine-3-carboxylate 44 (XLi 225). A solution of 43 (128 mg, 0.281 mmol), in THF (15 mL) was treated with Bu$_4$NF.H$_2$O (100.04 mg, 0.38 mmol). The mixture which resulted was allowed to stir for 5 min at room temperature after which the mixture was added to H$_2$O (10 mL) and extracted with EtOAc (3×15 mL). The combined organic extracts were washed with brine (15 mL) and dried (Na$_2$SO$_4$). After removal of solvent under reduced pressure, the residue was purified by a wash column (silica gel, EtOAc) to furnish 44 (XL1225) (92 mg, 85.4%) as a white solid: mp: 221°-223° C.; IR (KBr) 3159, 3107, 2092, 1721, 1606 cm$^{-1}$; $^1$H NMR (CDCl$_3$) δ 1.62 (s, 9H), 3.21 (s, 1H), 4.12 (d, 1H, J=10.2 Hz), 6.07 (d, 1H, J=12.5 Hz), 7.35-7.53 (m, 7H), 7.73 (dd, 1H, J=1.8 Hz and 8.3 Hz), 7.92 (s, 1H).

Scheme 9

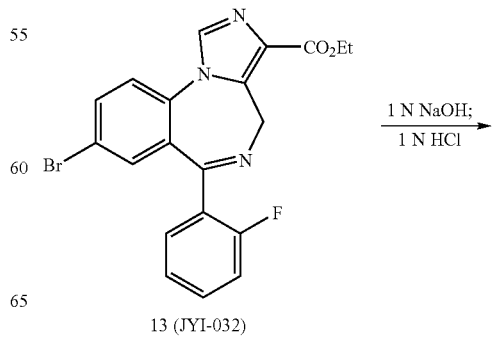

13 (JYI-032)

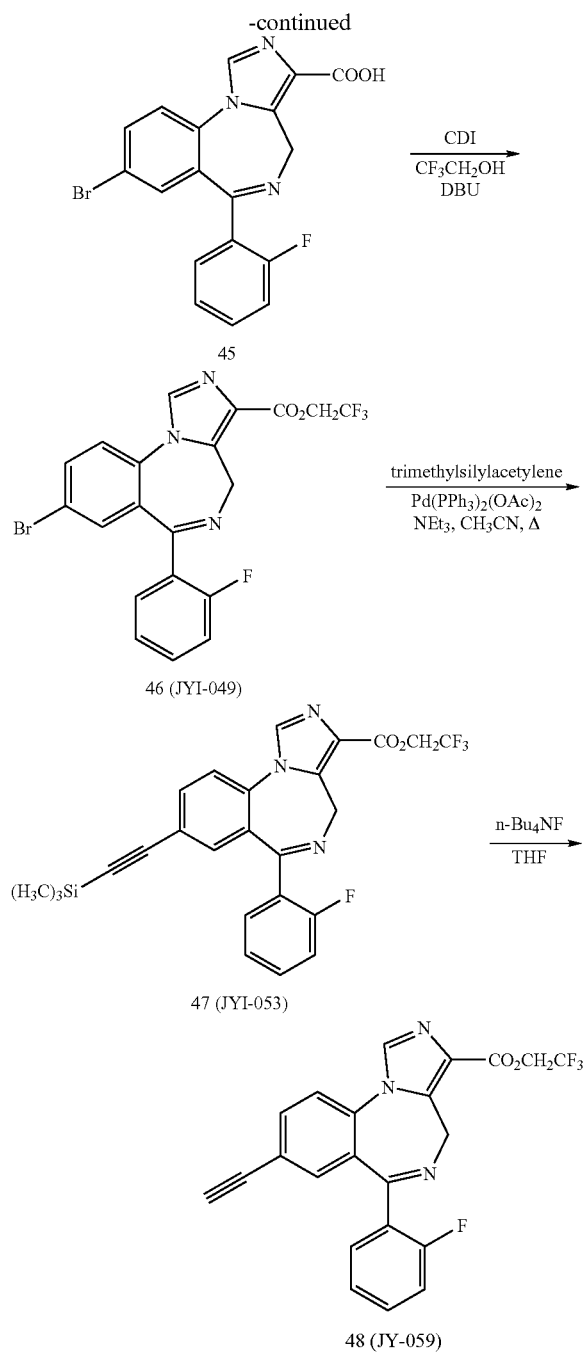

(8 mL) was added to the solution. The mixture was stirred at rt for 4 hours. After the EtOH was removed under reduced pressure, the solution was allowed to cool. The pH value was adjusted to 4 by adding 1 N HCl dropwise. The mixture was filtered and the solid was washed with cold water and ethyl ether. The solid was dried to afford 45 (0.96 g, 97%) as a white solid: mp 280° C. (dec); IR (KBr) 3419, 1740, 1611, 1491 cm$^{-1}$; $^1$H NMR (DMSO-d$_6$) δ 4.11 (bs, 1 H), 5.99 (bs, 1 H), 7.20 (t, 1 H, J=8.5 Hz), 7.32 (t, 1 H, J=7.5 Hz), 7.38 (d, 1 H, J=1.8 Hz), 7.55 (m, 2 H), 7.84 (d, 1 H, J=8.7 Hz), 7.95 (dd, 1 H, J=8.6, 1.9 Hz), 8.35 (s, 1 H). MS (EI) m/e (relative intensity) 400 (72), 399 (85), 381 (100), 355 (82).

Trifluoroethyl-8-bromo-6-(2'-fluorophenyl)-4H-benzo[f]imidazo[1,5-a][1,4]diazepine-3-carboxylate 46 (JYI-049). The carboxylic acid 45 (0.89 g, 2.23 mmol) was dissolved in dry DMF (20 mL), after which CDI (0.72 g, 4.45 mmol) was added at rt and the mixture was stirred for 12 hours. The trifluoroethanol (0.49 mL, 6.68 mmol) in DMF (1 mL) and DBU (0.37 mL, 2.45 mmol) in DMF (1 mL) were then added to the mixture and stirring continued overnight. The solvent was evaporated under reduced pressure and the residue was purified by flash chromatography (silica gel, hexanes/EtOAc: 3/1) to afford 46 (JYI-049, 0.81 g, 76%) as a white solid: mp 223-224° C.; IR (CHCl$_3$) 3063, 1732, 1611, 1492 cm$^{-1}$; $^1$H NMR (CDCl$_3$) δ 4.16 (bs, 1 H), 4.80 (bs, 2 H), 6.07 (bs, 1 H), 7.06 (dt, 1 H, J=8.3, 0.9 Hz), 7.30 (m, 2 H), 7.48 (m, 2 H), 7.68 (dt, 1 H, J=7.6, 1.8 Hz), 7.80 (dd, 1 H, J=8.6, 2.1 Hz), 8.11 (s, 1H). MS (EI) m/e (relative intensity) 483 (38), 383 (64), 355 (100). Anal. Calcd. for $C_{20}H_{12}N_3O_2F_4Br$: C, 49.81; H, 2.51; N, 8.71. Found: C, 49.97; H, 2.44; N, 8.68.

Trifluoroethyl-8-trimethylsilylacetylenyl-6-(2'-fluorophenyl)-4H-benzo[f]imidazo[1,5-a][1,4]diazepine-3-carboxylate 47 (JYI-053). A mixture of bromide 46 (JYI-049, 482 mg, 1.0 mmol), trimethylsilylacetylene (0.28 mL, 2.0 mmol) and bis(triphenylphosphine)palladium (II) acetate (75 mg, 0.1 mmol) in a mixed solvent system of CH$_3$CN (25 mL) and anhydrous triethylamine (25 mL) was heated to reflux under argon. After stirring for 12 h at reflux, the mixture was cooled to room temperature and the precipitate which formed was removed by filtration. The filtrate was concentrated under reduced pressure and the residue was treated with a saturated aq solution of NaHCO$_3$ (40 mL), and extracted with CHCl$_3$ (3×100 mL). The combined organic extracts were washed with brine (2×50 mL) and dried (Na$_2$SO$_4$). After removal of solvent under reduced pressure, the residue was purified by flash chromatography (silica gel, hexanes/EtOAc: 3/1) to afford 47 (JYI-053, 360 mg, 76%) as a gray solid: mp 220-221° C.; IR (CHCl$_3$) 2960, 1741, 1612, 1496 cm$^{-1}$; $^1$H NMR (CDCl$_3$) δ 0.25 (s, 9 H), 4.12 (bs, 1 H), 4.82 (bs, 2 H), 6.10 (bs, 1 H), 7.06 (t, 1 H, J=8.3 Hz), 7.30 (m, 1 H), 7.48 (m, 2 H), 7.56 (d, 1 H, J=8.3 Hz), 7.67 (m, 1 H), 7.73 (dd, 1 H, J=8.3, 1.8 Hz), 8.02 (s, 1 H); MS (EI) m/e (relative intensity) 499 (52), 399 (45), 371 (100), 235 (21), 178 (36). Anal. Calcd. for $C_{25}H_{21}N_3O_2F_4Si$: C, 60.11; H, 4.24; N, 8.41. Found: C, 60.27; H, 4.22; N, 8.33.

Trifluoroethyl-8-acetyleno-6-(2'-fluorophenyl)-4H-benzo[f]imidazo-[1,5-a][1,4]diazepine-3-carboxylate 48 (JYI-059). A solution of 47 (JYI-053, 475 mg, 1.0 mmol) in THF (15 mL) was treated with Bu$_4$NF (2 mL, 1.0M solution in THF). The mixture, which resulted, was allowed to stir for 5 min at room temperature after which the mixture was added to H$_2$O (5 mL) and extracted with EtOAc (3×10 mL). The combined organic extracts were washed with brine (2×10 mL) and dried (Na$_2$SO$_4$). The solvent was removed under reduced pressure and the residue was recrystallized from ethyl acetate/hexanes to afford 48 (JYI-059, 299 mg, 70%) as a pale yellow solid: mp 192-193° C.; IR (CHCl$_3$) 3295, 3052, 1741, 7-Bromo-2'-fluorobenzodiazepine 13 was hydrolyzed with aq 2 N sodium hydroxide in EtOH and acidified to pH 4 by adding 1 N HCl to afford the acid 45. The acid, obtained from the ester 13, was stirred with CDI in DMF, followed by stirring with trifluoroethanol and DBU to provide the ester 46 (JYI-049). This material 46 was heated with trimethysilylacetylene in a Heck-type coupling reaction[8] to provide the trimethylsilyl analog 47 (JYI-053). The silyl group was removed from 47 on treatment with tetrabutylammonium fluoride to furnish 48 (JYI-059) in 70% yield.

Procedure:

8-Bromo-6-(2'-fluorophenyl)-4H-benzo[f]imidazo[1,5-a][1,4]diaze-pine-3-carboxylic acid 45. The ester 13 (1.0 g, 2.36 mmol) was dissolved in EtOH (80 mL) and 2 N aq NaOH 1612, 1494, 1277, 1159 cm⁻¹; ¹H NMR (CDCl₃) δ 3.14 (s, 1 H), 4.17 (bs, 1 H), 4.78 (bs 2 H), 4.47 (s, 1 H), 6.05 (bs, 1 H), 7.05 (dt, 1 H, J=8.3, 0.8 Hz), 7.30 (m, 1 H), 7.48 (m, 2 H), 7.60 (d, 1 H, J=8.3 Hz), 7.68 (dt, 1 H, J=7.6, 1.8 Hz), 7.76 (dd, 1 H, J=10.1, 1.8 Hz), 8.02 (s, 1 H); MS (EI) m/e (relative intensity) 427 (37), 327 (26), 299 (100), 178 (50). Anal. Calcd. for C₂₂H₁₃N₃O₂F₄: C, 61.83; H, 3.07; N, 9.83. Found: C, 61.94; H, 3.03; N, 9.68.

(XHeII-053, 120 mg, 0.338 mmol) in THF (20 mL) was added. The mixture which resulted was heated to reflux for 8 hr. It was cooled to rt, after which acetic acid (40.6 mg, 0.676 mmol) was added. After the solution was stirred for 10 min, the mixture was filtered through celite. The filtrate was diluted with CH₂Cl₂ (50 mL) and washed with water, brine and dried (K₂CO₃). Evaporation of the solvent under reduced pressure afforded a pale yellow solid, which was purified by

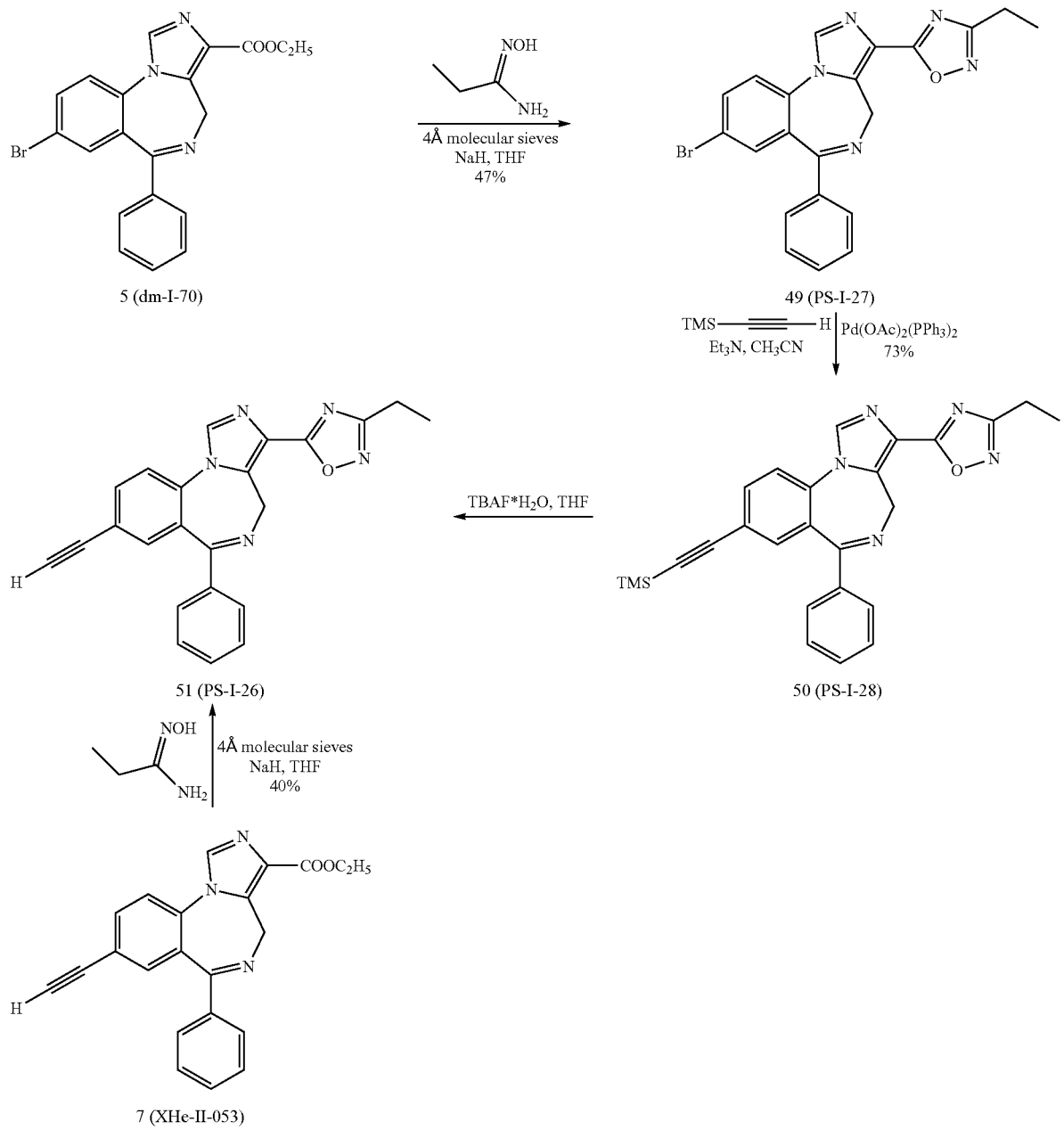

Scheme 10

Ethyl amido oxime (59.5 mg, 0.676 mmol) was added to a stirred suspension of powdered 4 Å molecular sieves (75 mg) in anhydrous THF (15 mL) under nitrogen. After the mixture was stirred at rt for 10 min, NaH (27 mg of 60% in mineral oil, 0.676 mmol) was added to the mixture. After the mixture was stirred for a further 30 min, a solution of the forgoing ester 7 flash column chromatography (silica gel, EtOAc/hexane, 2:3) to furnish 51 as a white solid (PS-I-26, 52 mg, 40%). mp: 221-222° C.; IR (KBr) 3297, 3105, 1631, 1570, 1495, 1310, 938 cm⁻¹; ¹H NMR (CDCl₃) δ 8.07 (s, 1H), 7.80 (dd, 1H, J=8.4 Hz, J=1.8 Hz), 7.64-7.60 (m, 2H), 7.53-7.37 (m, 5H), 6.12 (d, 1H, J=12.9 Hz), 4.21 (d, 1H, J=12.9 Hz), 3.20 (s, 1H), 2.88 and 2.83 (ABq, 2H, J=7.6 Hz), 1.41 (t, 3H, J=7.6 Hz); $^{13}$C NMR (CDCl$_3$) δ 171.8, 170.6, 168.8, 139.1, 136.6, 135.8, 135.4 (2C), 135.1, 130.7, 129.3 (2C), 128.3 (2C), 128.1, 124.7, 122.7, 121.6, 81.2, 80.0, 44.7, 19.7, 11.5; MS (m/z) 379 (100).

193-194° C.; IR (KBr) 3106, 2960, 2149, 1630, 1567, 1493, 938, 851, 701 cm$^{-1}$; $^1$H NMR (300 Hz, CDCl$_3$) δ 8.07 (s, 1H), 7.78 (dd, 1H, J=1.86, 8.34 Hz), 7.61-7.38 (m, 7H), 6.11 (d, J=12.78 Hz), 4.19 (d, J=12.78 Hz), 2.88 and 2.83 (ABq, 2H, J=7.56 Hz), 1.41 (t, 3H, J=7.56 Hz), 0.25 (s, 9H).

Scheme 11

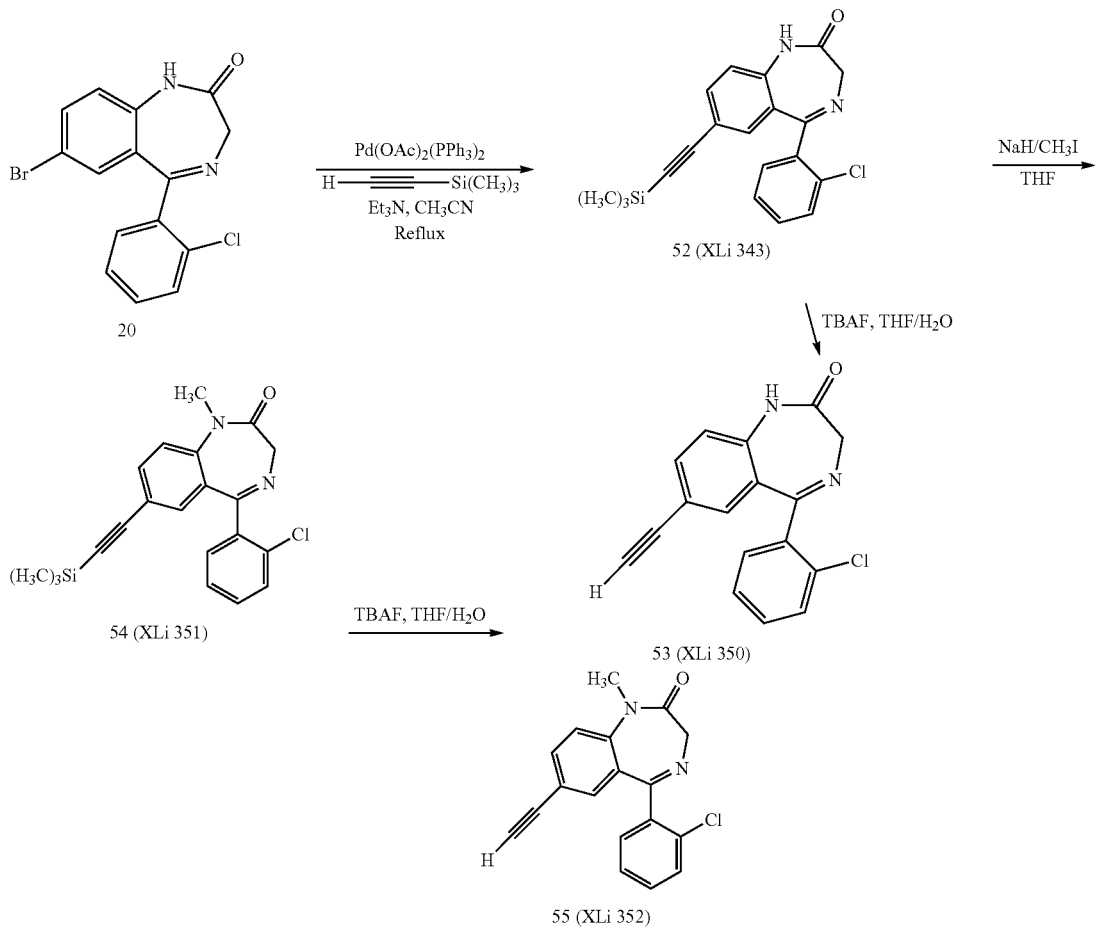

This compound 49 (PS-I-27) was obtained in 47% yield from 5 (dm-I-70) analogous to the procedure employed in Scheme 10 as a white solid. mp: 210° C.; IR (KBr) 3106, 1631, 1563, 1493, 1147, 931, 698 cm$^{-1}$; $^1$H NMR (CDCl$_3$) δ 8.06 (s, 1H), 7.84 (dd, 1H, J=8.6 Hz, J=2.25 Hz), 7.63-7.38 (m, 7H), 6.13 (d, 1H, J=12.9 Hz), 4.21 (d, 1H, J=12.9 Hz), 3.20 (s, 1H), 2.88 and 2.83 (ABq, 2H, J=7.6 Hz), 1.41 (t, 3H, J=7.6 Hz); MS (m/z) 435 (100).

To the suspension of compound 49 (PS-I-27, 0.5 g, 1.15 mmol) in acetonitrile (30 mL) and triethylamine (80 mL) was added bis(triphenylphosphine)palladium (II) acetate (0.086 g, 0.115 mmol). The solution was degassed and trimethylsilylacetylene (0.33 mL, 2.3 mmol) added. The mixture was heated to reflux and stirred overnight. After removal of the solvent, the residue was dissolved in CH$_2$Cl$_2$ and washed with a saturated aqueous solution NaHCO$_3$ and brine. The organic layer was dried (Na$_2$SO$_4$) filtered and concentrated under vacuum. The residue was purified by flash column chromatography (EtOAc:hexane 2:3) to furnish the trimethylsilyl analog 50 (PS-I-28, 380 mg, 73%) as a pale yellow solid: mp:

The bromide 20 available from references 9 and 10 was reacted with trimethylsilyacetylene in the presence of a palladium catalyst to provide trimethylsilyl analog 52. This product was methylated with methyl iodide/sodium hydride to give the N-methyl benzodiazepine 54 (XLi 351). This was subjected to fluoride-mediated desilation to furnish 53 (XLi 350) and 55 (XLi 352).

Procedure for XLi 350 and XLi 352:

7-Trimethylsilylacetyleno-5-phenyl-(2'-chlorophenyl)1, 3-dihydrobenzo[e]-1,4-diazepin-2-one 52 (XLi 343). A mixture of 20 (500 mg, 1.43 mmole) available in triethyl amine (10 mL) and CH$_3$CN (16 mL) with trimethyl-silylacetylene (126 mg, 1.28 mmole) and bis(triphenylphosphine)palladium (II) acetate (64.3 mg, 0.086 mmol) was heated to reflux under nitrogen. After 6 hours, the reaction mixture was cooled to room temperature and filtered. The filtrate was concentrated under vacuum and the residue was treated with a saturated aqueous NaHCO$_3$ solution (15 mL), and extracted with CH$_2$Cl$_2$ (3×20 mL). The organic layers were combined and washed with brine and dried (Na$_2$SO$_4$). After removal of solvent under reduced pressure, the residue was purified via flash chromatography (silica gel, EtOAc/hexanes: 1/1) to furnish 52 as a yellow powder (310 mg, 59%): mp: 225.8-228.2° C.; IR (KBr) 2953, 2358, 1685, 1616, 1490, 1328, 1248, 1058, 1011, 841, 746 cm$^{-1}$, $^1$H NMR (CDCl$_3$) δ 0.21 (s, 9H), 4.38 (s, 2H), 7.41 (d. 1H, J=8.37 Hz), 7.19-7.52 (br, 7H), 8.11 (s, 1H); MS (EI) m/e (relative intensity) 366 (M$^+$, 100), 331 (59), 229(18), 161(26).

7-Acetyleno-5-phenyl-(2'-chlorophenyl)-1,3-dihydro-benzo[e]-1,4-diazepin-2-one 53 (XLi 350): A solution of 52 (150 mg, 0.408 mol) in THF (30 mL) was treated with tetrabutylammonium fluoride (1M in THF). The mixture was stirred for 20 minutes at room temperature before water (30 mL) was added. The mixture was then extracted with EtOAc (3×30 mL). The combined organic extracts were washed with brine and dried over (Na$_2$SO$_4$). The solvent was removed under vacuum and the residue which resulted was passed through a wash column (silica gel, EtOAc/hexanes: 4/1) to give 55 as light yellow crystals (110 mg, 95.2%); mp: 215° C.; IR (KBr) 3290, 1685, 1615, 1491, 1328, 731 cm$^{-1}$, $^1$H NMR (CDCl$_3$) δ 3.06 (s, 1H), 4.40 (s, 3H), 7.03-7.61 (m, 7H), 7.58-7.86 (m, 2H), 7.99 (s, 1H); MS (EI) m/e (relative intensity) 294 (M$^+$, 100), 266(75), 265(87), 259(83), 231(40), 201(24), 176(23).

1-Methyl-7-trimethylsilylacetyleno-5-phenyl-(2'-chlorophenyl)-1,3-dihydro-benzo[e]-1,4-diazepin-2-one 54 (XLi 351). A mixture of 52 (300 mg, 0.82 mmol) was dissolved in dry THF (40 mL) at 0° C. and NaH (60% in mineral oil, 50 mg, 1.25 mmol) was added to the solution in one portion. The slurry was then stirred for 20 min at 0° C. and CH$_3$I (139 mg, 0.98 mmol) was added to the mixture and it was warmed up to room temperature. After the mixture stirred for 3 hours at room temperature, the THF was then removed under reduced pressure. The residue was purified by flash chromatography [hexanes/EtOAc (1:4)] to provide the title compound 54 (260 mg, 83%) as a white solid: mp: 196.9-198° C.; IR (KBr) 2953, 1676, 1611, 1489, 1346, 1125, 1078, 913, 742 cm−1; $^1$HNMR (CDCl$_3$)δ(ppm) 0.21(s, 9H) 3.46 (s, 3H), 3.54 (d, 1H, J=10.9 Hz), 4.60 (d, 1H. J=10.8 Hz), 7.20-7.43 (m, 5H), 7.58-7.65 (m, 3H). MS (EI) m/e (relative intensity) 380(M$^+$, 8), 366(10), 308(100), 280(88), 273(97), 245(61).

1-Methyl-7-acetyleno-5-phenyl-(2'-chlorophenyl)-1,3-dihydro-benzo[e]-1,4-diazepin-2-one 55 (XLi 352): A solution of 54 (100 mg, 0.262) in THF (30 mL) was treated with tetrabutylammonium fluoride (1M in THF). The mixture was stirred for 20 minutes at room temperature before water (30 mL) was added. The mixture was then extracted with EtOAc (3×30 mL). The combined organic extracts were washed with brine and dried (Na$_2$SO$_4$). The solvent was removed under vacuum and the residue which resulted was passed through a wash column (silica gel, EtOAc/hexanes: 4/1) to give 55 as light yellow crystals (71 mg, 90%): mp: 95.6-98.1° C.; IR (KBr) 2953, 1677, 1489, 1346, 1091, 791, 749 cm$^{-1}$, $^1$H NMR (CDCl$_3$) δ (ppm) 3.05(s, 1H), 3.46 (s, 3H), 3.83 (d, 1H, J=10.5 Hz), 4.87 (d, 1H, J=9.33 Hz), 5.28 (s, 1H), 7.20-7.43 (m, 5H), 7.58-7.86 (m, 2H); MS (EI) m/e (relative intensity) 308(M$^+$, 100), 294(19), 280(82), 273(99), 249(28), 245(61), 229(29), 201(32), 189(43).

Scheme 12

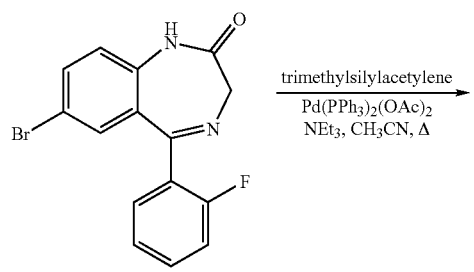

12

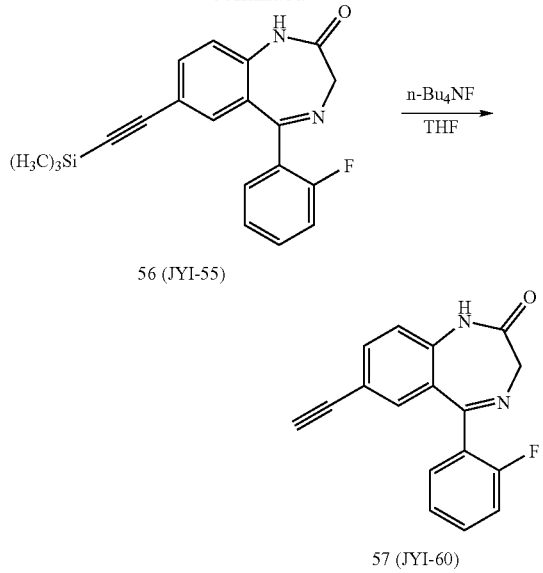

56 (JYI-55)

57 (JYI-60)

7-Trimethylsilylacetyleno-5-(2'-fluorophenyl)-1,3-dihydrobenzo[e]-1,4-diazepine-2-one 56 (JYI-55). A mixture of bromide 12 (1.6 g, 5.0 mmol), trimethylsilyl-acetylene (3.0 mL, 21.0 mmol) and bis(triphenylphosphine)palladium (II) acetate (375 mg, 0.5 mmol) in a mixed solvent system of CH$_3$CN (60 mL) and anhydrous triethylamine (40 mL) was heated to reflux under argon. After stirring for 3 h at reflux, the mixture was cooled to room temperature and the precipitate which formed was removed by filtration. The filtrate was concentrated under reduced pressure and the residue was treated with a saturated aq solution of NaHCO$_3$ (100 mL), and extracted with CHCl$_3$ (3×200 mL). The combined organic extracts were washed with brine (2×100 mL) and dried (Na$_2$SO$_4$). After removal of solvent under reduced pressure, the residue was purified by flash chromatography (silica gel, hexanes/EtOAc: 2/1) to afford 56 (JYI-55, 794 mg, 47%) as a gray solid: mp 168.5-169.5° C.; IR (CHCl$_3$) 3202, 3113, 2955, 1686, 1612, 1490 cm$^{-1}$; $^1$H NMR (CDCl$_3$) δ 0.22 (s, 9 H), 4.38 (s, 2 H), 7.04-7.33 (m, 3 H), 7.34 (s, 1 H), 7.45-7.53 (m, 1 H), 7.56-7.62 (m, 2 H), 8.73 (bs, 1 H). MS (EI) m/e (relative intensity) 350 (94), 322 (100), 167 (41), 153 (37). Anal. Calcd. for C$_{20}$H$_{19}$N$_2$OFSi: C, 68.54; H, 5.46; N, 7.99. Found: C, 68.23; H, 5.40; N, 8.34.

7-Acetyleno-5-(2'-fluorophenyl)-1,3-dihydrobenzo[e]1,4-diazepine-2-one 57 (JYI-60). A solution of 56 (JYI-55, 700 mg, 2.0 mmol) in THF (200 mL) was treated with Bu$_4$NF (2 mL, 1.0M solution in THF). The mixture, which resulted, was allowed to stir for 5 min at room temperature after which the mixture was added to H$_2$O (5 mL) and extracted with EtOAc (3×10 mL). The combined organic extracts were washed with brine (2×10 mL) and dried (Na$_2$SO$_4$). After the solvent was removed under reduced pressure, the residue was purified by flash chromatography (silica gel, hexanes/EtOAc: 2/1) to afford 57 (JYI-60, 400 mg, 72%) as a pale yellow solid: mp 208-209.5° C.; IR (CHCl$_3$) 3290, 3110, 2930, 1685, 1612, 1489 cm$^{-1}$; $^1$H NMR (CDCl$_3$) δ 3.04 (s, 1 H), 4.40 (s, 2 H), 7.06-7.28 (m, 3 H), 7.38 (s, 1 H), 7.44-7.51 (m, 1 H), 7.59-7.62 (m, 2 H), 9.43 (bs, 1 H). MS (EI) m/e (relative intensity) 278 (80), 250 (100). Anal. Calcd. for C$_{17}$H$_{11}$N$_2$OF: C, 73.37; H, 3.98; N, 10.07. Found: C, 73.64; H, 3.92; N, 9.78.

Scheme 13

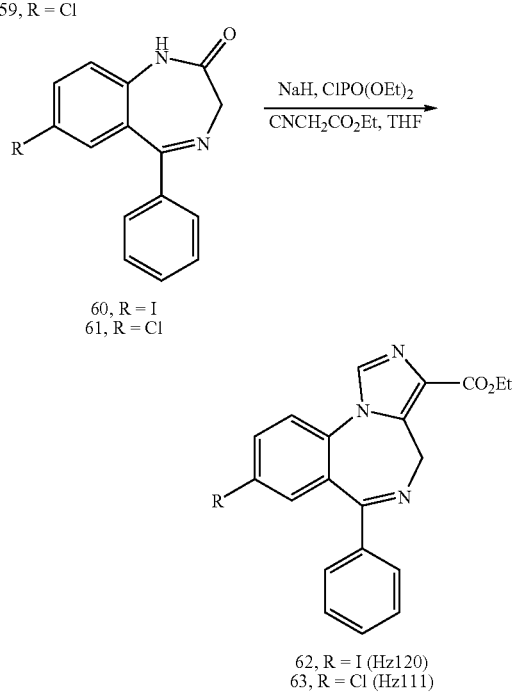

58, R = I
59, R = Cl

60, R = I
61, R = Cl

62, R = I (Hz120)
63, R = Cl (Hz111)

2-Amino-5-iodo-benzophenone was prepared from p-iodonitrobenzene and phenylacetonitrile according to the literature. 2-Amino-5-chloro-benzophenone was commercially available from Acros. The benzodiazepine 60 was reacted with diethylphosphorochloridate in the presence of sodium hydride, followed by the addition of ethyl isocyanoacetate to provide the ester 62 (Hz120), as shown in Scheme 13.

Ethyl 8-iodo-6-phenyl-4H-benzo[f]imidazo[1,5-a][1,4]diazepine-3-carboxylate 62. A solution of benzodiazepine 60 (3 g, 8.3 mmol) in dry THF (36 mL) was cooled to 0° C. and a 60% dispersion of sodium hydride (0.70 g, 17.4 mmol) was added in one portion. The mixture was allowed to warm to rt with stirring and the stirring was continued at rt until no more bubbles were evolved. The suspension was cooled to 0° C. after which diethylphosphorochloridate (2.29 g, 13.3 mmol) was added and this mixture was stirred for 30 min and allowed to warm to rt. The mixture was stirred for an additional 1.5 hr. In another flask, a 60% dispersion of sodium hydride (0.70 g, 17.4 mmol) in mineral oil was added in dry THF (36 mL) and cooled to 0° C. Ethyl isocyanoacetate (1.13 g, 9.94 mmol) was added and the stirring was continued until no more bubbles were evolved. This mixture was transferred to the above mixture at 0° C. The mixture was then stirred at rt for 6 h and quenched with HOAc (3.2 mL). The mixture was partitioned between EtOAc (200 mL) and H$_2$O (50 mL). The organic layer was washed with brine and dried (Na$_2$SO$_4$). After the solvent was removed under reduced pressure, the residue was purified by flash chromatography (silica gel, gradient elution, EtOAc:hexane 1:4, 1:1, 4:1) to provide the ester 62 (Hz120) in 43% yield as a light brown solid. mp: 221-222° C.; IR (KBr) 2977, 1717, 1608, 1489 cm$^{-1}$; $^1$H NMR (DMSO-d$_6$) δ 1.31 (t, 3H, J=7.1 Hz), 4.10 (d, 1H, J=12.5 Hz), 4.29 (q, 2H, J=6.7 Hz), 5.75 (d, 1H, J=12.4 Hz), 7.40-7.50 (m, 5H), 7.63 (d, 1H, J=1.8 Hz), 7.69 (d, 1H, J=8.5 Hz), 8.13 (dd, 1H, J=1.9, 8.5 Hz), 8.36 (s, 1H); MS (EI) m/e (relative intensity) 458 (23), 457 (M$^+$, 100), 411 (62), 384 (29), 383 (100), 257 (29). Anal. Calcd. for C$_{20}$H$_{16}$IN$_3$O$_2$: C, 52.53; H, 3.53; N, 9.19. Found: C, 52.57, H, 3.73; N, 8.64.

Ethyl 8-chloro-6-phenyl-4H-benzo[f]imidazo[1,5-a][1,4]diazepine-3-carboxylate 63. This ester 63 was obtained in 52% yield from 61 analogous to the procedure employed in Scheme 13 as a white solid. mp: 174-175° C. (lit.$^{12}$ 174-175° C.); $^1$H NMR (DMSO-d$_6$) δ 1.32 (t, 3H, J=7.1 Hz), 4.13 (d, 1H, J=12.3 Hz), 4.32 (q, 2H, J=6.7 Hz), 5.76 (d, 1H, J=12.3 Hz), 7.37-7.50 (m, 6H), 7.86-8.38 (m, 2H), 8.74 (s, 1H).

Scheme 14

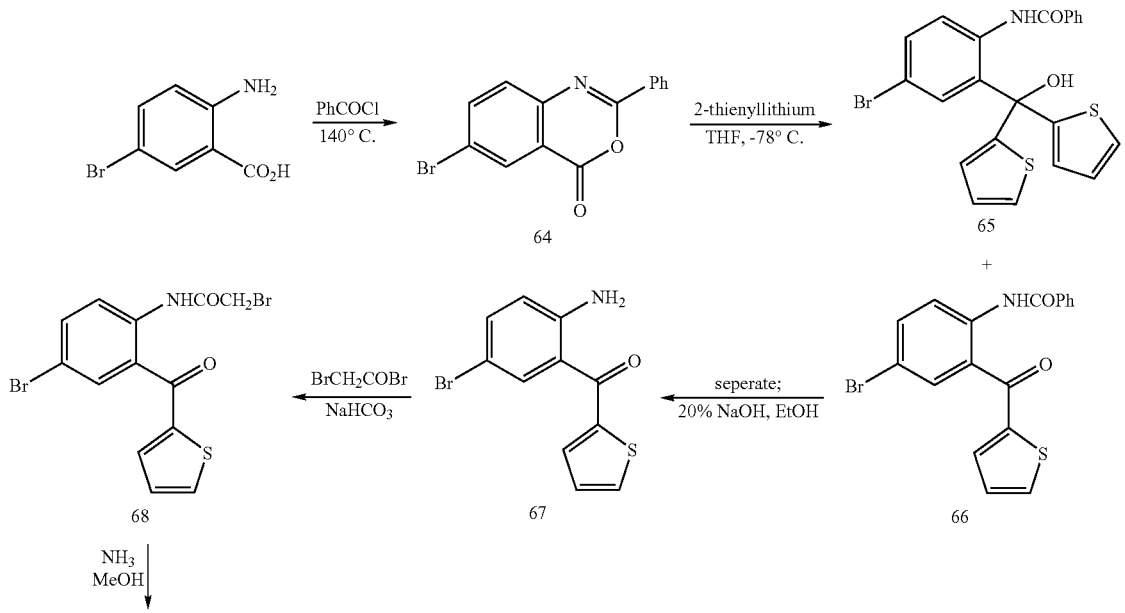

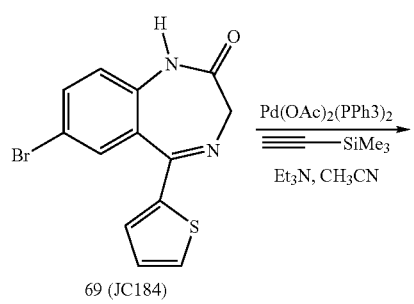
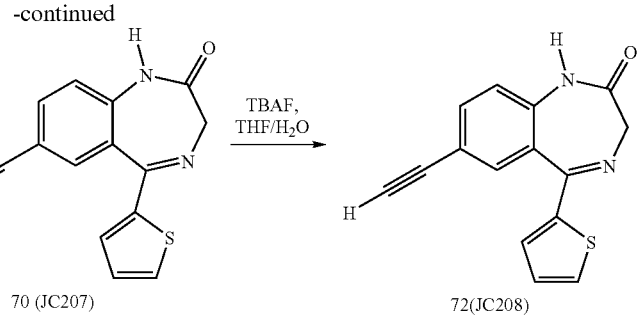
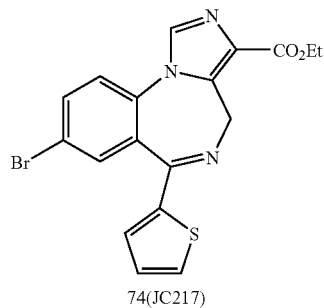
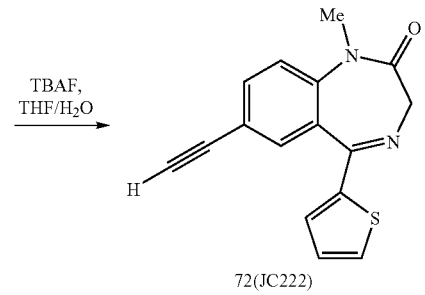
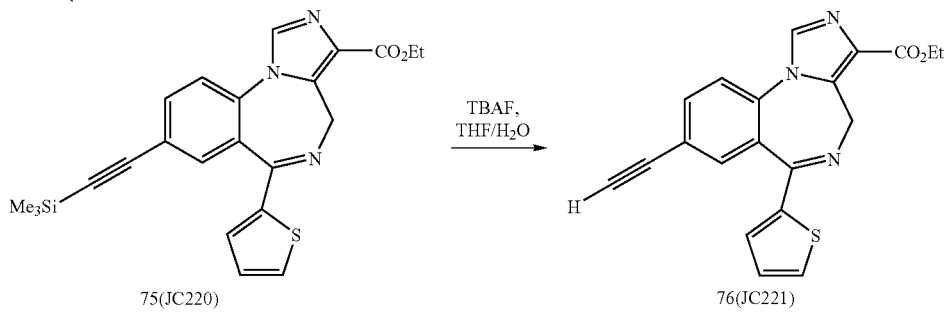

6-Bromo-2-phenyl-4H-benzo[2,3-d]-1,3-oxazin-4-one 64. The 2-amino-5-bromobenzoic acid (5 g, 23.1 mmol) was treated with benzoyl chloride (237 mL, 2.04 mol) at 140° C. for 3 h. After the reaction mixture was cooled to rt, the crystals that formed were collected by filtration and were washed with hexanes to provide 64 as light brown needles (6.8 g, 97%): $^1$H NMR (CDCl$_3$) δ 7.51-7.2 (m, 4H), 7.9 (dd, 1H, J=2.3, 8.6 Hz), 8.30-8.33 (m, 2H), 8.8 (d, 1H, J=2.2 Hz); $^{13}$C NMR (CDCl$_3$) δ 158.19, 157.35, 145.75, 139.58, 132.82, 130.97, 129.77, 128.82, 128.73, 128.29, 121.37, 118.27; MS (EI) m/e (relative intensity) 303 (M$^+$, 36), 301 (M$^+$, 36), 259 (14), 257 (14), 226 (6), 224 (6), 178 (9), 170 (9), 168 (9), 151 (4), 105 (100).

4-Bromo-2-(2'-thienylcarbonyl)-N-benzoylaniline 66 and bis-(2'-thienyl)-[5-bromo-2-(N-benzoyl)-amino]phenyl-methanol 65. The benzo-xazinone 64 (5.0 g, 16.6 mmol) was dissolved in dry THF (250 mL) and cooled to −78° C. for 45 min. The 2-thienyllithium (18.21 mL of 1M solution in THF) was added dropwise over 35 min and the reaction was stirred at −78° C. for 1.2 h. Saturated aq NH$_4$Cl solution (25 mL) and Et$_2$O (30 mL) were then added. The organic layer was separated, washed with brine and dried (MgSO$_4$). The solvent was removed under reduced pressure, and the residue was purified via flash chromatography (silica gel, hexanes/EtOAc: 1:0, 49:1, 20:1, 11:1, 5:1) to provide 66 as yellow crystals and the alcohol 65. 66: $^1$H NMR (CDCl$_3$) δ 7.23 (dd, 1H), 7.52-7.56 (m, 3H), 7.66 (dd, 1H, J=0.99, 3.8 Hz), 7.82 (d, 1H, J=5.0 Hz), 7.99-8.02 (m, 3H), 7.75 (d, 1H, J=9.0 Hz), 11.2 (s, 1H); $^{13}$C NMR (CDCl$_3$) δ 188.82, 165.45, 143.24, 138.79, 136.57, 135.90, 135.51, 134.25, 134.03, 132.17, 128.81, 128.31, 127.26, 125.65, 123.45, 114.95; MS (EI) m/e (relative intensity) 387 (M$^+$, 12), 385 (M$^+$, 12), 276 (18), 274 (18), 201 (7), 172 (7), 105 (100). 65: $^1$H NMR (CDCl$_3$) δ 4.20 (s, 1H), 6.82 (s, 2H), 6.96-7.01 (m, 3H), 7.33-7.38 (m, 7H), 7.65 (d, 2H, J=7.23 Hz), 8.43 (d, 1H, J=8.8 Hz), 9.92 (s, 1H); $^{13}$C NMR (CDCl$_3$) δ 165.04, 148.94, 136.44, 135.49, 134.49, 132.34, 131.59, 131.40, 128.40, 127.20, 126.89, 126.58, 124.18, 116.00, 79.35, 76.92, 76.50; MS (EI) m/e (relative intensity) 471 ($M^+$, 54), 469 ($M^+$, 51), 453 (100), 451 (93), 348 (98), 346 (92), 316 (54), 314 (58), 282 (20), 280 (19), 267 (88), 235 (12), 234 (12), 223 (15), 222 (17), 201 (56), 173 (20), 172 (12), 158 (10), 129 (10).

5-Bromo-2-(2'-thienylcarbonyl)aniline 67. The amide 66 (2 g, 635 mmol) was dissolved in EtOH (150 mL) and 20% NaOH solution (30 mL) was added. The mixture was heated to reflux for 5 h and the EtOH was removed under reduced pressure. The mixture was extracted with EtOAc and the organic phases were combined, washed with brine and dried ($Na_2SO_4$). The solvent was removed under reduced pressure, and the residue was purified via a wash column (silica gel, hexanes/EtOAc: 11:1 to 4:1) to provide 67 as a bright yellow solid: $^1$H NMR (DMSO-$d_6$) δ 6.28 (br s, 2H), 6.82 (s, 1H), 6.90 (s, 1H), 7.26 (dd, 1H, J=3.8, 5.0 Hz), 7.42 (dd, 1H, J=2.4, 8.9 Hz), 7.61 (dd, 1H, J=1.1, 3.8 Hz), 7.69 (dd, 1H, J=2.4 Hz), 8.04 (dd, 1H, J=1.1, 5.0 Hz); $^{13}$C NMR (DMSO) δ 187.42, 150.09, 143.87, 136.46, 134.75, 134.41, 133.93, 128.78, 119.36, 119.17, 104.95; MS (EI) m/e (relative intensity) 283 ($M^+$, 59), 282 ($M^+$, 87), 281 ($M^+$, 59), 280 ($M^+$, 79), 250 (23), 248 (23), 201 (13), 199 (49), 197 (48), 172 (25), 170 (23), 145 (13), 140 (1), 111 (100), 101 (33).

4-Bromo-2-(2'-thienylcarbonyl)-N-bromoacetylaniline 68. The thienylaniline 67 (3.3 g, 11.7 mmol) and $NaHCO_3$ (2.9 g, 34.5 mmol) were suspended in dry $CHCl_3$ (180 mL) and cooled to 0° C. A solution of bromoacetyl bromide (1.12 mL, 12.9 mmol) in dry $CHCl_3$ (30 mL) was added dropwise over 20 min at 0° C. and the mixture was stirred at rt for 3 h. The $CHCl_3$ solution was then washed with aq $NaHCO_3$ (5%) and dried ($Na_2SO_4$). The $CHCl_3$ was removed under reduced pressure, and $Et_2O$ was added to the flask. The solution was sonicated and filtered to provide 68 as a light solid: mp: 144.0-146.5° C.; $^1$H NMR ($CDCl_3$) δ 4.01 (s, 2H), 7.23-7.26 (m, 1H), 7.24 (d, 1H), 7.65 (d, 1H), 7.74 (d, 1H), 7.84 (d, 1H), 8.46 (d, 1H), 10.85 (br s, 1H); MS (EI) m/e (relative intensity) 405 ($M^+$, 69), 404 (40), 403 ($M^+$, 100), 401 ($M^+$, 66), 324 (39), 322 (38), 310 (33), 308 (33), 292 (32), 283 (65), 282 (72), 281 (65), 280 (67), 266 (10), 264 (10), 250 (34), 248 (35), 226 (55), 224 (55), 201 (43), 199 (27), 197 (27), 173 (32), 111 (73).

7-Bromo-5-(2'-thienyl)-1,3-dihydrobenzo[e][1,4]diazepine 69 (JC184). The bromoacetyl amide 68 (0.236 g, 0.586 mmol) was dissolved in a saturated solution of anhydrous ammonia in MeOH (50 mL) and the mixture was heated to reflux for 6 h. After the MeOH was removed under reduced pressure, EtOAc was added to the residue. The solution was sonicated and then filtered to provide 69 (JC184) as a light solid: MS (D) m/e (relative intensity) 322 ($M^+$, 54), 320 ($M^+$, 53), 294 (100), 292 (98), 211 (24), 185 (31), 140 (21). The material was used directly in the next step.

7-Trimethylsilylacetylenyl-5-(2'-thienyl)-1,3-dihydrobenzo[e][1,4]diazepine 70 (JC207). A mixture of 69 (1 g, 3.12 mmol) in $CH_3CN$ (20 mL) and $Et_3N$ (30 mL) was degassed and heated to reflux under nitrogen. Bis(triphenylphosphine)-palladium (II) acetate (0.26 g, 0.347 mmol) was then quickly added, followed by the addition of TMS acetylene (0.76 g, 7.78 mmol). The mixture was stirred at reflux for 4 h and the solvent was removed under reduced pressure. Water (25 mL) and EtOAc (25 mL) were added to the residue and the mixture was filtered through celite to remove the organometallic species. The filtrate was then extracted with EtOAc and the organic phases were combined, washed with brine and dried ($Na_2SO_4$). The solvent was removed under reduced pressure and the residue was purified via flash chromatography (silica gel, hexanes/EtOAc: 11:1, 5:1) to provide 70 (JC207) as a light yellow solid: mp: 198.5-201° C.; MS (EI) m/e (relative intensity) 338 ($M^+$, 68), 337 ($M^+$, 28), 310 (100), 295 (13), 161 (13), 147 (33), 105 (17). The material was used directly in the next step.

7-Acetylenyl-5-(2'-thienyl)-1,3-dihydrobenzo[e][1,4]diazepine 72 (JC208). A solution of 70 (150 mg, 0.457 mmol) in THF (30 mL) was treated with tetrabutylammonium fluoride (1M in THF) at 0° C. for 5 minutes. Water (20 mL) was subsequently added to quench the reaction and the THF was removed under reduced pressure. The remaining aq solution was then extracted with EtOAc and the organic phases were combined, washed with brine and dried ($Na_2SO_4$). Upon removal of the solvent, $Et_2O$ was added to the residue which was sonicated and then filtered to provide the title compound 72 (JC208, 111 mg, 91%) as an ivory colored solid: mp: 214-216° C.; MS (EI) m/e (relative intensity) 266 ($M^+$, 61), 265 ($M^+$, 30), 238 (100), 237 (49), 210 (13), 209 (10), 164 (6), 153 (7), 139 (7). This material was used in the next step.

1-N-methyl-7-trimethylsilylacetylenyl-5-(2'-thienyl)-1,3-dihydrobenzo[e][1,4]diazepine 71 (JC209). Thiophere 70 (500 g, 1.52 mmol) was dissolved in dry THF (25 mL) at 0° C. and NaH (60% in mineral oil, 76 mg, 1.50 mmol) was added to the solution in one portion. After the mixture was stirred at 0° C. for 30 min, MeI (0.14 mL, 2.25 mmol) was added and the ice bath was allowed to warm to rt. The mixture was allowed to stir for 3 h and the THF was then removed under reduced pressure. The residue was purified via flash chromatography (silica gel, hexanes/EtOAc 8:1, 4:1) to provide the title compound 71 (JC209) as a white solid: mp: 171.3-173.6° C.; $^1$H NMR ($CDCl_3$) δ 0.26 (br s, 9H), 3.38 (s, 3H), 4.71 (d, 1H), 7.09 (dd, 1H, J=3.7, 5.0 Hz), 7.17 (dd, 1H, J=1.1, 3.7 Hz), 7.30 (s, 1H), 7.49 (dd, 1H, J=1.1, 5.0 Hz), 7.65 (dd, 1H, J=2.0, 8.5 Hz), 7.75 (d, 1H); $^{13}$C NMR ($CDCl_3$) δ ($CDCl_3$) δ 170.12, 163.22, 143.65, 143.14, 134.69, 133.12, 131.38, 130.14, 127.77, 127.47, 121.01, 119.10, 103.01, 95.66, 56.38, 34.67; MS (EI) m/e (relative intensity) 352 ($M^+$, 71), 351 ($M^+$, 60), 337 (10), 324 (100), 309 (24), 168 (28), 154 (38).

1-N-methyl-7-acetyleno-5-(2'-thienyl)-1,3-dihydrobenzo[e][1,4]diazepine 73 (JC222). The same procedure for preparing 72 (JC208) was applied to 73 (JC222) and a very light brown solid resulted: mp: 218.3-220.4° C.; $^1$H NMR ($CDCl_3$) δ 3.16 (s, 1H), 3.39 (s, 3H), 3.78 (d, 1H, J=11.07 Hz), 4.72 (d, 1H, J=5.9 Hz), 7.08 (dd, 1H, J=3.8, 5.0 Hz), 7.31 (d, 1H, J=8.6 Hz), 7.49 (dd, 1H, J=1.0, 5.0 Hz), 7.67 (dd, 1H, J=2.0, 8.5 Hz), 7.79 (d, 1H, J=1.9 Hz); $^{13}$C NMR ($CDCl_3$) □ 171.04, 170.07, 163.12, 143.49, 134.79, 133.50, 131.34, 130.25, 127.85, 127.46, 121.16, 117.99, 81.83, 78.30, 56.34, 34.69. MS (EI) m/e (relative intensity) 281 (13), 280 ($M^+$, 60), 279 (51), 253 (19), 252 (100), 251 (2), 235 (11), 209 (10).

Ethyl 8-bromo-6-(2'-thienyl)-4H-benzo[f]imidazo[1,5-a][1,4]diazepine-3-carboxylate 74 (JC217). Dry THF (30 mL) was added to a flask containing the benzodiazepine 69 (1.27 g, 3.96 mmol) and the solution was allowed to cool to 0° C. and NaH (60% in mineral oil, 0.191 g, 4.76 mmol) was quickly added. The mixture was stirred for 30 min at 0° C. and then removed from an ice bath to stir another 1 h at rt. Prior to adding $ClPO(OEt)_2$ (1.06 g, 6.35 mmol), the mixture was again pre-cooled to 0° C. The solution was stirred another 3 h as the ice bath warmed to rt. Meanwhile, dry THF (10 mL) was added to a second flask containing NaH (60% in mineral oil, 0.229 g, 5.72 mmol). After the second mixture was cooled to 0° C., $CNCH_2CO_2Et$ was added dropwise and the solution continued to stir for 30 min at 0° C. After both reaction mixtures were again pre-cooled to 0° C., the two solutions were combined under Ar via cannula and the solution stirred at rt overnight. The reaction was quenched with ice water and worked up with EtOAc, and the combined organic phases were washed with brine and dried (Na$_2$SO$_4$). The solvent was removed under reduced pressure and the residue was purified via flash chromatography (silica gel, hexanes:EtOAc 4:1, 1:1, 1:3) to provide the title compound 74 (JC217) as an ivory solid (500 mg, 30% yield): mp: 204.0-205.3° C.; $^1$H NMR (CDCl$_3$) δ 1.45 (t, 3H, J=7.1, 14.3 Hz), 4.07 (d, 1H, J=8.8 Hz), 4.44 (dd, 2H, J=3.8, 4.7 Hz), 5.98 (d, 1H, J=12.8 Hz), 7.05 (d, 1H, J=1.0 Hz), 7.07 (s, 1H), 7.46-7.49 (m, 2H), 7.83 (dd, 1H, J=2.2, 8.5 Hz), 7.91 (s, 1H), 7.96 (d, 1H, J=2.2 Hz): MS (EI) m/e (relative intensity) 418 (M$^+$, 15), 417 (M$^+$, 68), 416 (M$^+$, 15), 415 (M$^+$, 64), 407 (22), 344 (26), 343 (100), 342 (30), 341 (93), 293 (15), 291 (21), 262 (18), 235 (15), 211 (12), 154 (10), 127 (11).

Ethyl 8-trimethylsilylacetylenyl-6-(2-thienyl)-4H-benzo[f]imidazo[1,5-a][1,4]diazepine-3-carboxylate 75 (JC220). The same procedure for preparing 70 (JC207) was applied to 75 (JC220) and an ivory colored solid resulted: $^1$H NMR (CDCl$_3$) δ 0.29 (s, 9H), 1.45 (t, 3H, J=7.1, 14.3 Hz), 4.0 (d, 1H, J=18.1 Hz), 4.45 (dd, 2H, J=7.2, 8.5 Hz), 5.97 (d, 1H, J=12.8 Hz), 7.06-7.11 (m, 2H), 7.49 (dd, 1H, J=1.2, 5.0 Hz), 7.52 (d, 1H, J=8.3 Hz), 7.77 (dd, 1H, J=1.9, 8.3 Hz), 7.90 (d, 1H, J=1.8 Hz), 7.93 (s, 1H). MS (EI) m/e (relative intensity) 433 (M$^+$, 74), 387 (49), 359 (100), 277 (28), 262 (19), 235 (24), 172 (19), 129(17).

Ethyl 8-acetyleno-6-(2'-thienyl)-4H-benzo[f]imidazo[1,5-a][1,4]diazepine-3-carboxylate 76 (JC221). The same procedure for preparing 72 (JC208) was applied to 76 (JC221) and an ivory colored solid resulted: mp: >198° C.; $^1$H NMR (CDCl$_3$) δ 1.43 (t, 3H, J=4.3, 11.4 Hz), 3.25 (s, 1H), 4.10 (d, 1H, J=12.8 Hz), 4.40-4.49 (m, 2H), 5.99 (d, 1H, J=12.9 Hz), 7.50 (d, 1H, J=5.0 Hz), 7.56 (d, 1H, J=8.3 Hz), 7.81 (dd, 1H, J=1.8, 8.3 Hz), 7.95 (s, 1H); MS (EI) m/e (relative intensity) 361 (M$^+$, 24), 315 (35), 287 (100), 237 (26), 178 (30), 153 (21), 126 (18). MS (EI) m/e (relative intensity) 361 (M$^+$, 29), 315 (41), 287 (100), 237 (31), 178 (40), 153 (26), 126 (21).

Scheme 15

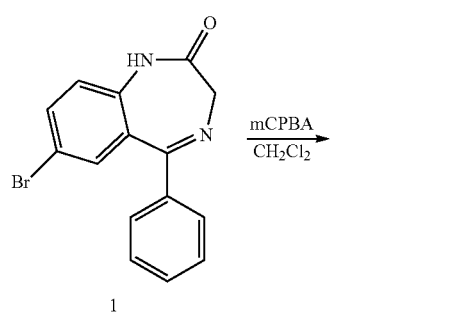

1

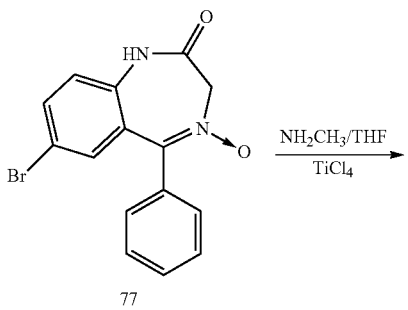

77

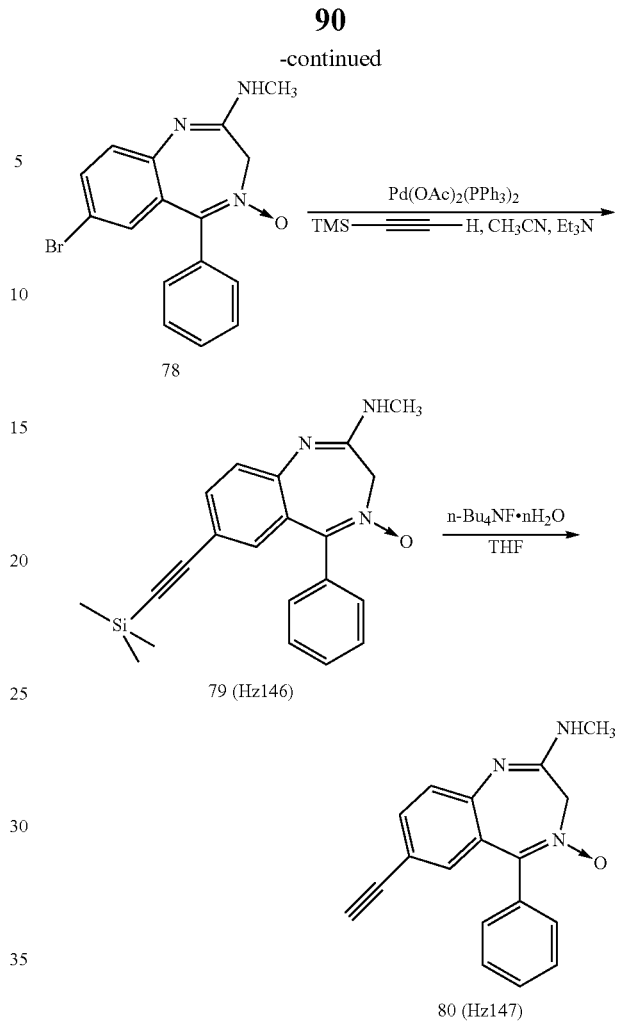

78

79 (Hz146)

80 (Hz147)

Scheme 16

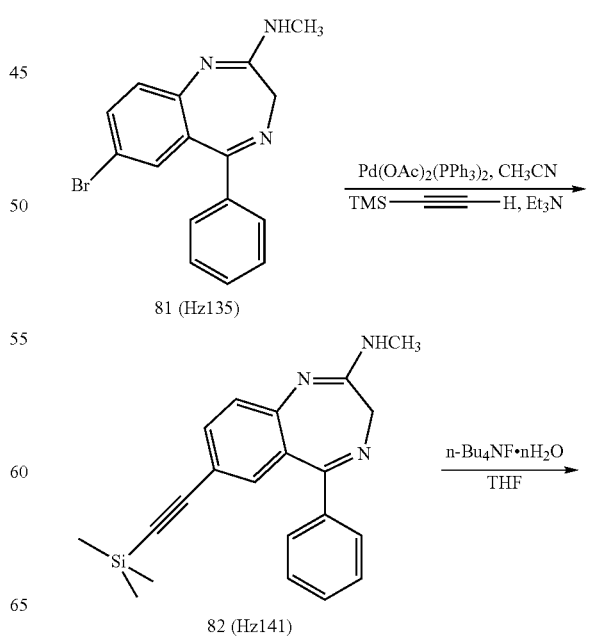

81 (Hz135)

82 (Hz141)

-continued

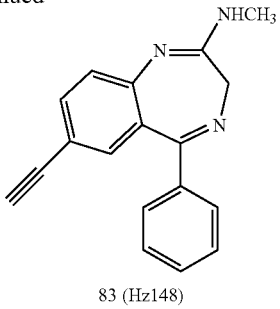

83 (Hz148)

The benzodiazepine 1 was oxidized with 3-chloroperoxybenzoic acid (mCPBA) to form 77, followed by the addition of methylamine to afford amidine 78. N-Oxide 78 was reacted with trimethylsilyacetylene in the presence of a palladium catalyst to provide the trimethylsilyl analog 79 (Hz146) which was subjected to fluoride-mediated desilation to afford 80 (Hz147), as shown in Scheme 15. In a related route, bromide 81 was converted into the trimethylsilylacetylene 82 (Hz141). This analog was then transformed into target 79 (Hz146) with mCPBA or the key target (Hz148) or treatment with fluoride (Scheme 16).

7-Bromo-4-oxy-5-phenyl-1,3-dihydro-benzo[e][1,4]diazepin-2-one 77. Bromide 1 (1.88 g, 5.95 mmol) was dissolved in $CH_2Cl_2$ (50 mL) and mCPBA (77% max) (1.76 g) was added at rt. The reaction mixture was stirred overnight. The mixture was diluted with $CH_2Cl_2$ (80 mL) and washed with a sat. solution of $NaHCO_3$ (50 mL), water (50 mL) and brine (40 mL). The organic layer was dried ($Na_2SO_4$) and concentrated. The residue was purified by flash chromatography (silica gel, EtOAc) to afford compound 77 in 90% yield as a white solid. mp: 230-231° C. (lit.[13] 230-231° C.); $^1$H NMR ($CDCl_3$) δ 4.69 (s, 2H), 7.16 (d, 1H, J=8.7 Hz), 7.24 (d, 1H, J=2.1 Hz), 7.45 (m, 3H), 7.54 (dd, 1H, J=8.6, 2.2 Hz), 7.64 (dd, 2H, J=7.3, 3.6 Hz), 10.02 (s, 1H).

(7-Bromo-4-oxy-5-phenyl-3H-benzo[e][1,4]diazepin-2-yl)-methyl-amine 78. Methylamine (50 mL, 2 M in THF) was added to 77 (1.9 g, 5.7 mmol) in a 100 mL round-bottom flask. The mixture was cooled to 0° C. after which $TiCl_4$ (0.54 g, 2.86 mmol) was added dropwise. The reaction mixture was allowed to warm to rt and stirred for 4 h. The mixture was quenched with water (5 mL), diluted with EtOAc (100 mL) and washed with dilute $NH_4OH$. The organic layer was washed with water, brine and dried ($Na_2SO_4$). After the solvent was removed under reduced pressure, the residue was purified by flash chromatography (silica gel, gradient elution, EtOAc, EtOAc:MeOH 10:1) to provide 78 in 86% yield as a white solid. mp: 236-237° C. (lit.[14] 242-243° C.); $^1$H NMR (300 MHz, $CDCl_3$) δ 0.21 (s, 9H), 2.91 (s, 3H), 4.17 (s, 1H), 4.85 (s, 1H), 7.13-7.66 (m, 9H).

(7-Trimethylsilylacetylenyl-4-oxy-5-phenyl-3H-benzo[e][1,4]diazepin-2-yl)-methyl-amine 79 (Hz146). Trimethylsilylacetylenyl analog 79 (Hz146) was obtained in 58% yield from 78 analogous to the procedure employed in Scheme 15 as a light gray solid. mp: 239-240° C.; IR (KBr) 3229, 3060, 2952, 2149, 1616, 1593, 1462, 1238, 868 cm$^{-1}$; $^1$H NMR (300 MHz, $CDCl_3$) δ 2.89 (d, 3H, J=4.4 Hz), 4.14 (d, 1H, J=10.6 Hz), 4.78 (d, 1H, J=10.4 Hz), 7.15 (d, 1H, J=1.7 Hz), 7.24-7.28 (m, 2H), 7.45 (m, 4H), 7.66 (m, 2H); MS (EI) m/e (relative intensity) 361 (M$^+$, 48), 344 (100), 303 (31), 165 (33).

(7-Acetylenyl-4-oxy-5-phenyl-3H-benzo[e][1,4]diazepin-2-yl)-methyl-amine 80 (Hz147). The 7-acetyleno target 80 was obtained in 90% yield from 79 analogous to the procedure employed in Scheme 15 as a light yellow solid. mp: 213-214° C.; IR (KBr) 3242, 3068, 2977, 1619, 1589, 1460, 1414 cm$^{-1}$; $^1$H NMR (300 MHz, $CDCl_3$) δ 2.89 (d, 2H, J=3.7 Hz), 2.98 (s, 1H), 4.13 (bs, 1H), 4.78 (bs, 1H), 7.18-7.71 (m, 9H); MS (EI) m/e (relative intensity) 289 (M$^+$, 47), 272 (100), 231 (42).

(7-Bromo-5-phenyl-3H-benzo[e][1,4]diazepin-2-yl)-methyl-amine 81 (Hz135). Bromide 81 was obtained in 70% yield from 1 analogous to the procedure employed in Scheme 15 as a white solid. mp: 234-235° C.; IR (KBr) 3253, 3076, 1609, 1571, 1415, 1326, 1230 cm$^{-1}$; $^1$H NMR (300 MHz, $CDCl_3$) δ 2.62 (s, 3H), 3.56 (bs, 1H), 4.68 (bs, 1H), 6.34 (s, 1H), 7.17 (d, 1H, J=8.7 Hz), 7.36-7.81 (m, 7H); MS (EI) m/e (relative intensity) 329 (80), 328 (M$^+$, 100), 327 (82), 326 (92), 220 (38), 219(48), 218(46), 205 (38).

(7-Trimethylsilylacetylenyl-5-phenyl-3H-benzo[e][1,4]diazepin-2-yl)-methyl-amine 82 (Hz141). Trimethylsilylacetylenyl analog 82 (Hz141) was obtained in 73% yield from 81 analogous to the procedure employed in Scheme 16 as a light yellow solid. mp: 210-211° C.; IR (KBr) 3257, 3079, 2956, 2150, 1619, 1610, 1580, 1416, 1237, 880, 843 cm$^{-1}$; $^1$H NMR (300 MHz, $CDCl_3$) δ 0.22 (s, 9H), 2.59 (d, 3H, J=3.5 Hz), 3.56 (bs, 1H), 4.66 (bs, 1H), 6.39 (s, 1H), 7.21 (d, 1H, J=8.4 Hz), 7.39-7.65 (m, 7H); MS (EI) m/e (relative intensity) 345 (M$^+$, 100), 344 (98), 164(50).

(7-Acetylenyl-4-oxy-5-phenyl-3H-benzo[e][1,4]diazepin-2-yl)-methylamine 83 (Hz148). The 7-acetyleno analog 83 (Hz148) was obtained in 92% yield from 82 analogous to the procedure employed in Scheme 16 as a white solid. mp: 226-227° C.; IR (KBr) 3275, 3245, 3075, 2102, 1618, 1599, 1580, 1467, 1416, 1333, 1235 cm$^{-1}$; $^1$H NMR (300 MHz, $CDCl_3$) δ 2.65 (d, 3H, J=4.4 Hz), 2.97 (s, 1H), 3.57 (bs, 1H), 4.65 (bs, 1H), 6.20 (d, 1H, J=3.7 Hz), 7.22 (d, 1H, J=8.4 Hz), 7.42-7.58 (m, 7H). MS (EI) m/e (relative intensity) 273 (M$^+$, 100), 272 (98).

Scheme 17

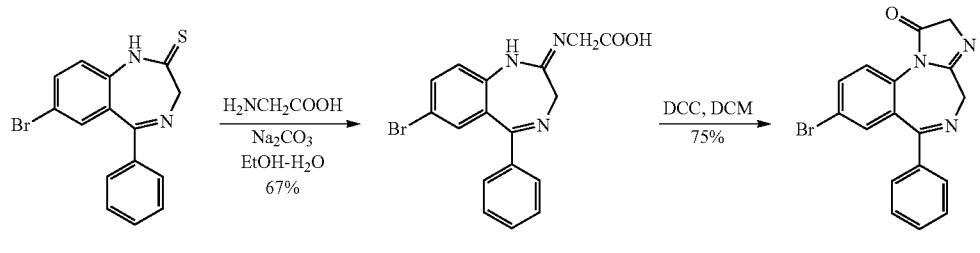

84[15]     85     86

Me$_2$NCH(OC$_2$H$_5$)$_2$
Et$_3$N, Benzene
70%

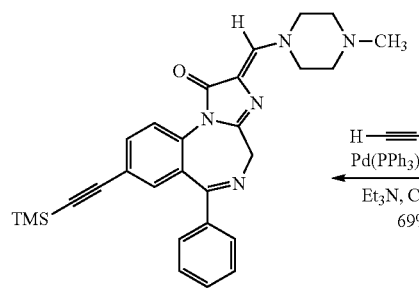

89 (PS-I-36)

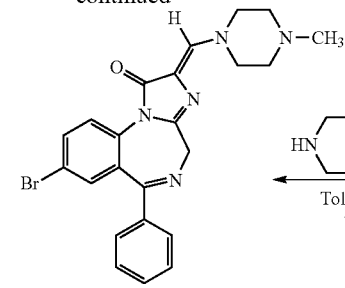

88 (PS-I-35)

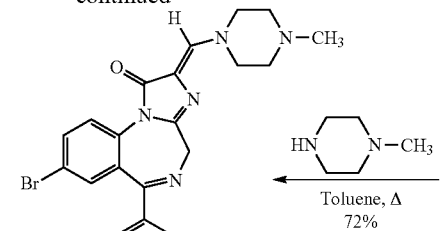

87

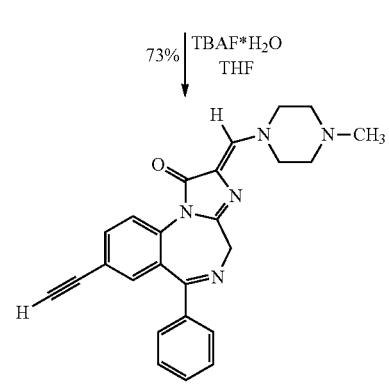

90 (PS-I-37)

A suspension of 7-bromo-1,3-dihydro-5-phenyl-2H-1,4-benzodiazepin-2-thione 84 (1.6 g, 4.83 mmol), glycine (1.81 g, 24.2 mmol) and $Na_2CO_3$ (1.84 g, 17.4 mmol) in EtOH (38 mL)-$H_2O$ (16 mL) was stirred at reflux for h, poured into water (100 mL), and then filtered to remove a small amount of 7-bromo-1,3-dihydro-5-phenyl-2H-1,4-benzodiazepin-2-one which remained. The filtrate was extracted with $CHCl_3$. The $CHCl_3$ extract was discarded; the aqueous layer was adjusted to pH 4 with 2N HCl and then extracted with $CHCl_3$ (3×25 mL). Evaporation of the $CHCl_3$ solution gave pure acid 85 (1.2 g, 67%) as a yellow solid. Acid 85 (350 mg, 0.941 mmol) was suspended in dry $CH_2Cl_2$ (10 mL) and DCC (223 mg, 1.08 mmol) was added. The suspension which resulted was stirred at 40° C. for 2 h and then cooled to 0° C. It was filtered, and the solvent was removed in vacuum to give 8-bromo-2,4-dihydro-6-phenyl-1H-imidazo[1,2-a][1,4]benzodiazepin-1-one 3 as a brown oil. The cyclized product 86 (ca. 250 mg) was dissolved in dry benzene (6 mL), dimethylformamide diethylacetal (130 mg, 0.883 mmol) and triethylamine (89 mg, 0.883 mmol) were added. The solution which resulted was stirred at room temperature for 1 h and the solvent was removed in vacuum, The residue was then crystallized from EtOAc-MeOH to give 87 (200 mg, 70%). A solution of 87 (180 mg, 0.440 mmol) in dry toluene (5 mL) was treated with 1-methyl piperazine (1 mL) and heated to reflux for 5 h. The solvent was removed in vacuum to give a gum which crystallized from $CH_2Cl_2$-$Et_2O$ to furnish 88 (PS-I-35, 146 mg, 72%). mp>250° C.; IR (KBr) 3324, 2932, 2787, 1692, 1624, 1475, 1402, 1297, 1137, 933 cm$^{-1}$; $^1$H NMR ($CDCl_3$) δ 7.95 (d, 1H, J=8.8 Hz), 7.72 (dd, 1H, J=2.3 Hz, J=8.8 Hz), 7.58-7.55 (m, 2H), 7.49-7.37 (m, 4H), 7.17 (s, 1H), 5.01 (d, 1H, J=12 Hz), 4.50-4.60 (m, 1H), 4.20-4.30 (m, 1H), 4.16 (d, 1H, J=12 Hz), 3.50-3.58 (m, 2H), 2.40-2.60 (m, 4H), 2.34 (s, 3H); MS (m/z) 465 (100).

To the suspension of compound 88 (PS-I-35, 140 mg, 0.302 mmol) in acetonitrile (4 mL) and triethylamine (3 mL) was added bis(triphenylphosphine)-palladium (II) acetate (22.6 mg, 0.03 mmol). The solution was degassed and trimethylsilylacetylene (0.1 mL, 0.7 mmol) was added. The mixture was heated to reflux and stirred overnight. After removal of the solvent in vacuum, the residue was dissolved in $CH_2Cl_2$ and washed with a saturated aqueous solution of $NaHCO_3$ and brine. The organic layer was dried ($Na_2CO_3$), filtered and concentrated under vacuum. The residue was purified by flash column chromatography (EtOAc:MeOH 9:1) to furnish the trimethylsilyl analogue 89 (PS-I-36, 100 mg, 69%) as a pale yellow solid. mp>250° C.; IR (KBr) 3436, 2936, 2794, 2154, 1682, 1625, 1489, 1136, 847 cm$^{-1}$; $^1$H NMR ($CDCl_3$) δ 8.0 (d, 1H, J=8.5 Hz), 7.68 (dd, 1H, J=1.9 Hz, J=8.5 Hz), 7.55-7.59 (m, 2H), 7.37-7.49 (m, 4H), 7.16 (s, 1H), 4.99 (d, 1H, J=12 Hz), 4.50-4.60 (m, 1H), 4.20-4.30 (m, 1H), 4.13 (d, 1H, J=12.4 Hz), 3.48-3.58 (m, 2H), 2.4-2.6 (m, 4H), 2.35 (s, 3H), 0.23 (s, 9H); MS (m/z) 482 (100).

A solution of the trimethylsilyl analog 89 (PS-I-36, 65 mg, 0.135 mmol) in THF (15 mL) was stirred with tetrabutylammonium fluoride hydrate (45 mg, 0.175 mmol) at −5° C. for 5 min. After this, $H_2O$ (5 mL) was added to the solution to quench the reaction and stirring continued at low temperature for one half hour. The solution was extracted with EtOAc (3×40 mL), and the organic layer was washed with water. After removal of the solvent under reduced pressure, ethyl ether was added to the residue to precipitate a solid. The mixture was filtered and the solid was washed with $CHCl_3$-$Et_2O$ (ca 1:15) to provide the acetyl target 90 (PS-I-37, 40 mg, 73%). mp 223-224° C.; IR (KBr) 3298, 2935, 2786, 1695, 1628, 1364, 1136, 1002, 778 cm$^{-1}$; $^1$H NMR ($CDCl_3$) δ 8.04 (d, 1H, J=8.5 Hz), 7.71 (dd, 1H, J=1.9 Hz, J=8.5 Hz), 7.55-7.58 (m, 2H), 7.36-7.48 (m, 4H), 7.17 (s, 1H), 5.0 (d, 1H, J=12.1 Hz), 4.5-4.6 (m, 1H), 4.2-4.3 (m, 1H), 4.16 (d, 1H, J=12.1 Hz), 3.5-3.6 (m, 2H), 3.08 (s, 1H), 2.4-2.6 (m, 4H), 2.35 (s, 3H); MS (m/z) (100).

Scheme 18

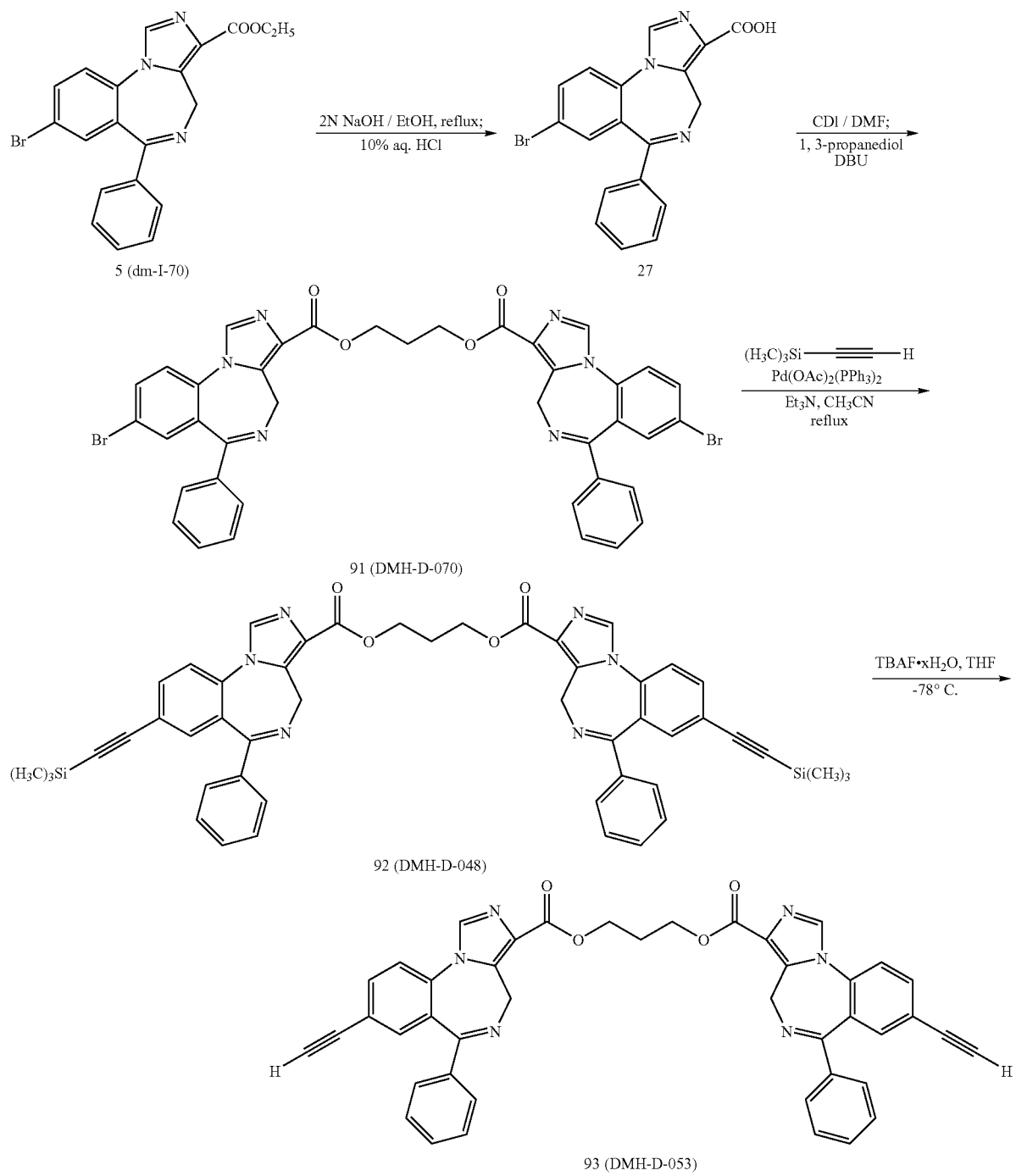

The acid 27, obtained from the ester 5 (dm-I-70), was stirred with CDI in DMF, followed by stirring with 1,3-propanediol and DBU to provide 91 (DMH-D-070, the dimer of dm-I-70). This was converted into the trimethylsilylacetylenyl compound 92 (DMH-D-048, the dimer of XLMHe048) under standard conditions (Pd-mediated, Heck-type coupling). The bisacetylene 93 (DMH-D-053, the dimer of XHeII-053) was easily obtained by treatment of trimethylsilyl compound 92 with fluoride anion as shown in Scheme 18.

8-Bromo-6-phenyl-4H-benzo[f]imidazo[1,5-a][1,4]diazepine-3-carboxylic acid 27. The ester 5 (2 g) was dissolved in EtOH (50 mL) and aq sodium hydroxide (10 mL, 2N) was added to the solution. The mixture was heated to reflux for half an hour. After the EtOH was removed under reduced pressure, the solution was allowed to cool. The pH value was adjusted to 4 by adding 10% aq HCl dropwise. The mixture was filtered and the solid was washed with water and ethyl ether. The solid was dried to provide 27 (1.8 g, 96.6%): mp>250° C.; IR (KBr) 3450 (b), 2844, 1707, 1615, 1493, 1166, 700 cm$^{-1}$; $^1$H NMR (300 MHz, DMSO-d$_6$) δ 4.14 (d, 1H, J=12.6 Hz), 5.79 (d, 1H, 12.6 Hz), 7.41-7.54 (m, 6H), 7.88 (d, 1H, J=8.7 Hz), 8.03 (dd, 1H, J=8.7 Hz, J=2.1 Hz), 8.47 (s, 1H); MS (EI) m/e (rel intensity) 381 (M$^+$, 20), 383 (19).

1,3-Bis(8-bromo-6-phenyl-4H-benzo[f]imidazo[1,5-a][1,4]diazepine-3-carb-oxy)propyl diester 91 (DMH-D-070). The carboxylic acid 27 (2 g, 5.2 mmol) was dissolved in DMF (20 mL), after which CDI (1.02 g, 6.3 mmol) was added at rt and the mixture was stirred for 2 h. Then 1,3-propanediol (0.19 mL, 2.6 mmol) and DBU (0.78 mL, 5.2 mmol) were added to the mixture and stirring continued overnight. The reaction solution was then cooled with an ice-water bath, after which water was added to precipitate a solid. This material was purified further by flash chromatography on silica gel (gradient elution, EtOAc:EtOH 20:1, 15:1, 10:1) to provide the bisbromide 91 (DMH-D-070) as a white solid (1.3 g, 61.9%): mp 187.5-189° C.; IR (KBr) 3112, 2968, 1708, 1610, 1559, 1491, 1269, 1160, 1123, 1073 cm$^{-1}$; $^1$H NMR (300 MHz, CDCl$_3$) δ 2.35 (m, 2H), 4.08 (d, 2H, J=12.6 Hz), 4.55 (m, 4H), 6.05 (d, 2H, J=12.6 Hz), 7.37-7.53 (m, 12H), 7.6 (d, 2H, J=2.1 Hz), 7.81 (dd, 2H, J=2.1 Hz, 8.6 Hz), 7.93 (s, 2H); $^{13}$C NMR (75.5 MHz, CDCl$_3$) δ 28.2, 44.9, 61.4, 120.7, 124.2, 128.3, 129.0, 129.3, 129.6, 130.6, 134.1, 134.4, 134.7, 135.0, 138.9, 138.9, 162.6, 167.9; MS (FAB, NBA) m/e (rel intensity) 803 (M$^+$+1, 15); Anal. Calcd. For C$_{39}$H$_{28}$N$_6$O$_4$Br$_2$: C, 58.23; H, 3.51; N, 10.45. Found: C, 57.92; H, 3.43; N, 10.29.

1,3-Bis(8-trimethylsilylacetylenyl-6-phenyl-4H-benzo[f]imidazo[1,5-a][1,4]-diazepine-3-carboxy)propyl diester 92 (DMH-D-048). To a suspension of bisbromide 91 (1.005 g, 1.25 mmol) in acetonitrile (50 mL) and triethylamine (65 mL), was added bis(triphenylphosphine)-palladium (II) acetate (0.15 g, 0.2 mmol). The solution was degassed and trimethylsilylacetylene (0.7 mL, 5 mmol) was added after which it was degassed again. The mixture was heated to reflux and stirring maintained overnight. After removal of the solvent under reduced pressure, the residue was dissolved in CH$_2$Cl$_2$ and washed with water. 3-Mercaptopropyl functionalized silica gel (0.6 g) was added into the organic layer and stirring continued for 1 hour. The silica gel/Pd complex was removed by filtration and the filtrate was concentrated under reduced pressure. The residue was purified by flash column chromatography on silica gel (gradient elution, EtOAc:EtOH 20:1, 15:1, 10:1) to furnish the bistrimethylsilyl dimer 92 (DMH-D-048, 680 mg, 60.8%) as a white solid: mp 169-172° C.; IR (KBr) 3449, 2950, 1725, 1720, 1715, 1496, 1250, 1160, 1080, 847 cm$^{-1}$; $^1$H NMR (300 MHz, CDCl$_3$) δ 0.25 (s, 18H), 2.35 (m, 2H), 4.05 (d, 2H, J=12.6 Hz), 4.55 (m, 4H), 6.02 (d, 2H, J=12.6 Hz), 7.37-7.55 (m, 14H), 7.75 (dd, 2H, J=1.8 Hz, 8.4 Hz), 7.94 (s, 2H); $^{13}$C NMR (75.5 MHz, CDCl$_3$) δ −0.3, 28.3, 44.9, 61.4, 97.4, 102.3, 122.4, 122.6, 128.0, 128.3, 129.0, 129.4, 130.5, 134.1, 134.9, 135.1, 139.0, 139.2, 139.2, 162.6, 168.5; MS (FAB, NBA) m/e (rel intensity) 839 (M$^+$+1, 100); Anal. Calcd. For C$_{49}$H$_{46}$N$_6$O$_4$Si$_2$: C, 70.14; H, 5.53; N, 10.02. Found: C, 69.97; H, 5.35; N, 9.77.

1,3-Bis(8-acetylenyl-6-phenyl-4H-benzo[f]imidazo[1,5-a][1,4]diazepine-3-carboxy)propyl diester 93 (DMH-D-053). A solution of bistrimethylsilyl dimer 92 (330 mg, 0.4 mmol) in THF (70 mL) was stirred with tetrabutylammonium fluoride hydrate (250 mg, 0.96 mmol) at −78° C. for 5 min. After this, H$_2$O (35 mL) was added to the solution to quench the reaction and stirring continued at low temperature for one half hour. The solution was extracted with EtOAc (3×100 mL), and the organic layer was washed with water. After removal of the solvent under reduced pressure, ethyl ether was added to the residue to precipitate a solid. The mixture was filtered and the solid was washed with CHCl$_3$-Et$_2$O (ca 1:15), the bisacetylenyl dimer 93 (DMH-D-053, 220 mg, 80%) was obtained as a yellow solid: mp 172-175° C.; IR (KBr) 3450, 3280, 2950, 1720, 1715, 1495, 1250, 1120, 1050 cm$^{-1}$; $^1$H NMR (300 MHz, CDCl$_3$) δ 2.35 (m, 2H), 3.18 (s, 2H), 4.08 (d, 2H, J=12.3 Hz), 4.56 (m, 4H), 6.04 (d, 2H, J=12.6 Hz), 7.36-7.59 (m, 14H), 7.78 (dd, 2H, J=8.4 Hz, 1.7 Hz), 7.95 (s, 2H); $^{13}$C NMR (75.5 MHz, CDCl$_3$) δ 28.8, 45.4, 61.9, 80.2, 81.3, 121.4, 122.7, 128.1, 128.3, 129.0, 129.3, 130.5, 134.2, 135.2, 135.3, 135.6, 138.9, 139.2, 162.6, 168.5; MS (FAB, NBA) m/e (rel intensity) 695 (M$^+$+1, 100).

Scheme 19

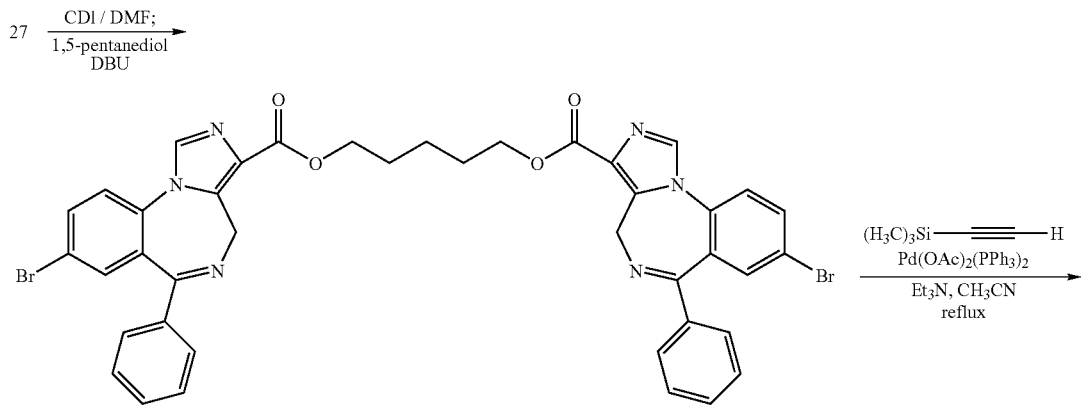

94 (dm-II-26)

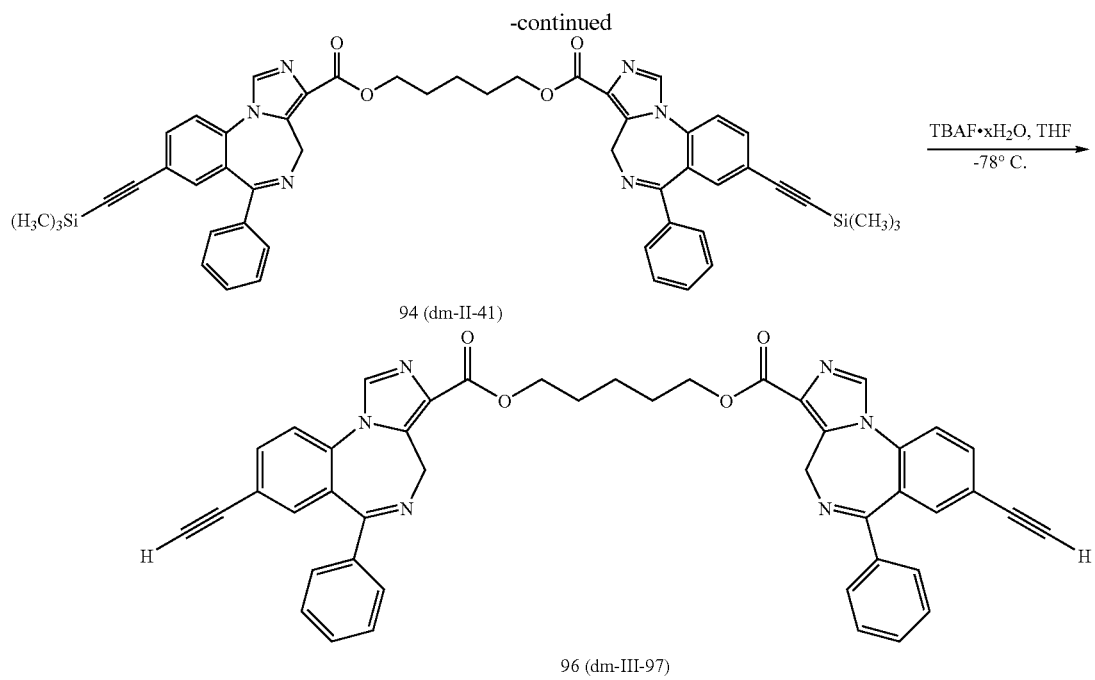

94 (dm-II-41)

96 (dm-III-97)

The 5-carbon linker bisbromide 94 (dm-II-26), bis-trimethylsilylacetylenyl dimer 95 (dm-II-41) and bisacetylene dimer 96 (dm-II-97), which are analogues of dimers DMH-D-070, DMH-D-048 and DMH-D-053, respectively, were prepared from acid 27 under the same conditions employed for preparing dimers 91 (DMH-D-070), 92 (DMH-D-048) and 93 (DMH-D-053), respectively, by using 1,5-pentanediol in place of 1,3-propanediol (Scheme 19).

1,5-Bis(8-bromo-6-phenyl-4H-benzo[f]imidazo[1,5-a][1,4]diazepine-3-carb-oxy)pentyl diester 94 (dm-II-26). A yellow powder (63.2%): mp 172-175° C.; IR (KBr) 3112, 2970, 1721, 1609, 1490, 1267, 1158, 1075, 754, 697 cm$^{-1}$; $^1$H NMR (300 MHz, CDCl$_3$) δ 1.62 (m, 2H), 1.90 (m, 4H), 4.07 (d, 2H, J=12.6 Hz), 4.39 (m, 4H), 6.05 (d, 2H, J=12.6 Hz), 7.37-7.53 (m, 12H), 7.58 (d, 2H, J=2.1 Hz), 7.78 (dd, 2H, J=2.1 Hz, 8.6 Hz), 7.92 (s, 2H); $^{13}$C NMR (75.5 MHz, CDCl$_3$) δ 22.5, 28.4, 44.9, 64.5, 120.7, 124.2, 128.3, 129.2, 129.3, 129.6, 130.6, 134.0, 134.5, 134.6, 135.0, 138.8, 138.9, 162.8, 167.9; MS (FAB, NBA) m/e (rel intensity) 831 (M$^+$+1, 5). Anal. Calcd. For C$_{41}$H$_{32}$N$_6$O$_4$Br$_2$·0.25H$_2$O: C, 58.95; H, 3.89; N, 10.07. Found: C, 58.69; H, 3.74; N, 9.70.

1,5-Bis(8-trimethylsilylacetylenyl-6-phenyl-4H-benzo[f]imidazo[1,5-a][1,4]-diazepine-3-carboxy)pentyl diester 95 (dm-II-41). A yellow solid (58.1%): mp 154-156° C.; IR (KBr) 3426, 2955, 1727, 1720, 1612, 1495, 1251, 1174, 1076, 846 cm$^{-1}$; $^1$H NMR (300 MHz, CDCl$_3$) δ 0.25 (s, 18H), 1.63 (m, 2H), 1.90 (m, 4H), 4.05 (d, 2H, J=12.6 Hz), 4.39 (m, 4H), 6.03 (d, 2H, J=12.6 Hz), 7.40-7.54 (m, 14H), 7.75 (dd, 2H, J=1.8 Hz, 8.4 Hz), 7.93 (s, 2H); $^{13}$C NMR (75.5 MHz, CDCl$_3$) δ −0.3, 22.5, 28.4, 44.9, 64.5, 97.4, 102.3, 122.4, 122.6, 128.0, 128.3, 129.2, 129.4, 130.5, 134.1, 135.0, 135.1, 135.1, 138.9, 139.3, 162.8, 168.5; MS (FAB, NBA) m/e (rel intensity) 867 (M$^+$+1, 100).

1,5-Bis(8-acetylenyl-6-phenyl-4H-benzo[f]imidazo[1,5-a][1,4]diazepine-3-carboxy)pentyl diester 96 (dm-III-97). A yellow solid: mp 150-153° C.; IR (KBr) 3290, 2953, 1718, 1611, 1493, 1253, 1172, 1120, 1076 cm$^{-1}$; $^1$H NMR (300 MHz, CDCl$_3$) δ 1.62 (m, 2H), 1.90 (m, 4H), 3.18 (s, 2H), 4.07 (d, 2H, J=12.3 Hz), 4.38 (m, 4H), 6.04 (d, 2H, J=12.3 Hz), 7.36-7.58 (m, 14H), 7.77 (dd, 2H, J=8.4 Hz, 1.6 Hz), 7.94 (s, 2H); $^{13}$C NMR (75.5 MHz, CDCl$_3$) δ 22.5, 28.4, 44.9, 64.5, 79.8, 81.3, 121.3, 122.7, 128.1, 128.3, 129.2, 129.3, 130.5, 134.1, 135.2, 135.3, 135.6, 138.8, 139.2, 162.8, 168.5; MS (FAB, NBA) m/e (rel intensity) 723 (M$^+$+1, 13).

Scheme 20

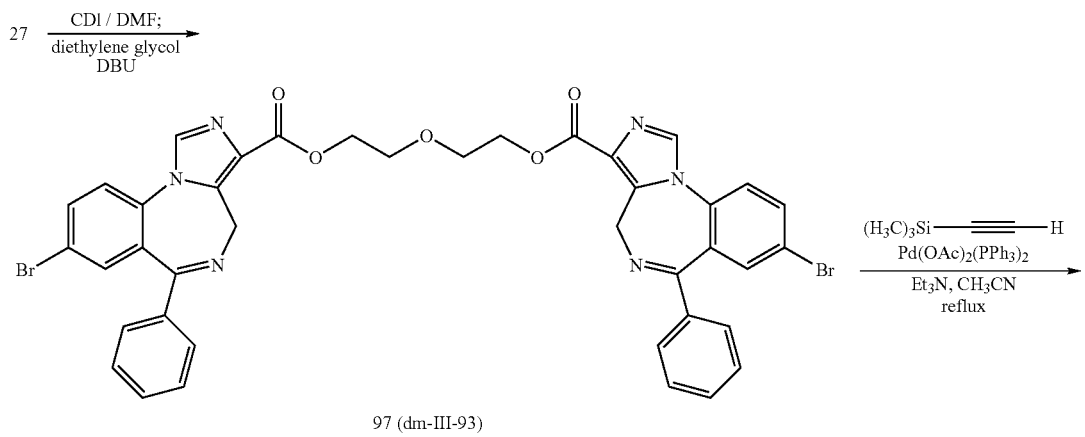

97 (dm-III-93)

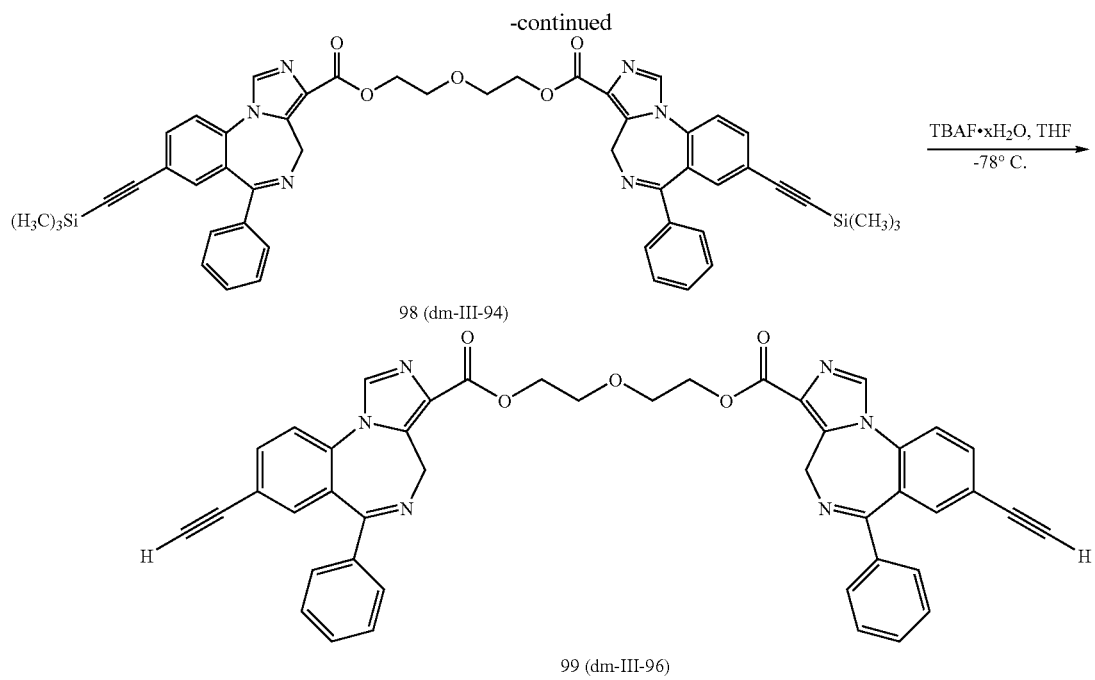

98 (dm-III-94)

99 (dm-III-96)

In order to improve the water solubility of the dimers, the oxygen-containing 5-atom linked dimers 97 (dm-III-93), 98 (dm-II-94) and 99 (dm-III-96), were designed and prepared from acid 27 under the same conditions employed for preparation of dimers DMH-D-070, DMH-D-048 and DMH-D-053, respectively, by replacing 1,3-propanediol with diethylene glycol (Scheme 20).

Bis(8-bromo-6-phenyl-4H-benzo[f]imidazo[1,5-a][1,4] diazepine-3-carboxy)diethylene glycol diester 97 (dm-III-93). A yellow solid (93.7%): mp 165-168° C.; IR (KBr) 3060, 2956, 1725, 1610, 1558, 1491, 1267, 1161, 1123, 1074 cm$^{-1}$; $^1$H NMR (300 MHz, CDCl$_3$) δ 3.93 (t, 4H, J=4.8 Hz), 4.06 (d, 2H, J=12.6 Hz), 4.54 (m, 4H), 6.05 (d, 2H, J=12.6 Hz), 7.39-7.50 (m, 12H), 7.57 (d, 2H, J=2.7 Hz), 7.80 (dd, 2H, J=2.1 Hz, 8.4 Hz), 7.90 (s, 2H); $^{13}$C NMR (75.5 MHz, CDCl$_3$) δ 44.9, 63.6, 69.0, 120.7, 124.2, 128.3, 129.0, 129.3, 129.6, 130.6, 134.1, 134.4, 134.6, 135.0, 138.9, 139.0, 162.5, 167.9; MS (FAB, NBA) m/e (rel intensity) 833 (M$^+$+1, 5).

Bis(8-trimethylsilylacetylenyl-6-phenyl-4H-benzo[f]imidazo[1,5-a][1,4]diazepine-3-carboxy)diethylene glycol diester 98 (dm-III-94). A yellow solid (49.5%): mp 205-208° C.; IR (KBr) 3433, 2960, 1730, 1700, 1612, 1493, 1255, 1169, 1120, 1071, 847 cm$^{-1}$; $^1$H NMR (300 MHz, CDCl$_3$) δ 0.25 (s, 18H), 3.93 (t, 4H, J=5.4 Hz), 4.04 (d, 2H, J=12.6 Hz), 4.55 (m, 4H), 6.04 (d, 2H, J=12.6 Hz), 7.37-7.53 (m, 14H), 7.74 (dd, 2H, J=1.2 Hz, 8.4 Hz), 7.91 (s, 2H); $^{13}$C NMR (75.5 MHz, CDCl$_3$) δ −0.3, 45.0, 63.6, 69.0, 97.5, 102.4, 122.5, 122.7, 128.1, 128.3, 129.0, 129.4, 130.5, 134.2, 135.0, 135.1, 135.2, 139.1, 139.3, 162.7, 168.6; MS (FAB, NBA) m/e (rel intensity) 869 (M$^+$+1, 100).

Bis(8-acetylenyl-6-phenyl-4H-benzo[f]imidazo[1,5-a][1,4]diazepine-3-carb-oxy)diethylene glycol diester 98 (dm-III-96). A yellow solid (81.6%): mp 173-177° C.; IR (KBr) 3432, 3280, 1720, 1715, 1496, 1254, 1175, 1120, 1074 cm$^{-1}$; $^1$H NMR (300 MHz, CDCl$_3$) δ 3.12 (s, 2H), 3.93 (t, 4H, J=4.5 Hz), 4.06 (d, 2H, J=12.6 Hz), 4.55 (m, 4H), 6.05 (d, 2H, J=12.6 Hz), 7.38-7.56 (m, 14H), 7.75 (dd, 2H, J=8.4 Hz, 1.8 Hz), 7.91 (s, 2H); $^{13}$C NMR (75.5 MHz, CDCl$_3$) δ 45.0, 63.6, 69.0, 79.8, 81.3, 121.3, 122.7, 128.1, 128.3, 129.0, 129.3, 130.5, 134.2, 135.2, 135.3, 135.6, 139.0, 139.1, 162.6, 168.4; MS (FAB, NBA) m/e (rel intensity) 725 (M$^+$+1, 63).

Scheme 21

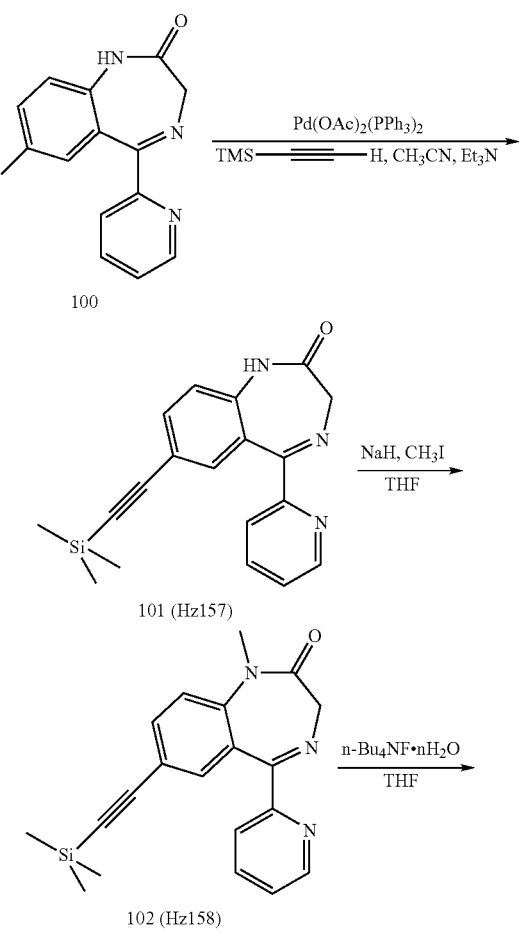

100

101 (Hz157)

102 (Hz158)

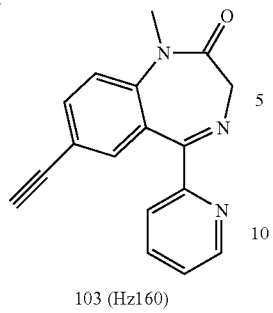

103 (Hz160)

The benzodiazepine 100 (bromazepam) was reacted with trimethylsilylacetylene in the presence of a palladium catalyst to provide trimethylsilyl analog 101 (Hz157) that was methylated with methyl iodide/sodium hydride to afford analog 102 (Hz158). This was subjected to fluoride-mediated desilation to achieve analog 103 (Hz160).

7-Trimethylsilylacetylenyl-5-pyridin-2-yl-1,3-dihydro-benzo[e][1,4]diazepin-2-one (Hz157). Trimethylsilylacetylenyl analog 101 (Hz157) was obtained in 76% yield from 100 analogous to the procedure employed above as a light gray solid. mp: 242-243° C.; IR (KBr) 2956, 2155, 1690, 1616, 1492, 1332, 1248, 1018, 842, 754 cm$^{-1}$; $^1$H NMR (300 MHz, CDCl$_3$) δ 0.23 (s, 9H), 4.39 (s, 2H), 7.06 (d, 1H, J=8.4 Hz), 7.41 (ddd, 1H, J=7.5, 4.8, 1.2 Hz), 7.46 (d, 1H, J=1.8 Hz), 7.57 (dd, 1H, J=8.4, 1.9 Hz), 7.83 (td, 1H, J=7.7, 1.7 Hz), 7.97 (d, 1H, J=7.9 Hz), 8.41 (b s, 1H), 8.68 (d, 1H, J=4.2 Hz); MS (EI) m/e (relative intensity) 334 (35), 333 (M$^+$, 100), 332 (57), 318 (21), 304 (31).

7-Trimethylsilylacetylenyl-1-methyl-5-pyridin-2-yl-1,3-dihydro-benzo[e][1,4]diazepin-2-one (Hz158). Trimethylsilylacetylenyl analog 102 (Hz158) was obtained in 74% yield from 101 analogous to the procedure employed above as a light grey solid. mp: 194-195° C.; IR (KBr) 2956, 2154, 1682, 1614, 1491, 1335, 1249, 881, 844, 747 cm$^{-1}$; $^1$H NMR (300 MHz, CDCl$_3$) δ 0.24 (s, 9H), 3.42 (s, 3H), 3.84 (d, 1H, J=10.6 Hz), 4.89 (d, 1H, J=10.6 Hz), 7.29 (d, 1H, J=7.6 Hz), 7.40 (m, 1H), 7.46 (d, 1H, J=1.9 Hz), 7.63 (dd, 1H, J=8.5, 1.9 Hz), 7.84 (td, 1H, J=7.7, 1.7 Hz), 8.09 (d, 1H, J=7.9 Hz), 8.68 (d, 1H, J=4.3 Hz); MS (EI) m/e (relative intensity) 348 (28), 347 (M$^+$, 100), 346 (44), 318 (34), 291 (23).

7-Acetylenyl-1-methyl-5-pyridin-2-yl-1,3-dihydro-benzo[e][1,4]diazepin-2-one (Hz160). The 7-acetyleno analog 103 (Hz160) was obtained in 63% yield from 102 analogous to the procedure employed above as a white solid. mp: 190-191° C.; IR (KBr) 3286, 3233, 1678, 1614, 1491, 1344, 1126, 750 cm$^{-1}$; $^1$H NMR (300 MHz, CDCl$_3$) δ 3.07 (s, 1H), 3.86 (d, 1H, J=10.6 Hz), 4.93 (d, 1H, J=10.2 Hz), 7.32 (d, 1H, J=8.6 Hz), 7.39 (m, 1H), 7.51 (d, 1H, J=1.8 Hz), 7.65 (dd, 1H, J=8.5, 1.9 Hz), 7.83 (td, 1H, J=7.7, 1.7 Hz), 8.11 (d, 1H, J=7.9 Hz), 8.65 (d, 1H, J=4.7 Hz); MS (EI) m/e (relative intensity) 275 (M$^+$, 100), 274 (35), 246 (43), 219 (30).

Scheme 22

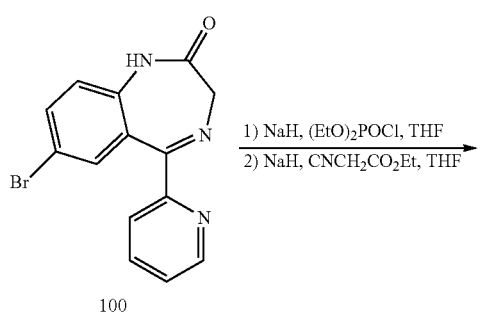

100

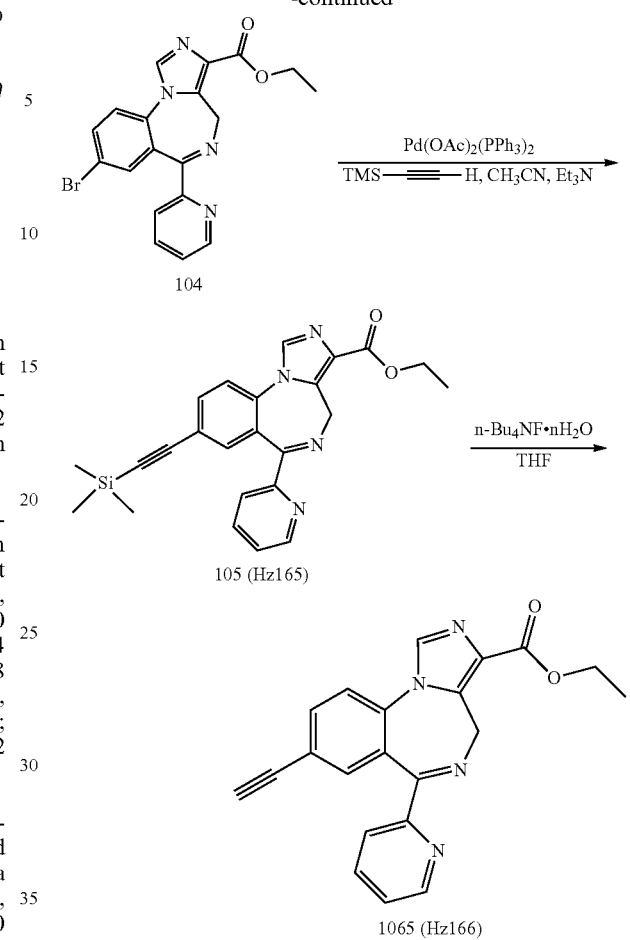

104

105 (Hz165)

1065 (Hz166)

The benzodiazepine 100 (bromazepam) was reacted with diethylphosphorochloridate, followed by the addition of ethyl isocyanoacetate to provide the ester 104. This was then reacted with trimethylsilyacetylene in the presence of a palladium catalyst to provide trimethylsilyl analog 105 (Hz165) which was subjected to fluoride-mediated desilylation to furnish analog 106 (Hz166).

8-Trimethylsilylacetylenyl-6-pyridin-2-yl-4H-benzo[f]imidazo[1,5-a][1,4]diazepine-3-carboxylic acid ethyl ester 105 (Hz165). Trimethylsilyacetylenyl analog 105 (Hz165) was obtained in 73% yield from 104 analogous to the procedure employed in Scheme 22 as a white solid. mp: 205-206° C.; $^1$H NMR (300 MHz, CDCl$_3$) δ 0.25 (s, 9H), 1.44 (t, 3H, J=7.1 Hz), 4.14 (d, 1H, J=11.0 Hz), 4.44 (m, 2H), 6.11 (d, 1H, J=10.9 Hz), 7.38 (ddd, 1H, J=7.5, 4.8, 1.1 Hz), 7.51 (s, 1H), 7.54 (d, 1H, J=8.4 Hz), 7.74 (dd, J=8.3, 1.8 Hz), 7.83 (td, 1H, J=7.7, 1.7 Hz), 7.93 (s, 1H), 8.05 (m, 1H), 8.61 (m, 1H).

8-Acetylenyl-6-pyridin-2-yl-4H-benzo[f]imidazo[1,5-a][1,4]diazepine-3-carboxylic acid ethyl ester 106 (Hz166). The 7-acetyleno analog 106 (Hz166) was obtained in 98% yield from 105 analogous to the procedure employed in Scheme 22 as a white solid. mp: 243-244° C.; $^1$H NMR (300 MHz, CDCl$_3$) δ 1.45 (t, 3H, J=7.1 Hz), 3.17 (s, 1H), 4.17 (d, 1H, J=10.0 Hz), 4.45 (m, 2H), 6.13 (d, 1H, J=10.4 Hz), 7.38 (ddd, 1H, J=7.5, 4.8, 1.1 Hz), 7.56 (d, 1H, J=8.2 Hz), 7.58 (s, 1H), 7.77 (dd, 1H, J=8.6, 1.8 Hz), 7.83 (td, 1H, J=7.7, 1.8 Hz), 7.93 (s, 1H), 8.08 (m, 1H), 8.59 (m, 1H).

Scheme 23 (SH-053-S-CH₃)
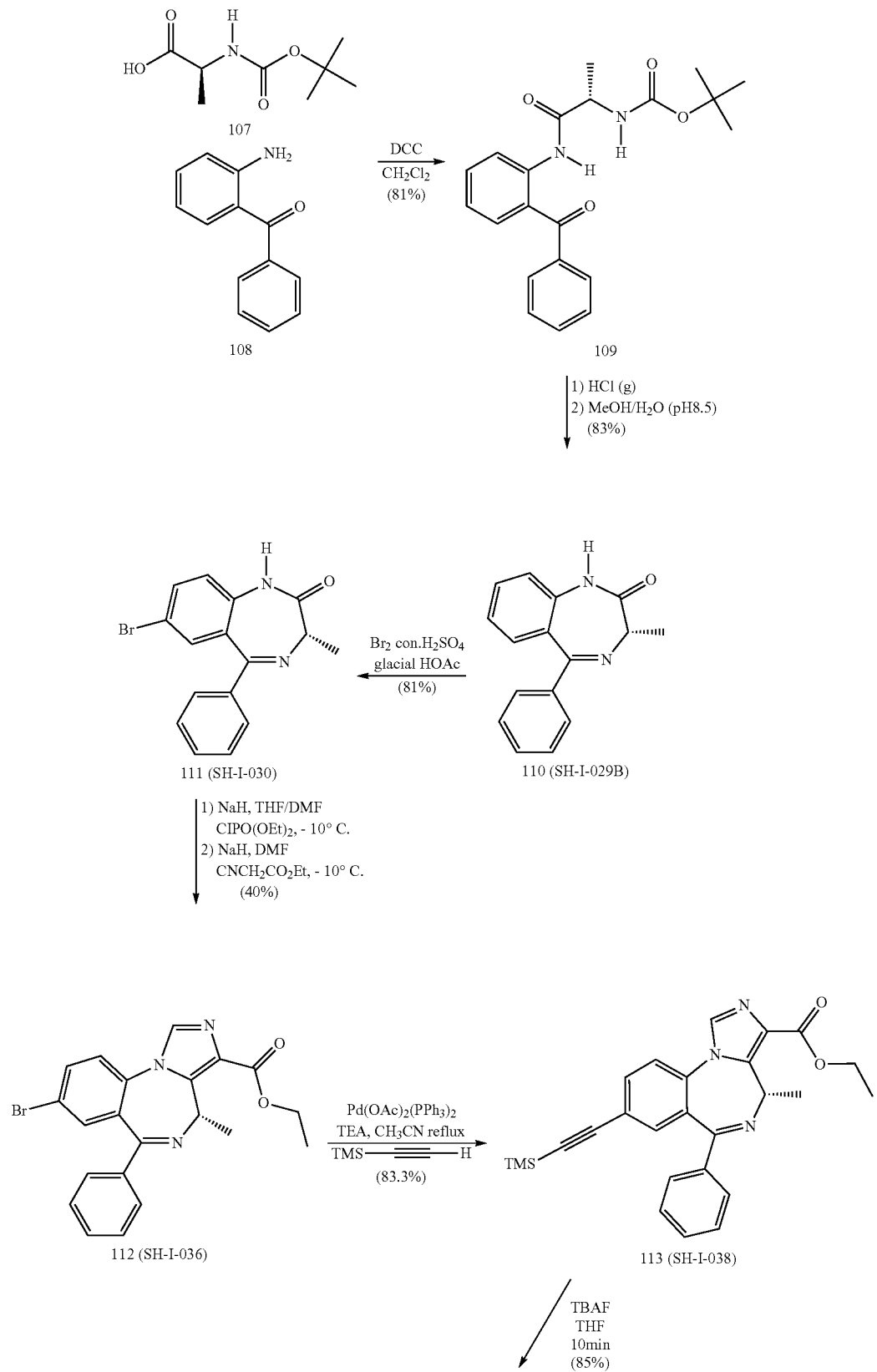

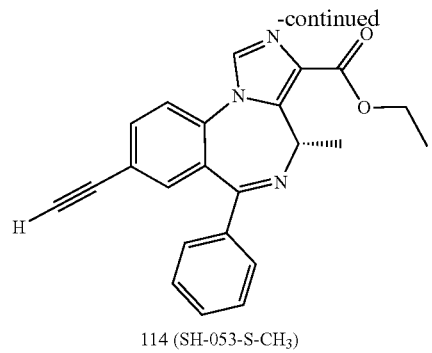

114 (SH-053-S-CH₃)

The benzophenone 108 was reacted with N—BOC-L-alanine 107 to give [1-(2-benzoyl-phenylcarbamoyl)-ethyl]-carbamic acid tert-butyl ester 109. See Bradley, R., et al., (2000) J. Am. Chem. Soc. 122: 460-465. This ester was treated with HCl(g) in CHCl₃ and then cyclized under basic conditions to give benzodiazepine 110. This amide 110 was regioselectively brominated at position-7 to give bromide 111. The bromide 111 was stirred with diethylphosphorochloridate in the presence of sodium hydride, followed by addition of ethyl isocyanoacetate to provide the ethyl ester 112 (SH-I-036). This was converted into the trimethylsilylacetylene analog 113 (SH-I-038) under standard conditions (Pd-mediated, Heck-type coupling). Treatment of 113 with fluoride anion gave the title compound 114 (SH-053-S—CH₃). The other analogs were prepared via the same process.

Procedure for SH-053-S—CH₃ (113):

[1-(2-Benzoyl-phenylcarbamoyl)-ethyl]-carbamic acid tert-butyl ester 109. To a stirred solution of 2-amino-5-bromobenzophenone 108 (5.73 g, 29.07 mmol) and the N-Boc-L-alanine 107 (5 g, 26.43 mmol) in CH₂Cl₂ (200 mL) was added dicyclohexylcarbodiimide (DCC) (5.99 g, 29.07 mmol) in CH₂Cl₂ (100 mL) dropwise, over 30 min at 0° C. The reaction mixture was stirred an additional 8 h at rt. The dicyclohexyl urea which formed was filtered off and the filtrate concentrated under reduced pressure. The crude solid 109 was purified by recrystallization from hexane to afford 109 (7.88 g, 81%), mp 127-129° C.; IR (KBr, cm⁻¹) 3288, 2475, 2352, 1684, 1636, 1576, 1507, 1447, 1264, 1165, 700; ¹H NMR (CDCl₃) δ 11.48 (s, 1H), 8.67 (d, J=8.22 Hz, 1H), 7.71-7.43 (m, 7H), 7.13-7.08 (m, 1H) 5.06 (br s, 1H), 4.36 (br s, 1H), 1.50 (d, J=7.1 Hz, 3H), 1.44 (s, 9H); MS (EI) m/e (relative intensity) 368 (M⁺, 6), 295 (10), 225 (27), 224 (79), 197 (83), 196 (77), 167 (15), 145 (46), 144 (88), 126 (17), 105 (38), 88 (94), 77(37), 57 (100); [α]²⁶_D=−67.7 (c 0.88, EtOAc).

3-Methyl-5-phenyl-1,3-dihydro-benzo[e][1,4]diazepin-2-one 110. To a stirred solution of the benzophenone 109 (10.65 g 29.38 mmol) in CHCl₃ (400 mL) at rt, hydrogen chloride gas was added in slowly. After 20 min, the addition was stopped and the solution was stirred overnight at rt. The reaction mixture was washed with a saturated solution of sodium bicarbonate (2×50 mL) and water (2×50 mL). The organic layer was concentrated under reduced pressure. The residual oil was dissolved in methanol-water (2:1, 500 mL) and the pH was adjusted to 8.5 by the addition of aqueous sodium hydroxide (1 N). The reaction mixture was stirred for 10 h at rt. The solution was concentrated under reduced pressure and water (100 mL) was added. The solution was extracted with CH₂Cl₂ (3×100 mL) and concentrated under reduced pressure. The crude solid 110 was purified by recrystallization from methanol/water to provide 110 (6.10 g, 83%). mp 160-162° C.; IR (KBr, cm⁻¹) 3215, 3059, 2974, 2932, 1681, 1574, 1478, 1445, 1372, 1321, 1242, 1160, 1131; ¹H NMR (CDCl₃) δ 9.65 (s, 1 H), 7.54-7.13 (m, 9 H), 3.78 (q, J=6.5 Hz, 1 H), 1.78 (d, J=7.1 Hz 3H); MS (EI) m/e (relative intensity) 250 (M⁺, 40), 249 (83), 234 (15), 209 (75), 208 (76), 207 (100), 180 (17), 152 (19) 103 (23), 77 (40); [α]²⁶_D=290.2 (c 0.78, EtOAc).

7-Bromo-3-methyl-5-phenyl-1,3-dihydro-benzo[e][1,4]diazepin-2-one 111. To a stirred solution of 110 (66.5 g, 265 mmol) in glacial acetic acid (400 mL), sulfuric acid (80 mL) was added to the solution. Bromine (28 mL, 530 mmol) dissolved in acetic acid (150 mL) was added dropwise into the mixture. The reaction mixture was allowed to stir until NMR spectroscopy indicated that all of the starting material 110 had been consumed. The solution was concentrated under reduced pressure and then neutralized by addition of 1N NaOH solution and then extracted with EtOAc. The crude product 111 was purified by recrystallization from CH₂Cl₂ to afford 5 (70.4 g, 81%). mp 210-212° C.; IR (KBr, cm⁻¹) 2931, 1692, 1603, 1563, 1475, 1445, 1375, 1259, 1235, 1130, 1090; ¹H NMR (CDCl₃) δ 9.36 (s, 1 H), 7.63 (dd, J=2.22, 8.58 Hz, 1 H), 7.54-7.39 (m, 6 H), 7.12 (d, J=8.61 1 H), 3.76 (q, J=6.3 Hz, 1 H), 1.76 (d, J=6.45 Hz, 3 H). MS (EI) m/e (relative intensity) 330 (M⁺+1, 21), 329 (M⁺, 50), 328 (22), 327 (48), 289 (44), 288 (46), 287 (100), 286 (49), 285 (60), 205 (25), 77 (49); [α]²⁶_D=313.1 (c 0.34, EtOAc).

8-Bromo-4-methyl-6-phenyl-4H-2,5,10b-triaza-benzo[e]azulene-3-carboxylic acid ethyl ester 112. 7-Bromo-3-methyl-5-phenyl-1,3-dihydrobenzo[e][1,4]diazepin-2-one 111 (16.6 g, 0.052 mol) was suspended in dry THF (250 mL) and cooled to −10° C. Sodium hydride (60% dispersion in mineral oil, 4.36 g, 0.109 mol) was added into the suspension in one portion. The reaction mixture was allowed to stir and warm to rt over a 3 h period. The reaction mixture was again cooled to −10° C. and diethyl chlorophosphate (12.7 ml, 0.09 mol) was added. The cooling bath was then removed and stirring continued for 3 h. At this time, sodium hydride (60% dispersion in mineral oil, 4.2 g, 0.1 mol) was suspended in dry THF (250 mL) at −10° C. in another flask. Ethyl isocyanoacetate (6.78 mL, 0.06 mol) was added to the NaH/THF suspension, the solution which resulted was allowed to stir for 3 h. After 3 h the first flask was cooled to −30° C. and the solution in the 2nd reaction flask was added to the first flask via a cannula. The reaction mixture was allowed to stir for 24 h, and then cooled with an ice-water bath and slowly quenched with acetic acid (10 mL). Water was added to the reaction mixture after which it was extracted with EtOAc. The EtOAc layers were combined, washed with aq NaHCO₃, brine and dried (Na₂SO₄). After removal of the solvent under reduced pressure, the solid was purified by flash chromatography (silica gel, EtOAc: hexane, gradient elution 1:2, 1:1, 2:1). The ester 112 was a white solid (8.76 g, 40%). mp 164-165° C.; IR (KBr, cm⁻¹) 2925, 1706, 1622, 1557, 1495, 1266, 1185; ¹H NMR (CDCl₃) δ 7.89 (s, 1 H), 7.73 (dd, J=1.73 Hz, 1 H), 7.51-7.36 (m, 7 H), 6.66 (q, J=7.30, 1 H), 4.45-4.30 (m, 2 H), 1.40 (t, J=7.11, 3 H), 1.25 (d, J=7.38 Hz, 3H). MS (EI) m/e (relative intensity) 426 (M⁺+2, 15), 425 (M⁺+1, 58), 424 (M⁺, 15), 423 (58), 380

(24), 379 (71), 378 (35), 377 (69), 352 (50), 351(100), 350 (67), 349 (92), 270 (38), 229 (16); [α]$^{26}_D$=−38.0 (c 0.45, EtOAc).

4-Methyl-6-phenyl-8-trimethylsilanylethynyl-4H-2,5,10b-triazabenzo[e]azulene-3-carboxylic acid ethyl ester 113. A mixture of ester 112 (3.0 g, 7.07 mmol) and bis(triphenylphosphine)palladium (II) acetate (0.42 g, 0.57 mmol) was dissolved in a mixed solvent system of acetonitrile (80 mL) and TEA (120 mL). The mixture was degassed under vacuum and argon gas was added, after which trimethylsilylacetylene (2 mL, 14.14 mmol) was added into the mixture. The mixture was degassed again under vacuum (argon) and heated to reflux. The mixture was heated at reflux until analysis by TLC (EtOAc) indicated that all of the starting material 112 had been consumed. The mixture was cooled to rt and the precipitate which formed was removed by filtration through celite. The filtrate was concentrated under reduced pressure and partitioned between H$_2$O and EtOAc. The combined layers of EtOAc were washed with brine and dried (Na$_2$SO$_4$), after which the solvent was removed under reduced pressure and the residue was purified by flash chromatography (silica gel, EtOAc:hexane 1:1). Conditions for TLC were EtOAc. A white solid 113 (2.60 g, 83.3%) was obtained. mp 160-162° C.; IR (KBr, cm$^{-1}$) 3365, 2925, 1706, 1616, 1553, 1498; $^1$H NMR (CDCl$_3$) δ 7.89 (s, 1 H), 7.73 (dd, J=1.73 Hz, 1 H), 7.51-7.36 (m, 7 H), 6.66 (q, J=7.30, 1 H), 4.45-4.30 (m, 2 H), 1.40 (t, J=7.11, 3 H), 1.25 (d, J=7.38 Hz, 3 H), 0.15 (s, 9 H). MS (EI) m/e (relative intensity) 441 (M$^+$, 15), 369 (25), 323 (55), 295 (100), 267 (15).

8-Ethynyl-4-methyl-6-phenyl-4H-2,5,10b-triaza-benzo[e]azulene-3-carboxylic acid ethyl ester 114 (SH-053-S—CH$_3$). The trimethylsilylacetylene intermediate 113 (SH-I-038) (2.8 g, 6.3 mmol) was dissolved in THF (60 mL) and was then treated with Bu$_4$NF.H$_2$O (1.9 g, 7.56 mmol). The mixture was allowed to stir for 30 min at rt, after which H$_2$O (10 mL) was added and the mixture was extracted with EtOAc (3×50 mL). The combined organic extracts were washed with brine (25 mL) and dried (Na$_2$SO$_4$). After removal of the solvent under reduced pressure, the residue was purified by a wash column (silica gel, EtOAc) to furnish 114 (SH-053-S—CH$_3$) (1.9 g, 85%) as a white solid: mp 197-199° C.; IR (KBr, cm$^{-1}$) 3285, 2928, 1708, 1616, 1553, 1498, 1445, 1374; $^1$H NMR (CDCl$_3$) δ 7.92 (s, 1 H), 7.73 (dd, J=1.72, 8.32 Hz, 1 H), 7.58-7.36 (m, 7 H), 6.67 (q, J=7.35, 1H), 4.46-4.34 (m, 2H), 3.16 (s, 1 H), 1.41 (t, J=7.11, 3 H), 1.25 (d, J=7.38, 3 H); MS (EI) m/e (relative intensity) 369 (M$^+$, 30), 323 (55), 295 (100), 267 (15). Anal. Calcd. for C$_{23}$H$_{19}$N$_3$O$_2$: C, 74.78; H, 5.18; N, 11.37. Found: C, 74.22; H, 5.11; N, 11.41. [α]$^{26}_D$=−74.8 (c 0.8, EtOAc).

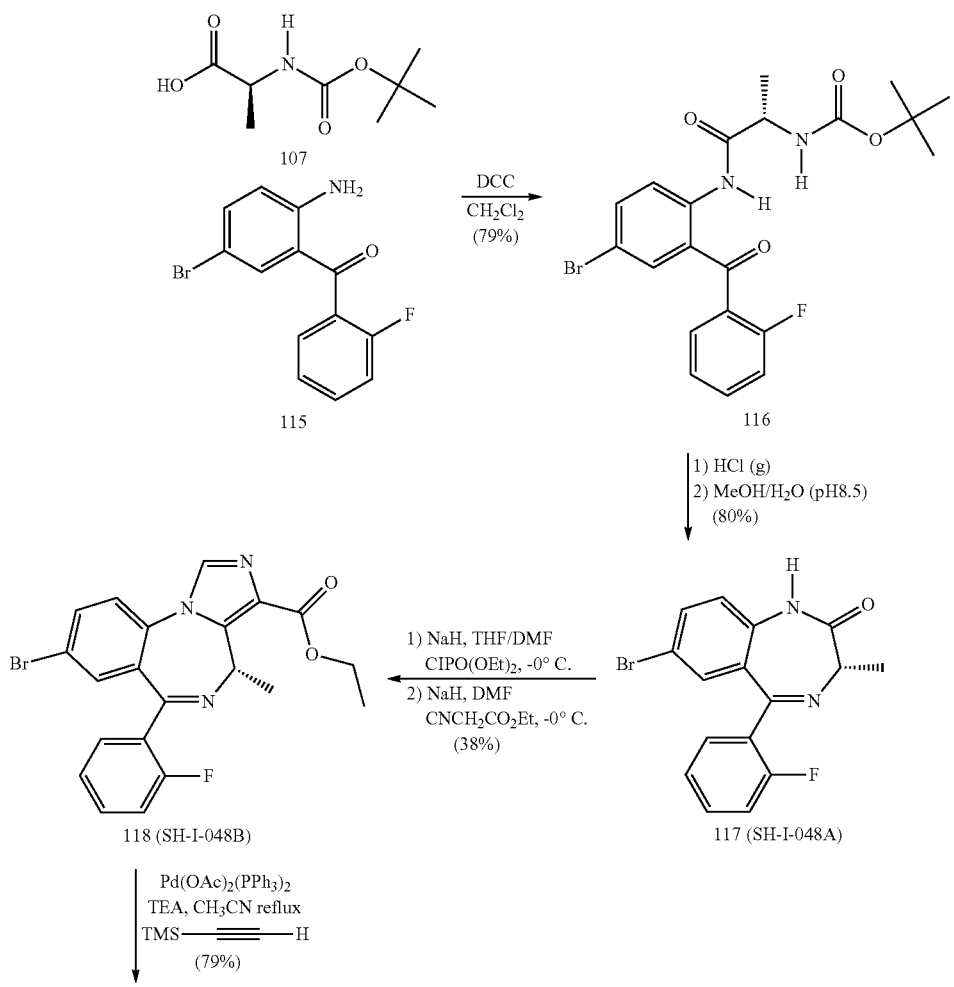

Scheme 24 (SH-053-2'F-S-CH$_3$)

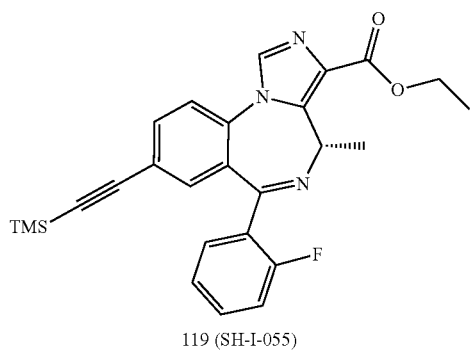

119 (SH-I-055)

-continued

TBAF
THF
10min
(87%)

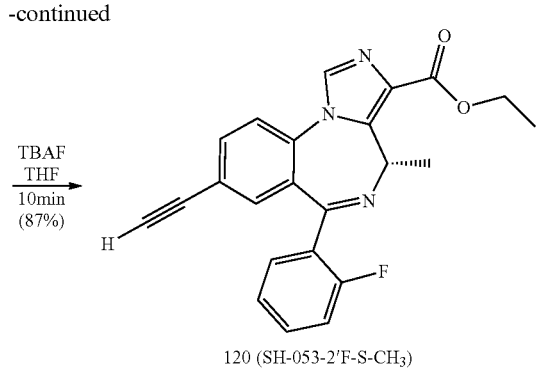

120 (SH-053-2'F-S-CH₃)

Procedure for SH-053-2'F—S—CH$_3$:

{1-[4-Bromo-2-(2-fluoro-benzoyl)-phenylcarbamoyl-ethyl}-carbamic acid tert-butyl ester 116. To a stirred solution of (2-amino-5-bromophenyl)-(2-fluoro-phenyl)-methanone (60 g, 204 mmol) 115 and the N-Boc-L-alanine 107 (38.59 g, 204 mmol) in CH$_2$Cl$_2$ (500 mL) was added dicyclohexylcarbodiimide (DCC) (42.09 g, 204 mmol) in CH$_2$Cl$_2$ (200 mL) dropwise, over a 30 min period at 0° C. The reaction mixture was allowed to stir an additional 8 h at rt. The dicyclohexyl urea which formed was filtered off and the filtrate concentrated under reduced pressure. The crude solid residue 116 was purified by recrystallization from hexane and EtOAc to afford 116 (74.9 g, 79%) mp 158-159° C.; IR (KBr, cm$^{-1}$) 3332, 2931, 255, 1694, 1643, 1613, 1582, 1537, 1450; $^1$H NMR (CDCl$_3$) δ 11.68 (s, 1 H), 8.71 (d, J=9.0 Hz, 1 H), 7.69 (dd, J=9.0, 2.3 Hz, 1 H), 7.55-7.62 (m, 2 H), 7.46 (td, J=7.6, 1.4 Hz, 1 H), 7.30 (t, J=7.5 Hz, 1 H), 7.21 (t, J=9.1 Hz, 1 H), 5.13 (b, 1 H), 4.37 (b, 1 H), 1.51 (d, J=7.2 Hz, 3 H), 1.45 (s, 9H). MS (EI) m/e (relative intensity) 467 (M$^+$+2, 14), 466 (M$^+$+1, 44), 465 (M$^+$, 14), 464 (42), 329 (15), 321 (60), 295 (100), 224 (26); [α]$^{26}_D$=−59.1 (c 0.51, EtOAc).

7-Bromo-5-(2-fluoro-phenyl)-3-methyl-1,3-dihydrobenzo[e]

[1,4]diazepin-2-one 117. To a stirred solution of the benzophenone 116 (30 g, 64.4 mmol) in CHCl$_3$ (300 mL) at rt, hydrogen chloride gas was added slowly. After 20 min, the addition was stopped and the solution was allowed to stir overnight at rt. The reaction mixture was washed with a saturated solution of sodium bicarbonate solution (2×70 mL) and water (2×70 mL). The organic layer was concentrated under reduced pressure. The residual oil was dissolved in methanol/water (1:1, 300 mL) and the pH was adjusted to 8.5 by the addition of aq sodium hydroxide (1 N). The reaction mixture was allowed to stir for 10 hr at rt. The solution was then concentrated under reduced pressure and water (100 mL) was added. The solution was extracted with CH$_2$Cl$_2$ (3×50 mL), the organic layer was dried (Na$_2$SO$_4$) and concentrated under reduced pressure. The crude solid 117 was purified by recrystallization from methanol/water to provide 117 (17.8 g, 80%). mp 183-185° C.; IR (KBr, cm$^{-1}$) 2928, 1694, 1611, 1479, 1450, 1377, 1315, $^1$H NMR (CDCl$_3$) δ 9.50 (bs, 1H), 7.62-7.65 (m, 2 H), 7.50 (q, J=6.5 Hz, 1 H), 7.40 (d, J=2.0 Hz, 1 H), 7.29 (t, J=7.5 Hz 1 H) 7.15 (d, J=8.6 Hz, 1 H), 7.11 (t, J=8.9 Hz, 1 H), 3.84 (q, J=6.5 Hz, 1 H), 1.82 (d, J=6.5 Hz, 3 H); MS (EI) m/e (relative intensity) 348 (M$^+$+1, 23), 347 (M$^+$, 38), 346 (24), 345 (36), 329 (19), 327 (20), 307 (40), 306 (41), 305 (100), 304 (37), 303 (63); [α]$^{26}_D$=168.8 (c 0.73, EtOAc).

8-Bromo-6-(2-fluorophenyl)-4-methyl-4H-2,5,10b-triaza-benzo[e]azulene-3-carboxylic acid ethyl ester 118.

7-Bromo-5-(2-fluorophenyl)-3-methyl-1,3-dihydro-benzo[e][1,4]diazepin-2-one 117 (3.78 g, 10.88 mmol) was suspended in dry THF (150 mL) and cooled to −10° C. Sodium hydride (60% dispersion in mineral oil, 0.52 g, 13.07 mol) was added into the suspension in one portion. The reaction mixture was allowed to stir and then warm to rt over a 3 h period. The reaction mixture was again cooled to −10° C. and diethyl chlorophosphate (2.65 mL, 17.42 mmol) was added. The cooling bath was then removed and stirring continued for 3 h. During this time, sodium hydride (60% dispersion in mineral oil, 0.61 g, 15.24 mmol) was suspended in dry THF (60 mL) at −10° C. in another flask. Ethyl isocyanoacetate (1.43 ml, 13.07 mnol) was added to the NaH/THF suspension and this mixture allowed to stir for 3 h. After 3 h the first flask was cooled to −30° C. with a cooling bath and the mixture in the second reaction flask was added to the first flask via a cannula. The reaction mixture was allowed to stir for 24 h, after which it was cooled to 0° C. with an ice-water bath and slowly quenched with acetic acid (5 mL). Water was then added to the reaction mixture and this was extracted with EtOAc. The EtOAc layers were combined, washed with aq NaHCO$_3$, brine and dried (Na$_2$SO$_4$). After removal of the solvent under reduced pressure, the solid was purified by flash chromatography (silica gel, EtOAc:hexane: gradient elution 1:2, 1:1, 2:1). The ethyl ester 118 was a white solid (1.82 g, 38%). mp 190-192° C.; IR (KBr, cm$^{-1}$) 3316, 2925, 1693, 1621, 1485, 1448, 1371; $^1$H NMR (CDCl$_3$) δ 7.92 (s, 1 H), 7.72 (dd, J=8.5, 1.5 Hz, 1 H), 7.6 (t, J=6.9 Hz, 1 H), 7.48 (d, J=8.5 Hz, 1 H), 7.42-7.49 (m, 2 H), 7.23-7.29 (m, 1 H), 7.05 (t, J=9.3 Hz, 1 H), 6.71 (q, J=7.3 Hz, 1 H), 4.41 (m, 2 H), 1.42 (t, J=7.1 Hz, 3 H), 1.29 (d, J=7.2, 3 H). MS (EI) m/e (relative intensity) 442 (M$^+$, 5), 428 (7), 381 (58), 355 (100), 303 (37); [α]$^{26}_D$=10.6 (c 0.53, EtOAc).

6-(2-Fluorophenyl)-4-methyl-8-trimethylsilanylethynyl-4H-2,5,10b-triaza-benzo[e]azulene-3-carboxylic acid ethyl ester 119. A mixture of 118 (69.3 mg, 0.16 mmol) and bis(triphenylphosphine) palladium (II) acetate (11.68 mg, 0.015 mmol) was dissolved in a mixed solvent system of acetonitrile (120 mL) and TEA (80 mL). The mixture was degassed under vacuum and argon gas was added, after which trimethylsilylacetylene (0.044 mL, 0.31 mmol) was added into the mixture. The mixture was degassed again under vacuum (argon) and heated to reflux. The mixture was heated at reflux until analysis by TLC (EtOAc) indicated that all of the starting material 118 had been consumed. The mixture was cooled to rt and the precipitate which formed was removed by filtration through celite. The filtrate was concentrated under reduced pressure and partitioned between H$_2$O and EtOAc. The combined layers of EtOAc were washed with brine and dried (Na$_2$SO$_4$), after which the solvent was removed under reduced pressure and the residue was purified by flash chromatography (silica gel, EtOAc:hexane 1:1). The conditions for TLC were EtOAc on silica gel. A white solid 119 (58.1 mg, 7 9%) was obtained. mp 186-187° C.; IR (KBr, cm$^{-1}$) 2410, 2358, 1716, 1497, 1253; $^1$H NMR (CDCl$_3$) δ 7.92 (s, 1 H), 7.72 (dd, 1.5 Hz, 1 H), 7.6 (t, J=6.9 Hz, 1H), 7.48 (d, J=8.5 Hz, 1 H), 7.42-7.49 (m, 2 H), 7.23-7.29 (m, 1 H), 7.05 (t, J=9.3 Hz, 1 H), 6.71 (q, J=7.3 Hz, 1 H), 4.41 (m, 2 H), 1.42 (t, J=7.1 Hz, 3 H), 1.29 (d, J=7.2, 3 H), 0.24 (s, 9 H). MS (EI) m/e (relative intensity) 459 (M$^+$, 28), 445 (32), 399 (51), 371 (100), 235 (71), 178 (75); [α]$^{26}_D$=−27.8 (c 0.46, EtOAc).

8-Ethynyl-6-(2-fluorophenyl)-4-methyl-4H-2,5,10b-triazabenzo[e]azulene-3-carboxylic acid ethyl ester 110 (SH-053-2'F—S—CH$_3$). The trimethylsilylacetylene intermediate 119 (SH-1-055) (0.17 g, 0.37 mmol) was dissolved in THF (30 mL) and was then treated with Bu$_4$NF.H$_2$O (0.114 g, 0.44 mmol). The mixture was allowed to stir for 30 min at rt, after which H$_2$O (10 mL) was added and the mixture was extracted with EtOAc (3×25 mL). The combined organic extracts were washed with brine (25 mL) and dried (Na$_2$SO$_4$). After removal of the solvent under reduced pressure, the residue was purified by a wash column (silica gel, EtOAc) to furnish 120 (SH-053-2'F—S—CH$_3$) (0.12 g, 87%) as a white solid: mp 212-214° C.; IR (KBr, cm$^{-1}$) 3288, 2979, 1716, 1497, 1257, 1255; $^1$H NMR (CDCl$_3$) δ 7.98 15 (s, 1H), 7.72 (d, J=8.3 Hz, 1 H) 77.63 (d, J=8.5 Hz, 1 H), 7.59 (d, J=8.3 Hz, 1 H), 7.42-7.49 (m, 1 H), 7.42 (s, 1 H), 7.23-7.28 (m, 1 H), 7.05 (t, J=9.2 Hz, 1 H), 6.71 (q, J=7.2, 1 H), 4.41 (m, 2 H), 3.16 (s, 1 H), J=7.1 Hz, 3 H) 1.29 (d, J=7.3 Hz, 3 H). MS (EI) m/e (relative intensity) 387 (M$^+$, 20), 373 (21), 327 (47), 299 (100); [α]$^{26}_D$=−0.95 (c 0.84, EtOAc).

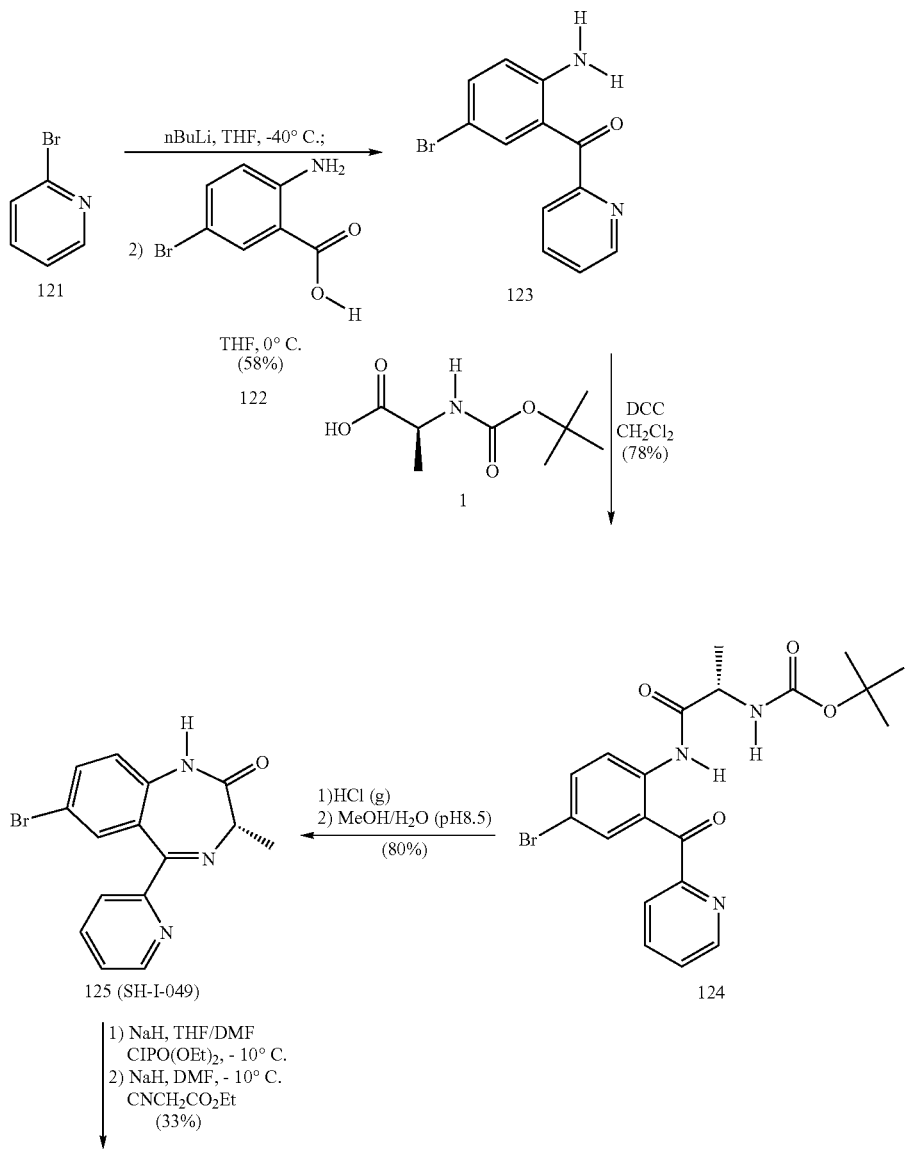

Scheme 25 (SH-053-2'N-S-CH$_3$)

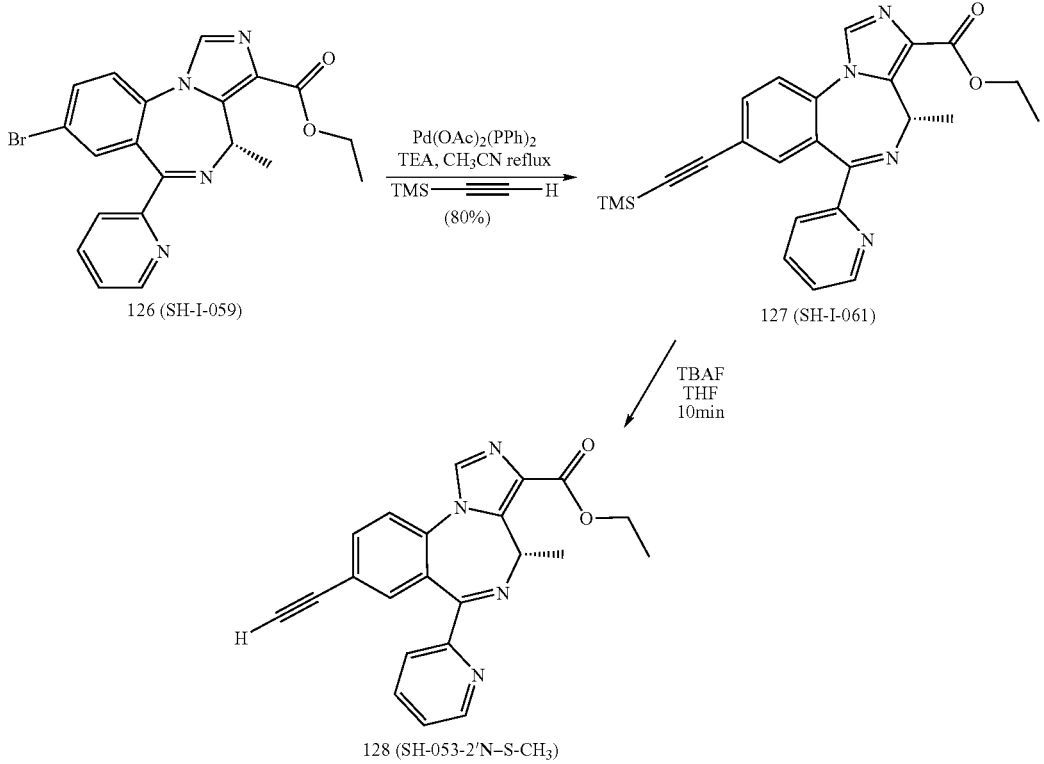

126 (SH-I-059)

127 (SH-I-061)

128 (SH-053-2'N–S–CH₃)

Procedure for SH-053-2'N—S—CH₃ (128):

(2-Amino-5-bromo-phenyl)-pyridin-2-yl-methanone 123. The anion of 2-bromo-pyridine 121 and 2-amino-5-bromobenzoic acid 122 were condensed to provide the 2'-pyridylketone 123.

{1-[4-Bromo-2-(pyridine-2-carbonyl)-phenylcarbamoyl]-ethyl}-carbamic acid tert-butyl ester 124. To a stirred solution of (2-amino-5-bromophenyl)-pyridin-2-yl-methanone 123 (16 g, 57.33 mmol) and the N-Boc-L-alanine 107 (10.92 g, 57.73 mmol) in $CH_2Cl_2$ (100 mL) was added dicyclohexyl-carbodiimide (DCC) (11.91 g, 57.73 mmol) in $CH_2Cl_2$ (60 mL) dropwise, over a 30 min period at 0° C. The reaction mixture was allowed to stir an additional 8 h at rt. The dicyclohexyl urea which formed was filtered off and the filtrate concentrated under reduced pressure. The crude solid 124 was purified by recrystallization from hexane and EtOAc to afford 124 (7.88 g, 81%). mp 208-210° C.; IR (KBr, cm⁻¹) 3332, 2931, 1694, 1507, 1287, 1163; ¹H NMR (CDCl₃) δ 11.68 (s, 1 H), 8.71 (d, J=9.0 Hz, 1 H), 7.69 (dd, J=9.0, 2.3 Hz, 1 H), 7.55-7.62 (m, 2 H), 7.46 (td, J=7.6, 1.4 Hz, 1 H), 7.30 (t, J=7.5 Hz, 1 H), 7.21 (t, J=9.1 Hz, 1 H), 5.13 (b, 1 H), 4.37 (b, 1 H), 1.51 (d, J=7.2 Hz, 3 H), 1.45 (s, 9H). MS (EI) m/e (relative intensity) 449 (M⁺+1, 5), 448 (M⁺, 5), 376 (10), 329 (20), 304 (100), 228 (25); [α]²⁶$_D$=−36.1 (c 0.61, EtOAc).

7-Bromo-3-methyl-5-pyridin-2-yl-1,3-dihydro-benzo[e][1,4]diazepin-2-one 125. To a stirred solution of ester 124 (16 g, 35.69 mmol) in CHCl₃ (300 mL) at rt, hydrogen chloride gas was added in slowly. After 20 min, the addition was stopped and the solution was allowed to stir overnight at rt. The reaction mixture was washed with a saturated solution of sodium bicarbonate (2×50 mL) and water (2×50 mL). The organic layer was concentrated under reduced pressure. The residual oil was dissolved in methanol-water (3:1, 300 mL) and the pH was adjusted to 8.5 by the addition of aq sodium hydroxide (1 N). The reaction mixture was stirred for 10 h at rt. The solution was concentrated under reduced pressure and water (80 mL) was added. The solution was extracted with CH₂Cl₂ (3×70) and concentrated under reduced pressure. The crude solid 125 was purified by recrystallization from methanol/water to provide pure 125 (9.42 g, 80%). mp 227-229° C.; IR (KBr, cm⁻¹) 2928, 1684, 1611, 1476; ¹H NMR (CDCl₃) δ 9.47 (bs, 1 H), 8.62 (d, J=4.7 Hz, 1 H), 8.0 (d, J=7.90 Hz, 1 H), 7.81 (td, J=7.7, 1.6 Hz, 1 H), 7.56 (dd, J=8.6, 2.2 Hz 1 H), 7.50 (dd, J=2.1 Hz, 1 H), 7.36 (dd, J=7.4 Hz, 1 H), 7.06 (d, J=8.6 Hz, 1 H), 3.85 (q, J=6.5 Hz, 1 H), 1.76 (d, J=6.5 Hz, 3 H); MS (EI) m/e (relative intensity) 330 (M⁺, 50), 329 (50), 314 (52), 288 (100), 250 (30), 208 (32), 179(50), 88(72); [α]²⁶$_D$=403.2 (c 0.50, EtOAc).

8-Bromo-4-methyl-6-pyridin-2-yl-4H-2,5,10b-triaza-benzo[e]azulene-3-carboxylic acid ethyl ester 126. The 7-bromo-3-methyl-5-pyridin-2-yl-1,3-dihydro-benzo[e][1,4]diazepin-2-one 125 (3.3 g, 10 mmol) was suspended in dry THF (200 mL) and cooled to −10° C. Sodium hydride (60% dispersion in mineral oil, 0.48 g, 12 mmol) was added into the suspension in one portion. The reaction mixture was allowed to stir and warm to rt over a 3 h period. The reaction mixture was again cooled to −10° C. and diethyl chlorophosphate (2.31 mL, 16 mmol) was added. The cooling bath was then removed and stirring continued for 3 h. At this time, sodium hydride (60% dispersion in mineral oil, 0.56 g, 14 mmol) was suspended in dry THF (150 mL) at −10° C. in another flask. Ethyl isocyanoacetate (1.31 mL, 12 mmol) was added to the NaH/THF suspension, the solution which resulted was allowed to stir for 3 h. After 3 h, the first flask was cooled to −30° C. and the solution in the 2nd reaction flask was added to the first flask via a cannula. The reaction mixture was allowed to stir for 24 h, and then cooled with an ice-water bath and slowly quenched with acetic acid (10 mL). Water was added to the reaction mixture after which it was extracted with EtOAc. The EtOAc layers were combined, washed with aq NaHCO₃, brine and dried (Na₂SO₄). After removal of the solvent under reduced pressure, the solid was purified by flash chromatography (silica gel, EtOAc:hexane, gradient elution 1:1, 2:1, 3:1). The ester 126 was a white solid (1.40 g, 33%). mp 193-195° C.; IR (KBr, cm$^{-1}$) 2962, 1719, 1260, 1021; $^1$H NMR (CDCl$_3$) δ 7.92 (s, 1 H), 7.72 (dd, J=8.5, 1.5 Hz, 1 H), 7.6 (t, J=6.9 Hz, 1 H), 7.48 (d, J=8.5 Hz, 1 H), 7.42-7.49 (m, 2 H), 7.23-7.29 (m, 1 H), 7.05 (t, J=9.3 Hz, 1 H), 6.71 (q, J=7.3 Hz, 1 H), 4.41 (m, 2 H), 1.42 (t, J=7.1 Hz, 3 H), 1.29 (d, J=7.2, 3 H).

4-Methyl-6-pyridin-2-yl-8-trimethylsilanylethynyl-4H-2,5,10b-triazabenzo[e]azulene-3-carboxylic acid ethyl ester 127 (SH-I-061). A mixture of 126 (2.73 g, 6.42 mmol) and bis(triphenylphosphine)palladium (II) acetate (0.48 g, 0.64 mmol) was dissolved in a mixed solvent system of acetonitrile (80 mL) and TEA (120 mL). The mixture was degassed under vacuum and argon gas was added, after which trimethylsilylacetylene (1.8 mL, 12.85 nmol) was added into the mixture. The mixture was degassed again under vacuum (argon) and heated to reflux. The mixture was heated at reflux until analysis by TLC (EtOAc) indicated that all of the starting material 126 had been consumed. The mixture was cooled to rt and the precipitate which formed was removed by filtration through celite. The filtrate was concentrated under reduced pressure and partitioned between H$_2$O and EtOAc. The combined layers of EtOAc were washed with brine and dried (Na$_2$SO$_4$), after which the solvent was removed under reduced pressure and the residue was purified by flash chromatography (silica gel, EtOAc:hexane 2:1). A white solid 127 (SH-I-061) (2.27 g, 80%) was obtained. mp 197-198° C.; IR (KBr, cm$^{-1}$) 3477, 2982, 2158, 1713, 1643; $^1$H NMR (CDCl$_3$) δ 7.92 (s, 1H), 7.72 (dd, J=8.5, 1.5 Hz, 1 H), 7.6 (t, J=6.9 Hz, 1H), 7.48 (d, J=8.5 Hz, 1 H), 7.42-7.49 (m, 2 H), 7.23-7.29 (m, 1 H), 7.05 (t, J=9.3 Hz, 1 H), 6.71 (q, J=7.3 Hz, 1 H), 4.41 (m, 2 H), 1.42 (t, J=7.1 Hz, 3 H), 1.29 (d, J=7.2, 3 H), 0.24 (s, 9 H); [α]$^{26}_D$=304.4 (c 0.41, EtOAc).

8-Ethynyl-4-methyl-6-pyridin-2-yl-4H-2,5,10b-triazabenzo[e]azulene-3-carboxylic acid ethyl ester 128 (SH-053-2'N—S—CH$_3$). The trimethylsilylacetylene intermediate 127 (1.5 g, 3.39 mmol) was dissolved in THF (150 mL) and was then stirred with Bu$_4$NF.H$_2$O (1.06 g, 4.06 mmol). The mixture was allowed to stir for 30 min at rt, after which H$_2$O (10 mL) was added and the mixture was extracted with EtOAc (3×50 mL). The combined organic extracts were washed with brine (25 mL) and dried (Na$_2$SO$_4$). After removal of the solvent under reduced pressure, the residue was purified by a wash column (silica gel, EtOAc) to furnish 128 (SH-053-2'N—S—CH$_3$) (1.01 g, 81%) as a white solid: mp 235-237° C.; IR (KBr, cm$^{-1}$) 3321, 2979, 2933, 1647, 1597; $^1$H NMR (CDCl$_3$) δ 8.61 (d, J=4.2 Hz, 1 H), 8.01 (d, J=7.8 Hz, 1 H), 7.91 (s, 1 H), 7.81 (t, J=7.8 Hz, 1 H), 7.72 (d, J=9.5 Hz, 1 H), 7.55 (d, J=12 Hz, 1 H), 7.59 (s, 1 H), 7.37 (t, J=9.8 Hz, 1 H), 6.71 (q, J=7.3, 1H), 4.41 (m, 2 H), 3.16 (s, 1 H), 1.42 (t, J=7.1 Hz, 3 H) 1.28 (d, J=7.3 Hz, 3 H); [α]$^{26}_D$=−85.2 (c 0.69, EtOAc).

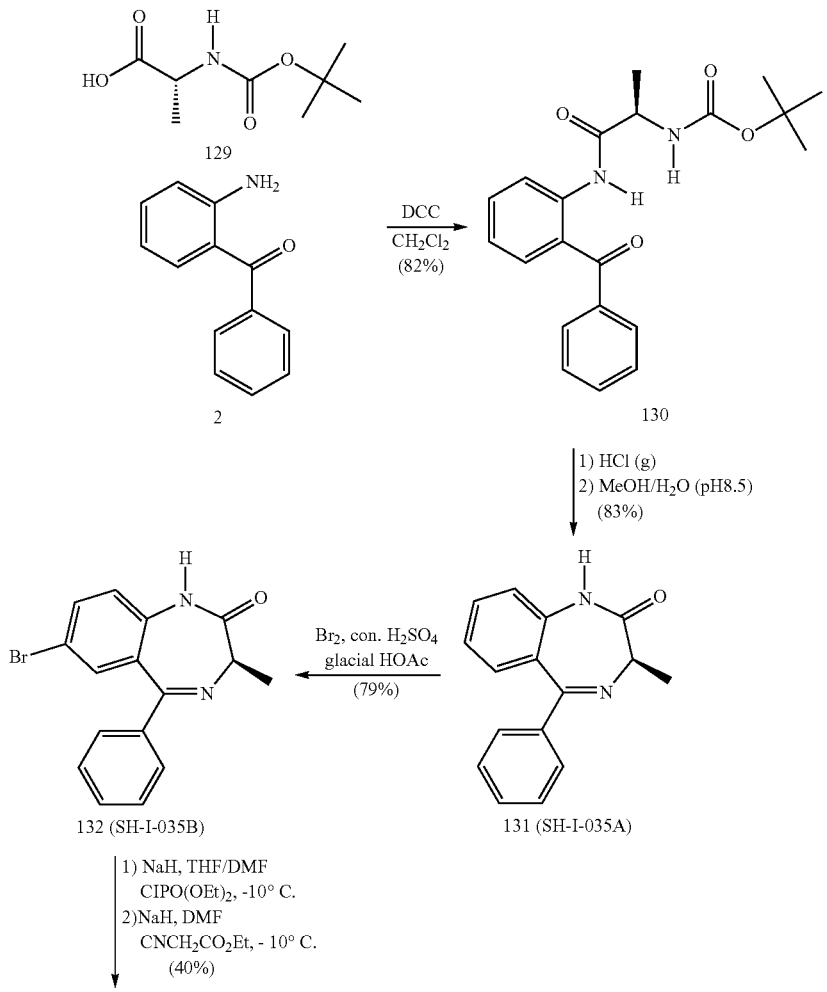

Scheme 26 (SH-053-R-CH$_3$)

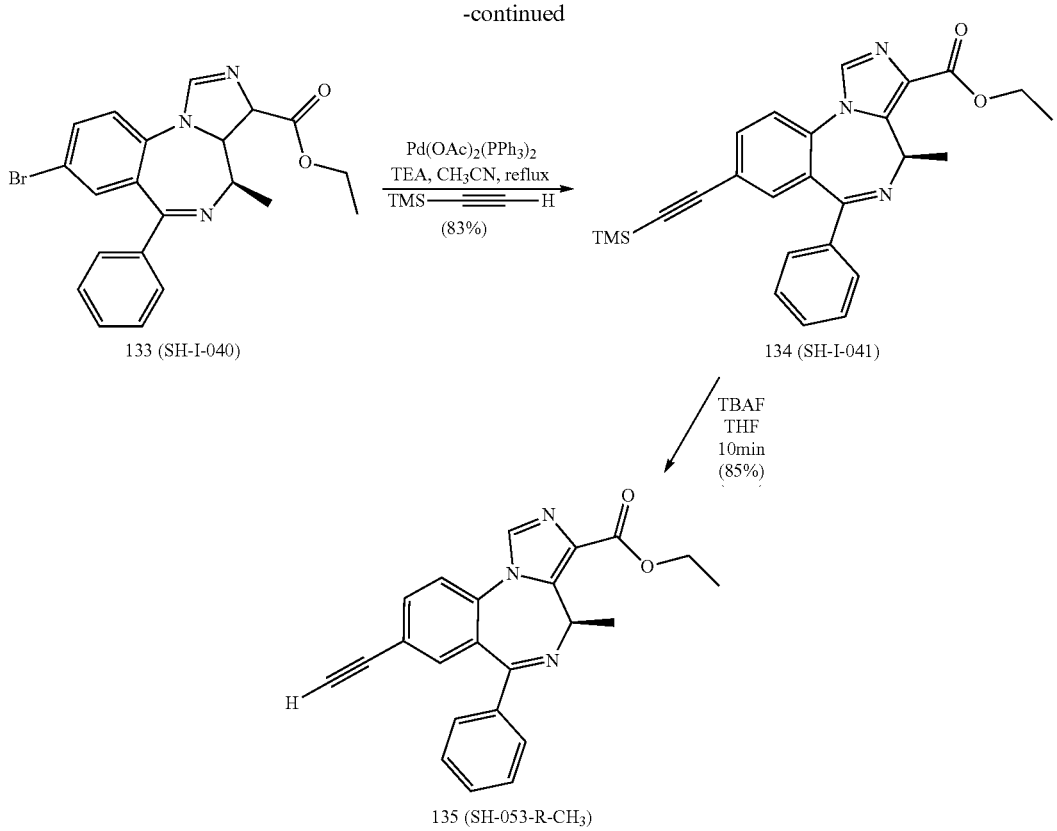

Procedure for SH-053-R—CH₃ (135):

1-(2-Benzoyl-phenylcarbamoyl)-ethyl]-carbamic acid tert-butyl ester 130. To a stirred solution of 2-amino-5-bromobenzophenone (5.73 g, 29.07 mol) and the N-Boc-D-alanine 129 (5 g, 26.43 mmol) in CH₂Cl₂ (200 mL) was added dicyclohexylcarbodiimide (DCC) (5.99 g, 29.07 mmol) in CH₂Cl₂ (100 mL) dropwise, over a 30 min period at 0° C. The reaction mixture was allowed to stir an additional 8 h at rt. The dicyclohexyl urea which formed was filtered off and the filtrate concentrated under reduced pressure. The crude solid 130 was purified by 10 recrystallization from hexane to afford 130 (7.97 g, 82%). mp 127-129° C.; IR (KBr, cm⁻¹) 3288, 2475, 2352, 1684, 1636, 1576, 1507, 1447, 1264, 1165, 700; ¹H NMR (CDCl₃) δ 11.48 (s, 1 H), 8.67 (d, J=8.22 Hz, 1 H), 7.71-7.43 (m, 7 H), 7.13-7.08 (m, J=1 H) 5.06 (br s, 1 H), 4.36 (br s, 1 H), 1.50 (d, J=7.1 Hz, 3 H), 1.44 (s, 9H); MS (EI) m/e (relative intensity) 368 (M⁺, 6), 295 (10), 225 (27), 224 (79), 197 (83), 196 (77), 167 (15), 145 (46), 144 (88), 126 (17), 105 (38), 88 (94), 77 (37), 57 (100); [α]²⁶_D=67.3 (c 0.44, EtOAc).

3-Methyl-5-phenyl-1,3-dihydro-benzo[e][1,4]diazepin-2-one 131. To a stirred solution of the benzophenone 130 (10.65 g, 29.38 mmol) in CHCl₃ (400 mL) at rt, hydrogen chloride gas was added in slowly. After 20 min, the addition was stopped and the solution was allowed to stir overnight at rt. The reaction mixture was then washed with a saturated solution of sodium bicarbonate (2×50 mL) and water (2×50 mL). The organic layer was concentrated under reduced pressure. The residual oil was dissolved in methanol-water (2:1, 500 mL) and the pH was adjusted to 8.5 by the addition of aq sodium hydroxide (1 N). The reaction mixture was stirred for 10 h at rt. The solution was concentrated under reduced pressure and water (100 mL) was added. The solution was extracted with CH₂Cl₂ (3×100 mL) and concentrated under reduced pressure. The crude solid 131 was purified by recrystallization from methanol/water to provide 131 (6.10 g, 83%). mp 160-162° C.; IR (KBr, cm⁻¹) 3215, 3059, 2974, 2932, 1681, 1574, 1478, 1445, 1372, 1321, 1242, 1160, 1131; ¹H NMR (CDCl₃) δ 9.65 (s, 1 H), 7.54-7.13 (m, 9 H), 3.78 (q, J=6.45 Hz, 1 H), 1.78 (d, J=7.1 Hz, 3 H); MS (EI) m/e (relative intensity) 250 (M⁺, 40), 249 (83), 234 (15), 209 (75), 208 (76), 207 (100), 180 (17), 152 (19) 103 (23), 77 (40).

7-Bromo-3-methyl-5-phenyl-1,3-dihydro-benzo[e][1,4]diazepin-2-one 132. To a stirred solution of 131 (66.5 g, 265 m mol) in glacial acetic acid (400 mL), sulfuric acid (80 mL) was added to the solution. Bromine (28 mL, 530 mmol) dissolved in acetic acid (150 mL) was added dropwise into the mixture. The reaction mixture was allowed to stir until analysis by NMR spectroscopy indicated that all of the starting material 131 had been consumed. The solution was concentrated under reduced pressure and then brought to pH 7 by addition of 1N aq NaOH solution and then extracted with EtOAc. The crude product 132 was purified by recrystallization from CH₂Cl₂ to afford 132 (68.66 g, 79%). mp 210-212° C.; IR (KBr, cm⁻¹) 2931, 1692, 1603, 1563, 1475, 1445, 1375, 1259, 1235, 1130, 1090; ¹H NMR (CDCl₃) δ 9.36 (s, 1 H), 7.63 (dd, J=2.22, 8.58 Hz, 1 H), 7.54-7.39 (m, 6 H), 7.12 (d, J=8.61 1 H), 3.76 (q, J=6.3 Hz, 1 H), 1.76 (d, J=6.45 Hz, 3 H). MS (EI) m/e (relative intensity) 330 (M⁺+1, 21), 329 (M⁺, 50), 328 (22), 327 (48), 289 (44), 288 (46), 287 (100), 286 (45), 285 (60), 205 (25), 77 (49).

8-Bromo-4-methyl-6-phenyl-4H-2,5,10b-triaza-benzo[e]azulene-3-carboxylic acid ethyl ester 133. 7-Bromo-3-methyl-5-phenyl-1,3-dihydro-benzo[e][1,4]diazepin-2-one 132 (16.6 g, 0.052 mol) was suspended in dry THF (250 mL) and cooled to −10° C. Sodium hydride (60% dispersion in mineral oil, 4.36 g, 0.109 mol) was added into the suspension in one portion. The reaction mixture was allowed to stir and warm to rt over a 3 h period. The reaction mixture was again cooled to −10° C. and diethyl chlorophosphate (12.7 mL, 0.09 mol) was added. The cooling bath was then removed and stirring continued for 3 h. At this time, sodium hydride (60% dispersion in mineral oil, 4.2 g, 0.1 mol) was suspended in dry THF (250 mL) at −10° C. in another flask. Ethyl isocyanoacetate (6.78 mL, 0.06 mol) was added to the NaH/THF suspension, after which the solution which resulted was allowed to stir for 3 h. After 3 h the first flask was cooled to −30° C. and the solution in the 2nd reaction flask was added to the first flask via a cannula. The reaction mixture was allowed to stir for 24 h, and then cooled with an ice-water bath and slowly quenched with acetic acid (10 mL). Water was added to the reaction mixture after which it was extracted with EtOAc. The EtOAc layers were combined, washed with aq $NaHCO_3$, brine and dried ($Na_2SO_4$). After removal of the solvent under reduced pressure, the solid was purified by flash chromatography (silica gel, EtOAc:hexane, gradient elution 1:2, 1:1, 2:1). The ester 133 was a white solid (8.76 g, 40%). mp 164-165° C.; IR (KBr, cm$^{-1}$) 2925, 1706, 1622, 1557, 1495, 1266, 1185; $^1$H NMR (CDCl$_3$) δ 7.89 (s, 1 H), 7.73 (dd, J=1.73 Hz, 1 H), 7.51-7.36 (m, 7 H), 6.66 (q, J=7.30, 1 H), 4.45-4.30 (m, 2 H), 1.40 (t, J=7.11, 3 H), 1.25 (d, J=7.38 Hz, 3 H). MS (EI) m/e (relative intensity) 426 (M$^+$+2, 15), 425 (M$^+$+1, 58), 424 (M$^+$, 15), 423 (58), 380 (24), 379 (71), 378 (35), 377 (69), 352 (50), 351(100), 350 (67), 349 (92), 270 (38), 229 (16); [α]$^{26}_D$=38.2 (c 0.45, EtOAc).

4-Methyl-6-phenyl-8-trimethylsilanylethynyl-4H-2,5,10b-triazabenzo[e]azulene-3-carboxylic acid ethyl ester 134 (SH-I-041). A mixture of ester 133 (3.0 g, 7.07 mmol) and bis(triphenylphosphine) palladium (II) acetate (0.42 g, 0.57 mmol) was dissolved in a mixed solvent system of acetonitrile (80 mL) and TEA (120 mL). The mixture was degassed under vacuum and argon was added, after which trimethylsilylacetylene (2 mL, 14.14 mmol) was added into the mixture. The mixture was degassed again under vacuum (argon) and heated to reflux. The mixture was heated at reflux until analysis by TLC (EtOAc) indicated that all of the starting material 133 had been consumed. The mixture was cooled to rt and the precipitate which formed was removed by filtration through celite. The filtrate was concentrated under reduced pressure and partitioned between $H_2O$ and EtOAc. The combined layers of EtOAc were washed with brine and dried ($Na_2SO_4$), after which the solvent was removed under reduced pressure and the residue was purified by flash chromatography (silica gel, EtOAc:hexane 1:1). The conditions for TLC were EtOAc on silica gel. A white solid 134 (SH-I-041) (2.59 g, 83%) was obtained. mp 160-162° C.; IR (KBr, cm$^{-1}$) 3365, 2925, 1706, 1616, 1553, 1498; $^1$H NMR (CDCl$_3$) δ 7.89 (s, 1 H), 7.73 (dd, J=1.73 Hz, 1 H), 7.51-7.36 (m, 7 H), 6.66 (q, J=7.30, 1 H), 4.45-4.30 (m, 2 H), 1.40 (t, J=7.11, 3 H), 1.25 (d, J=7.38 Hz, 3 H), 0.15 (S, 9 H). MS (EI) m/e (relative intensity) 441 (M$^+$, 15), 369 (25), 323 (55), 295 (100), 267 (15).

8-Ethynyl-4-methyl-6-phenyl-4H-2,5,10b-triaza-benzo[e]azulene-3-carboxylic acid ethyl ester 135 (SH-053-R—CH$_3$) The trimethylsilylacetylene intermediate 134 (2.8 g, 6.3 mmol) was dissolved in THF (20 mL) and was then treated with Bu$_4$NF.H$_2$O (1.9 g, 7.56 mmol). The mixture was allowed to stir for 30 min at rt, after which H$_2$O (10 mL) was added and the mixture was extracted with EtOAc (3×50 mL). The combined organic extracts were washed with brine (25 mL) and dried (Na$_2$SO$_4$). After removal of the solvent under reduced pressure, the residue was purified by a wash column (silica gel, EtOAc) to furnish 135 (SH-053-R—CH$_3$) (1.9 g, 85%) as a white solid: mp 197-199° C.; IR (KBr, cm$^{-1}$) 3285, 2928, 1708, 1616, 1553, 1498, 1445, 1374; $^1$H NMR (CDCl$_3$) δ 7.92 (s, 1H), 7.73 (dd, J=1.72, 8.32 Hz, 1 H), 7.58-7.36 (m, 7 H), 6.67 (q, J=7.35, 1 H), 4.46-4.34 (m, 2 H), 3.16 (s, 1 H), 1.41 (t, J=7.11, 3 H), 1.25 (d, J=7.38, 3 H); MS (EI) m/e (relative intensity) 369 (M$^+$, 30), 323 (55), 295 (100), 267 (15). Anal. Calcd. for C$_{23}$H$_{19}$N$_3$O$_2$: C, 74.78; H, 5.18; N, 11.37. Found: C, 74.43; H, 5.67; N, 11.39. [α]$^{26}_D$=75.0 (c 0.8, EtOAc).

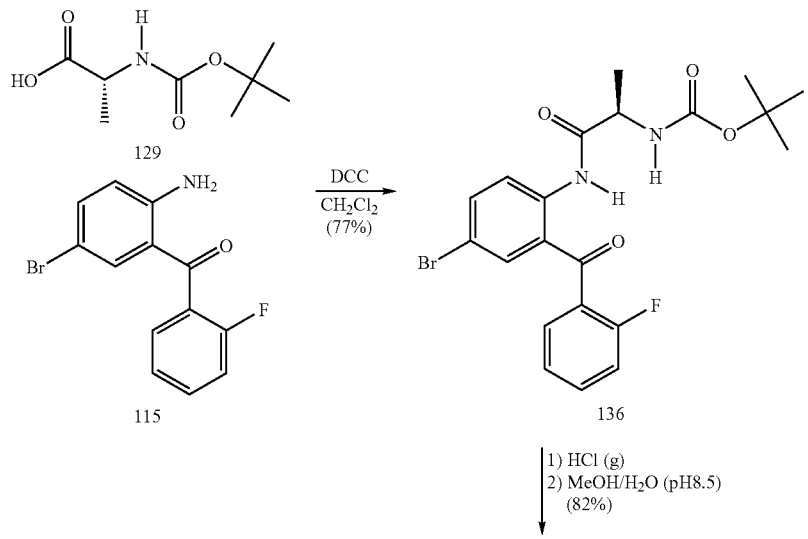

Scheme 27 (SH-053-2′F-R-CH$_3$)

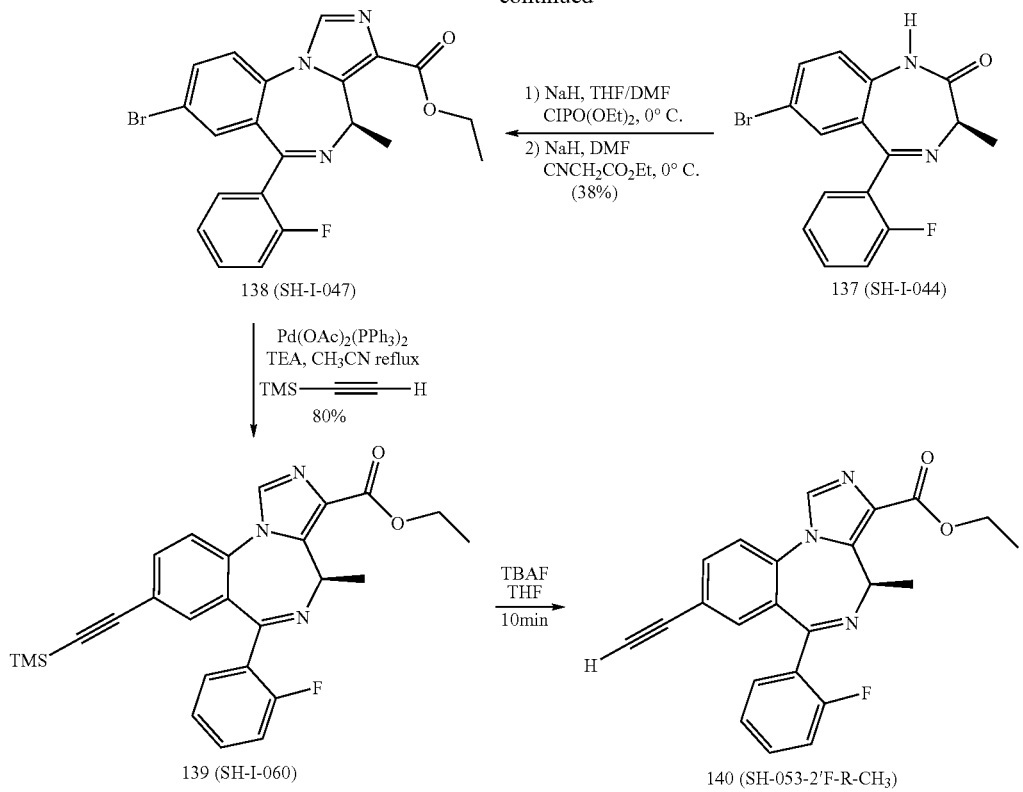

138 (SH-I-047)

137 (SH-I-044)

139 (SH-I-060)

140 (SH-053-2'F-R-CH₃)

Procedure for SH-053-2'F—R—CH₃ (140):

{1-[4-Bromo-2-(2-fluorobenzoyl)-phenylcarbamoyl]-ethyl}-carbamic acid tert-butyl ester 136. To a stirred solution of (2-amino-5-bromophenyl)-(2'-fluoro-phenyl)-methanone 115 (60 g, 204 mmol) and the N-Boc-D-alanine 129 (38.59 g, 2 04 mmol) in CH$_2$Cl$_2$ (500 mL) was added dicyclohexylcarbodiimide (DCC) (42.09 g, 204 mmol) in CH$_2$Cl$_2$ (200 mL) dropwise, over a 30 min period at 0° C. The reaction mixture was allowed to stir an additional 8 h at rt. The dicyclohexyl urea which formed was filtered off and the filtrate concentrated under reduced pressure. The crude solid product 136 was purified by recrystallization from hexane and EtOAc to afford 136 (73 g, 77%). mp 158-159° C.; IR (KBr, cm$^{-1}$) 3332, 2931, 255, 1694, 1643, 1613, 1582, 1537, 1450; $^1$H NMR (CDCl$_3$) δ 11.68 (s, 1 H), 8.71 (d, J=9.0 Hz, 1 H), 7.69 (dd, J=9.0, 2.3 Hz, 1 H), 7.55-7.62 (m, 2 H), 7.46 (td, J=7.6, 1.4 Hz, 1 H), 7.30 (t, J=7.5 Hz, 1 H), 7.21 (t, J=9.1 Hz, 1 H), 5.13 (b, 1 H), 4.37 (b, 1 H), 1.51 (d, J=7.2 Hz, 3 H), 1.45 (s, 9H). MS (EI) m/e (relative intensity) 467 (M$^+$+2, 14), 466 (M$^+$+1, 44), 465 (M$^+$, 14), 464 (42), 329 (15), 321 (60), 295 (100), 224 (26); [α]$^{26}_D$=59.6 (c 0.51, EtOAc).

7-Bromo-5-(2-fluoro-phenyl)-3-methyl-1,3-dihydro-benzo[e][1,4]diazepin-2-one 137. To a stirred solution of the benzophenone 136 (30 g, 64.4 mmol) in CHCl$_3$ (300 mL) at rt, hydrogen chloride gas was added slowly. After 20 min, the addition was stopped and the solution was allowed to stir overnight at rt. The reaction mixture was then washed with a saturated solution of sodium bicarbonate (2×70 mL) and water (2×70 mL). The organic layer was concentrated under reduced pressure. The residual oil was dissolved in methanol-water (1:1, 300 mL) and the pH was adjusted to 8.5 by the addition of aq sodium hydroxide (1 N). The reaction mixture was allowed to stir for 10 h at rt. The solution was then concentrated under reduced pressure and water (100 mL) was added. The solution was extracted with CH$_2$Cl$_2$ (3×50 mL), and the organic layer was dried (Na$_2$SO$_4$) and concentrated under reduced pressure. The crude solid 137 was purified by recrystallization from methanol/water to provided 137 (18.2 g, 82%). mp 183-185° C.; IR (KBr, cm$^{-1}$) 2928, 1694, 1611, 1479, 1450, 1377, 1315; $^1$H NMR (CDCl$_3$) δ 9.50 (bs, 1 H), 7.62-7.65 (m, 2 H), 7.50 (q, J=6.5 Hz, 1H), 7.40 (d, J=2.0 Hz, 1 H), 7.29 (t, J=7.5 Hz 1 H) 7.15 (d, J=8.6 Hz, 1 H), 7.11 (t, J=8.9 Hz, 1 H), 3.84 (q, J=6.5 Hz, 1 H), 1.82 (d, J=6.5 Hz, 3 H); MS (EI) m/e (relative intensity) 348 (M$^+$+1, 23), 347 (M$^+$, 38), 346 (24), 345 (36), 329 (19), 327 (20), 307 (40), 306 (41), 305(100), 304 (37), 303 (63); [α]$^{26}_D$=−169.1 (c 0.71, EtOAc).

8-Bromo-6-(2-fluorophenyl)-4-methyl-4H-2,5,10b-triaza-benzo[e]azulene-3-carboxylic acid ethyl ester 138. 7-Bromo-5-(2'-fluorophenyl)-3-methyl-1,3-dihydro-benzo[e][1,4]diazepin-2-one 137 (3.78 g, 10.88 mmol) was suspended in dry THF (150 mL) and cooled to −10° C. Sodium hydride (60% dispersion in mineral oil, 0.52 g, 13.07 mol) was added into the suspension in one portion. The reaction mixture was allowed to stir and then warm to rt over 3 h period. The reaction mixture was again cooled to −10° C. and diethyl chlorophosphate (2.65 mL, 17.42 mmol) was added. The cooling bath was then removed and stirring continued for 3 h. During this time, sodium hydride (60% dispersion in mineral oil, 0.61 g, 15.24 mmol) was suspended in dry THF (60 mL) at −10° C. in another flask. Ethyl isocyanoacetate (1.43 mL, 13.07 mmol) was added to the NaH/THF suspension and this mixture allowed to stir for 3 h. After 3 h the first flask was cooled to −30° C. with a cooling bath and the mixture in the second reaction flask was added to the first flask via a cannula. The reaction mixture was allowed to stir for 24 h, after which it was cooled to 0° C. with an ice-water bath and slowly quenched 5 with acetic acid (5 mL). Water was then added to the reaction mixture and this was extracted with EtOAc. The EtOAc layers were combined, washed with aq NaHCO$_3$, brine and dried (Na$_2$SO$_4$). After removal of the solvent under reduced pressure the solid was purified by flash chromatography (silica gel, EtOAc:hexane: gradient elution 1:2, 1:1, 2:1). The ethyl ester 138 was a white solid (1.82 g, 38%). mp 190-192° C.; IR (KBr, cm$^{-1}$) 3316, 2925, 1693, 1621, 1485, 1448, 1371; $^1$H NMR (CDCl$_3$) δ 7.92 (s, 1 H), 7.72 (dd, J=8.5, 1.5 Hz, 1 H), 7.6 (t, J=6.9 Hz, 1 H), 7.48 (d, J=8.5 Hz, 1 H), 7.42-7.49 (m, 2 H), 7.23-7.29 (m, 1 H), 7.05 (t, J=9.3 Hz, 1 H), 6.71 (q, J=7.3 Hz, 1 H), 4.41 (m, 2 H), 1.42 (t, J=7.1 Hz, 3 H), 1.29 (d, 3 H). MS (EI) m/e (relative intensity) 442 (M$^+$, 5), 428 (7), 381 (58), 355 (100), 303 (37); [α]$^{26}_D$=−10.9 (c 0.54, EtOAc).

6-(2-Fluorophenyl)-4-methyl-8-trimethylsilanylethynyl-4H-2,5,10b-triazabenzo[e]azulene-3-carboxylic acid ethyl ester 139. A mixture of 138 (69.3 mg, 0.16 mmol) and bis(triphenylphosphine)palladium (II) acetate (11.68 mg, 0.015 mmol) was dissolved in a mixed solvent system of acetonitrile (120 mL) and TEA (80 mL). The mixture was degassed under vacuum and argon gas was added, after which trimethylsilylacetylene (0.044 mL, 0.31 mmol) was added into the mixture. The mixture was degassed again under vacuum (argon) and heated to reflux. The mixture was heated at reflux until analysis by TLC (EtOAc) indicated that all of the starting material 138 had been consumed. The mixture was cooled to rt and the precipitate which formed was removed by filtration through celite. The filtrate was concentrated under reduced pressure and partitioned between H$_2$O and EtOAc. The combined layers of EtOAc were washed with brine and dried (Na$_2$SO$_4$), after which the solvent was removed under reduced pressure and the residue was purified by flash chromatography (silica gel, EtOAc:hexane 1:1). The conditions for TLC were EtOAc on silica gel. A white solid 139 (58.8 mg, 80%) was obtained. mp 186-187° C.; IR (KBr, cm$^{-1}$) 2410, 2358, 1716, 1497, 1253; $^1$H NMR (CDCl$_3$) δ 7.92 (s, 1 H), 7.72 (dd, J=8.5, 1.5 Hz, 1 H), 7.6 (t, J=6.9 Hz, 1H), 7.48 (d, J=8.5 Hz, 1 H), 7.42-7.49 (m, 2H), 7.23-7.29 (m, 1 H), 7.05 (t, J=9.3 Hz, 1H), 6.71 (q, J=7.3 Hz, 1 H), 4.41 (m, 2 H), 1.42 (t, J=7.1 Hz, 3 H), 1.29 (d, J=7.2, 3 H), 0.24 (s, 9 H). MS (EI) m/e (relative intensity) 459 (M$^+$, 28), 445 (32), 399 (51), 371 (100), 235 (71), 178 (75); [α]$^{26}_D$=28.2 (c 0.48, EtOAc).

8-Ethynyl-6-(2-fluorophenyl)-4-methyl-4H-2,5,10b-triaza-benzo[e]azulene-3-carboxylic acid ethyl ester 140 (SH-053-2'F—R—CH$_3$). The trimethylsilylacetylene intermediate 139 was converted to 140 (SH-053-2'F—R—CH$_3$) by using the same procedure described above for the synthesis of compound 10.

Assays of Competitive Binding to αxβ3γ2 GABA$_A$ Receptors

The GABA$_A$ subunit selectivity of several compounds prepared as described above were determined using competitive binding assays. The assays were performed in a total volume of 0.5 mL at 4° C. for 1 hour using [$^3$H]flunitrazepam as the radiolabel. For these binding assays, 20-50 mg of membrane protein harvested with hypotonic buffer (50 mM Tris-acetate pH 7.4 at 4 degree) was incubated with the radiolabel as previously described (Choudhary, M. S., Craigo. S., Roth, B. L., Identification of receptor domains that modify ligand binding to 5-hydroxy-tryptamine-2 and 5-hydroxytryptamine-1c serotonin receptors, Mol Pharmacol. 1992 October; 42(4):627-33). Nonspecific binding was defined as radioactivity bound in the presence of 100 μM diazepam and represented less than 20% of total binding. Membranes were harvested with a Brandel cell harvester followed by three ice-cold washes onto polyethyleneimine-pretreated (0.3%) Whatman GF/C filters. Filters were dried overnight and then soaked in Ecoscint, a liquid scintillation cocktail (National Diagnostics; Atlanta, Ga.). Bound radioactivity was quantified by liquid scintillation counting. Membrane protein concentrations were determined using an assay kit from Bio-Rad (Hercules, Calif.) with bovine serum albumin as the standard. The results are summarized in Table 3, below.

TABLE 3

Results of Competitive Binding Assays
Binding Affinity (nM) at αxβ3γ2 GABA$_A$ Receptors

| | GABA$_A$/α1 | GABA$_A$/α2 | GABA$_A$/α3 | GABA$_A$/α4 | GABA$_A$/α5 | GABA$_A$/α6 |
|---|---|---|---|---|---|---|
| Diazepam | 14 | 20 | 15 | >1000 | 11 | >1000 |
| QH-II-066 | 76.3 | 42.1 | 47.4 | >1000 | 6.8 | >1000 |
| XHE-II-012 | 49 | 24 | 31 | 1042 | 14 | 2038 |
| XHE-II-053 | 287 | 45 | 96 | 1504 | 13.8 | 1000 |
| PS-I-37 | 193 | 35 | 434 | >5000 | 22 | >5000 |
| PS-I-26 | 933.5 | 366 | 260 | ND | 393.5 | >5000 |
| HZ 166 | 118 | 148 | 365 | >5000 | 76.88 | >5000 |
| SH-053-2'N | 300 | 160 | 527 | ND | 82 | >5000 |
| JY-XHE-053 | 21.99 | 12.34 | 34.9 | ND | 0.671 | ND |
| HZ 120 | >5000 | 35 | 78.5 | ND | 20.6 | 32.2 |
| XLI-JY-DMH | 3.3 | 0.58 | 1.9 | ND | 4.4 | >5000 |
| PS-I-72 | 123 | 31 | 386 | >5000 | 34 | >5000 |
| JC-221 | 146 | 35 | 182 | ND | 14.3 | 362 |
| DM-II-20 | 5717 | 177 | 35.68 | 5000 | 197.7 | 5000 |
| JYI-53 | 77.4 | 40.4 | 183 | 5000 | 133 | 3650 |
| JYI-49 | 1.87 | 2.38 | ND | 5000 | 6.7 | 3390 |
| EMJ-I-026 | >5000 | 135 | 1027 | ND | 152 | >5000 |
| YT-TC-3 | 141.4 | 11.43 | 118.1 | ND | 29.22 | ND |
| YT-II-94 | 4536 | 126.2 | 4981 | ND | 932.8 | ND |

Table 4 summarizes the results of similar competitive binding assays performed using stereoisomers.

TABLE 4

Results of Competitive Binding Assays
Binding Affinity (nM) at αxβ3γ2 GABA$_A$ Receptors

| | GABA$_A$/α1 | GABA$_A$/α2 | GABA$_A$/α3 | GABA$_A$/α4 | GABA$_A$/α5 | GABA$_A$/α6 |
|---|---|---|---|---|---|---|
| SH-053-S-CH3 | 1666 | 1263 | 1249 | >5000 | 206.4 | >5000 |
| SH-053-R-CH3 | 2026 | 2377 | 1183 | >5000 | 949.1 | >5000 |

TABLE 4-continued

Results of Competitive Binding Assays
Binding Affinity (nM) at αxβ3γ2 GABA$_A$ Receptors

| | GABA$_A$/α1 | GABA$_A$/α2 | GABA$_A$/α3 | GABA$_A$/α4 | GABA$_A$/α5 | GABA$_A$/α6 |
|---|---|---|---|---|---|---|
| SH-053-2'F-S-CH3 | 350 | 141 | 1237 | >5000 | 16 | 5000 |
| SH-053-2'F-S-CH3 | 468.2 | 33.27 | 291.5 | >5000 | 19.2 | >5000 |
| SH-053-2'F-R-CH3 | 759.1 | 948.2 | 768.8 | >5000 | 95.17 | >5000 |
| SH-053-2'N-S-CH3 | 6951 | 2331 | 2655 | ND | 744.1 | ND |
| SH-TS-CH3 | 107.2 | 50.09 | 20.95 | ND | 8.068 | ND |

Subunit Selective Efficacy Determined from Voltage Clamp Recordings from *Xenopus* Oocytes Expressing αxβ3γ2 GABA$_A$ Receptors The GABA$_A$ subunit selectivity of several compounds prepared as described above were determined using voltage clamp recordings from *Xenopus* oocytes that expressed that αxβ3γ2 GABA$_A$ receptor.

Figure 5:
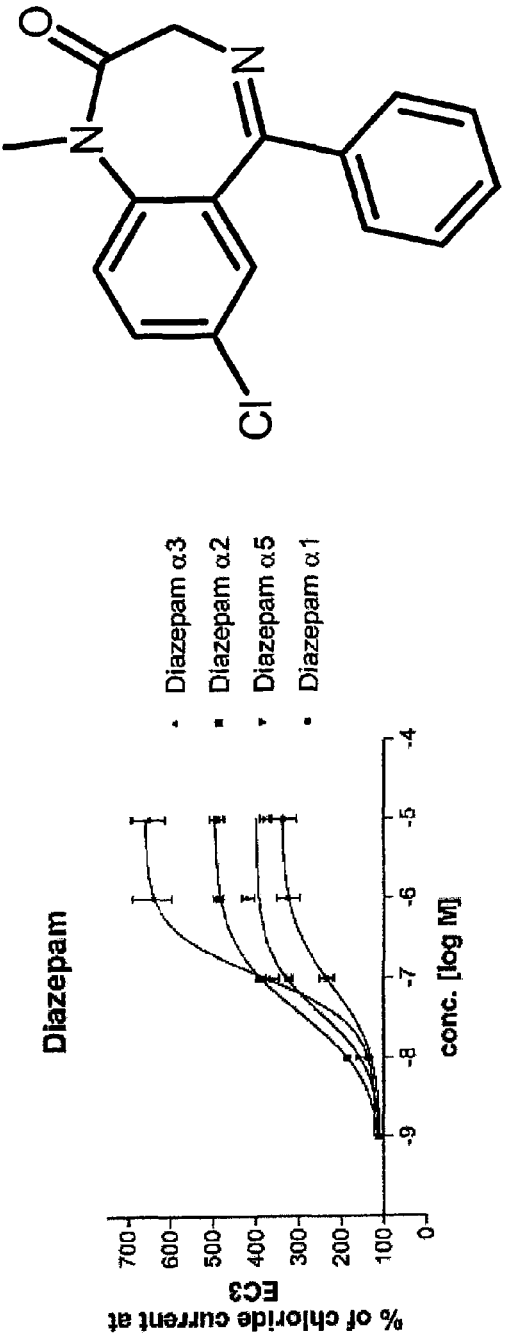
FIG. 5 is a graph of dose-response curves of the patch clamp current (expressed as percent of the control current) produced by various concentrations of diazepam when applied to $Xenopus$ oocytes expressing $\alpha1\beta3\gamma2$ (●), $\alpha2\beta3\gamma2$ (■), $\alpha3\beta3\gamma2$ (▲) or $\alpha5\beta3\gamma2$ (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 5 is a graph of dose-response curves of the patch clamp current (expressed as percent of the control current) produced by various concentrations of diazepam when applied to *Xenopus* oocytes expressing α1β3γ2 (●), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

Figure 6:
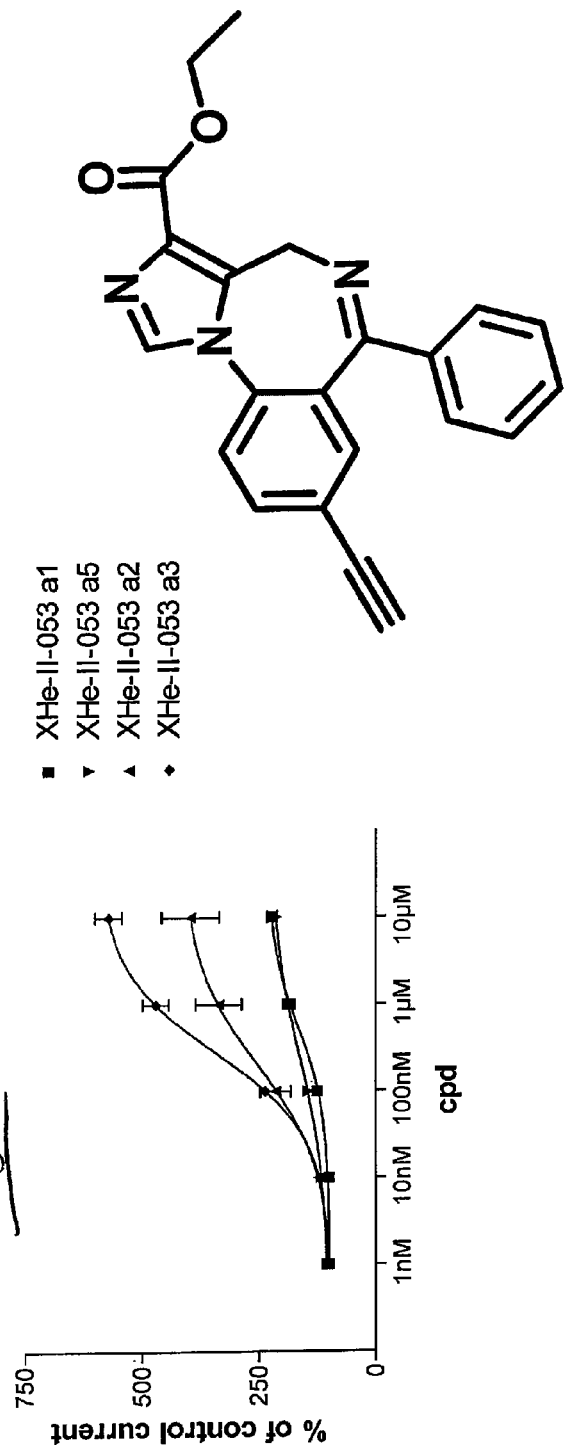
FIG. 6 is a graph of dose-response curves of the patch clamp current (expressed as percent of the control current) produced by various concentrations of XHE-II-053 when applied to $Xenopus$ oocytes expressing $\alpha1\beta3\gamma2$ (●), $\alpha2\beta3\gamma2$ (■), $\alpha3\beta3\gamma2$ (▲) or $\alpha5\beta3\gamma2$ (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 6 is a graph of dose-response curves of the patch clamp current (expressed as percent of the control current) produced by various concentrations of XHE-II-053 when applied to *Xenopus* oocytes expressing α1β3γ2 (●), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

FIG. 7 is a graph of dose-response curves of the patch clamp current (expressed as percent of the control current) produced by various concentrations of HZ-166 (SH-053'2'N) when applied to *Xenopus* oocytes expressing α1β3γ2 (●), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

FIG. 8 is a graph of dose-response curves of the patch clamp current (expressed as percent of the control current) produced by various concentrations of JY-XHE-053 when applied to *Xenopus* oocytes expressing α1β3γ2 (●), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

Figure 9:
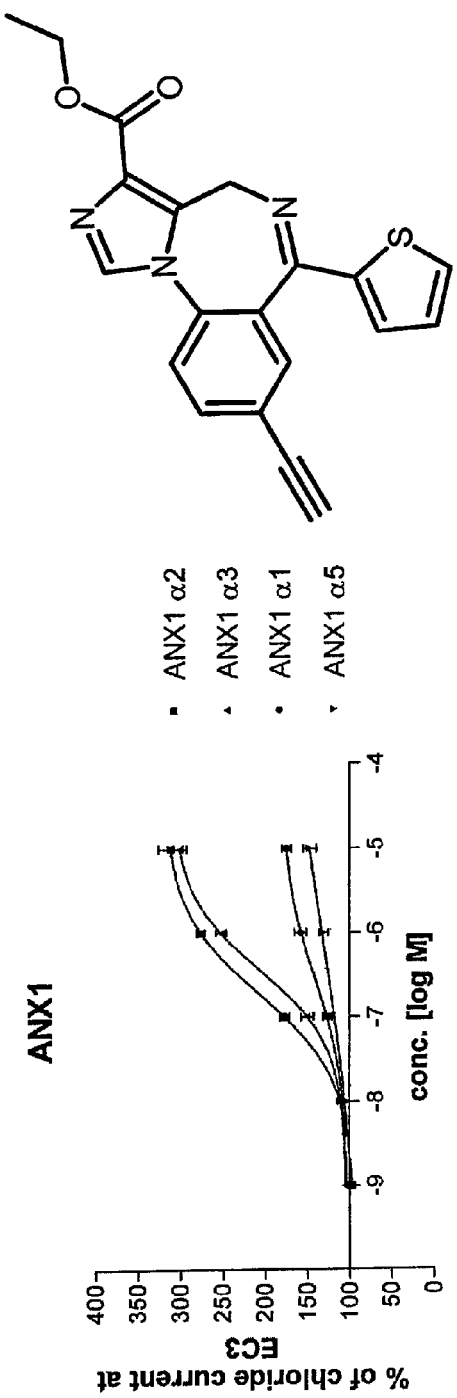
FIG. 9 is a graph of dose-response curves of the patch clamp current (expressed as percent of the control current) produced by various concentrations of JC-221 when applied to $Xenopus$ oocytes expressing $\alpha1\beta3\gamma2$ (●), $\alpha2\beta3\gamma2$ (■), $\alpha3\beta3\gamma2$ (▲) or $\alpha5\beta3\gamma2$ (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 9 is a graph of dose-response curves of the patch clamp current (expressed as percent of the control current) produced by various concentrations of JC-221 when applied to *Xenopus* oocytes expressing α1β3γ2 (●), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

Figure 10:
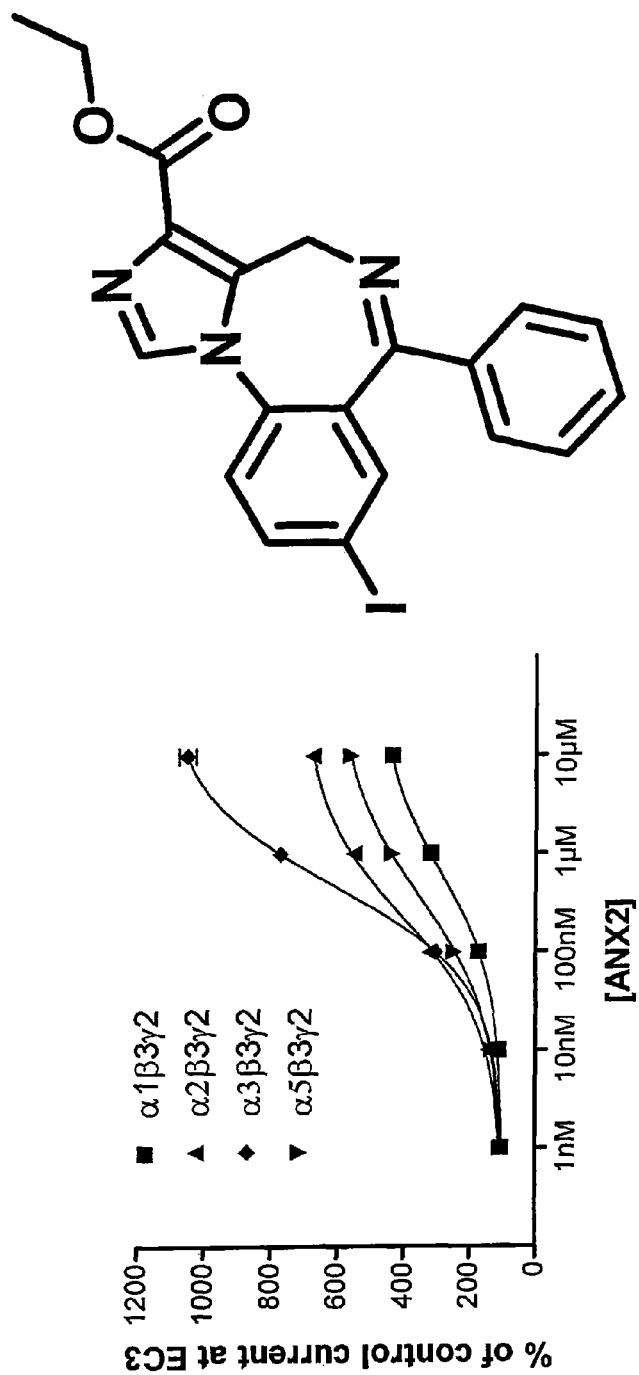
FIG. 10 is a graph of dose-response curves of the patch clamp current (expressed as percent of the control current) produced by various concentrations of Hz-120 (ANX2) when applied to $Xenopus$ oocytes expressing $\alpha1\beta3\gamma2$ (●), $\alpha2\beta3\gamma2$ (■), $\alpha3\beta3\gamma2$ (▲) or $\alpha5\beta3\gamma2$ (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 10 is a graph of dose-response curves of the patch clamp current (expressed as percent of the control current) produced by various concentrations of Hz-120 (ANX2) when applied to *Xenopus* oocytes expressing α1β3γ2 (●), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

Figure 11:
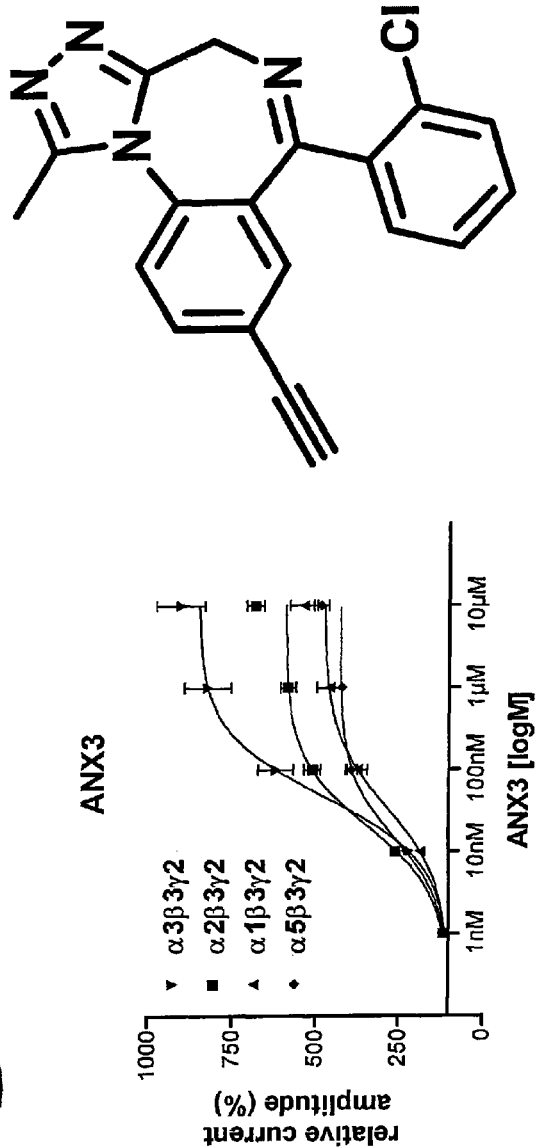
FIG. 11 is a graph of dose-response curves of the patch clamp current (expressed as percent of the control current) produced by various concentrations of XLi-JY-DMH when applied to $Xenopus$ oocytes expressing $\alpha1\beta3\gamma2$ (●), $\alpha2\beta3\gamma2$ (■), $\alpha3\beta3\gamma2$ (▲) or $\alpha5\beta3\gamma2$ (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 11 is a graph of dose-response curves of the patch clamp current (expressed as percent of the control current) produced by various concentrations of XLi-JY-DMH when applied to *Xenopus* oocytes expressing α1β3γ2 (●), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

FIG. 12 is a graph of dose-response curves of the patch clamp current (expressed as percent of the control current) produced by various concentrations of SH-053-2'F—S—CH3 when applied to *Xenopus* oocytes expressing recombinant GABA$_A$/α$_1$ receptors, GABA$_A$/α$_2$ receptors, GABA$_A$/α$_3$ receptors or GABA$_A$/α$_5$ receptors.

Figure 13:
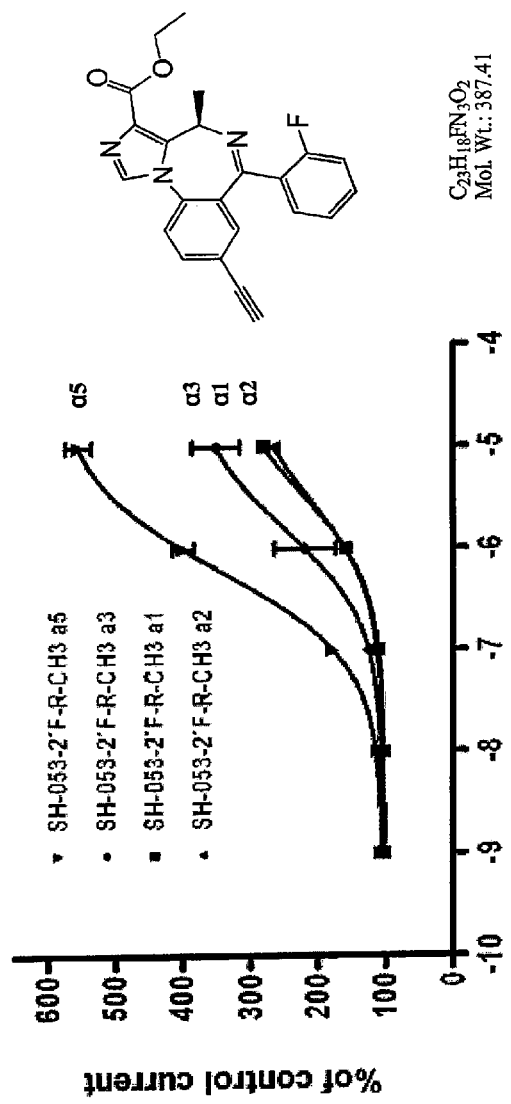
FIG. 13 is a graph of dose-response curves of the patch clamp current (expressed as percent of the control current) produced by various concentrations of SH-053-2'F—R—CH3 when applied to $Xenopus$ oocytes expressing recombinant $GABA_A/\alpha_1$ receptors, $GABA_A/\alpha_2$ receptors, $GABA_A/\alpha_3$ receptors or $GABA_A/\alpha_5$ receptors.

FIG. 13 is a graph of dose-response curves of the patch clamp current (expressed as percent of the control current) produced by various concentrations of SH-053-2'F—R—CH3 when applied to *Xenopus* oocytes expressing recombinant GABA$_A$/α$_1$ receptors, GABA$_A$/α$_2$ receptors, GABA$_A$/α$_3$ receptors or GABA$_A$/α$_5$ receptors.

FIG. 14 is a graph of dose-response curves of the patch clamp current (expressed as percent of the control current) produced by various concentrations of SH-053-2'N—S—CH3 when applied to *Xenopus* oocytes expressing recombinant GABA$_A$/α$_1$ receptors, GABA$_A$/α$_2$ receptors, GABA$_A$/α$_3$ receptors or GABA$_A$/α$_5$ receptors.

Figure 15:
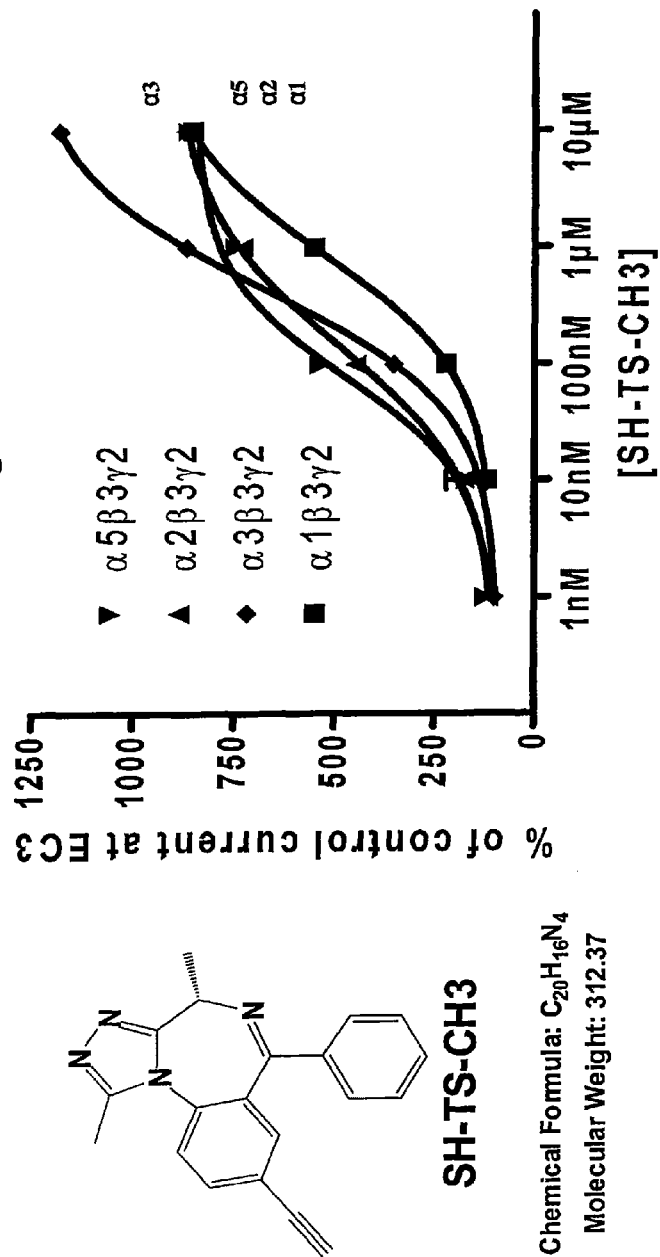
FIG. 15 is a graph of dose-response curves of the patch clamp current (expressed as percent of the control current) produced by various concentrations of SH-TS-CH3 when applied to $Xenopus$ oocytes expressing $\alpha1\beta3\gamma2$ (■), $\alpha2\beta3\gamma2$ (▲), $\alpha3\beta3\gamma2$ (♦) or $\alpha5\beta3\gamma2$ (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 15 is a graph of dose-response curves of the patch clamp current (expressed as percent of the control current) produced by various concentrations of SH-TS-CH3 when applied to *Xenopus* oocytes expressing α1β3γ2 (■), α2β3γ2 (▲), α3β3γ2 (♦) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

Figure 16:
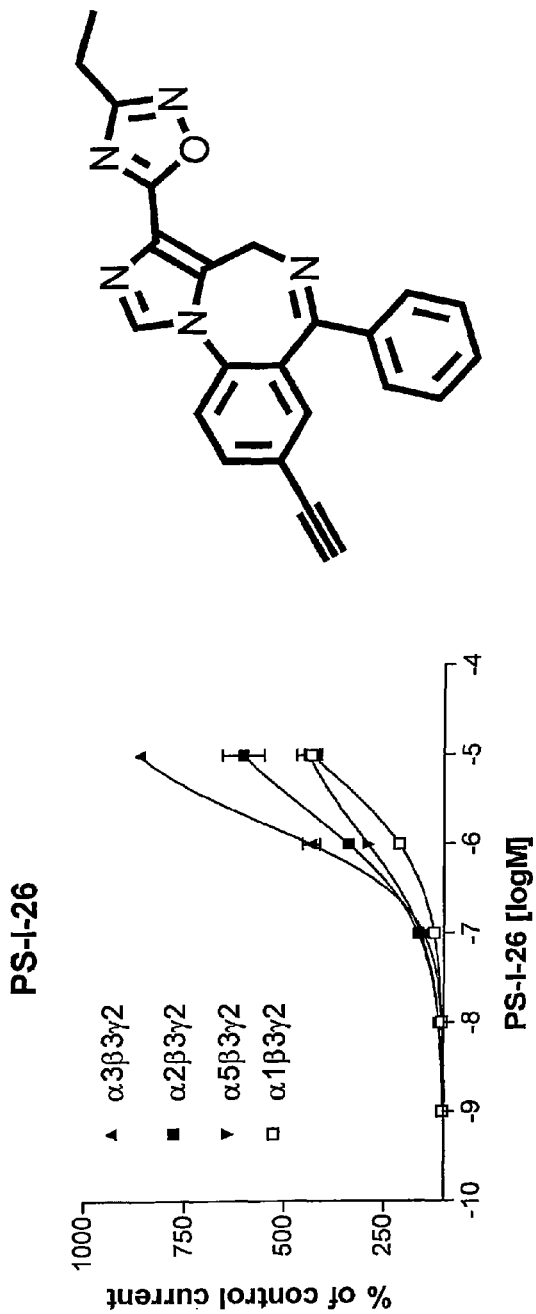
FIG. 16 is a graph of dose-response curves of the patch clamp current (expressed as percent of the control current) produced by various concentrations of PS-1-26 when applied to $Xenopus$ oocytes expressing $\alpha1\beta3\gamma2$ (□), $\alpha2\beta3\gamma2$ (■), $\alpha3\beta3\gamma2$ (▲) or $\alpha5\beta3\gamma2$ (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 16 is a graph of dose-response curves of the patch clamp current (expressed as percent of the control current) produced by various concentrations of PS-1-26 when applied to *Xenopus* oocytes expressing α1β3γ2 (□), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

Figure 17:
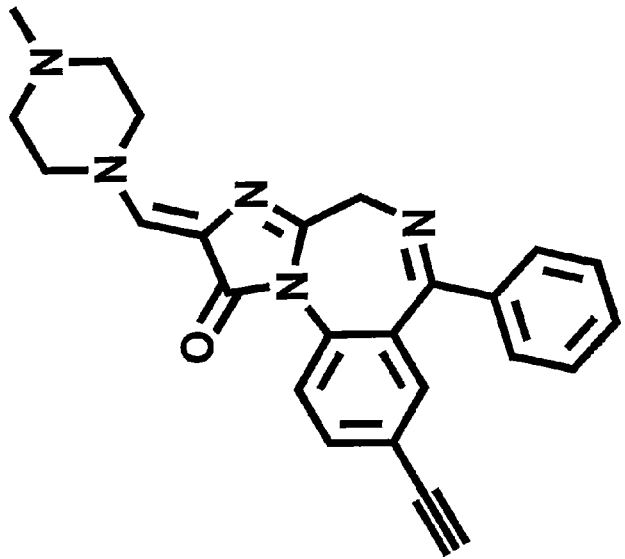
FIG. 17 is a representation of the binding affinity of a structure of PS-1-37.

FIG. 17 is a representation of the binding affinity an structure of PS-1-37.

FIG. 18 is a graph of dose-response curves of the patch clamp current (expressed as percent of the control current) produced by various concentrations of EMJ-I-026 when applied to *Xenopus* oocytes expressing α1β3γ2 (□), α2β3γ2 (■), α3β3γ2 (▲) or α5β3γ2 (▼) GABA$_A$ receptors. Values are presented as mean±SEM of at least four oocytes from at FIG. 19 is a graph of dose-response curves of the patch clamp current (expressed as percent of the control current) produced by various concentrations of YT-TC-3 when applied to *Xenopus* oocytes expressing α1β3γ2 (□), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

FIG. 20 is a graph of dose-response curves of the patch clamp current (expressed as percent of the control current) produced by various concentrations of YT-II-794 when applied to *Xenopus* oocytes expressing α1β3γ2 (□), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

FIGS. 21A-21F are graphs of the results for rates of non-suppressed and suppressed responses at various dosage concentrations of diazepam, XHE-II-053, JY-XHE-053, Hz-166, SH-053-2'F—S—CH3 and SH-053-2'F—R—CH3. The data in FIGS. 21A-21F reflect the ability of the compounds or drugs to exert an anxioyic effect in rhesus monkeys (J. Rowlett, J. M. Cook et al., unpublished results) when given intravenously in propylene glycol/water solution. This is the conflict model of anxiolytic activity which also measures sedation. In FIG. 21A, diazepam is anxiolytic (non-suppressed responding), but is also sedating (mean responses dropped) at greater than 1.2 mg/kg. In FIG. 21B, SH-053-2'F (JY-XHE-053) is anxiolytic at a dose of greater than 0.13 mg/kg, but exerts only some slight sedation at doses greater than 1.2 mg/kg (responses decrease). In FIG. 21C it is clear the S-enantiomer of SH-053-2'F—S—CH$_3$ is anxiolytic with no sedation up to 10-18 mg/kg, which is the highest dose tested. The ligand XHE-II-053 in FIG. 21D is also an anxiolytic with no sedative activity. The same is true for SH-053-2'N(HZ-166) which is anxiolytic with no sedative activity, as shown in FIG. 21E. However, in FIG. 21F, the R-enantiomer, SH-053-2'F—R—CH$_3$, is only a weak anxiolytic at high doses (10 mg/kg) but is not sedating. This compound is not very active as an anxiolytic and could be termed inactive relative to the ligands whose testing results are illustrated in FIGS. 21A-21E.

FIG. 34 is a graph of dose-response curves of the patch clamp current (expressed as percent of the control current) produced by various concentrations of SR-II-57 when applied to *Xenopus* oocytes expressing α1β3γ2 (■), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

FIG. 35 is a graph of dose-response curves of the patch clamp current (expressed as percent of the control current) produced by various concentrations of SR-II-54 when applied to *Xenopus* oocytes expressing α1β3γ2 (■), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

FIG. 36 is a graph of dose-response curves of the patch clamp current (expressed as percent of the control current) produced by various concentrations of YT-III-271 when applied to *Xenopus* oocytes expressing α1β3γ2 (□), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

FIG. 37 is a graph of dose-response curves of the patch clamp current (expressed as percent of the control current) produced by various concentrations of YT-III-15 when applied to *Xenopus* oocytes expressing α1β3γ2 (■), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

FIG. 38 is a graph of dose-response curves of the patch clamp current (expressed as percent of the control current) produced by various concentrations of YT-TC-4 when applied to *Xenopus* oocytes expressing α1β3γ2 (■), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

Figure 39:
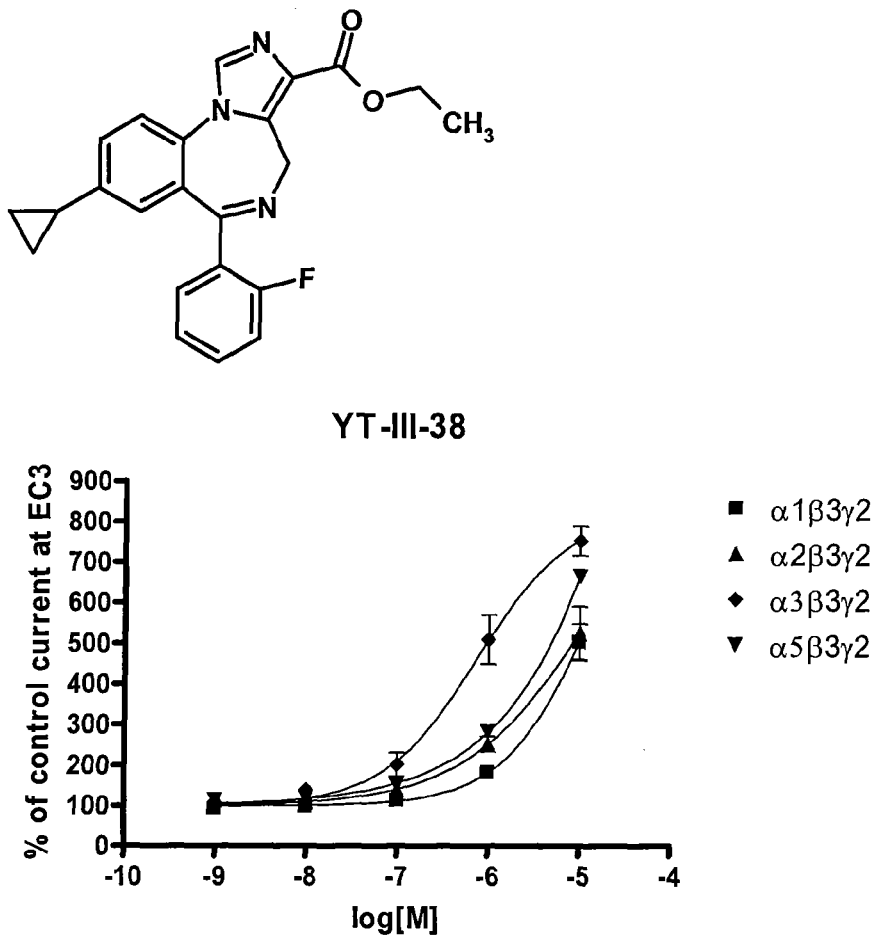
FIG. 39 is a graph of dose-response curves of the patch clamp current (expressed as percent of the control current) produced by various concentrations of YT-III-38 when applied to *Xenopus* oocytes expressing α1β3γ2 (■), α2β3γ2 (■), α3β3γ2 (▲) or α5β3γ2 (▼) $GABA_A$ receptors. Values are presented as mean±SEM of at least four oocytes from at least two batches expressing recombinant $GABA_A/\alpha_1$ receptors, $GABA_A/\alpha_2$ receptors, $GABA_A/\alpha_3$ receptors or $GABA_A/\alpha_5$ receptors.

FIG. 39 is a graph of dose-response curves of the patch clamp current (expressed as percent of the control current) produced by various concentrations of YT-III-38 when applied to *Xenopus* oocytes expressing α1β3γ2 (■), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

FIG. 40 is a graph of dose-response curves of the patch clamp current (expressed as percent of the control current) produced by various concentrations of YT-II-76 when applied to *Xenopus* oocytes expressing α1β3γ2 (■), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

FIG. 41 is a graph of dose-response curves of the patch clamp current (expressed as percent of the control current) produced by various concentrations of YT-III-31 when applied to *Xenopus* oocytes expressing α1β3γ2 (■), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

FIG. 42 is a graph of dose-response curves of the patch clamp current (expressed as percent of the control current) produced by various concentrations of YT-III-42 when applied to *Xenopus* oocytes expressing α1β3γ2 (■), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

FIG. 43 is a graph of dose-response curves of the patch clamp current (expressed as percent of the control current) produced by various concentrations of HJ-I-40 when applied to *Xenopus* oocytes expressing α1β3γ2 (■), α2β3γ2 (■), α3β3γ2 (▲) or α5β3γ2 (▼) GABA$_A$ receptors. Values are presented as mean±SEM of at least four oocytes from at least two batches expressing recombinant GABA$_A$/α$_1$ receptors, GABA$_A$/α$_2$ receptors, GABA$_A$/α$_3$ receptors or GABA$_A$/α$_5$ receptors.

FIG. 44 is a graph of dose-response curves of the patch clamp current (expressed as percent of the control current) produced by various concentrations of ZJW-II-40 when applied to *Xenopus* oocytes expressing α1β3γ2 (■), α2β3γ2 (■), α3β3γ2 (▲) or α5β3γ2 (▼) $GABA_A$ receptors. Values are presented as mean±SEM of at least four oocytes from at least two batches expressing recombinant $GABA_A/α_1$ receptors, $GABA_A/α_2$ receptors, $GABA_A/α_3$ receptors or $GABA_A/α_5$ receptors.

FIG. 45 is a graph of dose-response curves of the patch clamp current (expressed as percent of the control current) produced by various concentrations of HJ-I-037 when applied to *Xenopus* oocytes expressing α1β3γ2 (■), α2β3γ2 (■), α3β3γ2 (▲) or α5β3γ2 (▼) $GABA_A$ receptors. Values are presented as mean±SEM of at least four oocytes from at least two batches expressing recombinant $GABA_A/α_1$ receptors, $GABA_A/α_2$ receptors, $GABA_A/α_3$ receptors or $GABA_A/α_5$ receptors.

FIGS. 46-48 is a representation of the binding affinities of ZJW-II-061, ZJW-II-063 and ZJW-II-065.

FIG. 49 illustrates both the binding affinities and oocyte efficacies of JY-XHE-053, XHE-II-053, HZ-166, SH-053-2'F—S—CH3 and SH-053-2'F—R—CH3, and the binding affinity of diazepam.

Utility of Benzodiazepine Derivative Compounds Selective for $GABA_A$ Receptor Subunits Compound for Suppression of Neuropathic Pain & Inflammatory Pain The benzodiazepine derivative compounds listed in Table 5 are tested for the ability to suppress pain in the neuropathic pain model of chronic constriction injury (CCI) and the zymosan A inflammatory pain model and the formalin test model, as described above. The ability of these benzodiazepine derivative compounds to suppress pain with minimal ataxic and sedative side effects corresponds to their greater binding affinity at $GABA_A/α_2$ receptors or $GABA_A/α_3$ receptors compared to $GABA_A/α_1$ receptors, or to their efficacy in increasing current through membrane channels in oocytes or spinal neurons modulated by $GABA_A/α_2$ receptors or $GABA_A/α_3$ receptors compared to $GABA_A/α_1$ receptors. In certain embodiments, the ability of these benzodiazepine derivative compounds to suppress neuropathic pain or inflammatory pain with minimal ataxic and sedative side effects corresponds subtype selective efficacy at α3 over α1 and α5 $GABA_A$ receptors.

TABLE 5

Benzodiazepine Derivative Compounds Selective At $GABA_A$ Receptor Subunits

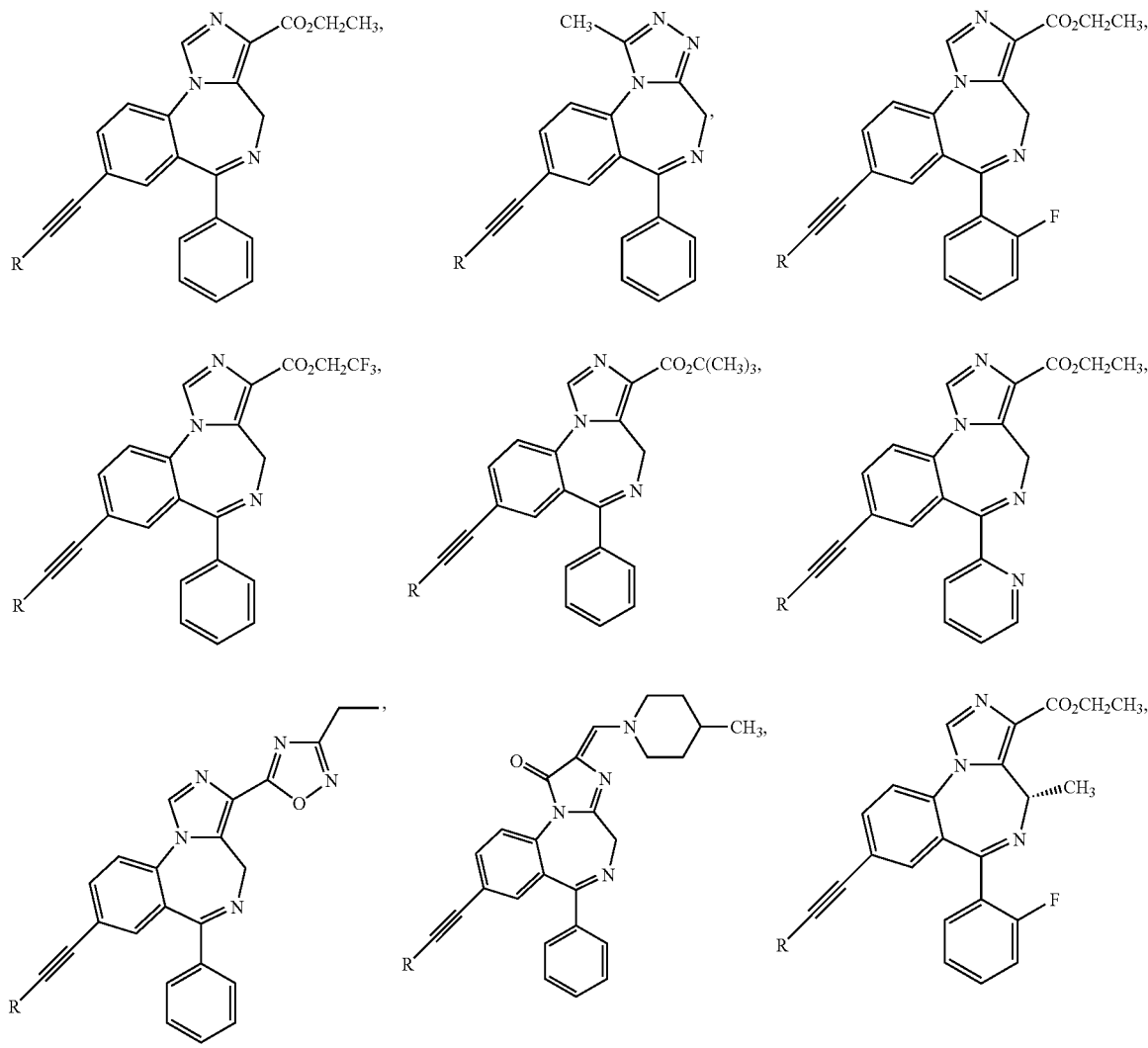

TABLE 5-continued
Benzodiazepine Derivative Compounds Selective At GABA$_A$ Receptor Subunits
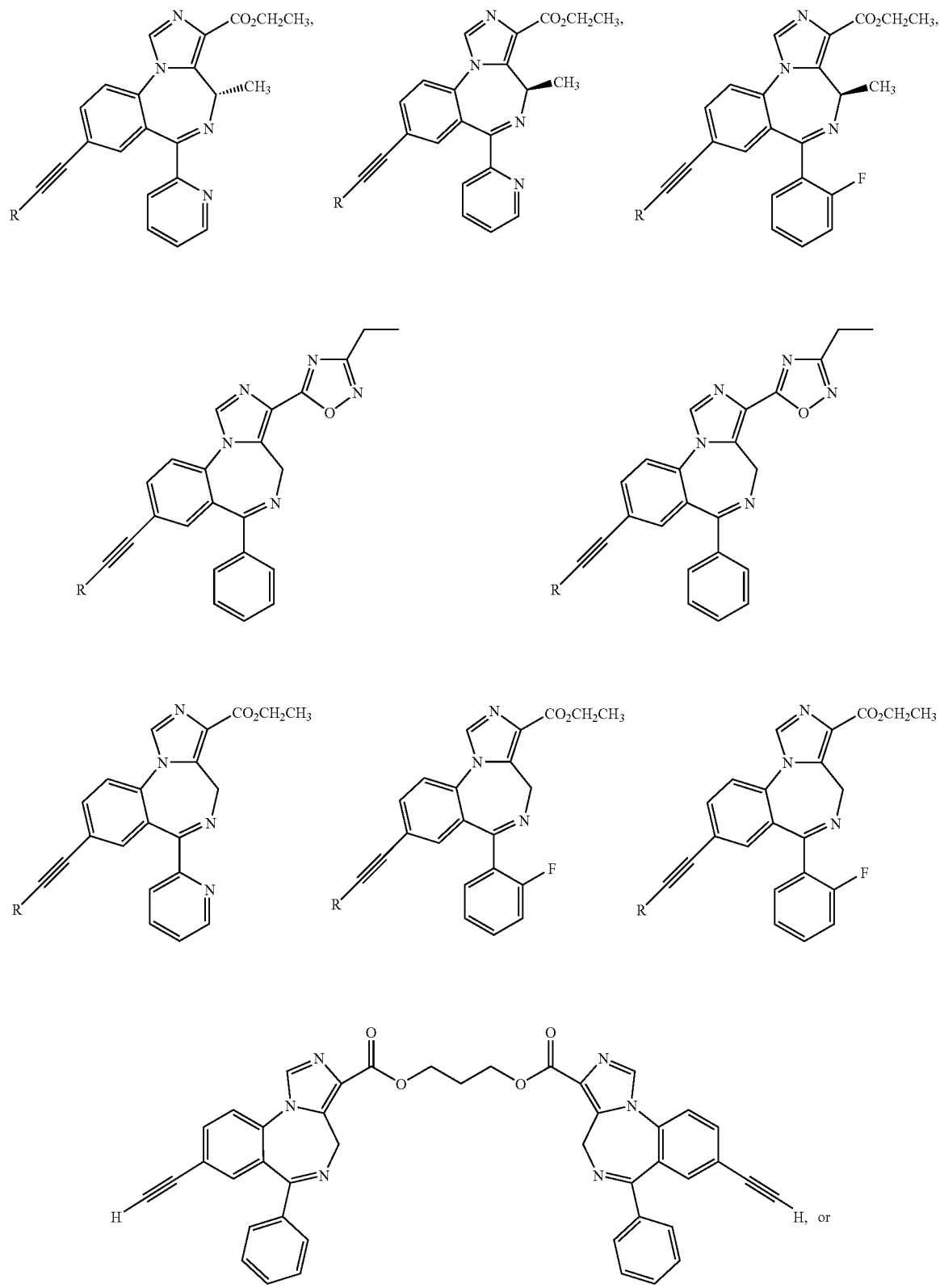

TABLE 5-continued

Benzodiazepine Derivative Compounds Selective At $GABA_A$ Receptor Subunits

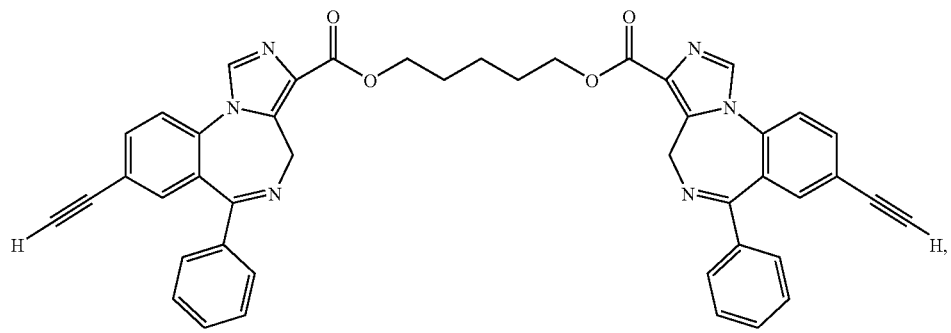

where R is H or $Si(CH_3)_3$, $R_6$ is a branched or straight chain $C_1$ to $C_4$ alkyl, e.g., $CH(CH_3)_2$ (isopropyl group), $CH_2CH_3$, or $CH_3$, or a methyl cyclopropyl, and $R_2$ is $CO_2CH(CH_3)_2$, $CO_2CH_2CH(CH_3)_2$, $CON(CH_3)_2$, $CONHCH_3$, or $COSCH_3$.

The invention claimed is:

1. A method for the treatment and suppression of neuropathic pain, inflammatory pain and migraine-associated pain comprising administering to a patient in need of such treatment an effective amount of a compound of the formula wherein the compound is

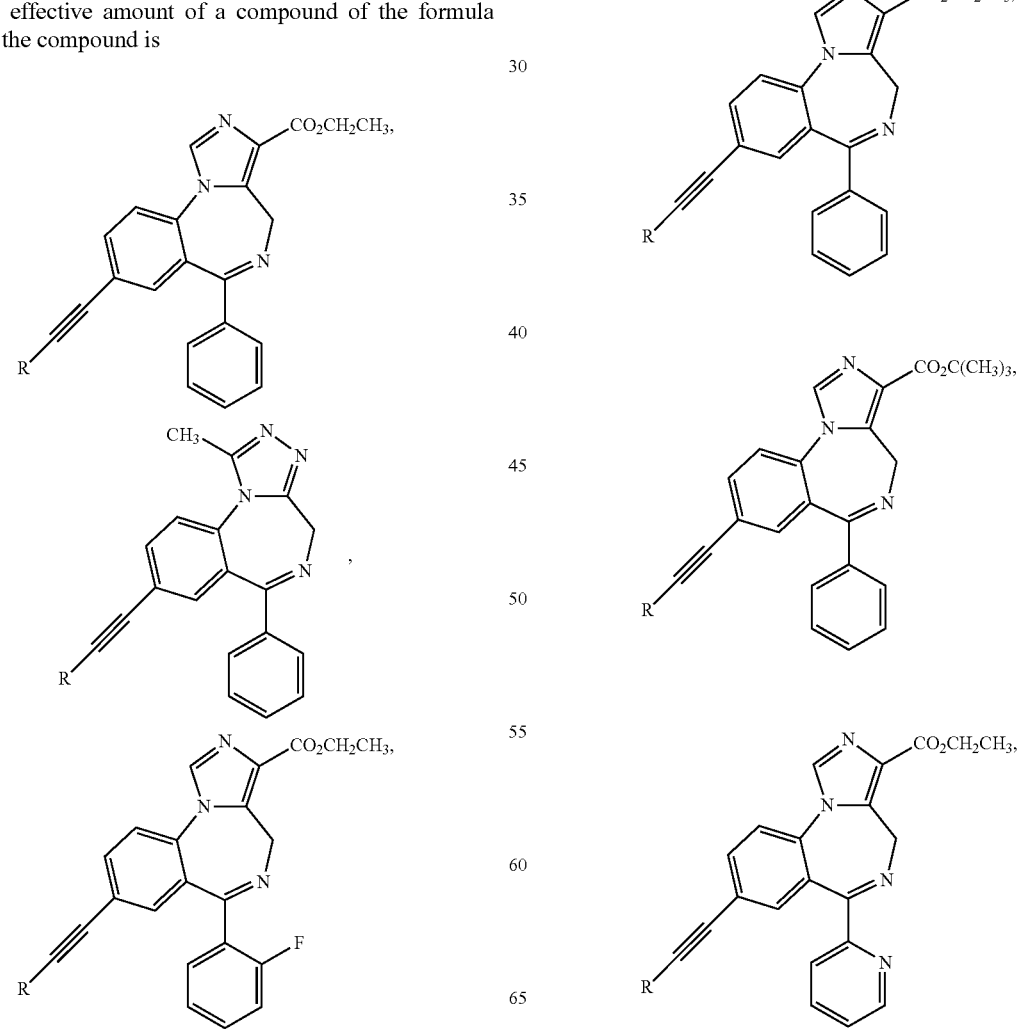

137
-continued
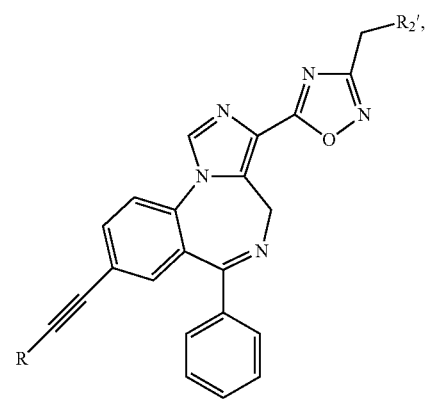
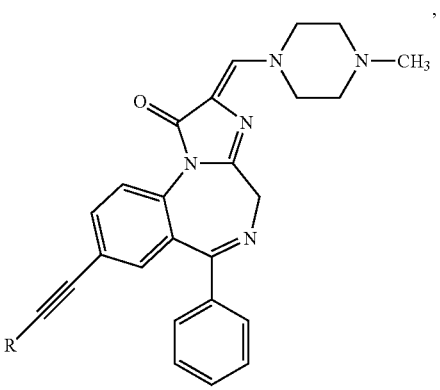
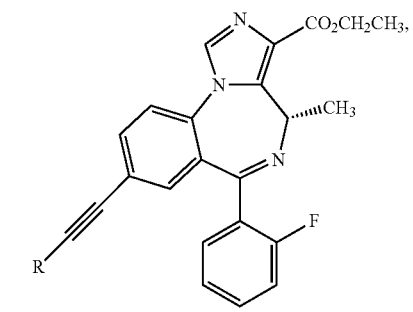
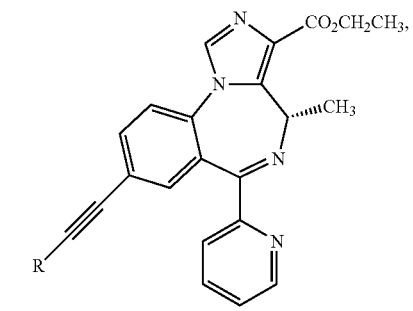
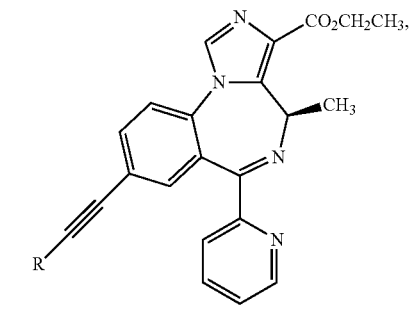
138
-continued
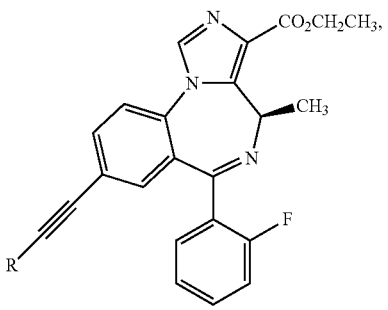
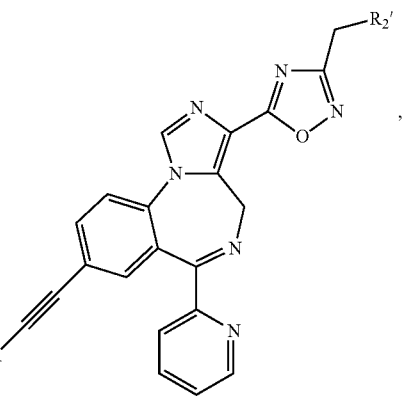
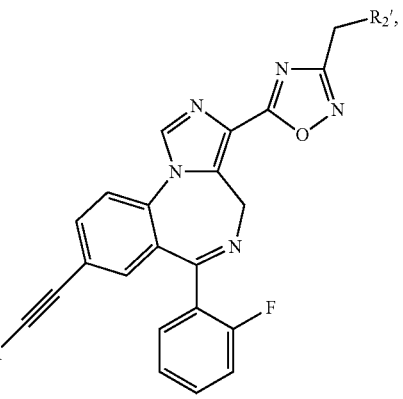
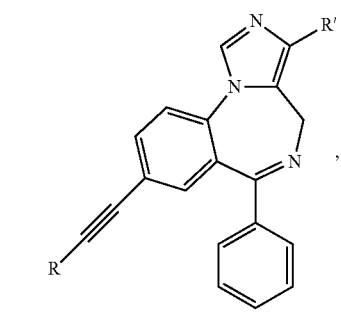
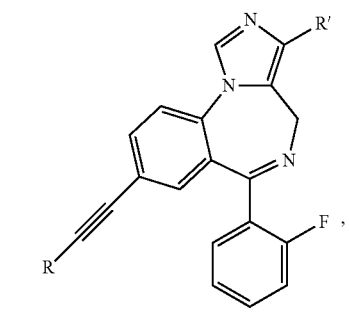

139
-continued

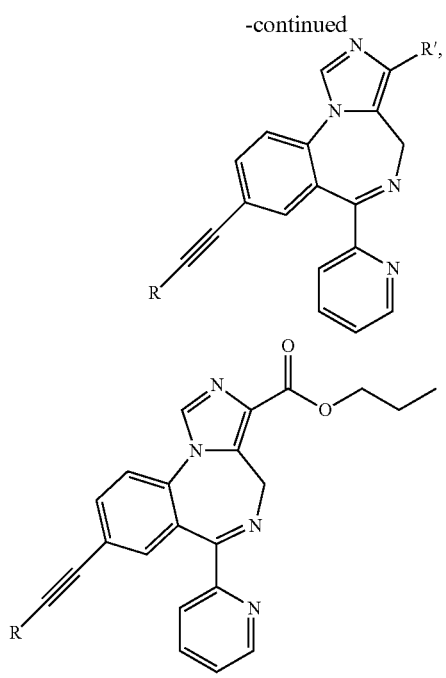

140 and salts thereof where R is H or $Si(CH_3)_3$, R' is $CO_2CH_2CH_3$, $CO_2CH(CH_3)_2$, $CO_2CH_2CH(CH_3)_2$, $CON(CH_3)_2$, $CONHCH_3$, or $COSCH_3$ and where $R'_2$ is $CH(CH_3)_2$, $CH_2CH_3$, or $CH_3$.

2. The method of claim 1 wherein the compound is

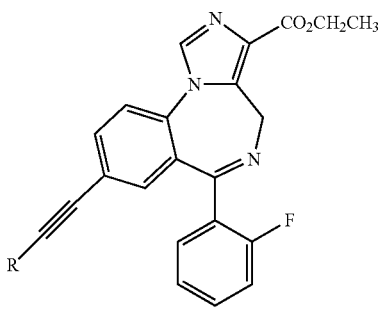

and salts thereof where R is H or $Si(CH_3)_3$.

3. The method of claim 1 wherein the compound is

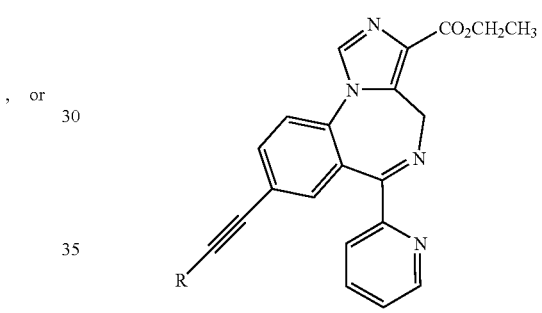

and salts thereof where R is H or $Si(CH_3)_3$.

4. A method for the treatment and suppression of neuropathic pain, inflammatory pain and migraine-associated pain comprising administering to a patient in need of such treatment an effective amount of a compound of the formula, wherein the compound is

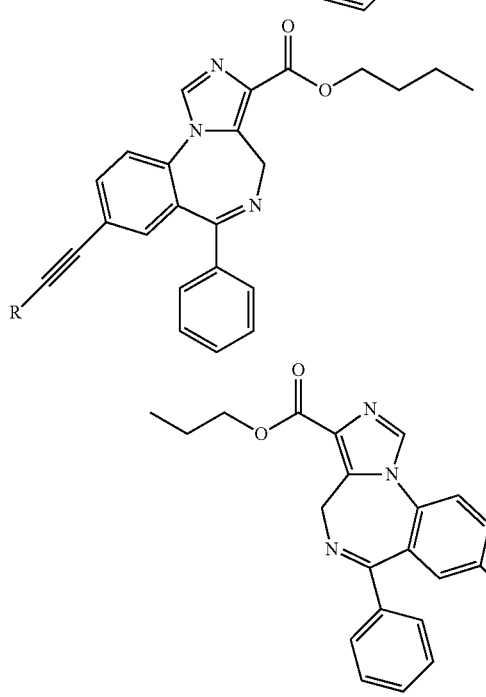

and salts thereof where R is H or $Si(CH_3)_3$.

5. A method for the treatment and suppression of neuropathic pain, inflammatory pain and migraine-associated pain comprising administering to a patient in need of such treatment an effective amount of a compound of the formula wherein the compound is

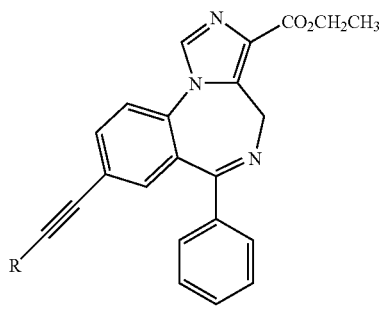

and salts thereof where R is H or Si(CH$_3$)$_3$.

6. A method for the treatment and suppression of neuropathic pain, inflammatory pain and migraine-associated pain comprising administering to a patient in need of such treatment an effective amount of a compound of the formula wherein the compound is

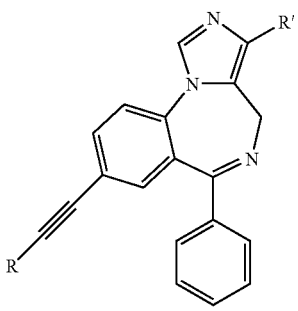

and salts thereof where R is H or Si(CH$_3$)$_3$ and R' is CO$_2$CH(CH$_3$)$_2$, CO$_2$CH$_2$CH(CH$_3$)$_2$, CON(CH$_3$)$_2$, CONHCH$_3$, or COSCH$_3$.

7. A method for the treatment and suppression of neuropathic pain, inflammatory pain and migraine-associated pain comprising administering a patient in need of such treatment an effective amount of a compound of the formula wherein the compound is

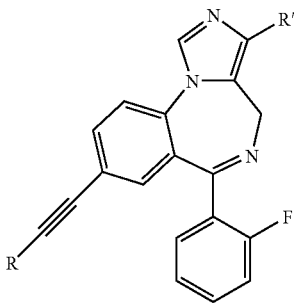

and salts thereof where R is H or Si(CH$_3$)$_3$ and R' is CO$_2$CH(CH$_3$)$_2$, CO$_2$CH$_2$CH(CH$_3$)$_2$, CON(CH$_3$)$_2$, CONHCH$_3$, or COSCH$_3$.

8. A method for the treatment and suppression of neuropathic pain, inflammatory pain and migraine-associated pain comprising administering to a patient in need of such treatment an effective amount of a compound of the formula wherein the compound is

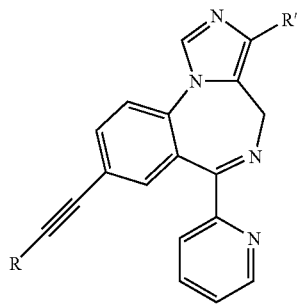

and salts thereof where R is H or Si(CH$_3$)$_3$ and R' is CO$_2$CH(CH$_3$)$_2$, CO$_2$CH$_2$CH$_2$(CH$_3$)$_2$, CON(CH$_3$)$_2$, CONHCH$_3$, or COSCH$_3$.

9. A method for the treatment and suppression of neuropathic pain, inflammatory pain and migraine-associated pain comprising administering to a patient in need of such treatment an effective amount of a compound of the formula wherein the compound is

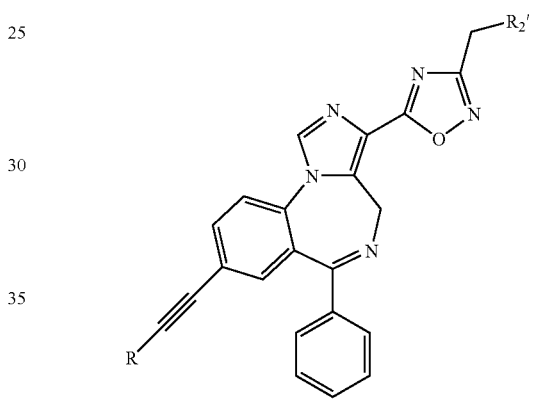

and salts thereof where R is H or Si(CH$_3$)$_3$, and where R'$_2$ is CH(CH$_3$)$_2$, CH$_2$CH$_3$, or CH$_3$.

10. A method for the treatment and suppression of neuropathic pain, inflammatory pain and migraine-associated pain comprising administering to a patient in need of such treatment an effective amount of a compound of the formula wherein the compound is

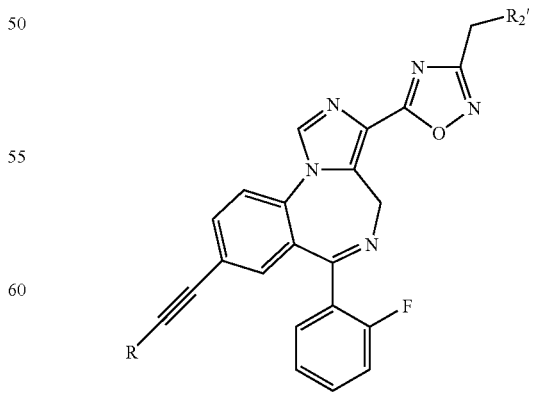

and salts thereof where R is H or Si(CH$_3$)$_3$, and where R'$_2$ is CH(CH$_3$)$_2$, CH$_2$CH$_3$, or CH$_3$.

11. A method for the treatment and suppression of neuropathic pain, inflammatory pain and migraine-associated pain comprising administering to a patient in need of such treatment an effective amount of a compound of the formula wherein the compound is
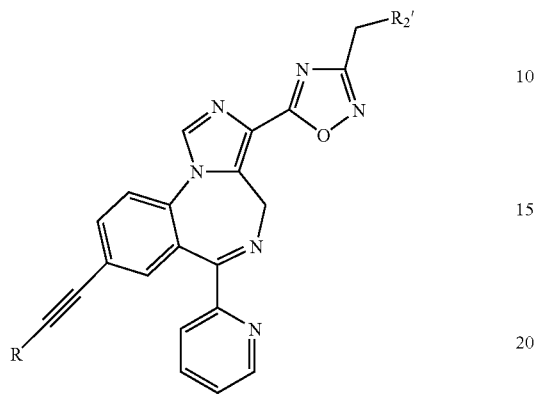
and salts thereof where R is H or Si(CH$_3$)$_3$, and where R'$_2$ is CH(CH$_3$)$_2$, CH$_2$CH$_3$, or CH$_3$.
* * * * *

UNITED STATES PATENT AND TRADEMARK OFFICE
CERTIFICATE OF CORRECTION

PATENT NO. : 8,835,424 B2  Page 1 of 1
APPLICATION NO. : 12/779449
DATED : September 16, 2014
INVENTOR(S) : Cook et al.

It is certified that error appears in the above-identified patent and that said Letters Patent is hereby corrected as shown below:

IN THE CLAIMS

Claim 8, column 142, line 16, delete "$CO_2CH_2CH_2(CH_3)_2$" and substitute therefor

-- $CO_2CH_2CH(CH_3)_2$ --

Signed and Sealed this
Second Day of December, 2014

Michelle K. Lee
*Deputy Director of the United States Patent and Trademark Office*